United States Patent
Singh et al.

(10) Patent No.: US 9,732,070 B2
(45) Date of Patent: Aug. 15, 2017

(54) PROTEIN KINASE C INHIBITORS AND USES THEREOF

(71) Applicant: Rigel Pharmaceuticals, Inc., South San Francisco, CA (US)

(72) Inventors: Rajinder Singh, Belmont, CA (US); Kin Tso, San Francisco, CA (US); Jing Zhang, Mercer Island, WA (US); Matthew Duncton, San Bruno, CA (US); Salvador Alvarez, Fremont, CA (US); Rao Kolluri, Foster City, CA (US); John Ramphal, Union City, CA (US); Sacha Holland, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 15/261,294

(22) Filed: Sep. 9, 2016

(65) Prior Publication Data

US 2017/0152246 A1    Jun. 1, 2017

Related U.S. Application Data

(63) Continuation of application No. 12/958,284, filed on Dec. 1, 2010, now abandoned.

(60) Provisional application No. 61/265,648, filed on Dec. 1, 2009, provisional application No. 61/366,469, filed on Jul. 21, 2010, provisional application No. 61/405,968, filed on Oct. 22, 2010.

(51) Int. Cl.
   C07D 401/14    (2006.01)
   A61K 31/506    (2006.01)
   C07D 405/14    (2006.01)
   A61K 31/41     (2006.01)

(52) U.S. Cl.
   CPC ............ C07D 405/14 (2013.01); A61K 31/41 (2013.01); A61K 31/506 (2013.01); C07D 401/14 (2013.01)

(58) Field of Classification Search
   CPC .... C07D 401/14; C07D 405/14; A61K 31/41; A61K 31/506
   USPC ................................. 544/323, 324; 514/275
   See application file for complete search history.

(56) References Cited

U.S. PATENT DOCUMENTS

| | | |
|---|---|---|
| 5,136,868 A | 8/1992 | Theodoridis |
| 5,958,935 A | 9/1999 | Davis et al. |
| 6,235,746 B1 | 5/2001 | Davis et al. |
| 6,545,030 B1 | 4/2003 | Barrett |
| 7,517,886 B2 | 4/2009 | Singh et al. |
| 8,178,671 B2 | 5/2012 | Singh et al. |
| 2003/0171359 A1 | 9/2003 | Dahmann et al. |
| 2004/0029902 A1 | 2/2004 | Singh et al. |
| 2006/0270694 A1 | 11/2006 | Wong |
| 2007/0293494 A1 | 12/2007 | Djung et al. |
| 2008/0027045 A1 | 1/2008 | Argade et al. |
| 2008/0096892 A1 | 4/2008 | Cheng et al. |
| 2010/0130486 A1 | 5/2010 | Singh et al. |

FOREIGN PATENT DOCUMENTS

| | | |
|---|---|---|
| WO | 9719065 | 5/1997 |
| WO | 03032997 | 4/2003 |
| WO | 03063794 | 8/2003 |
| WO | 2004014382 | 2/2004 |
| WO | 2005013996 | 2/2005 |
| WO | 2005016893 | 2/2005 |
| WO | 2007146981 | 12/2007 |
| WO | 2009012421 | 1/2009 |
| WO | 2009158571 | 12/2009 |
| WO | 2010090875 | 8/2010 |

OTHER PUBLICATIONS

Abboushi et al. (2004) "Ceramide inhibits IL-2 production by preventing protein kinase C-dependent NF-kappaB activation: possible role in protein kinase Ctheta regulation" J Immunol 173(5):3193-3200.
Duncton et al. (2010) "Dibutyl 2-(Trifluoromethyl)Cyclopropylboronate as a Useful (Trifluoromethyl)-Cyclopropyl Donor: Application to antagonists of TRPV1" Tetrahedron Lett 51:1009-1011.
Gupta et al. (2004) "1-(2-Iodophenyl)-1H-Tetrazole as a Ligand for Pd(II) Catalyzed Heck reaction" Tetrahedron Left 45(21):4113.
Hoyer et al. (2008) "Interleukin-2 in the development and control of inflammatory disease" Immunol Rev 266:19-28.
Mondiano et al. (1991) "Protein kinase C regulates both production and secretion of interleukin 2" J Biol Chem 266 (16):10552-10561.
Newton (1995) "Protein kinase C: structure, function, and regulation" J Biol Chem 270(48):28495-28498.
Potewar et al. (2007) "Efficient and Rapid Synthesis of 1-Substituted-1H-1,2,3,4-Tetrazoles in the Acidic Ionic Liquid 1-n-Butylimidazolium Tetrafluoroborate" Tetrahedron Lett 48(10):1721-1724.
Satoh et al. (1995) "Application of 5-Lithiotetrazoles in Organic Synthesis" Tetrahedron Lett 36(11):1759-1762.
Su et al. (2006) "A Facile Synthesis of 1-Substituted-1H-1,2,314-Tetrazoles Catalyzed by Ytterbium Triflate Hydrate" Eur J Org Chem 2006(12):2723-2726.
Damasio, Alzheimer's Disease and Related Dementias, Cecil Textbook of Medicine, 20th Edition, vol. 2, pp. 1992-1996 (1996).
Gura, Systems for identifying New Drugs are Often Faulty, Cancer Models, Science, vol. 278, No. 5340, pp. 1041-1042, Nov. 1997.

(Continued)

*Primary Examiner* — Deepak Rao
(74) *Attorney, Agent, or Firm* — Rudy J. Ng; Carol L. Francis; Bozicevic, Field & Francis LLP

(57) ABSTRACT

This disclosure concerns compounds which are useful as inhibitors of protein kinase C (PKC) and are thus useful for treating a variety of diseases and disorders that are mediated or sustained through the activity of PKC. This disclosure also relates to pharmaceutical compositions comprising these compounds, methods of using these compounds in the treatment of various diseases and disorders, processes for preparing these compounds and intermediates useful in these processes.

27 Claims, No Drawings

(56) References Cited

OTHER PUBLICATIONS

Hayashi et al., Protein Kinase C theta (PKCe): A key role in T cell life and death, Pharmacological Research 55 (2007), pp. 537-544.
Johnson et al., Relationships between drug activity in NCI preclinical in vitro and in vivo models and early clinical trials, British Journal of Cancer (2001) 64(1 0): 1424-1431.
Layzer, Degenerative Diseases of the Nervous System, Cecil Textbook of Medicine, 20th Edition, vol. 2, pp. 2050-2057 (1996).
Pearce et al., Failure modes in anticancer drug discovery and development, Cancer Drug Design and Discovery Edited by Stephen Neidle, Chapter 18, pp. 424-435 (2008).
Simone, Oncology: Introduction, Cecil Textbook of Medicine, 20th Edition, vol. 1, pp. 1004-1010, 1996.

PROTEIN KINASE C INHIBITORS AND USES THEREOF

CROSS-REFERENCE TO RELATED APPLICATIONS

This application is a continuation of U.S. application Ser. No. 12/958,284, filed Dec. 1, 2010, which claims the benefit of Provisional Application Ser. Nos. 61/265,648, filed Dec. 1, 2009; 61/366,469, filed Jul. 21, 2010; and 61/405,968, filed Oct. 22, 2010, each which application is incorporated by reference in their entireties.

BACKGROUND

Protein kinase C ("PKC") is a key enzyme in signal transduction involved in a variety of cellular functions, including cell growth, regulation of gene expression, and ion channel activity. The PKC family of isozymes includes at least 11 different protein kinases that can be divided into at least three subfamilies based on their homology and sensitivity to activators. Each isozyme includes a number of homologous ("conserved" or "C") domains interspersed with isozyme-unique ("variable" or "V") domains. Members of the "classical" or "cPKC" subfamily, PKC α, $β_i$, $β_{ii}$ and γ, contain four homologous domains (C1, C2, C3 and C4) and require calcium, phosphatidylserine, and diacylglycerol or phorbol esters for activation. Members of the "novel" or "nPKC" subfamily, PKC δ, ε, η and θ, lack the C2 homologous domain and do not require calcium for activation. Finally, members of the "atypical" or "aPKC" subfamily, PKC ζ and λ/i, lack both the C2 and one-half of the C1 homologous domains and are insensitive to diacylglycerol, phorbol esters and calcium.

SUMMARY

This disclosure concerns compounds which are useful as inhibitors of protein kinase C (PKC) and are thus useful for treating a variety of diseases and disorders that are mediated or sustained through the activity of PKC. This disclosure also relates to pharmaceutical compositions comprising these compounds, methods of using these compounds in the treatment of various diseases and disorders, processes for preparing these compounds and intermediates useful in these processes.

Exemplary chemical structures are provided throughout the disclosure. By way of example, such compounds are represented by the following formula:

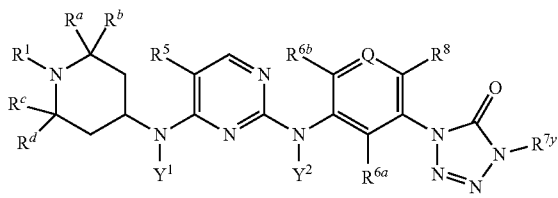

(I)

wherein $R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen, alkyl, and acyl;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is selected from N and $CR^{7b}$;

$R^{6a}$, $R^{6b}$, $R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

alk is a bond, alkylene or substituted alkylene;

A is selected from aryl, cycloalkyl, heteroaryl, and heterocyclyl;

wherein the A ring can be substituted or unsubstituted;

$R^{7y}$ is selected from hydrogen, alkyl, cycloalkyl, and substituted alkyl;

or a salt or stereoisomer thereof.

DETAILED DESCRIPTION

This disclosure concerns compounds which are useful as inhibitors of protein kinase C (PKC) and are thus useful for treating a variety of diseases and disorders that are mediated or sustained through the activity of PKC. This disclosure also relates to pharmaceutical compositions comprising these compounds, methods of using these compounds in the treatment of various diseases and disorders, processes for preparing these compounds and intermediates useful in these processes.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is specifically contemplated. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978.

The nomenclature used herein to name the subject compounds is illustrated in the Examples herein. This nomenclature has generally been derived using the commercially-available AutoNom software (MDL, San Leandro, Calif.).

TERMS

The following terms have the following meanings unless otherwise indicated. Any undefined terms have their art recognized meanings.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O) substituted alkyl, NR$^{20}$C(O)cycloalkyl, —NR$^{20}$C(O) substituted cycloalkyl, —NR$^{20}$C(O)cycloalkenyl, —NR$^{20}$C(O) substituted cycloalkenyl, —NR$^{20}$C(O) alkenyl, —NR$^{20}$C(O) substituted alkenyl, —NR$^{20}$C(O) alkynyl, —NR$^{20}$C(O) substituted alkynyl, —NR$^{20}$C(O)aryl, —NR$^{20}$C(O) substituted aryl, —NR$^{20}$C(O)heteroaryl, —NR$^{20}$C(O) substituted heteroaryl, —NR$^{20}$C(O)heterocyclic, and —NR$^{20}$C(O) substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$ wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic, provided that the point of attachment is through an atom of the aromatic aryl group. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O— alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen, and sulfur within the ring. Such heteroaryl groups can have a single ring (e.g., pyridinyl, imidazolyl or furyl) or multiple condensed rings (e.g., indolizinyl, quinolinyl, benzimidazolyl or benzothienyl), wherein the condensed rings may or may not be aromatic and/or contain a heteroatom, provided that the point of attachment is through an atom of the aromatic heteroaryl group. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein.

This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocilooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocilooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $M^+$ may independently be, for example, an alkali ion, such as $K^+$, $Na^+$, $Li+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means e.g. that one of the counter ions for such divalent alkali earth ions can be an ionized form of a compound of the invention and the other a typical counter ion such as chloride, or two ionized compounds of the invention can serve as counter ions for such divalent alkali earth ions, or a doubly ionized compound of the invention can serve as the counter ion for such divalent alkali earth ions). As specific examples, —$NR^{80}R^{80}$ is meant to include —$NH_2$, —NH-alkyl, N-pyrrolidinyl, N-piperazinyl, 4N-methyl-piperazin-1-yl and N-morpholinyl.

In addition to the groups disclosed with respect to the individual terms herein, substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —$P(O)(OR^{70})O^-M^+$, —$P(O)(OR^{70})_2$, —$C(O)R^{70}$, —C(S)$R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})NR^{80}R^{80}$, —$OC(O)R^{70}$, —OC(S)$R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

In addition to the disclosure herein, substituent groups for hydrogens on nitrogen atoms in "substituted" heteroalkyl and cycloheteroalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (e.g., salts having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when the hydrogen of an acid is replaced by a cation, such as a metal cation or an organic cation and the like. Where applicable, the salt is a pharmaceutically acceptable salt, although this is not required for salts of compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Patient" refers to human and non-human animals, especially mammals.

The term "treating" or "treatment" as used herein means the treating or treatment of a disease or medical condition in a patient, such as a mammal (particularly a human) that includes: (a) preventing the disease or medical condition from occurring, i.e., prophylactic treatment of a patient; (b) ameliorating the disease or medical condition, i.e., eliminating or causing regression of the disease or medical condition in a patient; (c) suppressing the disease or medical condition, i.e., slowing or arresting the development of the disease or medical condition in a patient; or (d) alleviating the symptoms of the disease or medical condition in a patient.

REPRESENTATIVE EMBODIMENTS

The following substituents and values are intended to provide representative examples of various aspects and embodiments. These representative values are intended to further define and illustrate such aspects and embodiments and are not intended to exclude other embodiments or to limit the scope of this invention. In this regard, the representation that a particular value or substituent is preferred is not intended in any way to exclude other values or substituents from this invention unless specifically indicated.

These compounds may contain one or more chiral centers and therefore, the embodiments are directed to racemic mixtures; pure stereoisomers (i.e., enantiomers or diastereomers); stereoisomer-enriched mixtures and the like unless otherwise indicated. When a particular stereoisomer is shown or named herein, it will be understood by those skilled in the art that minor amounts of other stereoisomers may be present in the compositions unless otherwise indicated, provided that the desired utility of the composition as a whole is not eliminated by the presence of such other isomers.

The compositions of the present disclosure include compounds of formula I, shown below. Pharmaceutical compositions and methods of the present disclosure also contemplate compounds of formula I.

Formula I

In one of its composition aspects, the present embodiments provide a compound of formula (I):

wherein $R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen, alkyl, and acyl;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is selected from N and $CR^{7b}$;

$R^{6a}$, $R^{6b}$, $R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

alk is a bond, alkylene or substituted alkylene;

A is selected from aryl, cycloalkyl, heteroaryl, and heterocyclyl;

wherein the A ring can be substituted or unsubstituted;

$R^{7y}$ is selected from hydrogen, alkyl, cycloalkyl, and substituted alkyl;

or a salt or stereoisomer thereof.

In formula I, $R^5$ can be selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl. In certain instances, $R^5$ is cyano, halogen, acyl, aminoacyl, or nitro. In certain instances, $R^5$ is halogen. In certain instances, $R^5$ is fluoro. In certain instances, $R^5$ is cyano. In certain instances, $R^5$ is fluoro, cyano, or aminoacyl. In certain instances, $R^5$ is cyano or aminoacyl.

In formula I, $Y^1$ and $Y^2$ can be independently selected from hydrogen, alkyl, and acyl. In certain instances, $Y^1$ is hydrogen. In certain instances, $Y^1$ is alkyl. In certain instances, $Y^1$ is acyl. In certain instances, $Y^2$ is hydrogen. In certain instances, $Y^2$ is alkyl. In certain instances, $Y^2$ is acyl.

In formula I, $R^1$ can be selected from hydrogen, alkyl, substituted alkyl, cycloalkyl, acyl, and oxy radical. In certain instances, $R^1$ is hydrogen or alkyl. In certain instances, $R^1$ is hydrogen. In certain instances, $R^1$ is alkyl. In certain instances, $R^1$ is methyl. In certain instances, $R^1$ is hydrogen, alkyl, substituted alkyl, or oxy radical. In certain instances, $R^1$ is hydrogen, alkyl, substituted alkyl, acyl, or cycloalkyl.

In formula I, $R^a$ and $R^b$ can be independently selected from hydrogen and alkyl. In certain instances, $R^a$ and $R^b$ are both alkyl. In certain instances, $R^a$ and $R^b$ are both methyl. In certain instances, at least one of $R^a$ and $R^b$ is alkyl.

In formula I, $R^c$ and $R^d$ can be independently selected from hydrogen and alkyl. In certain instances, $R^c$ and $R^d$ are both alkyl. In certain instances, $R^c$ and $R^d$ are both methyl. In certain instances, at least one of $R^c$ and $R^d$ is alkyl.

In formula I, Q can be selected from N and $CR^{7b}$. In certain instances, Q is $CR^{7b}$. In certain instances, Q is N.

In formula I, $R^{6a}$, $R^{6b}$, $R^{7b}$ and $R^8$ can be independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A.

In certain instances, in formula I, $R^{6a}$, $R^{6b}$, $R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, cycloalkyl, substituted cycloalkyl, and —O-alk-A.

In certain instances, in formula I, $R^{6a}$, $R^{6b}$, $R^{7b}$ and $R^8$ are independently selected from hydrogen, alkyl, substituted alkyl, halogen, cyano, alkoxy, substituted alkoxy, cycloalkyl, substituted cycloalkyl, acyl, carboxyl, carboxyl ester, aminoacyl, and —O-alk-A. In certain instances, at least one of $R^{6a}$, $R^{6b}$, $R^{7b}$ and $R^8$ is alkyl or substituted alkyl. In certain instances, at least one of $R^{6a}$, $R^{6b}$, $R^{7b}$ and $R^8$ is halogen. In certain instances, at least one of $R^{6a}$, $R^{6b}$, $R^{7b}$ and R is alkoxy, substituted alkoxy, or —O-alk-A. In certain instances, at least one of $R^{6a}$, $R^{6b}$, $R^{7b}$ and $R^8$ is cyano, acyl, carboxyl, carboxyl ester, or aminoacyl. In certain instances, at least one of $R^{6a}$, $R^{6b}$, $R^{7b}$ and $R^8$ is cycloalkyl or substituted cycloalkyl.

In certain instances, at least one of $R^{6a}$, $R^{6b}$, $R^{7b}$ and $R^8$ are independently selected from fluoro, trifluoromethyl, difluoromethoxy, hydroxyl, and isopropoxy.

In certain instances, one of $R^{6a}$ and $R^{6b}$ is fluoro and the other is hydrogen.

In certain instances, $R^{6a}$ is selected from hydrogen, alkyl, substituted alkyl, halogen, alkoxy, substituted alkoxy, cycloalkyl, and substituted cycloalkyl. In certain instances, $R^{6a}$ is selected from hydrogen, alkyl, substituted alkyl, and halogen. In certain instances, $R^{6a}$ is hydrogen. In certain instances, $R^{6a}$ is selected from alkyl and substituted alkyl. In certain instances, $R^{6a}$ is halogen. In certain instances, $R^{6a}$ is fluoro.

In certain instances, $R^{6b}$ is selected from hydrogen, alkyl, substituted alkyl, halogen, alkoxy, substituted alkoxy, cycloalkyl, and substituted cycloalkyl. In certain instances, $R^{6b}$ is selected from hydrogen, alkyl, substituted alkyl, and halogen. In certain instances, $R^{6b}$ is hydrogen. In certain instances, $R^{6b}$ is selected from alkyl and substituted alkyl. In certain instances, $R^{6b}$ is halogen. In certain instances, $R^{6b}$ is fluoro.

In certain instances, $R^{7b}$ is selected from hydrogen, alkyl, substituted alkyl, halogen, alkoxy, substituted alkoxy, cycloalkyl, and substituted cycloalkyl. In certain instances, $R^{7b}$ is selected from hydrogen, alkyl, and substituted alkyl. In certain instances, $R^{7b}$ is hydrogen. In certain instances, $R^{7b}$ is selected from alkyl and substituted alkyl.

In certain instances, $R^{7b}$ is selected from hydrogen, alkyl, substituted alkyl, halogen, cyano, alkoxy, substituted alkoxy, cycloalkyl, substituted cycloalkyl, acyl, carboxyl, carboxyl ester, aminoacyl, and —O-alk-A.

In certain instances, $R^8$ is selected from hydrogen, alkyl, substituted alkyl, halogen, alkoxy, substituted alkoxy, cycloalkyl, and substituted cycloalkyl. In certain instances, $R^8$ is hydrogen. In certain instances, $R^8$ is alkyl or substituted alkyl. In certain instances, $R^8$ is methyl. In certain instances, $R^8$ is halogen. In certain instances, $R^8$ is fluoro. In certain instances, $R^8$ is alkoxy or substituted alkoxy. In certain instances, $R^8$ is fluoro. In certain instances, $R^8$ is cycloalkyl or substituted cycloalkyl. In certain instances, $R^8$ is cyclopropyl.

In certain instances, any of $R^{7b}$ or $R^8$ is selected from hydrogen, alkyl, substituted alkyl, halogen, cyano, alkoxy, substituted alkoxy, cycloalkyl, substituted cycloalkyl, acyl, carboxyl, carboxyl ester, aminoacyl, and —O-alk-A. In certain instances, at least one of $R^{7b}$ or $R^8$ is cycloalkyl, or substituted cycloalkyl. In certain instances, at least one of $R^{7b}$ or $R^8$ is alkoxy, substituted alkoxy, or —O-alk-A. In certain instances, at least one of $R^{7b}$ or $R^8$ is alkyl, substituted alkyl, or halogen.

In formula I, for "—O-alk-A," alk is a bond, alkylene or substituted alkylene. In certain instances, alk is a bond. In certain instances, alk is alkylene. In certain instances, alk is ethylene or propylene. In certain instances, alk is substituted alkylene. In certain instances, alk is substituted ethylene or substituted propylene.

In certain instances, in formula I, for "—O-alk-A," alk is a bond or alk is ethylene, substituted ethylene, propylene, or —C(CH$_3$)$_2$CH$_2$—. In certain instances, in formula I, for "—O-alk-A," alk is a bond or alk is substituted propylene, —C(CH$_3$)$_2$CH$_2$CH$_2$—, or —C(CH$_3$)$_2$CH$_2$C(O)—.

In formula I, A can be selected from aryl, cycloalkyl, heteroaryl, and heterocyclyl; wherein the A ring can be substituted or unsubstituted. In certain instances, A is aryl or substituted aryl. In certain instances, A is cycloalkyl or substituted cycloalkyl. In certain instances, A is heteroaryl or substituted heteroaryl. In certain instances, A is heterocyclyl or substituted heterocyclyl. In certain instances, A is heteroaryl, substituted heteroaryl, heterocyclyl, or substituted heterocyclyl.

In certain instances, in formula I, A is selected from azetidine, imidazole, pyrazole, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, pteridine, carbazole, carboline, isothiazole, phenazine, isoxazole, imidazolidine, imidazoline, oxazole, oxazolidine, piperidine, piperazine, indoline, phthalimide, 1,2,3,4-tetrahydroisoquinoline, tetrazole, triazole, thiazole, thiazolidine, thiophene, thiomorpholinyl, 1,1-dioxothiomorpholinyl, piperidinyl, 3-pyrrolidine; wherein the A ring can be substituted or unsubstituted.

In certain instances, in formula I, A is selected from 1-triazole, 3-pyrrolidine, 4-piperidine, and 1-imidazolidine; wherein the A ring can be substituted or unsubstituted.

In certain instances, in formula I, A is selected from piperidine, tetrahydropyranyl, tetrahydrothiopyranyl, azetidinyl, azepanyl, and furanyl; wherein the A ring can be substituted or unsubstituted.

In formula I, $R^{7y}$ is selected from hydrogen, alkyl, cycloalkyl, and substituted alkyl. In certain instances, $R^{7y}$ is hydrogen. In certain instances, $R^{7y}$ is alkyl. In certain instances, $R^{7y}$ is methyl. In certain instances, $R^{7y}$ is isopropyl. In certain instances, $R^{7y}$ is cycloalkyl. In certain instances, $R^{7y}$ is substituted alkyl.

Formula II

In one of its composition aspects, the present embodiments provide a compound of formula (II):

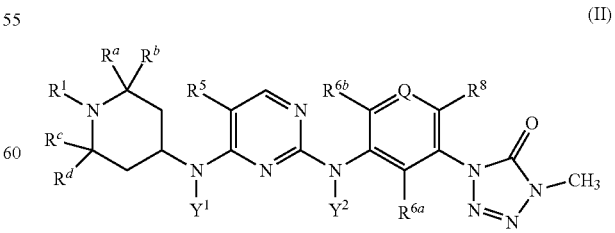

wherein $R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen, alkyl, and acyl;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is selected from N and $CR^{7b}$;

$R^{6a}$, $R^{6b}$, $R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

alk is a bond, alkylene or substituted alkylene;

A is selected from aryl, cycloalkyl, heteroaryl, and heterocyclyl;

wherein the A ring can be substituted or unsubstituted;

or a salt or stereoisomer thereof.

In formula II, $R^5$ can be selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl. In certain instances, $R^5$ is cyano, halogen, acyl, aminoacyl, or nitro. In certain instances, $R^5$ is halogen. In certain instances, $R^5$ is fluoro. In certain instances, $R^5$ is fluoro, cyano, or aminoacyl. In certain instances, $R^5$ is cyano or aminoacyl.

In formula II, $Y^1$ and $Y^2$ can be independently selected from hydrogen, alkyl, and acyl. In certain instances, $Y^1$ is hydrogen. In certain instances, $Y^1$ is alkyl. In certain instances, $Y^1$ is acyl. In certain instances, $Y^2$ is hydrogen. In certain instances, $Y^2$ is alkyl. In certain instances, $Y^2$ is acyl.

In formula II, $R^1$ can be selected from hydrogen, alkyl, substituted alkyl, cycloalkyl, acyl, and oxy radical. In certain instances, $R^1$ is hydrogen or alkyl. In certain instances, $R^1$ is hydrogen. In certain instances, $R^1$ is alkyl. In certain instances, $R^1$ is methyl. In certain instances, $R^1$ is hydrogen, alkyl, substituted alkyl, or oxy radical. In certain instances, $R^1$ is hydrogen, alkyl, substituted alkyl, acyl, or cycloalkyl.

In formula II, $R^a$ and $R^b$ can be independently selected from hydrogen and alkyl. In certain instances, $R^a$ and $R^b$ are both alkyl. In certain instances, $R^a$ and $R^b$ are both methyl. In certain instances, at least one of $R^a$ and $R^b$ is alkyl.

In formula II, $R^c$ and $R^d$ can be independently selected from hydrogen and alkyl. In certain instances, $R^c$ and $R^d$ are both alkyl. In certain instances, $R^c$ and $R^d$ are both methyl. In certain instances, at least one of $R^c$ and $R^d$ is alkyl.

In formula II, Q can be selected from N and $CR^{7b}$. In certain instances, Q is $CR^{7b}$ In certain instances, Q is N.

In formula II, $R^{7b}$ and $R^8$ can be independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A.

In certain instances, in formula II, $R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, and —O-alk-A.

In certain instances, $R^{7b}$ and $R^8$ are independently selected from fluoro, trifluoromethyl, difluoromethoxy, hydroxyl, and isopropoxy.

In certain instances, $R^{7b}$ is selected from hydrogen, alkyl, and substituted alkyl. In certain instances, $R^{7b}$ is hydrogen. In certain instances, $R^{7b}$ is selected from alkyl and substituted alkyl.

In certain instances, $R^8$ is selected from hydrogen, alkyl, substituted alkyl, halogen, alkoxy, and substituted alkoxy. In certain instances, $R^8$ is hydrogen. In certain instances, $R^8$ is alkyl or substituted alkyl. In certain instances, $R^8$ is methyl. In certain instances, $R^8$ is halogen. In certain instances, $R^8$ is fluoro. In certain instances, $R^8$ is alkoxy or substituted alkoxy.

In formula II, for "—O-alk-A," alk can be present or not present and is alkyl or substituted alkyl. In certain instances, alk is not present. In certain instances, alk is present and is alkyl. In certain instances, alk is present and is ethylene or propylene. In certain instances, alk is present and is substituted alkyl. In certain instances, alk is present and is substituted ethylene or substituted propylene.

In certain instances, in formula II, for "—O-alk-A," alk is not present or alk is present and is ethylene, substituted ethylene, propylene, or —C(CH$_3$)$_2$CH$_2$—. In certain instances, in formula I, for "—O-alk-A," alk is not present or alk is present and is substituted propylene, —C(CH$_3$)$_2$CH$_2$CH$_2$—, or —C(CH$_3$)$_2$CH$_2$C(O)—.

In formula II, A can be selected from aryl, cycloalkyl, heteroaryl, and heterocyclyl; wherein the A ring can be substituted or unsubstituted. In certain instances, A is aryl or substituted aryl. In certain instances, A is cycloalkyl or substituted cycloalkyl. In certain instances, A is heteroaryl or substituted heteroaryl. In certain instances, A is heterocyclyl or substituted heterocyclyl. In certain instances, A is heteroaryl, substituted heteroaryl, heterocyclyl, or substituted heterocyclyl.

In certain instances, in formula II, A is selected from azetidine, imidazole, pyrazole, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, pteridine, carbazole, carboline, isothiazole, phenazine, isoxazole, imidazolidine, imidazoline, oxazole, oxazolidine, piperidine, piperazine, indoline, phthalimide, 1,2,3,4-tetrahydroisoquinoline, tetrazole, triazole, thiazole, thiazolidine, thiophene, thiomorpholinyl, 1,1-dioxothiomorpholinyl, piperidinyl, 3-pyrrolidine; wherein the A ring can be substituted or unsubstituted.

In certain instances, in formula II, A is selected from 1-triazole, 3-pyrrolidine, 4-piperidine, and 1-imidazolidine; wherein the A ring can be substituted or unsubstituted.

In certain instances, in formula II, A is selected from piperidine, tetrahydropyranyl, tetrahydrothiopyranyl, azetidinyl, azepanyl, and furanyl; wherein the A ring can be substituted or unsubstituted.

Formula III

In one of its composition aspects, the present embodiments provide a compound of formula (III):

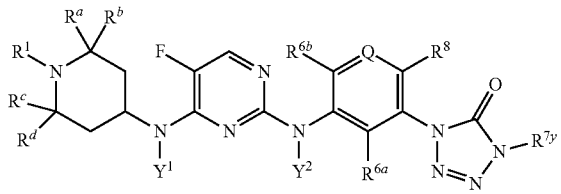

(III)

wherein $Y^1$ and $Y^2$ are independently selected from hydrogen, alkyl, and acyl;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is selected from N and $CR^{7b}$ $R^{6a}$, $R^{6b}$, $R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

alk is a bond, alkylene or substituted alkylene;

A is selected from aryl, cycloalkyl, heteroaryl, and heterocyclyl;

wherein the A ring can be substituted or unsubstituted;

$R^{7y}$ is selected from hydrogen, alkyl, and substituted alkyl;

or a salt or stereoisomer thereof.

In formula III, $Y^1$ and $Y^2$ can be independently selected from hydrogen, alkyl, and acyl. In certain instances, $Y^1$ is hydrogen. In certain instances, $Y^1$ is alkyl. In certain instances, $Y^1$ is acyl. In certain instances, $Y^2$ is hydrogen. In certain instances, $Y^2$ is alkyl. In certain instances, $Y^2$ is acyl.

In formula III, $R^1$ can be selected from hydrogen, alkyl, substituted alkyl, cycloalkyl, acyl, and oxy radical. In certain instances, $R^1$ is hydrogen or alkyl. In certain instances, $R^1$ is hydrogen. In certain instances, $R^1$ is alkyl. In certain instances, $R^1$ is methyl. In certain instances, $R^1$ is hydrogen, alkyl, substituted alkyl, or oxy radical. In certain instances, $R^1$ is hydrogen, alkyl, substituted alkyl, acyl, or cycloalkyl.

In formula III, $R^a$ and $R^b$ can be independently selected from hydrogen and alkyl. In certain instances, $R^a$ and $R^b$ are both alkyl. In certain instances, $R^a$ and $R^b$ are both methyl. In certain instances, at least one of $R^a$ and $R^b$ is alkyl.

In formula III, $R^c$ and $R^d$ can be independently selected from hydrogen and alkyl. In certain instances, $R^c$ and $R^d$ are both alkyl. In certain instances, $R^c$ and $R^d$ are both methyl. In certain instances, at least one of $R^c$ and $R^d$ is alkyl.

In formula III, Q can be selected from N and $CR^{7b}$. In certain instances, Q is $CR^{7b}$. In certain instances, Q is N.

In formula III, $R^{7b}$ and $R^8$ can be independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A.

In certain instances, in formula III, $R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, and —O-alk-A.

In certain instances, $R^{7b}$ and $R^8$ are independently selected from fluoro, trifluoromethyl, difluoromethoxy, hydroxyl, and isopropoxy.

In certain instances, $R^{7b}$ is selected from hydrogen, alkyl, and substituted alkyl. In certain instances, $R^{7b}$ is hydrogen. In certain instances, $R^{7b}$ is selected from alkyl and substituted alkyl.

In certain instances, $R^8$ is selected from hydrogen, alkyl, substituted alkyl, halogen, alkoxy, and substituted alkoxy. In certain instances, $R^8$ is hydrogen. In certain instances, $R^8$ is alkyl or substituted alkyl. In certain instances, R is methyl. In certain instances, $R^8$ is halogen. In certain instances, $R^8$ is fluoro. In certain instances, $R^8$ is alkoxy or substituted alkoxy.

In formula III, for "—O-alk-A," alk can be present or not present and is alkyl or substituted alkyl. In certain instances, alk is not present. In certain instances, alk is present and is alkyl. In certain instances, alk is present and is ethylene or propylene. In certain instances, alk is present and is substituted alkyl. In certain instances, alk is present and is substituted ethylene or substituted propylene.

In certain instances, in formula III, for "—O-alk-A," alk is not present or alk is present and is ethylene, substituted ethylene, propylene, or —C(CH$_3$)$_2$CH$_2$—. In certain instances, in formula I, for "—O-alk-A," alk is not present or alk is present and is substituted propylene, —C(CH$_3$)$_2$CH$_2$CH$_2$—, or —C(CH$_3$)$_2$CH$_2$C(O)—.

In formula III, A can be selected from aryl, cycloalkyl, heteroaryl, and heterocyclyl; wherein the A ring can be substituted or unsubstituted. In certain instances, A is aryl or substituted aryl. In certain instances, A is cycloalkyl or substituted cycloalkyl. In certain instances, A is heteroaryl or substituted heteroaryl. In certain instances, A is heterocyclyl or substituted heterocyclyl. In certain instances, A is heteroaryl, substituted heteroaryl, heterocyclyl, or substituted heterocyclyl.

In certain instances, in formula III, A is selected from azetidine, imidazole, pyrazole, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, pteridine, carbazole, carboline, isothiazole, phenazine, isoxazole, imidazolidine, imidazoline, oxazole, oxazolidine, piperidine, piperazine, indoline, phthalimide, 1,2,3,4-tetrahydroisoquinoline, tetrazole, triazole, thiazole, thiazolidine, thiophene, thiomorpholinyl, 1,1-dioxothiomorpholinyl, piperidinyl, 3-pyrrolidine; wherein the A ring can be substituted or unsubstituted.

In certain instances, in formula III, A is selected from 1-triazole, 3-pyrrolidine, 4-piperidine, and 1-imidazolidine; wherein the A ring can be substituted or unsubstituted.

In certain instances, in formula III, A is selected from piperidine, tetrahydropyranyl, tetrahydrothiopyranyl, azetidinyl, azepanyl, and furanyl; wherein the A ring can be substituted or unsubstituted.

In formula III, $R^{7y}$ is selected from hydrogen, alkyl, and substituted alkyl. In certain instances, $R^{7y}$ is hydrogen. In certain instances, $R^{7y}$ is alkyl. In certain instances, $R^{7y}$ is methyl. In certain instances, $R^{7y}$ is isopropyl. In certain instances, $R^{7y}$ is substituted alkyl.

Formula IV

In one of its composition aspects, the present embodiments provide a compound of formula (IV):

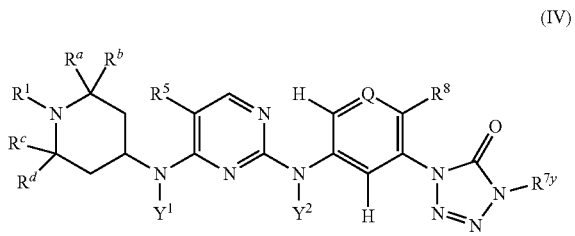

(IV)

wherein
$R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen, alkyl, and acyl;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is selected from N and $CR^{7b}$ $R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

alk is a bond, alkylene or substituted alkylene;

A is selected from aryl, cycloalkyl, heteroaryl, and heterocyclyl;

wherein the A ring can be substituted or unsubstituted;

$R^{7y}$ is selected from hydrogen, alkyl, and substituted alkyl;

or a salt or stereoisomer thereof.

Formula V

In one of its composition aspects, the present embodiments provide a compound of formula (V):

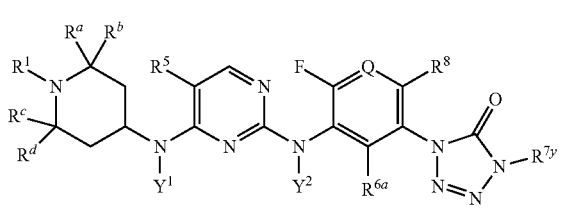

(V)

wherein
$R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ and $Y^2$ are independently selected from hydrogen, alkyl, and acyl;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is selected from N and $CR^{7b}$;

$R^{6a}$, $R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

alk is a bond, alkylene or substituted alkylene;

A is selected from aryl, cycloalkyl, heteroaryl, and heterocyclyl;

wherein the A ring can be substituted or unsubstituted;

$R^{7y}$ is selected from hydrogen, alkyl, and substituted alkyl;

or a salt or stereoisomer thereof.

In formula V, Q can be selected from N and $CR^{7b}$. In certain instances, Q is $CR^{7b}$ In certain instances, Q is N.

In certain instances, in formula V, $R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, and —O-alk-A.

In certain instances, $R^{7b}$ and $R^8$ are independently selected from fluoro, trifluoromethyl, difluoromethoxy, hydroxyl, and isopropoxy.

In certain instances, $R^{7b}$ is selected from hydrogen, alkyl, and substituted alkyl. In certain instances, $R^{7b}$ is hydrogen. In certain instances, $R^{7b}$ is selected from alkyl and substituted alkyl.

In certain instances, $R^8$ is selected from cycloalkyl, substituted cycloalkyl, heterocyclyl, substituted heterocyclyl, and —O-alk-A. In certain instances, $R^8$ is cycloalkyl or substituted cycloalkyl. In certain instances, $R^8$ is cycloalkyl. In certain instances, $R^8$ is substituted cycloalkyl. In certain instances, $R^8$ is heterocyclyl or substituted heterocyclyl. In certain instances, $R^8$ is heterocyclyl. In certain instances, $R^8$ is substituted heterocyclyl. In certain instances, $R^8$ is —O-alk-A.

In certain instances, $R^8$ is selected from hydrogen, alkyl, substituted alkyl, halogen, alkoxy, and substituted alkoxy. In certain instances, $R^8$ is hydrogen. In certain instances, $R^8$ is alkyl or substituted alkyl. In certain instances, $R^8$ is methyl. In certain instances, $R^8$ is halogen. In certain instances, $R^8$ is fluoro. In certain instances, $R^8$ is alkoxy or substituted alkoxy.

In formula V, for "—O-alk-A," alk can be present or not present and is alkyl or substituted alkyl. In certain instances, alk is not present. In certain instances, alk is present and is alkyl. In certain instances, alk is present and is ethylene or propylene. In certain instances, alk is present and is substituted alkyl. In certain instances, alk is present and is substituted ethylene or substituted propylene.

In certain instances, in formula V, for "—O-alk-A," alk is not present or alk is present and is ethylene, substituted ethylene, propylene, or —C(CH$_3$)$_2$CH$_2$—. In certain instances, in formula I, for "—O-alk-A," alk is not present or alk is present and is substituted propylene, —C(CH$_3$)$_2$CH$_2$CH$_2$—, or —C(CH$_3$)$_2$CH$_2$C(O)—.

In formula V, A can be selected from aryl, cycloalkyl, heteroaryl, and heterocyclyl; wherein the A ring can be substituted or unsubstituted. In certain instances, A is aryl or substituted aryl. In certain instances, A is cycloalkyl or substituted cycloalkyl. In certain instances, A is heteroaryl or substituted heteroaryl. In certain instances, A is heterocyclyl or substituted heterocyclyl. In certain instances, A is heteroaryl, substituted heteroaryl, heterocyclyl, or substituted heterocyclyl.

Formula VI

In one of its composition aspects, the present embodiments provide a compound of formula (VI):

(VI)

wherein

R$^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y$^1$ and Y$^2$ are independently selected from hydrogen, alkyl, and acyl;

R$^1$ is selected from hydrogen, alkyl, substituted alkyl, cycloalkyl, acyl, and oxy radical;

R$^a$ and R$^b$ are independently selected from hydrogen and alkyl;

R$^c$ and R$^d$ are independently selected from hydrogen and alkyl;

Q is selected from N and CR$^{7b}$

R$^{6a}$, R$^{6b}$, and R$^{7b}$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

alk is a bond, alkylene or substituted alkylene;

A is selected from aryl, cycloalkyl, heteroaryl, and heterocyclyl;

wherein the A ring can be substituted or unsubstituted;

R$^{7y}$ is selected from hydrogen, alkyl, and substituted alkyl;

or a salt or stereoisomer thereof.

In certain instances, in formula VI, at least one of R$^{6a}$ and R$^{6b}$ is selected from fluoro, trifluoromethyl, difluoromethoxy, hydroxyl, and isopropoxy.

In certain instances, one of R$^{6a}$ and R$^{6b}$ is fluoro and the other is hydrogen.

In certain instances, in formula VI, R$^{6a}$ is selected from hydrogen, alkyl, substituted alkyl, halogen, alkoxy, substituted alkoxy, cycloalkyl, and substituted cycloalkyl. In certain instances, R$^{6a}$ is selected from hydrogen, alkyl, substituted alkyl, and halogen. In certain instances, R$^{6a}$ is hydrogen. In certain instances, R$^{6a}$ is selected from alkyl and substituted alkyl. In certain instances, R$^{6a}$ is halogen. In certain instances, R$^{6a}$ is fluoro.

In certain instances, in formula VI, R$^{6b}$ is selected from hydrogen, alkyl, substituted alkyl, halogen, alkoxy, substituted alkoxy, cycloalkyl, and substituted cycloalkyl. In certain instances, R$^{6b}$ is selected from hydrogen, alkyl, substituted alkyl, and halogen. In certain instances, R$^{6b}$ is hydrogen. In certain instances, R$^{6b}$ is selected from alkyl and substituted alkyl. In certain instances, R$^{6b}$ is halogen. In certain instances, R$^{6b}$ is fluoro.

In formula VI, for "—O-alk-A," alk is a bond, alkylene or substituted alkylene. In certain instances, alk is a bond. In certain instances, alk is alkylene. In certain instances, alk is ethylene or propylene. In certain instances, alk is substituted alkylene. In certain instances, alk is substituted ethylene or substituted propylene.

In certain instances, in formula VI, for "—O-alk-A," alk is a bond or alk is ethylene, substituted ethylene, propylene, or —C(CH$_3$)$_2$CH$_2$—. In certain instances, in formula I, for "—O-alk-A," alk is a bond or alk is substituted propylene, —C(CH$_3$)$_2$CH$_2$CH$_2$—, or —C(CH$_3$)$_2$CH$_2$C(O)—.

In formula VI, A can be selected from aryl, cycloalkyl, heteroaryl, and heterocyclyl; wherein the A ring can be substituted or unsubstituted. In certain instances, A is aryl or substituted aryl. In certain instances, A is cycloalkyl or substituted cycloalkyl. In certain instances, A is heteroaryl or substituted heteroaryl. In certain instances, A is heterocyclyl or substituted heterocyclyl. In certain instances, A is substituted heterocyclyl. In certain instances, A is heteroaryl, substituted heteroaryl, heterocyclyl, or substituted heterocyclyl.

Formula VII

In one of its composition aspects, the present embodiments provide a compound of formula (VII):

(VII)

wherein

R$^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y$^1$ and Y$^2$ are independently selected from hydrogen, alkyl, and acyl;

R$^1$ is selected from hydrogen, alkyl, substituted alkyl, cycloalkyl, acyl, and oxy radical;

R$^a$ and R$^b$ are independently selected from hydrogen and alkyl;

$R^c$ and $R^d$ are independently selected from hydrogen and alkyl;

Q is selected from N and $CR^{7b}$ $R^{6a}$, $R^{6b}$, and $R^{7b}$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

alk is a bond, alkylene or substituted alkylene;

A is selected from aryl, cycloalkyl, heteroaryl, and heterocyclyl;

wherein the A ring can be substituted or unsubstituted;

$R^{7y}$ is selected from hydrogen, alkyl, and substituted alkyl;

or a salt or stereoisomer thereof.

In certain instances, in formula VII, at least one of $R^{6a}$ and $R^{6b}$ is selected from fluoro, trifluoromethyl, difluoromethoxy, hydroxyl, and isopropoxy.

In certain instances, one of $R^{6a}$ and $R^{6b}$ is fluoro and the other is hydrogen.

In certain instances, in formula VII, $R^{6a}$ is selected from hydrogen, alkyl, substituted alkyl, halogen, alkoxy, substituted alkoxy, cycloalkyl, and substituted cycloalkyl. In certain instances, $R^{6a}$ is selected from hydrogen, alkyl, substituted alkyl, and halogen. In certain instances, $R^{6a}$ is hydrogen. In certain instances, $R^{6a}$ is selected from alkyl and substituted alkyl. In certain instances, $R^{6a}$ is halogen. In certain instances, $R^{6a}$ is fluoro.

In certain instances, in formula VII, $R^{6b}$ is selected from hydrogen, alkyl, substituted alkyl, halogen, alkoxy, substituted alkoxy, cycloalkyl, and substituted cycloalkyl. In certain instances, $R^{6b}$ is selected from hydrogen, alkyl, substituted alkyl, and halogen. In certain instances, $R^{6b}$ is hydrogen. In certain instances, $R^{6b}$ is selected from alkyl and substituted alkyl. In certain instances, $R^{6b}$ is halogen. In certain instances, $R^{6b}$ is fluoro.

Formulae IV-VII

In formulae IV-VII, $R^5$ can be selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl. In certain instances, $R^5$ is cyano, halogen, acyl, aminoacyl, or nitro. In certain instances, $R^5$ is halogen. In certain instances, $R^5$ is fluoro. In certain instances, $R^5$ is fluoro, cyano, or aminoacyl. In certain instances, $R^5$ is cyano or aminoacyl.

In formulae IV-VII, $Y^1$ and $Y^2$ can be independently selected from hydrogen, alkyl, and acyl. In certain instances, $Y^1$ is hydrogen. In certain instances, $Y^1$ is alkyl. In certain instances, $Y^1$ is acyl. In certain instances, $Y^2$ is hydrogen. In certain instances, $Y^2$ is alkyl. In certain instances, $Y^2$ is acyl.

In formulae IV-VII, $R^1$ can be selected from hydrogen, alkyl, substituted alkyl, cycloalkyl, acyl, and oxy radical. In certain instances, $R^1$ is hydrogen or alkyl. In certain instances, $R^1$ is hydrogen. In certain instances, $R^1$ is alkyl. In certain instances, $R^1$ is methyl. In certain instances, $R^1$ is hydrogen, alkyl, substituted alkyl, or oxy radical. In certain instances, $R^1$ is hydrogen, alkyl, substituted alkyl, acyl, or cycloalkyl.

In formulae IV-VII, $R^a$ and $R^b$ can be independently selected from hydrogen and alkyl. In certain instances, $R^a$ and $R^b$ are both alkyl. In certain instances, $R^a$ and $R^b$ are both methyl. In certain instances, at least one of $R^a$ and $R^b$ is alkyl.

In formulae IV-VII, $R^c$ and $R^d$ can be independently selected from hydrogen and alkyl. In certain instances, $R^c$ and $R^d$ are both alkyl. In certain instances, $R^c$ and $R^d$ are both methyl. In certain instances, at least one of $R^c$ and $R^d$ is alkyl.

In formulae IV-VII, Q can be selected from N and $CR^{7b}$. In certain instances, Q is $CR^{7b}$. In certain instances, Q is N.

Formula VIII

In one of its composition aspects, the present embodiments provide a compound of formula (VIII):

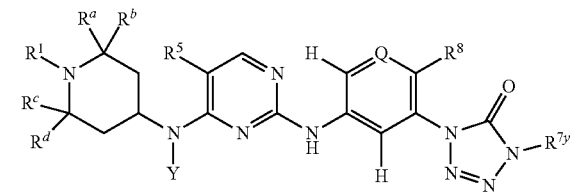

(VIII)

wherein $R^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

$Y^1$ is selected from hydrogen and alkyl;

$R^1$ is selected from hydrogen, alkyl, substituted alkyl, cycloalkyl, acyl, and oxy radical;

$R^a$ and $R^b$ are independently selected from hydrogen and alkyl;

$R^c$ and $R^d$ are independently selected from hydrogen and alkyl;

Q is selected from N and $CR^{7b}$ $R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteraryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A;

alk, if present, is alkyl or substituted alkyl;

A is selected from aryl, cycloalkyl, heteroaryl, and heterocyclyl;

wherein the A ring can be substituted or unsubstituted;

$R^{7y}$ is selected from hydrogen, alkyl, and substituted alkyl;

or a salt or stereoisomer thereof.

In formula VIII, $R^5$ can be selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl. In certain instances, $R^5$ is cyano, halogen, acyl, aminoacyl, or nitro. In certain instances, $R^5$ is halogen. In certain instances, $R^5$ is fluoro. In certain instances, $R^5$ is fluoro, cyano, or aminoacyl. In certain instances, $R^5$ is cyano or aminoacyl.

In formula VIII, Y can be selected from hydrogen and alkyl. In certain instances, Y is hydrogen. In certain instances, Y is alkyl.

In formula VIII, $R^1$ can be selected from hydrogen, alkyl, substituted alkyl, cycloalkyl, acyl, and oxy radical. In certain instances, $R^1$ is hydrogen or alkyl. In certain instances, $R^1$ is hydrogen. In certain instances, $R^1$ is alkyl. In certain instances, $R^1$ is methyl. In certain instances, $R^1$ is hydrogen, alkyl, substituted alkyl, or oxy radical. In certain instances, $R^1$ is hydrogen, alkyl, substituted alkyl, acyl, or cycloalkyl.

In formula VIII, $R^a$ and $R^b$ can be independently selected from hydrogen and alkyl. In certain instances, $R^a$ and $R^b$ are both alkyl. In certain instances, $R^a$ and $R^b$ are both methyl. In certain instances, at least one of $R^a$ and $R^b$ is alkyl.

In formula VIII, $R^c$ and $R^d$ can be independently selected from hydrogen and alkyl. In certain instances, $R^c$ and $R^d$ are both alkyl. In certain instances, $R^c$ and $R^d$ are both methyl. In certain instances, at least one of $R^c$ and $R^d$ is alkyl.

In formula VIII, Q can be selected from N and $CR^{7b}$. In certain instances, Q is $CR^{7b}$ In certain instances, Q is N.

In formula VIII, $R^{7b}$ and $R^8$ can be independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted aryl, alkoxycarbonylamino, aminocarbonylamino, acyl, carboxyl, carboxyl ester, aminoacyl, sulfonyl, sulfonylamino, aminosulfonyl, and —O-alk-A.

In certain instances, in formula VIII, $R^{7b}$ and $R^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, and —O-alk-A.

In certain instances, $R^{7b}$ and $R^8$ are independently selected from fluoro, trifluoromethyl, difluoromethoxy, hydroxyl, and isopropoxy.

In certain instances, $R^{7b}$ is selected from hydrogen, alkyl, and substituted alkyl. In certain instances, $R^{7b}$ is hydrogen. In certain instances, $R^{7b}$ is selected from alkyl and substituted alkyl.

In certain instances, $R^8$ is selected from hydrogen, alkyl, substituted alkyl, halogen, alkoxy, and substituted alkoxy. In certain instances, $R^8$ is hydrogen. In certain instances, $R^8$ is alkyl or substituted alkyl. In certain instances, $R^8$ is methyl. In certain instances, $R^8$ is halogen. In certain instances, $R^8$ is fluoro. In certain instances, $R^8$ is alkoxy or substituted alkoxy.

In formula VIII, for "—O-alk-A," alk can be present or not present and is alkyl or substituted alkyl. In certain instances, alk is not present. In certain instances, alk is present and is alkyl. In certain instances, alk is present and is ethylene or propylene. In certain instances, alk is present and is substituted alkyl. In certain instances, alk is present and is substituted ethylene or substituted propylene.

In certain instances, in formula VIII, for "—O-alk-A," alk is not present or alk is present and is ethylene, substituted ethylene, propylene, or —C(CH$_3$)$_2$CH$_2$—. In certain instances, in formula I, for "—O-alk-A," alk is not present or alk is present and is substituted propylene, —C(CH$_3$)$_2$CH$_2$CH$_2$—, or —C(CH$_3$)$_2$CH$_2$C(O)—.

In formula VIII, A can be selected from aryl, cycloalkyl, heteroaryl, and heterocyclyl; wherein the A ring can be substituted or unsubstituted. In certain instances, A is aryl or substituted aryl. In certain instances, A is cycloalkyl or substituted cycloalkyl. In certain instances, A is heteroaryl or substituted heteroaryl. In certain instances, A is heterocyclyl or substituted heterocyclyl. In certain instances, A is heteroaryl, substituted heteroaryl, heterocyclyl, or substituted heterocyclyl.

In certain instances, in formula VIII, A is selected from azetidine, imidazole, pyrazole, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, pteridine, carbazole, carboline, isothiazole, phenazine, isoxazole, imidazolidine, imidazoline, oxazole, oxazolidine, piperidine, piperazine, indoline, phthalimide, 1,2,3,4-tetrahydroisoquinoline, tetrazole, triazole, thiazole, thiazolidine, thiophene, thiomorpholinyl, 1,1-dioxothiomorpholinyl, piperidinyl, 3-pyrrolidine; wherein the A ring can be substituted or unsubstituted.

In certain instances, in formula VIII, A is selected from 1-triazole, 3-pyrrolidine, 4-piperidine, and 1-imidazolidine; wherein the A ring can be substituted or unsubstituted.

In certain instances, in formula VIII, A is selected from piperidine, tetrahydropyranyl, tetrahydrothiopyranyl, azetidinyl, azepanyl, and furanyl; wherein the A ring can be substituted or unsubstituted.

In formula VIII, $R^{7y}$ is selected from hydrogen, alkyl, and substituted alkyl. In certain instances, $R^{7y}$ is hydrogen. In certain instances, $R^{7y}$ is alkyl. In certain instances, $R^{7y}$ is methyl. In certain instances, $R^{7y}$ is isopropyl. In certain instances, $R^{7y}$ is substituted alkyl.

Particular compounds of interest are shown illustrated the following table.

TABLE 1

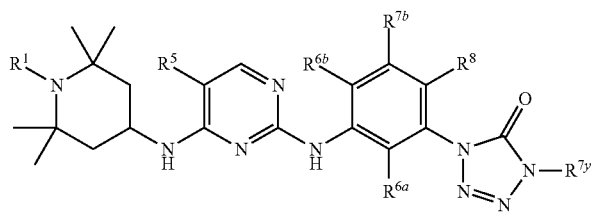

| cmpd | $R^1$ | $R^5$ | $R^{6a}$ | $R^{6b}$ | $R^{7b}$ | $R^8$ | $R^{7y}$ | salt |
|---|---|---|---|---|---|---|---|---|
| I-1 | —CH$_3$ | —F | —H | —H | —H | —F | —H | |
| I-2 | —H | —F | —H | —H | —H | —F | —H | |
| I-3 | —CH$_3$ | —F | —H | —H | —H | —F | —CH$_3$ | |
| I-4 | —H | —F | —H | —H | —H | —F | —CH$_3$ | |

TABLE 1-continued

| cmpd | R¹ | R⁵ | R⁶ᵃ | R⁶ᵇ | R⁷ᵇ | R⁸ | R⁷ʸ | salt |
|---|---|---|---|---|---|---|---|---|
| I-5 | —CH₃ | —F | —H | —H | —H | —F | —CH(CH₃)₂ | |
| I-6 | —H | —F | —H | —H | —H | —F | —CH(CH₃)₂ | |
| I-7 | —H | —F | —H | —H | —H | —F | —CH₂CH₂F | |
| I-8 | —CH₃ | —F | —H | —H | —H | —CH₃ | —CH₃ | |
| I-9 | —H | —F | —H | —H | —H | —CH₃ | —CH₃ | |
| I-10 | —CH₃ | —F | —H | —H | —H | —O—CH(CH₃)₂ | —CH₃ | |
| I-11 | —H | —F | —H | —H | —H | —O—CH(CH₃)₂ | —CH₃ | |
| I-12 | —CH₃ | —F | —H | —H | —H | —H | —CH₃ | |
| I-13 | —H | —F | —H | —H | —H | —H | —CH₃ | |
| I-14 | —H | —F | —H | —F | —H | cyclopropyl | —CH₃ | |
| I-15 | —H | —CN | —H | —F | —H | cyclopropyl | —CH₃ | |
| I-16 | —CH₃ | —F | —H | —F | —H | cyclopropyl | —CH₃ | |
| I-17 | —CH₃ | —CN | —H | —F | —H | cyclopropyl | —CH₃ | |
| I-18 | —CH₃ | —F | —H | —H | —H | —O—C(CH₃)₂—CF₃ | —CH₃ | |
| I-19 | —H | —F | —H | —H | —H | —O—C(CH₃)₂—CF₃ | —CH₃ | |
| I-20 | —CH₃ | —F | —H | —H | —H | —O-oxetanyl | —CH₃ | |
| I-21 | —H | —F | —H | —H | —H | —O-oxetanyl | —CH₃ | |
| I-22 | —H | —F | —H | —H | —F | —H | —CH₃ | |
| I-23 | —CH₃ | —F | —H | —H | —F | —H | —CH₃ | |
| I-24 | —H | —F | —H | —H | —O-oxetanyl | —H | —CH₃ | |
| I-25 | —CH₃ | —F | —H | —H | —O-oxetanyl | —H | —CH₃ | |
| I-26 | —CH₃ | —F | —H | —H | —H | —O-tetrahydropyranyl | —CH₃ | |

TABLE 1-continued

| cmpd | R$^1$ | R$^5$ | R$^{6a}$ | R$^{6b}$ | R$^{7b}$ | R$^8$ | R$^{7y}$ | salt |
|---|---|---|---|---|---|---|---|---|
| I-27 | —H | —F | —H | —H | —H | —O-(tetrahydropyran-4-yl) | —CH$_3$ | |
| I-28 | —H | —F | —H | —H | —H | —OCH$_2$-(3-methyloxetan-3-yl) | —CH$_3$ | |
| I-29 | —CH$_3$ | —F | —H | —H | —H | —Cl | —CH$_3$ | |
| I-30 | —H | —F | —H | —H | —H | —Cl | —CH$_3$ | |
| I-31 | —CH$_3$ | —F | —H | —H | —OCH$_3$ | —H | —CH$_3$ | |
| I-32 | —H | —F | —H | —H | —OCH$_3$ | —H | —CH$_3$ | |
| I-33 | —H | —F | —H | —H | —H | cyclopropyl | —CH$_3$ | |
| I-34 | —CH$_3$ | —F | —H | —H | —H | cyclopropyl | —CH$_3$ | |
| I-35 | —H | —F | —H | —H | cyclopropyl | —H | —CH$_3$ | |
| I-36 | —CH$_3$ | —F | —H | —H | cyclopropyl | —H | —CH$_3$ | |
| I-37 | —H | —F | —H | —H | —Cl | —H | —CH$_3$ | |
| I-38 | —H | —F | —H | —H | —CF$_3$ | —Cl | —CH$_3$ | |
| I-39 | —H | —F | —H | —H | —CF$_3$ | cyclopropyl | —CH$_3$ | |
| I-40 | —CH$_3$ | —F | —H | —H | —CF$_3$ | cyclopropyl | —CH$_3$ | |
| I-41 | —H | —CN | —H | —H | —CF$_3$ | cyclopropyl | —CH$_3$ | |
| I-42 | —CH$_3$ | —CN | —H | —H | —CF$_3$ | cyclopropyl | —CH$_3$ | |

TABLE 1-continued

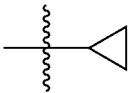 [SMILES: *C1CC1]

| cmpd | R¹ | R⁵ | R⁶ᵃ | R⁶ᵇ | R⁷ᵇ | R⁸ | R⁷ʸ | salt |
|---|---|---|---|---|---|---|---|---|
| I-43 | —H | —F | —H | —H | cyclopropyl | —F | —CH₃ | |
| I-44 | —H | —CN | —H | —H | cyclopropyl | —F | —CH₃ | |
| I-45 | —CH₃ | —F | —H | —H | —CH₃ | —CH₃ | —CH₃ | |
| I-46 | —H | —F | —H | —H | —CH₃ | —CH₃ | —CH₃ | |
| I-47 | —CH₃ | —F | —H | —H | —CF₃ | —H | —CH₃ | |
| I-48 | —H | —F | —H | —H | —CF₃ | —H | —CH₃ | |
| I-49 | —CH₃ | —F | —H | —H | —CN | —H | —CH₃ | |
| I-50 | —H | —F | —H | —H | —CN | —H | —CH₃ | |
| I-51 | —H | —F | —H | —H | —CF₃ | —O—CH(CH₃)₂ | —CH₃ | |
| I-52 | —CH₃ | —F | —H | —H | —CF₃ | —O—CH(CH₃)₂ | —CH₃ | |
| I-53 | —H | —F | —H | —H | —CF₃ | —CH₃ | —CH₃ | |
| I-54 | —CH₃ | —F | —H | —H | —CF₃ | —CH₃ | —CH₃ | |
| I-55 | —H | —F | —H | —H | —Cl | —CH₃ | —CH₃ | |
| I-56 | —CH₃ | —F | —H | —H | —Cl | —CH₃ | —CH₃ | |
| I-57 | —H | —CONH₂ | —H | —H | —F | cyclopropyl | —CH₃ | |
| I-58 | —H | —F | —H | —H | —H | —CN | —CH₃ | |
| I-59 | —H | —F | —H | —H | —F | cyclopropyl | —CH₃ | |
| I-60 | —H | —F | —H | —H | —COOCH₃ | —CH₃ | —CH₃ | |
| I-61 | —H | —F | —H | —H | —COOH | —CH₃ | —CH₃ | |
| I-62 | —H | —CN | —H | —H | —F | cyclopropyl | —CH₃ | |
| I-63 | —CH₃ | —F | —H | —H | —COOCH₃ | —CH₃ | —CH₃ | |
| I-64 | —CH₃ | —F | —H | —H | —CONHCH₃ | —CH₃ | —CH₃ | |
| I-65 | —CH₃ | —F | —H | —H | —COOH | —CH₃ | —CH₃ | |
| I-66 | —CH₃ | —F | —F | —H | —H | —F | —CH₃ | |
| I-67 | —H | —F | —F | —H | —H | —F | —CH₃ | |
| I-68 | —H | —F | —H | —F | —H | —Cl | —CH₃ | |
| I-69 | —CH₃ | —F | —H | —F | —H | —Cl | —CH₃ | |
| I-70 | —H | —F | —H | —F | —H | trans-2-(CF₃)cyclopropyl | —CH₃ | |
| I-71 | —H | —F | —H | —F | —H | —H | —CH₃ | |
| I-72 | —H | —F | —H | —F | —H | cyclopropyl | —CD₃ | |

TABLE 1-continued
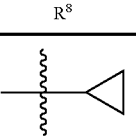
| cmpd | R¹ | R⁵ | R⁶ᵃ | R⁶ᵇ | R⁷ᵇ | R⁸ | R⁷ʸ | salt |
|---|---|---|---|---|---|---|---|---|
| I-73 | —H | —F | —H | —F | —H | 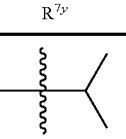 | 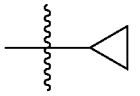 [SMILES: *C1CC1] | |
| I-74 | —H | —F | —H | —F | —H | 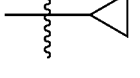 | —H | formate salt |
| I-75 | —H | —F | —H | —F | —H | 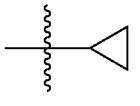 [SMILES: *C1CC1] | —H | citrate salt |
| I-76 | —H | —F | —H | —F | —H | 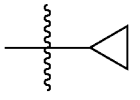 [SMILES: *C1CC1] | —H | maleate salt |
| I-77 | —H | —F | —H | —F | —H | 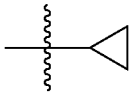 [SMILES: *C1CC1] | —H | fumarate salt (2:1 ratio) |
| I-78 | —H | —F | —H | —F | —H | 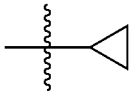 [SMILES: *C1CC1] | —H | L-tartarate salt |
| I-79 | —H | —F | —H | —F | —H | 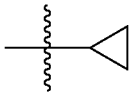 [SMILES: *C1CC1] | —H | $HSO_4^-$ salt |
| I-80 | —H | —F | —H | —F | —H | 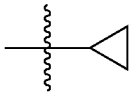 [SMILES: *C1CC1] | —H | HCl salt |
| I-81 | —H | —F | —H | —F | —H | 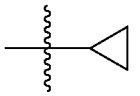 [SMILES: *C1CC1] | —H | benzoate salt |
| I-82 | —H | —F | —H | —F | —H | 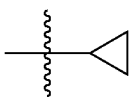 [SMILES: *C1CC1] | —H | Tosylate salt |
| I-83 | —H | —F | —H | —F | —H | 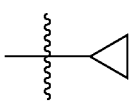 [SMILES: *C1CC1] | —H | Besylate salt |
| I-84 | —H | —F | —H | —F | —H |  | —H | Mesylate salt |

TABLE 1-continued

| cmpd | R$^1$ | R$^5$ | R$^{6a}$ | R$^{6b}$ | R$^{7b}$ | R$^8$ | R$^{7y}$ | salt |
|---|---|---|---|---|---|---|---|---|
| I-85 | —H | —F | —H | —F | —H | cyclopropylmethyl | —H | Acetate salt |
| I-86 | —H | —F | —H | —F | —H | —OCH$_3$ | —CH$_3$ | |
| I-87 | —CH$_3$ | —F | —H | —F | —H | —OCH$_3$ | —CH$_3$ | |

Particular compounds of interest, and salts or solvates or stereoisomers thereof, include:

I-1: 5-Fluoro-N2-{4-fluoro-[3-(4-H)-1,2,3,4-tetrazol-5-one-1-yl]}phenyl-N4-(1,2,2,6,6-pentamethylpiperidin-4-yl)-2,4-pyrimidinediamine;

I-2: 5-Fluoro-N2-{4-fluoro-[3-(4-H)-1,2,3,4-tetrazol-5-one-1-yl]}phenyl-N4-(2,2,6,6-tetramethylpiperidin-4-yl)-2,4-pyrimidinediamine;

I-3: 5-Fluoro-N2-{4-fluoro-[3-(4-methyl)-1,2,3,4-tetrazol-5-one-1-yl]}phenyl-N4-(1,2,2,6,6-pentamethylpiperidin-4-yl)-2,4-pyrimidinediamine;

I-4: 5-Fluoro-N2-{4-fluoro-[3-(4-isopropyl)-1,2,3,4-tetrazol-5-one-1-yl]}phenyl-N4-(2,2,6,6-tetramethylpiperidin-4-yl)-2,4-pyrimidinediamine;

I-5: 5-Fluoro-N2-{4-fluoro-[3-(4-isopropyl)-1,2,3,4-tetrazol-5-one-1-yl]}phenyl-N4-(1,2,2,6,6-pentamethylpiperidin-4-yl)-2,4-pyrimidinediamine;

I-6: 5-Fluoro-N2-{4-fluoro-3-[4-(2-fluoroethyl)-1,2,3,4-tetrazol-5-one-1-yl]}phenyl-N4-(2,2,6,6-tetramethylpiperidin-4-yl)-2,4-pyrimidinediamine;

I-7: 5-Fluoro-N2-{4-fluoro-3-[4-(2-fluoroethyl)-1,2,3,4-tetrazol-5-one-1-yl]}phenyl-N4-(2,2,6,6-tetramethylpiperidin-4-yl)-2,4-pyrimidinediamine;

I-8: 5-Fluoro-N2-{4-methyl-[3-(4-methyl)-1,2,3,4-tetrazol-5-one-1-yl]}phenyl-N4-(1,2,2,6,6-pentamethylpiperidin-4-yl)-2,4-pyrimidinediamine;

I-9: 5-Fluoro-N2-{4-methyl-[3-(4-methyl)-1,2,3,4-tetrazol-5-one-1-yl]}phenyl-N4-(2,2,6,6-tetramethylpiperidin-4-yl)-2,4-pyrimidinediamine;

I-10: 5-Fluoro-N2-{4-isopropoxy-[3-(4-methyl)-1,2,3,4-tetrazol-5-one-1-yl]}phenyl-N4-(1,2,2,6,6-pentamethylpiperidin-4-yl)-2,4-pyrimidinediamine;

I-11: 5-Fluoro-N2-{4-isopropoxy-[3-(4-methyl)-1,2,3,4-tetrazol-5-one-1-yl]}phenyl-N4-(2,2,6,6-tetramethylpiperidin-4-yl)-2,4-pyrimidinediamine;

I-12: 5-Fluoro-N2-[3-(4-methyl)-1,2,3,4-tetrazol-5-one-1-yl]phenyl-N4-(1,2,2,6,6-pentamethylpiperidin-4-yl)-2,4-pyrimidinediamine;

I-13: 5-Fluoro-N2-[3-(4-methyl)-1,2,3,4-tetrazol-5-one-1-yl]phenyl-N4-(2,2,6,6-tetramethylpiperidin-4-yl)-2,4-pyrimidinediamine;

I-14: 1-(2-cyclopropyl-4-fluoro-5-(5-fluoro-4-(2,2,6,6-tetramethylpiperidin-4-ylamino)pyrimidin-2-ylamino)phenyl)-4-methyl-1H-tetrazol-5(4H)-one;

I-15: 2-(4-cyclopropyl-2-fluoro-5-(4-methyl-5-oxo-4,5-dihydro-1H-tetrazol-1-yl)phenylamino)-4-(2,2,6,6-tetramethylpiperidin-4-ylamino)pyrimidine-5-carbonitrile;

I-16: 1-{2-Cyclopropyl-4-fluoro-5-[5-fluoro-4-(1,2,2,6,6-pentamethyl-piperidin-4-ylamino)-pyrimidin-2-ylamino]-phenyl}-4-methyl-1,4-dihydro-tetrazol-5-one;

I-17: 2-[4-Cyclopropyl-2-fluoro-5-(4-methyl-5-oxo-4,5-dihydro-tetrazol-1-yl)-phenylamino]-4-(1,2,2,6,6-pentamethyl-piperidin-4-ylamino)-pyrimidine-5-carbonitrile;

I-18: 1-(5-(5-fluoro-4-(1,2,2,6,6-pentamethylpiperidin-4-ylamino)pyrimidin-2-ylamino)-2-(1,1,1-trifluoro-2-methylpropan-2-yloxy)phenyl)-4-methyl-1H-tetrazol-5(4H)-one;

I-19: 1-(5-(5-fluoro-4-(2,2,6,6-tetramethylpiperidin-4-ylamino)pyrimidin-2-ylamino)-2-(1,1,1-trifluoro-2-methylpropan-2-yloxy)phenyl)-4-methyl-1H-tetrazol-5(4H)-one;

I-20: 1-(5-(5-fluoro-4-(1,2,2,6,6-pentamethylpiperidin-4-ylamino)pyrimidin-2-ylamino)-2-(oxetan-3-yloxy)phenyl)-4-methyl-1H-tetrazol-5(4H)-one;

I-21: 1-(5-(5-fluoro-4-(2,2,6,6-tetramethylpiperidin-4-ylamino)pyrimidin-2-ylamino)-2-(oxetan-3-yloxy)phenyl)-4-methyl-1H-tetrazol-5(4H)-one;

I-22: 1-(3-fluoro-5-(5-fluoro-4-(2,2,6,6-tetramethylpiperidin-4-ylamino)pyrimidin-2-ylamino)phenyl)-4-methyl-1H-tetrazol-5(4H)-one;

I-23: 1-(3-fluoro-5-(5-fluoro-4-(1,2,2,6,6-pentamethylpiperidin-4-ylamino)pyrimidin-2-ylamino)phenyl)-4-methyl-1H-tetrazol-5 (4H)-one;

I-24: 1-(3-(5-fluoro-4-(2,2,6,6-tetramethylpiperidin-4-ylamino)pyrimidin-2-ylamino)-5-(oxetan-3-yloxy)phenyl)-4-methyl-1H-tetrazol-5 (4H)-one;

I-25: 1-(3-(5-fluoro-4-(1,2,2,6,6-pentamethylpiperidin-4-ylamino)pyrimidin-2-ylamino)-5-(oxetan-3-yloxy)phenyl)-4-methyl-1H-tetrazol-5 (4H)-one;

I-26: 1-(5-(5-fluoro-4-(1,2,2,6,6-pentamethylpiperidin-4-ylamino)pyrimidin-2-ylamino)-2-(tetrahydro-2H-pyran-4-yloxy)phenyl)-4-methyl-1H-tetrazol-5 (4H)-one;

I-27: 1-(5-(5-fluoro-4-(2,2,6,6-tetramethylpiperidin-4-ylamino)pyrimidin-2-ylamino)-2-(tetrahydro-2H-pyran-4-yloxy)phenyl)-4-methyl-1H-tetrazol-5 (4H)-one;

I-28: 1-(5-(5-fluoro-4-(2,2,6,6-tetramethylpiperidin-4-ylamino)pyrimidin-2-ylamino)-2-((3-methyloxetan-3-yl)methoxy)phenyl)-4-methyl-1H-tetrazol-5 (4H)-one;

I-29: 1-(2-chloro-5-(5-fluoro-4-(1,2,2,6,6-pentamethylpiperidin-4-ylamino)pyrimidin-2-ylamino)phenyl)-4-methyl-1H-tetrazol-5 (4H)-one;

I-30: 1-(2-chloro-5-(5-fluoro-4-(2,2,6,6-tetramethylpiperidin-4-ylamino)pyrimidin-2-ylamino)phenyl)-4-methyl-1H-tetrazol-5 (4H)-one;

I-31: 1-(3-(5-fluoro-4-(1,2,2,6,6-pentamethylpiperidin-4-ylamino)pyrimidin-2-ylamino)-5-methoxyphenyl)-4-methyl-1H-tetrazol-5 (4H)-one;

I-32: 1-(3-(5-fluoro-4-(2,2,6,6-tetramethylpiperidin-4-ylamino)pyrimidin-2-ylamino)-5-methoxyphenyl)-4-methyl-1H-tetrazol-5(4H)-one;

I-33: 1-(2-cyclopropyl-5-(5-fluoro-4-(2,2,6,6-tetramethylpiperidin-4-ylamino)pyrimidin-2-ylamino)phenyl)-4-methyl-1H-tetrazol-5 (4H)-one;

I-34: 1-(2-cyclopropyl-5-(5-fluoro-4-(2,2,6,6-tetramethylpiperidin-4-ylamino)pyrimidin-2-ylamino)phenyl)-4-methyl-1H-tetrazol-5 (4H)-one;

I-35: 1-(3-cyclopropyl-5-(5-fluoro-4-(2,2,6,6-tetramethylpiperidin-4-ylamino)pyrimidin-2-ylamino)phenyl)-4-methyl-1H-tetrazol-5 (4H)-one;

I-36: 1-(3-cyclopropyl-5-(5-fluoro-4-(1,2,2,6,6-pentamethylpiperidin-4-ylamino)pyrimidin-2-ylamino)phenyl)-4-methyl-1H-tetrazol-5 (4H)-one;

I-37: 1-(3-chloro-5-(5-fluoro-4-(2,2,6,6-tetramethylpiperidin-4-ylamino)pyrimidin-2-ylamino)phenyl)-4-methyl-1H-tetrazol-5 (4H)-one;

I-38: 1-(2-chloro-5-(5-fluoro-4-(2,2,6,6-tetramethylpiperidin-4-ylamino)pyrimidin-2-ylamino)-3-(trifluoromethyl)phenyl)-4-methyl-1H-tetrazol-5 (4H)-one;

I-39: 1-(2-cyclopropyl-5-(5-fluoro-4-(2,2,6,6-tetramethylpiperidin-4-ylamino)pyrimidin-2-ylamino)-3-(trifluoromethyl)phenyl)-4-methyl-1H-tetrazol-5(4H)-one;

I-40: 1-(2-cyclopropyl-5-(5-fluoro-4-(1,2,2,6,6-pentamethylpiperidin-4-ylamino)pyrimidin-2-ylamino)-3-(trifluoromethyl)phenyl)-4-methyl-1H-tetrazol-5(4H)-one;

I-41: 2-(4-cyclopropyl-3-(4-methyl-5-oxo-4,5-dihydro-1H-tetrazol-1-yl)-5-(trifluoromethyl)phenylamino)-4-(2,2,6,6-tetramethylpiperidin-4-ylamino)pyrimidine-5-carbonitrile;

I-42: 2-(4-cyclopropyl-3-(4-methyl-5-oxo-4,5-dihydro-1H-tetrazol-1-yl)-5-(trifluoromethyl)phenylamino)-4-(1,2,2,6,6-pentamethylpiperidin-4-ylamino)pyrimidine-5-carbonitrile;

I-43: 1-(3-cyclopropyl-2-fluoro-5-(5-fluoro-4-(2,2,6,6-tetramethylpiperidin-4-ylamino)pyrimidin-2-ylamino)phenyl)-4-methyl-1H-tetrazol-5(4H)-one;

I-44: 2-(3-cyclopropyl-4-fluoro-5-(4-methyl-5-oxo-4,5-dihydro-1H-tetrazol-1-yl)phenylamino)-4-(2,2,6,6-tetramethylpiperidin-4-ylamino)pyrimidine-5-carbonitrile;

I-45: 1-(5-(5-fluoro-4-(1,2,2,6,6-pentamethylpiperidin-4-ylamino)pyrimidin-2-ylamino)-2,3-dimethylphenyl)-4-methyl-1H-tetrazol-5(4H)-one;

I-46: 1-(5-(5-fluoro-4-(2,2,6,6-tetramethylpiperidin-4-ylamino)pyrimidin-2-ylamino)-2,3-dimethylphenyl)-4-methyl-1H-tetrazol-5(4H)-one;

I-47: 1-(3-(5-fluoro-4-(1,2,2,6,6-pentamethylpiperidin-4-ylamino)pyrimidin-2-ylamino)-5-(trifluoromethyl)phenyl)-4-methyl-1H-tetrazol-5(4H)-one;

I-48: 1-(3-(5-fluoro-4-(2,2,6,6-tetramethylpiperidin-4-ylamino)pyrimidin-2-ylamino)-5-(trifluoromethyl)phenyl)-4-methyl-1H-tetrazol-5(4H)-one;

I-49: 3-(5-fluoro-4-(1,2,2,6,6-pentamethylpiperidin-4-ylamino)pyrimidin-2-ylamino)-5-(4-methyl-5-oxo-4,5-dihydro-1H-tetrazol-1-yl)benzonitrile;

I-50: 3-(5-fluoro-4-(2,2,6,6-tetramethylpiperidin-4-ylamino)pyrimidin-2-ylamino)-5-(4-methyl-5-oxo-4,5-dihydro-1H-tetrazol-1-yl)benzonitrile;

I-51: 1-(5-(5-fluoro-4-(2,2,6,6-tetramethylpiperidin-4-ylamino)pyrimidin-2-ylamino)-2-isopropoxy-3-(trifluoromethyl)phenyl)-4-methyl-1H-tetrazol-5(4H)-one;

I-52: 1-(5-(5-fluoro-4-(1,2,2,6,6-pentamethylpiperidin-4-ylamino)pyrimidin-2-ylamino)-2-isopropoxy-3-(trifluoromethyl)phenyl)-4-methyl-1H-tetrazol-5(4H)-one;

I-53: 1-(5-(5-fluoro-4-(2,2,6,6-tetramethylpiperidin-4-ylamino)pyrimidin-2-ylamino)-2-methyl-3-(trifluoromethyl)phenyl)-4-methyl-1H-tetrazol-5(4H)-one;

I-54: 1-(5-(5-fluoro-4-(1,2,2,6,6-pentamethylpiperidin-4-ylamino)pyrimidin-2-ylamino)-2-methyl-3-(trifluoromethyl)phenyl)-4-methyl-1H-tetrazol-5(4H)-one;

I-55: 1-(3-chloro-5-(5-fluoro-4-(2,2,6,6-tetramethylpiperidin-4-ylamino)pyrimidin-2-ylamino)-2-methylphenyl)-4-methyl-1H-tetrazol-5(4H)-one;

I-56: 1-(3-chloro-5-(5-fluoro-4-(1,2,2,6,6-pentamethylpiperidin-4-ylamino)pyrimidin-2-ylamino)-2-methylphenyl)-4-methyl-1H-tetrazol-5(4H)-one;

I-57: 2-(4-cyclopropyl-3-fluoro-5-(4-methyl-5-oxo-4,5-dihydro-1H-tetrazol-1-yl)phenylamino)-4-(2,2,6,6-tetramethylpiperidin-4-ylamino)pyrimidine-5-carboxamide;

I-58: 4-(5-fluoro-4-(2,2,6,6-tetramethylpiperidin-4-ylamino)pyrimidin-2-ylamino)-2-(4-methyl-5-oxo-4,5-dihydro-1H-tetrazol-1-yl)benzonitrile;

I-59: 1-(2-cyclopropyl-3-fluoro-5-(5-fluoro-4-(2,2,6,6-tetramethylpiperidin-4-ylamino)pyrimidin-2-ylamino)phenyl)-4-methyl-1H-tetrazol-5(4H)-one;

I-60: methyl 5-(5-fluoro-4-(2,2,6,6-tetramethylpiperidin-4-ylamino)pyrimidin-2-ylamino)-2-methyl-3-(4-methyl-5-oxo-4,5-dihydro-1H-tetrazol-1-yl)benzoate;

I-61: 5-(5-fluoro-4-(2,2,6,6-tetramethylpiperidin-4-ylamino)pyrimidin-2-ylamino)-2-methyl-3-(4-methyl-5-oxo-4,5-dihydro-1H-tetrazol-1-yl)benzoic acid;

I-62: 2-(4-cyclopropyl-3-fluoro-5-(4-methyl-5-oxo-4,5-dihydro-1H-tetrazol-1-yl)phenylamino)-4-(2,2,6,6-tetramethylpiperidin-4-ylamino)pyrimidine-5-carbonitrile;

I-63: methyl 5-(5-fluoro-4-(1,2,2,6,6-pentamethylpiperidin-4-ylamino)pyrimidin-2-ylamino)-2-methyl-3-(4-methyl-5-oxo-4,5-dihydro-1H-tetrazol-1-yl)benzoate;

I-64: 5-(5-fluoro-4-(1,2,2,6,6-pentamethylpiperidin-4-ylamino)pyrimidin-2-ylamino)-N,2-dimethyl-3-(4-methyl-5-oxo-4,5-dihydro-1H-tetrazol-1-yl)benzamide;

I-65: 5-(5-fluoro-4-(1,2,2,6,6-pentamethylpiperidin-4-ylamino)pyrimidin-2-ylamino)-2-methyl-3-(4-methyl-5-oxo-4,5-dihydro-1H-tetrazol-1-yl)benzoic acid;

I-66: 1-(2,6-difluoro-3-(5-fluoro-4-(1,2,2,6,6-pentamethylpiperidin-4-ylamino)pyrimidin-2-ylamino)phenyl)-4-methyl-1H-tetrazol-5(4H)-one;

I-67: 1-(2,6-difluoro-3-(5-fluoro-4-(2,2,6,6-tetramethylpiperidin-4-ylamino)pyrimidin-2-ylamino)phenyl)-4-methyl-1H-tetrazol-5(4H)-one;

I-68: 1-(2-chloro-4-fluoro-5-(5-fluoro-4-(2,2,6,6-tetramethylpiperidin-4-ylamino)pyrimidin-2-ylamino)phenyl)-4-methyl-1H-tetrazol-5(4H)-one;

I-69: 1-(2-chloro-4-fluoro-5-(5-fluoro-4-(1,2,2,6,6-pentamethylpiperidin-4-ylamino)pyrimidin-2-ylamino)phenyl)-4-methyl-1H-tetrazol-5(4H)-one;

I-70: 1-(4-fluoro-5-(5-fluoro-4-(2,2,6,6-tetramethylpiperidin-4-ylamino)pyrimidin-2-ylamino)-2-((1 S,2S)-2-(trifluoromethyl)cyclopropyl)phenyl)-4-methyl-1H-tetrazol-5(4H)-one;

I-71: 1-(4-fluoro-3-(5-fluoro-4-(2,2,6,6-tetramethylpiperidin-4-ylamino)pyrimidin-2-ylamino)phenyl)-4-methyl-1H-tetrazol-5(4H)-one;

I-72: 1-(2-cyclopropyl-4-fluoro-5-(5-fluoro-4-(2,2,6,6-tetramethylpiperidin-4-ylamino)pyrimidin-2-ylamino)phenyl)-4-(trideuteromethyl)-1H-tetrazol-5(4H)-one;

I-73: N2-{4-Cyclopropyl-6-fluoro-[3-(4-isopropyl)-1,2,3,4-tetrazol-5-one-1-yl]}phenyl-5-fluoro-N4-(2,2,6,6-tetramethylpiperidin-4-yl)-2,4-pyrimidinediamine;

I-74: N2-{4-Cyclopropyl-6-fluoro-3-(1,2,3,4-tetrazol-5-one-1-yl)}phenyl-5-fluoro-N4-(2,2,6,6-tetramethylpiperidin-4-yl)-2,4-pyrimidinediamine, formate salt;

I-75: N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine, citrate salt;

I-76: N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine, maleate salt;

I-77: N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine, fumarate salt;

I-78: N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine, L-tartarate salt;

I-79: N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine, hydrogen sulfate salt;

I-80: N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine, hydrogen chloride salt;

I-81: N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine, benzoate salt;

I-82: N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine, tosylate salt;

I-83: N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine, besylate salt;

I-84: N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine, mesylate salt;

I-85: N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine, acetate salt;

I-86: N2-(4-fluoro-2-methoxy-3-(4-methyl-4,5-dihydro-5-oxo-1H-tetrazol-1-yl)phenyl)-5-fluoro-N4-(2,2,6,6-tetramethylpiperidin-4-yl)pyrimidine-2,4-diamine; and I-87: N2-(4-fluoro-2-methoxy-3-(4-methyl-4,5-dihydro-5-oxo-1H-tetrazol-1-yl)phenyl)-5-fluoro-N4-(1,2,2,6,6-pentamethylpiperidin-4-yl)pyrimidine-2,4-diamine.

Particular compounds of interest, and salts or solvates or stereoisomers thereof, include:

I-1: 5-Fluoro-N2-{4-fluoro-[3-(4-H)-1,2,3,4-tetrazol-5-one-1-yl]}phenyl-N4-(1,2,2,6,6-pentamethylpiperidin-4-yl)-2,4-pyrimidinediamine;

I-2: 5-Fluoro-N2-{4-fluoro-[3-(4-H)-1,2,3,4-tetrazol-5-one-1-yl]}phenyl-N4-(2,2,6,6-tetramethylpiperidin-4-yl)-2,4-pyrimidinediamine;

I-3: 5-Fluoro-N2-{4-fluoro-[3-(4-methyl)-1,2,3,4-tetrazol-5-one-1-yl]}phenyl-N4-(1,2,2,6,6-pentamethylpiperidin-4-yl)-2,4-pyrimidinediamine;

I-4: 5-Fluoro-N2-{4-fluoro-[3-(4-isopropyl)-1,2,3,4-tetrazol-5-one-1-yl]}phenyl-N4-(2,2,6,6-tetramethylpiperidin-4-yl)-2,4-pyrimidinediamine;

I-5: 5-Fluoro-N2-{4-fluoro-[3-(4-isopropyl)-1,2,3,4-tetrazol-5-one-1-yl]}phenyl-N4-(1,2,2,6,6-pentamethylpiperidin-4-yl)-2,4-pyrimidinediamine;

I-6: 5-Fluoro-N2-{4-fluoro-3-[4-(2-fluoroethyl)-1,2,3,4-tetrazol-5-one-1-yl]}phenyl-N4-(2,2,6,6-tetramethylpiperidin-4-yl)-2,4-pyrimidinediamine;

I-7: 5-Fluoro-N2-{4-fluoro-3-[4-(2-fluoroethyl)-1,2,3,4-tetrazol-5-one-1-yl]}phenyl-N4-(2,2,6,6-tetramethylpiperidin-4-yl)-2,4-pyrimidinediamine;

I-8: 5-Fluoro-N2-{4-methyl-[3-(4-methyl)-1,2,3,4-tetrazol-5-one-1-yl]}phenyl-N4-(1,2,2,6,6-pentamethylpiperidin-4-yl)-2,4-pyrimidinediamine;

I-9: 5-Fluoro-N2-{4-methyl-[3-(4-methyl)-1,2,3,4-tetrazol-5-one-1-yl]}phenyl-N4-(2,2,6,6-tetramethylpiperidin-4-yl)-2,4-pyrimidinediamine;

I-10: 5-Fluoro-N2-{4-isopropoxy-[3-(4-methyl)-1,2,3,4-tetrazol-5-one-1-yl]}phenyl-N4-(1,2,2,6,6-pentamethylpiperidin-4-yl)-2,4-pyrimidinediamine;

I-11: 5-Fluoro-N2-{4-isopropoxy-[3-(4-methyl)-1,2,3,4-tetrazol-5-one-1-yl]}phenyl-N4-(2,2,6,6-tetramethylpiperidin-4-yl)-2,4-pyrimidinediamine;

I-12: 5-Fluoro-N2-[3-(4-methyl)-1,2,3,4-tetrazol-5-one-1-yl]phenyl-N4-(1,2,2,6,6-pentamethylpiperidin-4-yl)-2,4-pyrimidinediamine; and I-13: 5-Fluoro-N2-[3-(4-methyl)-1,2,3,4-tetrazol-5-one-1-yl]phenyl-N4-(2,2,6,6-tetramethylpiperidin-4-yl)-2,4-pyrimidinediamine.

Particular compounds of interest, and salts or solvates or stereoisomers thereof, include:

I-14: 1-(2-cyclopropyl-4-fluoro-5-(5-fluoro-4-(2,2,6,6-tetramethylpiperidin-4-ylamino)pyrimidin-2-ylamino)phenyl)-4-methyl-1H-tetrazol-5(4H)-one;

I-15: 2-(4-cyclopropyl-2-fluoro-5-(4-methyl-5-oxo-4,5-dihydro-1H-tetrazol-1-yl)phenylamino)-4-(2,2,6,6-tetramethylpiperidin-4-ylamino)pyrimidine-5-carbonitrile;

I-16: 1-{2-Cyclopropyl-4-fluoro-5-[5-fluoro-4-(1,2,2,6,6-pentamethyl-piperidin-4-ylamino)-pyrimidin-2-ylamino]-phenyl}-4-methyl-1,4-dihydro-tetrazol-5-one; and I-17: 2-[4-Cyclopropyl-2-fluoro-5-(4-methyl-5-oxo-4,5-dihydro-tetrazol-1-yl)-phenylamino]-4-(1,2,2,6,6-pentamethyl-piperidin-4-ylamino)-pyrimidine-5-carbonitrile.

Particular compounds of interest, and salts or solvates or stereoisomers thereof, include:

I-18: 1-(5-(5-fluoro-4-(1,2,2,6,6-pentamethylpiperidin-4-ylamino)pyrimidin-2-ylamino)-2-(1,1,1-trifluoro-2-methylpropan-2-yloxy)phenyl)-4-methyl-1H-tetrazol-5(4H)-one;

I-19: 1-(5-(5-fluoro-4-(2,2,6,6-tetramethylpiperidin-4-ylamino)pyrimidin-2-ylamino)-2-(1,1,1-trifluoro-2-methylpropan-2-yloxy)phenyl)-4-methyl-1H-tetrazol-5(4H)-one;

I-20: 1-(5-(5-fluoro-4-(1,2,2,6,6-pentamethylpiperidin-4-ylamino)pyrimidin-2-ylamino)-2-(oxetan-3-yloxy)phenyl)-4-methyl-1H-tetrazol-5(4H)-one;

I-21: 1-(5-(5-fluoro-4-(2,2,6,6-tetramethylpiperidin-4-ylamino)pyrimidin-2-ylamino)-2-(oxetan-3-yloxy)phenyl)-4-methyl-1H-tetrazol-5(4H)-one;

I-22: 1-(3-fluoro-5-(5-fluoro-4-(2,2,6,6-tetramethylpiperidin-4-ylamino)pyrimidin-2-ylamino)phenyl)-4-methyl-1H-tetrazol-5(4H)-one;

I-23: 1-(3-fluoro-5-(5-fluoro-4-(1,2,2,6,6-pentamethylpiperidin-4-ylamino)pyrimidin-2-ylamino)phenyl)-4-methyl-1H-tetrazol-5(4H)-one;

I-24: 1-(3-(5-fluoro-4-(2,2,6,6-tetramethylpiperidin-4-ylamino)pyrimidin-2-ylamino)-5-(oxetan-3-yloxy)phenyl)-4-methyl-1H-tetrazol-5(4H)-one;

I-25: 1-(3-(5-fluoro-4-(1,2,2,6,6-pentamethylpiperidin-4-ylamino)pyrimidin-2-ylamino)-5-(oxetan-3-yloxy)phenyl)-4-methyl-1H-tetrazol-5(4H)-one;

I-26: 1-(5-(5-fluoro-4-(1,2,2,6,6-pentamethylpiperidin-4-ylamino)pyrimidin-2-ylamino)-2-(tetrahydro-2H-pyran-4-yloxy)phenyl)-4-methyl-1H-tetrazol-5(4H)-one;

I-27: 1-(5-(5-fluoro-4-(2,2,6,6-tetramethylpiperidin-4-ylamino)pyrimidin-2-ylamino)-2-(tetrahydro-2H-pyran-4-yloxy)phenyl)-4-methyl-1H-tetrazol-5(4H)-one;

I-28: 1-(5-(5-fluoro-4-(2,2,6,6-tetramethylpiperidin-4-ylamino)pyrimidin-2-ylamino)-2-((3-methyloxetan-3-yl)methoxy)phenyl)-4-methyl-1H-tetrazol-5 (4H)-one;

I-29: 1-(2-chloro-5-(5-fluoro-4-(1,2,2,6,6-pentamethylpiperidin-4-ylamino)pyrimidin-2-ylamino)phenyl)-4-methyl-1H-tetrazol-5 (4H)-one;

I-30: 1-(2-chloro-5-(5-fluoro-4-(2,2,6,6-tetramethylpiperidin-4-ylamino)pyrimidin-2-ylamino)phenyl)-4-methyl-1H-tetrazol-5 (4H)-one;

I-31: 1-(3-(5-fluoro-4-(1,2,2,6,6-pentamethylpiperidin-4-ylamino)pyrimidin-2-ylamino)-5-methoxyphenyl)-4-methyl-1H-tetrazol-5 (4H)-one;

I-32: 1-(3-(5-fluoro-4-(2,2,6,6-tetramethylpiperidin-4-ylamino)pyrimidin-2-ylamino)-5-methoxyphenyl)-4-methyl-1H-tetrazol-5(4H)-one;

I-33: 1-(2-cyclopropyl-5-(5-fluoro-4-(2,2,6,6-tetramethylpiperidin-4-ylamino)pyrimidin-2-ylamino)phenyl)-4-methyl-1H-tetrazol-5 (4H)-one;

I-34: 1-(2-cyclopropyl-5-(5-fluoro-4-(2,2,6,6-tetramethylpiperidin-4-ylamino)pyrimidin-2-ylamino)phenyl)-4-methyl-1H-tetrazol-5 (4H)-one;

I-35: 1-(3-cyclopropyl-5-(5-fluoro-4-(2,2,6,6-tetramethylpiperidin-4-ylamino)pyrimidin-2-ylamino)phenyl)-4-methyl-1H-tetrazol-5 (4H)-one;

I-36: 1-(3-cyclopropyl-5-(5-fluoro-4-(1,2,2,6,6-pentamethylpiperidin-4-ylamino)pyrimidin-2-ylamino)phenyl)-4-methyl-1H-tetrazol-5 (4H)-one;

I-37: 1-(3-chloro-5-(5-fluoro-4-(2,2,6,6-tetramethylpiperidin-4-ylamino)pyrimidin-2-ylamino)phenyl)-4-methyl-1H-tetrazol-5 (4H)-one;

I-38: 1-(2-chloro-5-(5-fluoro-4-(2,2,6,6-tetramethylpiperidin-4-ylamino)pyrimidin-2-ylamino)-3-(trifluoromethyl)phenyl)-4-methyl-1H-tetrazol-5 (4H)-one;

I-39: 1-(2-cyclopropyl-5-(5-fluoro-4-(2,2,6,6-tetramethylpiperidin-4-ylamino)pyrimidin-2-ylamino)-3-(trifluoromethyl)phenyl)-4-methyl-1H-tetrazol-5 (4H)-one;

I-40: 1-(2-cyclopropyl-5-(5-fluoro-4-(1,2,2,6,6-pentamethylpiperidin-4-ylamino)pyrimidin-2-ylamino)-3-(trifluoromethyl)phenyl)-4-methyl-1H-tetrazol-5 (4H)-one;

I-41: 2-(4-cyclopropyl-3-(4-methyl-5-oxo-4,5-dihydro-1H-tetrazol-1-yl)-5-(trifluoromethyl)phenylamino)-4-(2,2,6,6-tetramethylpiperidin-4-ylamino)pyrimidine-5-carbonitrile;

I-42: 2-(4-cyclopropyl-3-(4-methyl-5-oxo-4,5-dihydro-1H-tetrazol-1-yl)-S-(trifluoromethyl)phenylamino)-4-(1,2,2,6,6-pentamethylpiperidin-4-ylamino)pyrimidine-5-carbonitrile;

I-43: 1-(3-cyclopropyl-2-fluoro-5-(5-fluoro-4-(2,2,6,6-tetramethylpiperidin-4-ylamino)pyrimidin-2-ylamino)phenyl)-4-methyl-1H-tetrazol-5(4H)-one;

I-44: 2-(3-cyclopropyl-4-fluoro-5-(4-methyl-5-oxo-4,5-dihydro-1H-tetrazol-1-yl)phenylamino)-4-(2,2,6,6-tetramethylpiperidin-4-ylamino)pyrimidine-5-carbonitrile;

I-45: 1-(5-(5-fluoro-4-(1,2,2,6,6-pentamethylpiperidin-4-ylamino)pyrimidin-2-ylamino)-2,3-dimethylphenyl)-4-methyl-1H-tetrazol-5(4H)-one;

I-46: 1-(5-(5-fluoro-4-(2,2,6,6-tetramethylpiperidin-4-ylamino)pyrimidin-2-ylamino)-2,3-dimethylphenyl)-4-methyl-1H-tetrazol-5(4H)-one;

I-47: 1-(3-(5-fluoro-4-(1,2,2,6,6-pentamethylpiperidin-4-ylamino)pyrimidin-2-ylamino)-5-(trifluoromethyl)phenyl)-4-methyl-1H-tetrazol-5(4H)-one;

I-48: 1-(3-(5-fluoro-4-(2,2,6,6-tetramethylpiperidin-4-ylamino)pyrimidin-2-ylamino)-5-(trifluoromethyl)phenyl)-4-methyl-1H-tetrazol-5(4H)-one;

I-49: 3-(5-fluoro-4-(1,2,2,6,6-pentamethylpiperidin-4-ylamino)pyrimidin-2-ylamino)-5-(4-methyl-5-oxo-4,5-dihydro-1H-tetrazol-1-yl)benzonitrile;

I-50: 3-(5-fluoro-4-(2,2,6,6-tetramethylpiperidin-4-ylamino)pyrimidin-2-ylamino)-5-(4-methyl-5-oxo-4,5-dihydro-1H-tetrazol-1-yl)benzonitrile;

I-51: 1-(5-(5-fluoro-4-(2,2,6,6-tetramethylpiperidin-4-ylamino)pyrimidin-2-ylamino)-2-isopropoxy-3-(trifluoromethyl)phenyl)-4-methyl-1H-tetrazol-5(4H)-one;

I-52: 1-(5-(5-fluoro-4-(1,2,2,6,6-pentamethylpiperidin-4-ylamino)pyrimidin-2-ylamino)-2-isopropoxy-3-(trifluoromethyl)phenyl)-4-methyl-1H-tetrazol-5(4H)-one;

I-53: 1-(5-(5-fluoro-4-(2,2,6,6-tetramethylpiperidin-4-ylamino)pyrimidin-2-ylamino)-2-methyl-3-(trifluoromethyl)phenyl)-4-methyl-1H-tetrazol-5(4H)-one;

I-54: 1-(5-(5-fluoro-4-(1,2,2,6,6-pentamethylpiperidin-4-ylamino)pyrimidin-2-ylamino)-2-methyl-3-(trifluoromethyl)phenyl)-4-methyl-1H-tetrazol-5(4H)-one;

I-55: 1-(3-chloro-5-(5-fluoro-4-(2,2,6,6-tetramethylpiperidin-4-ylamino)pyrimidin-2-ylamino)-2-methylphenyl)-4-methyl-1H-tetrazol-5(4H)-one;

I-56: 1-(3-chloro-5-(5-fluoro-4-(1,2,2,6,6-pentamethylpiperidin-4-ylamino)pyrimidin-2-ylamino)-2-methylphenyl)-4-methyl-1H-tetrazol-5(4H)-one;

I-57: 2-(4-cyclopropyl-3-fluoro-5-(4-methyl-5-oxo-4,5-dihydro-1H-tetrazol-1-yl)phenylamino)-4-(2,2,6,6-tetramethylpiperidin-4-ylamino)pyrimidine-5-carboxamide;

I-58: 4-(5-fluoro-4-(2,2,6,6-tetramethylpiperidin-4-ylamino)pyrimidin-2-ylamino)-2-(4-methyl-5-oxo-4,5-dihydro-1H-tetrazol-1-yl)benzonitrile;

I-59: 1-(2-cyclopropyl-3-fluoro-5-(5-fluoro-4-(2,2,6,6-tetramethylpiperidin-4-ylamino)pyrimidin-2-ylamino)phenyl)-4-methyl-1H-tetrazol-5(4H)-one;

I-60: methyl 5-(5-fluoro-4-(2,2,6,6-tetramethylpiperidin-4-ylamino)pyrimidin-2-ylamino)-2-methyl-3-(4-methyl-5-oxo-4,5-dihydro-1H-tetrazol-1-yl)benzoate;

I-61: 5-(5-fluoro-4-(2,2,6,6-tetramethylpiperidin-4-ylamino)pyrimidin-2-ylamino)-2-methyl-3-(4-methyl-5-oxo-4,5-dihydro-1H-tetrazol-1-yl)benzoic acid;

I-62: 2-(4-cyclopropyl-3-fluoro-5-(4-methyl-5-oxo-4,5-dihydro-1H-tetrazol-1-yl)phenylamino)-4-(2,2,6,6-tetramethylpiperidin-4-ylamino)pyrimidine-5-carbonitrile;

I-63: methyl 5-(5-fluoro-4-(1,2,2,6,6-pentamethylpiperidin-4-ylamino)pyrimidin-2-ylamino)-2-methyl-3-(4-methyl-5-oxo-4,5-dihydro-1H-tetrazol-1-yl)benzoate;

I-64: 5-(5-fluoro-4-(1,2,2,6,6-pentamethylpiperidin-4-ylamino)pyrimidin-2-ylamino)-N,2-dimethyl-3-(4-methyl-5-oxo-4,5-dihydro-1H-tetrazol-1-yl)benzamide;

I-65: 5-(5-fluoro-4-(1,2,2,6,6-pentamethylpiperidin-4-ylamino)pyrimidin-2-ylamino)-2-methyl-3-(4-methyl-5-oxo-4,5-dihydro-1H-tetrazol-1-yl)benzoic acid;

I-66: 1-(2,6-difluoro-3-(5-fluoro-4-(1,2,2,6,6-pentamethylpiperidin-4-ylamino)pyrimidin-2-ylamino)phenyl)-4-methyl-1H-tetrazol-5(4H)-one;

I-67: 1-(2,6-difluoro-3-(5-fluoro-4-(2,2,6,6-tetramethylpiperidin-4-ylamino)pyrimidin-2-ylamino)phenyl)-4-methyl-1H-tetrazol-5(4H)-one;

I-68: 1-(2-chloro-4-fluoro-5-(5-fluoro-4-(2,2,6,6-tetramethylpiperidin-4-ylamino)pyrimidin-2-ylamino)phenyl)-4-methyl-1H-tetrazol-5(4H)-one; and I-69: 1-(2-chloro-4-fluoro-5-(5-fluoro-4-(1,2,2,6,6-pentamethylpiperidin-4-ylamino)pyrimidin-2-ylamino)phenyl)-4-methyl-1H-tetrazol-5(4H)-one.

Particular compounds of interest, and salts or solvates or stereoisomers thereof, include:

I-70: 1-(4-fluoro-5-(5-fluoro-4-(2,2,6,6-tetramethylpiperidin-4-ylamino)pyrimidin-2-ylamino)-2-((1 S,2S)-2-(trifluoromethyl)cyclopropyl)phenyl)-4-methyl-1H-tetrazol-5(4H)-one;

I-71: 1-(4-fluoro-3-(5-fluoro-4-(2,2,6,6-tetramethylpiperidin-4-ylamino)pyrimidin-2-ylamino)phenyl)-4-methyl-1H-tetrazol-5(4H)-one;

I-72: 1-(2-cyclopropyl-4-fluoro-5-(5-fluoro-4-(2,2,6,6-tetramethylpiperidin-4-ylamino)pyrimidin-2-ylamino)phenyl)-4-(trideuteromethyl)-1H-tetrazol-5(4H)-one;

I-73: N2-{4-Cyclopropyl-6-fluoro-[3-(4-isopropyl)-1,2,3,4-tetrazol-5-one-1-yl]}phenyl-5-fluoro-N4-(2,2,6,6-tetramethylpiperidin-4-yl)-2,4-pyrimidinediamine;

I-74: N2-{4-Cyclopropyl-6-fluoro-3-(1,2,3,4-tetrazol-5-one-1-yl)}phenyl-5-fluoro-N4-(2,2,6,6-tetramethylpiperidin-4-yl)-2,4-pyrimidinediamine, formate salt;

I-75: N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine, citrate salt;

I-76: N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine, maleate salt;

I-77: N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine, fumarate salt;

I-78: N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine, L-tartarate salt;

I-79: N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine, hydrogen sulfate salt;

I-80: N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine, hydrogen chloride salt;

I-81: N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine, benzoate salt;

I-82: N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine, tosylate salt;

I-83: N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine, besylate salt;

I-84: N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine, mesylate salt;

I-85: N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine, acetate salt;

I-86: N2-(4-fluoro-2-methoxy-3-(4-methyl-4,5-dihydro-5-oxo-1H-tetrazol-1-yl)phenyl)-5-fluoro-N4-(2,2,6,6-tetramethylpiperidin-4-yl)pyrimidine-2,4-diamine; and I-87: N2-(4-fluoro-2-methoxy-3-(4-methyl-4,5-dihydro-5-oxo-1H-tetrazol-1-yl)phenyl)-5-fluoro-N4-(1,2,2,6,6-pentamethylpiperidin-4-yl)pyrimidine-2,4-diamine.

The compounds described also include isotopically labeled compounds where one or more atoms have an atomic mass different from the atomic mass conventionally found in nature. Examples of isotopes that may be incorporated into the compounds disclosed herein include, but are not limited to, $^{2}H$, $^{3}H$, $^{11}C$, $^{13}C$, $^{14}C$, $^{15}N$, $^{18}O$, $^{17}O$, etc. Thus, the disclosed compounds may be enriched in one or more of these isotopes relative to the natural abundance of such isotope. By way of example, deuterium ($^{2}H$) has a natural abundance of about 0.015%. Accordingly, for approximately every 6,500 hydrogen atoms occurring in nature, there is one deuterium atom. Specifically contemplated herein are compounds enriched in deuterium at one or more positions. Thus, deuterium containing compounds of the disclosure have deuterium at one or more positions (as the case may be) in an abundance of greater than 0.015%.

The present disclosure also provides pharmaceutical compositions comprising a pharmaceutically acceptable carrier and a therapeutically effective amount of a compound of formula I-VIII or a pharmaceutically acceptable salt or solvate or stereoisomer thereof.

A disclosed compound can be administered alone, as the sole active pharmaceutical agent, or in combination with one or more additional compounds of formula I-VIII or in conjunction with other agents. When administered as a combination, the therapeutic agents can be formulated as separate compositions that are administered simultaneously or at different times, or the therapeutic agents can be administered together as a single composition combining two or more therapeutic agents. Thus, the pharmaceutical compositions disclosed herein containing a compound of formula I-VIII optionally contain other therapeutic agents. Accordingly, certain embodiments are directed to such pharmaceutical compositions, wherein the composition further comprises a therapeutically effective amount of an agent selected as is known to those of skill in the art.

The subject compounds can inhibit a protein kinase C activity. Accordingly, the compounds are useful for treating a disease or disorder that is mediated through the activity of a PKC activity in a subject. Also, the compounds are useful for treating a disease or disorder that is associated with the activation of T-cells in a subject.

The present disclosure provides a method of treating an inflammatory disease in a subject, the method comprising administering to the subject with a compound of formula I-VIII or a salt or solvate or stereoisomer thereof.

The present disclosure also provides a method of treating an autoimmune disease in a subject, the method comprising administering to the subject with a compound of formula I-VIII or a salt or solvate or stereoisomer thereof.

The present disclosure also provides a method of treating an ocular disease or disorder involving inflammatory and/or neovascular events.

The present disclosure also provides a method of treating diseases or conditions of interest including, but are not limited to, atherosclerosis, vascular occlusion due to vascular injury, angioplasty, restenosis, obesity, syndrome X, impaired glucose tolerance, polycystic ovary syndrome, hypertension, heart failure, chronic obstructive pulmonary disease, CNS diseases, Alzheimer disease, amyotrophic lateral sclerosis, bipolar disease, cancer, infectious disease, AIDS, septic shock, adult respiratory distress syndrome, ischemia/reperfusion injury, myocardial infarction, stroke, gut ischemia, renal failure, hemorrhage shock, and traumatic shock, and traumatic brain injury.

The present disclosure also provides a method of treating diseases or conditions of interest including, but are not limited to, T-cell mediated acute or chronic inflammatory diseases or disorders or autoimmune diseases, rheumatoid arthritis, osteoarthritis, systemic lupus erythematosus, Hashimoto's thyroiditis, multiple sclerosis, myasthenia gravis, diabetes type I or II and the disorders associated therewith, transplant rejection, graft versus host disease, respiratory diseases, asthma, inflammatory lung injury, inflammatory liver injury, inflammatory glomerular injury, cutaneous manifestations of immunologically-mediated disorders or illnesses, inflammatory and hyperproliferative skin diseases, psoriasis, atopic dermatitis, allergic contact dermatitis, irritant contact dermatitis and further eczematous dermatitises, seborrhoeic dermatitis, inflammatory eye diseases, Sjoegren's syndrome, keratoconjunctivitis, uveitis, inflammatory bowel disease, Crohn's disease or ulcerative colitis, Guillain-Barre syndrome, and allergies.

The subject compounds can be used for treating a cell proliferative disorder. The present disclosure also provides a method of treating diseases or conditions of interest including, but are not limited to, hematopoietic neoplasm, lymphoid neoplasm, T cell neoplasm, T lymphoblastic leukemia, B cell neoplasm, B-lymphoblastic leukemia, Burkitt's lymphoma, myeloid neoplasm, myeloproferative disease, chronic myelogenous leukemia (CML), myelodysplastic disease, chronic myelomonocytic leukemia, myelodysplastic syndrome, and acute myeloid leukemia.

Since subject compounds possess PKC inhibitory properties, such compounds are also useful as research tools. Accordingly, the disclosure also provides for a method for using a compound of formula I-VIII or a salt or solvate or stereoisomer thereof as a research tool for studying a biological system or sample, or for discovering new chemical compounds having PKC inhibitory properties.

The embodiments are also directed to processes and novel intermediates useful for preparing compounds of formula I-VIII or a salt or solvate or stereoisomer thereof.

In one embodiment, the above process further comprises the step of forming a salt of a compound of formula I-VIII. Embodiments are directed to the other processes described herein; and to the product prepared by any of the processes described herein.

The embodiments are also directed to a compound of formula I-VIII or a salt or solvate or stereoisomer thereof, for use in therapy or as a medicament.

Additionally, the embodiments are directed to the use of a compound of formula I-VIII or a salt or solvate or stereoisomer thereof, for the manufacture of a medicament; especially for the manufacture of a medicament for the inhibition of protein kinase C (PKC) activity. The embodiments are also directed to the use of a compound of formula I-VIII or a salt or solvate or stereoisomer thereof for the manufacture of a medicament for the treatment of a disease or disorder mediated or sustained through the activity of PKC activity. The embodiments are also directed to the use of a compound of formula I-VIII or a salt or solvate or stereoisomer thereof for the manufacture of a medicament for the treatment of a disease or disorder associated with the activation of T-cells. Diseases or conditions of interest include, but are not limited to, an inflammatory disease, an immunological disorder, an autoimmune disease, an ocular disease or disorder involving inflammatory and/or neovascular events, organ and bone marrow transplant rejection, acute or chronic inflammation, allergies, contact dermatitis, psoriasis, rheumatoid arthritis, multiple sclerosis, type I diabetes, type II diabetes, inflammatory bowel disease, Guillain-Barre syndrome, Crohn's disease, ulcerative colitis, graft versus host disease, and lupus erythematosus.

The embodiments are also directed to the use of a compound of formula I-VIII or a salt or solvate or stereoisomer thereof for the manufacture of a medicament for the treatment of a cell proliferative disorder. Diseases or conditions of interest include, but are not limited to, hematopoietic neoplasm, lymphoid neoplasm, T cell neoplasm, T lymphoblastic leukemia, B cell neoplasm, B-lymphoblastic leukemia, Burkitt's lymphoma, myeloid neoplasm, myeloproferative disease, chronic myelogenous leukemia (CML), myelodysplastic disease, chronic myelomonocytic leukemia, myelodysplastic syndrome, acute myeloid leukemia.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, $4^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. Suitable exemplary methods that can be routinely adapted to synthesize the 2,4-pyrimidinediamine compounds and prodrugs of the invention are found in U.S. Pat. No. 5,958,935, the disclosure of which is incorporated herein by reference. Specific examples describing the synthesis of numerous 2,4-pyrimidinediamine compounds and prodrugs, as well as intermediates therefore, are described in the U.S. publication No. US2004/0029902A1, the contents of which are incorporated herein by reference. Suitable exemplary methods that can be routinely used and/or adapted to synthesize active 2,4-pyrimidinediamine compounds can also be found in WO 03/063794, U.S.

application Ser. No. 10/631,029 filed Jul. 29, 2003, WO2004/014382, U.S. publication No. 2005-0234049 A1, and WO005/016893, the disclosures of which are incorporated herein by reference. All of the compounds described herein (including prodrugs) can be prepared by routine adaptation of these methods.

Exemplary synthetic methods for the 2,4-substituted pyrimidinediamines described herein are described below. Those of skill in the art will also be able to readily adapt these methods for the synthesis of specific 2,4-substituted pyrimidinediamines as described herein.

A variety of exemplary synthetic routes that can be used to synthesize the 2,4-pyrimidinediamine compounds of the invention are described in scheme below. These methods can be routinely adapted to synthesize the 2,4-pyrimidinediamine compounds and prodrugs described herein.

Synthesis of Compounds

In a certain embodiment, the compounds can be synthesized from substituted or unsubstituted uracils as illustrated in Scheme 1, below:

In Scheme 1, $R^1$, $R^a$, $R^b$, $R^c$, $R^d$, $R^5$, $R^{6a}$, $R^{6b}$, $R^{7b}$, $R^{7y}$, $R^8$ are as set forth hereinbefore.

According to Scheme 1, uracil A-1 is dihalogenated at the 2- and 4-positions using a standard dehydrating-halogenating agent such as $POCl_3$ (phosphorus oxychloride) (or other standard halogenating agent) under standard conditions to yield 2,4 dichloropyrimidine A-2. Depending upon the substituents in pyrimidinediamine A-2, the chloride at the C4 position is more reactive towards nucleophiles than the chloride at the C2 position. This differential reactivity can be exploited by first reacting 2,4 dichloropyrimidine A-2 with one equivalent of amine A-3, yielding 4N-substituted-2-chloro-4-pyrimidineamine A-4, followed by amine A-5 to yield a 2,4-pyrimidinediamine derivative A-6.

Typically, the C4 halide is more reactive towards nucleophiles, as illustrated in the scheme. However, as will be recognized by skilled artisans, the identity of the substituent may alter this reactivity. For example, when the substituent is trifluoromethyl, a 50:50 mixture of 4N-substituted-4-pyrimidineamine A-4 and the corresponding 2N-substituted-

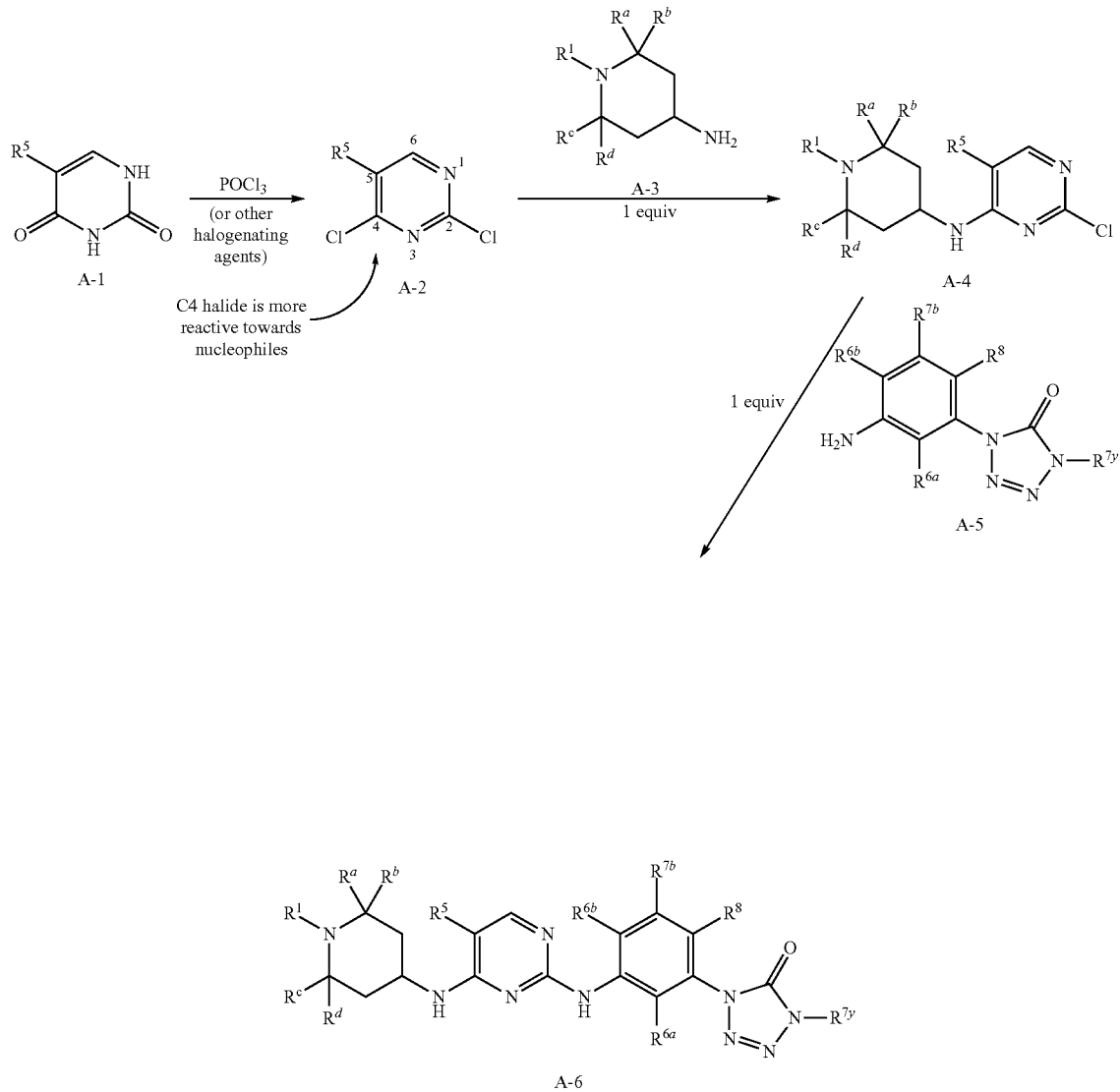

2-pyrimidineamine is obtained. The regioselectivity of the reaction can also be controlled by adjusting the solvent and other synthetic conditions (such as temperature), as is well-known in the art.

In a certain embodiment, to couple compounds with an electrophilic leaving group, such as halides or pseudohalides, and compounds with an amino group, nucleophilic aromatic substitution can be used. For example, a halogen substituent on Compound A-2 and the amino group on Compound A-3 can react. Also for example, a halogen substituent on Compound A-4 and the amino group on Compound A-5 can react. Conditions for nucleophilic aromatic substitution include the compounds reacting in a polar aprotic solvent or polar protic solvent. Suitable solvents include alcohols (such as isopropanol, methanol, ethanol), formic acid, dimethylsulfoxide, dimethylformamide, dioxane, and tetrahydrofuran. The reaction can be run at room temperature or can be heated.

In a certain embodiment, to couple compounds with an electrophilic leaving group, such as halides or pseudohalides, and aryl compounds with an amino group, a coupling reaction, such as a Buchwald coupling reaction, can be used. The Buchwald coupling reaction involves palladium-catalyzed synthesis of aryl amines. Starting materials are aryl halides or pseudohalides (for example, triflates) and primary or secondary amines. Such reaction can be performed using a variety of methods well known in the art and specific examples can be had by reference to the Examples hereunder described.

The reactions depicted in Scheme 1 may proceed more quickly when the reaction mixtures are heated via microwave. When heating in this fashion, the following conditions can be used: heat to 175° C. in ethanol for 5-20 minutes in a Smith Reactor (Personal Chemistry, Uppsala, Sweden) in a sealed tube (at 20 bar pressure).

A specific embodiment of Scheme 1 utilizing 5-fluorouracil (Aldrich #32,937-1) as a starting material is illustrated in Scheme 2, below.

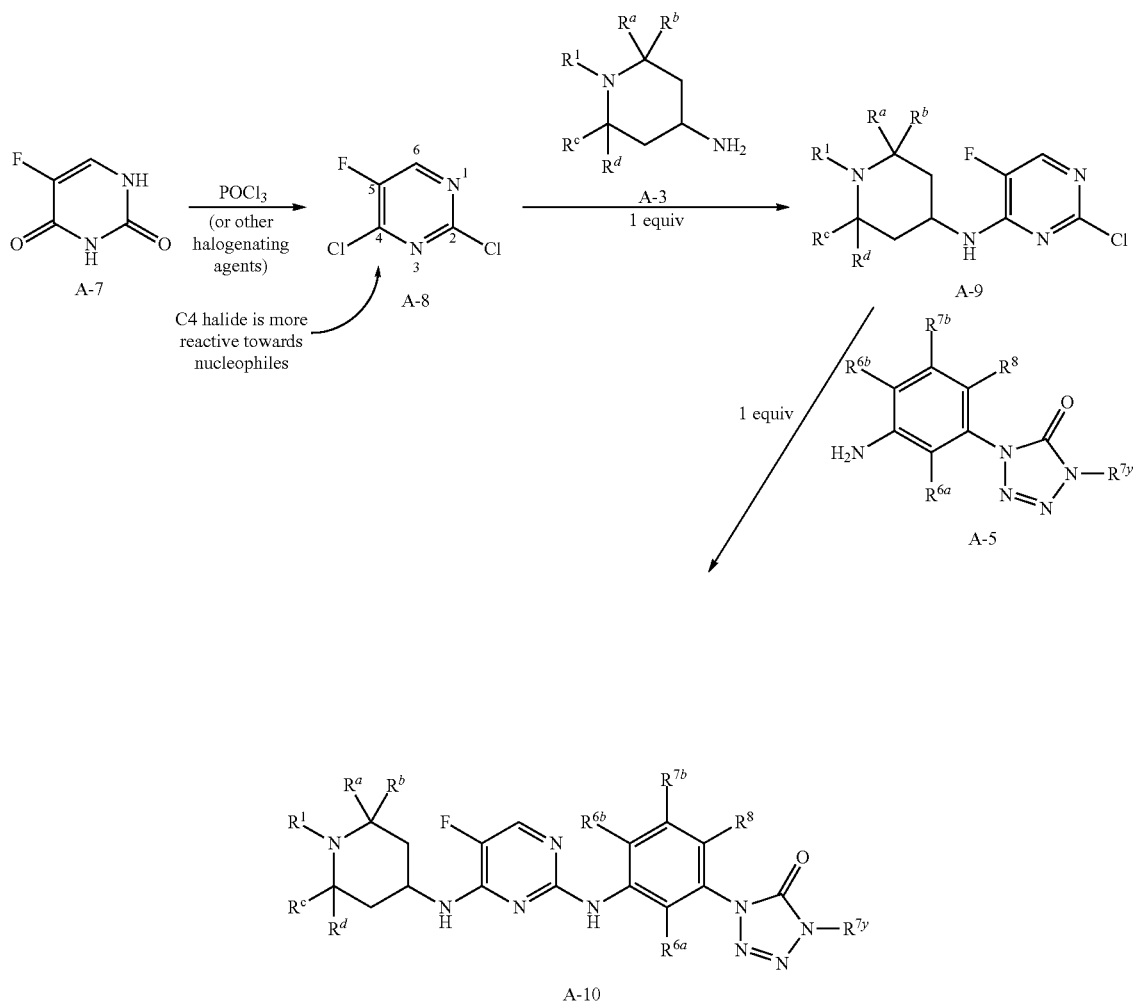

Scheme 2

In Scheme 2, $R^1$, $R^a$, $R^b$, $R^c$, $R^d$, $R^{6a}$, $R^{6b}$, $R^{7b}$, $R^{7y}$, $R^8$ are as set forth hereinbefore.

Asymmetric 2N,4N-disubstituted-5-fluoro-2,4-pyrimidinediamine A-10 can be obtained by reacting 2,4-dichloro-5-fluoropyrimidine A-8 with one equivalent of amine A-3 (to yield 2-chloro-N4-substituted-5-fluoro-4-pyrimidineamine A-9) followed by one or more equivalents of amine A-5.

A specific embodiment of Scheme 1 to form cyano derivatives is illustrated in Scheme 3, below.

Scheme 3

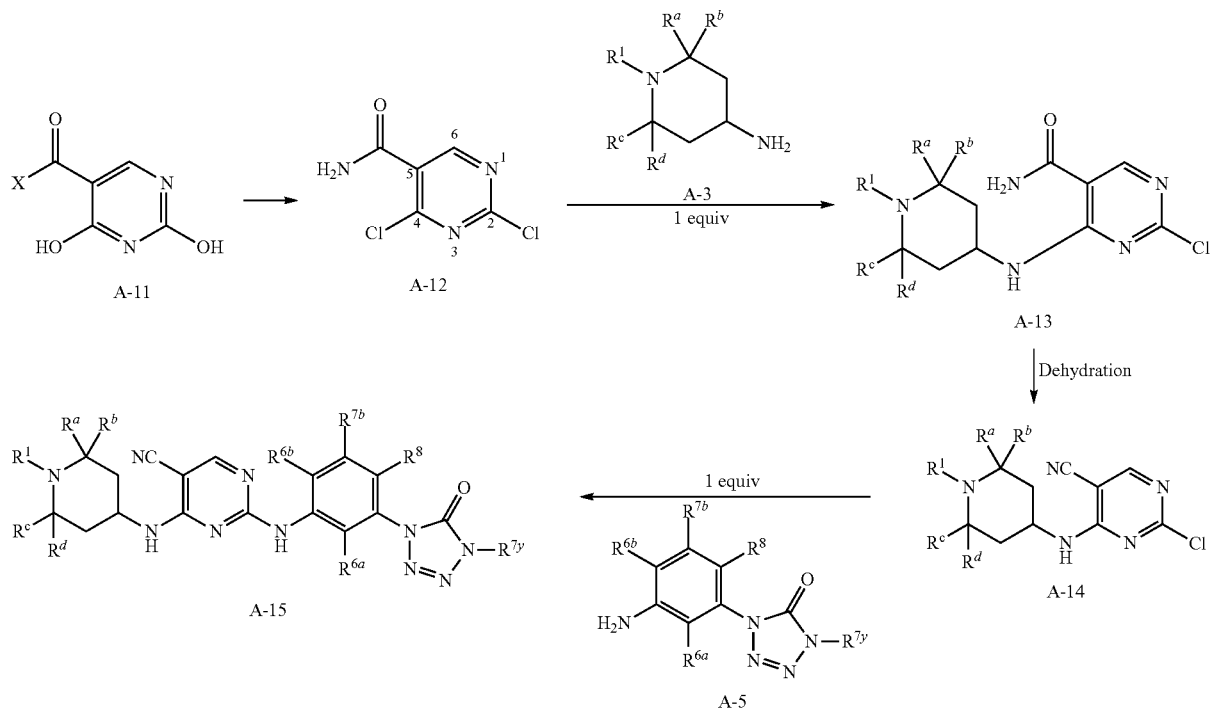

In Scheme 3, $R^1$, $R^a$, $R^b$, $R^c$, $R^d$, $R^{6a}$, $R^{6b}$, $R^{7b}$, $R^{7y}$, $R^8$ are as set forth hereinbefore.

Asymmetric 2N,4N-disubstituted-5-cyano-2,4-pyrimidinediamine A-15 can be obtained by reacting 2,4-dichloro-5-carbamoylpyrimidine A-12 with one equivalent of amine A-3 (to yield 2-chloro-N4-substituted-5-carbamoyl-4-pyrimidineamine A-13). The amide group of Compound A-13 is converted to a cyano group to yield Compound A-14, followed by reaction with one or more equivalents of amine A-5. Conversion of the amide group to the cyano group can be accomplished with dehydration, such as with use of Burgess reagent or trifluoroacetic anhydride. As will be recognized by those of skill in the art and exemplified herein, aniline A-5 may also be reacted with intermediate A-13, and the resultant N2,N4-disubstituted diaminopyrimidine-5-carbamoylpyrimidine can be dehydrated to yield the corresponding 5-cyano compound A-15.

Uracil Starting Materials and Intermediates

The uracil A-1, A-7, and A-11 starting materials can be purchased from commercial sources or prepared using standard techniques of organic chemistry. Commercially available uracils that can be used as starting materials in the schemes disclosed herein include, by way of example and not limitation, uracil (Aldrich #13,078-8; CAS Registry 66-22-8); 5 bromouracil (Aldrich #85,247-3; CAS Registry 51-20-7; 5 fluorouracil (Aldrich #85,847-1; CAS Registry 51-21-8); 5 iodouracil (Aldrich #85,785-8; CAS Registry 696-07-1); 5 nitrouracil (Aldrich #85,276-7; CAS Registry 611-08-5); 5 (trifluoromethyl)-uracil (Aldrich #22,327-1; CAS Registry 54-20-6). Additional 5-substituted uracils are available from General Intermediates of Canada, Inc., Edmonton, CA and/or Interchim, Cedex, France, or can be prepared using standard techniques. Myriad textbook references teaching suitable synthetic methods are provided infra.

Amino Starting Materials and Intermediates

Amines, such as A-3 and A-5 can be purchased from commercial sources or, alternatively, can be synthesized utilizing standard techniques. For example, suitable amines can be synthesized from nitro precursors using standard chemistry. See also Vogel, 1989, Practical Organic Chemistry, Addison Wesley Longman, Ltd. and John Wiley & Sons, Inc.

Tetrazole Intermediates

Compound A-5 with an N-linked tetrazole in Schemes 1-3 was prepared as illustrated in Scheme 4 and may be incorporated into the present compounds according to the procedure illustrated in Scheme 4.

Scheme 4

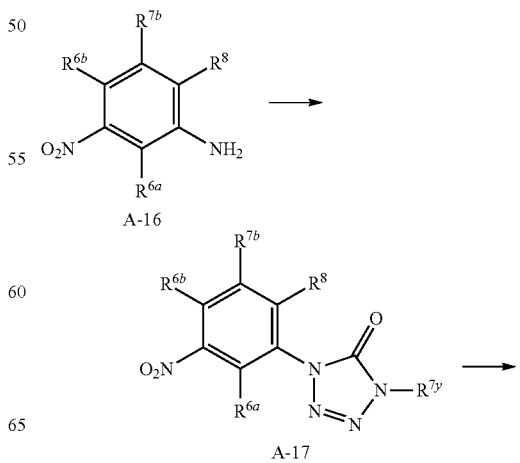

-continued

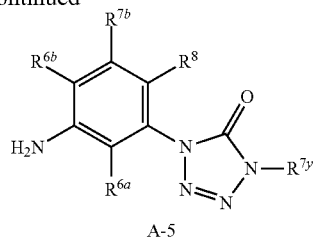

A-5

In Scheme 4, $R^{6a}$, $R^{6b}$, $R^{7b}$, $R^8$, and $R^{7y}$ are as previously defined.

To prepare Compound A-5, Compound A-16 was reacted to form tetrazolone Compound A-17 by treatment with phosgene and azidotrimethylsilane. The reaction is general to any appropriate aminophenyl compound. Compound A-17 was reacted to reduce the nitro group to form Compound A-5. Compound A-5 can also be prepared according to the procedures provided by Satoh et al., Tetrahedron Lett, 1995, 36, 1749; Gupta et al. Tetrahedron Lett, 2004, 45, 4113; Su et al. Eur. J. Org. Chem., 2006, 2723; and Potewar et al., Tetrahedron Lett, 2007, 48, 172.

Substitution of the ring with substituents can be performed with standard chemistry. In certain embodiment, substitution of the ring with substituents can be performed with nucleophilic aromatic substitution. For example, a halogen substituent can be replaced with another substituent with nucleophilic aromatic substitution. In certain embodiment, substitution of the ring with substituents can be performed with a metal catalyzed coupling reaction. For example, a halogen substituent can be replaced with another substituent with utilization of a metal catalyst. Suitable metal catalyzed reactions to place appropriate substituents include Suzuki coupling, Stille coupling, and Buchwald coupling.

The nitro group of Compound A-17 was converted to an amino group to produce Compound A-5. The conversion of the nitro group to an amino group can be accomplished by various methods. A suitable method for reduction of nitro group is catalytic hydrogenation which uses hydrogen and a catalyst, such as, but not limited to, palladium on carbon, platinum oxide, Raney nickel, and samarium diiodide.

Compound A-16 can be purchased from commercial sources or prepared using standard techniques of organic chemistry. For example, Compound A-16 can be prepared from the corresponding amine with standard techniques of organic chemistry. In certain embodiment, Compound A-16 can be prepared from the corresponding dinitro compound in which one of the nitro groups is reduced to an amino group. Myriad textbook references teaching suitable synthetic methods are provided infra.

Although many of the synthetic schemes discussed above do not illustrate the use of protecting groups, skilled artisans will recognize that in some instances certain substituents may include functional groups requiring protection. The exact identity of the protecting group used will depend upon, among other things, the identity of the functional group being protected and the reaction conditions used in the particular synthetic scheme, and will be apparent to those of skill in the art. Guidance for selecting protecting groups, their attachment and removal suitable for a particular application can be found, for example, in Greene & Wuts, supra.

Prodrugs as described herein can be prepared by routine modification of the above-described methods. Alternatively, such prodrugs can be prepared by reacting a suitably protected 2,4-pyrimidinediamine with a suitable progroup. Conditions for carrying out such reactions and for deprotecting the product to yield prodrugs as described herein are well-known.

Myriad references teaching methods useful for synthesizing pyrimidines generally, as well as starting materials described in Schemes (I)-(VII), are known in the art. For specific guidance, the reader is referred to Brown, D. J., "The Pyrimidines", in The Chemistry of Heterocyclic Compounds, Volume 16 (Weissberger, A., Ed.), 1962, Interscience Publishers, (A Division of John Wiley & Sons), New York ("Brown I"); Brown, D. J., "The Pyrimidines", in The Chemistry of Heterocyclic Compounds, Volume 16, Supplement I (Weissberger, A. and Taylor, E. C., Ed.), 1970, Wiley-Interscience, (A Division of John Wiley & Sons), New York (Brown II"); Brown, D. J., "The Pyrimidines", in The Chemistry of Heterocyclic Compounds, Volume 16, Supplement II (Weissberger, A. and Taylor, E. C., Ed.), 1985, An Interscience Publication (John Wiley & Sons), New York ("Brown III"); Brown, D. J., "The Pyrimidines" in The Chemistry of Heterocyclic Compounds, Volume 52 (Weissberger, A. and Taylor, E. C., Ed.), 1994, John Wiley & Sons, Inc., New York, pp. 1-1509 (Brown IV"); Kenner, G. W. and Todd, A., in Heterocyclic Compounds, Volume 6, (Elderfield, R. C., Ed.), 1957, John Wiley, New York, Chapter 7 (pyrimidines); Paquette, L. A., Principles of Modern Heterocyclic Chemistry, 1968, W. A. Benjamin, Inc., New York, pp. 1-401 (uracil synthesis pp. 313, 315; pyrimidinediamine synthesis pp. 313-316; amino pyrimidinediamine synthesis pp. 315); Joule, J. A., Mills, K. and Smith, G. F., Heterocyclic Chemistry, 3rd Edition, 1995, Chapman and Hall, London, UK, pp. 1-516; Vorbrüggen, H. and Ruh-Pohlenz, C., Handbook of Nucleoside Synthesis, John Wiley & Sons, New York, 2001, pp. 1-631 (protection of pyrimidines by acylation pp. 90-91; silylation of pyrimidines pp. 91-93); Joule, J. A., Mills, K. and Smith, G. F., Heterocyclic Chemistry, 4th Edition, 2000, Blackwell Science, Ltd, Oxford, UK, pp. 1-589; and Comprehensive Organic Synthesis, Volumes 1-9 (Trost, B. M. and Fleming, I., Ed.), 1991, Pergamon Press, Oxford, UK.

Pharmaceutical Compositions

The disclosed compounds are useful, at least, for the inhibition of PKC activity and the treatment of a disease or disorder that is mediated through the activity of a PKC activity. Accordingly, pharmaceutical compositions comprising at least one disclosed compound are also described herein.

A pharmaceutical composition comprising a subject compound may be administered to a patient alone, or in combination with other supplementary active agents. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilisate, tablet, pill, pellet, capsule, powder, syrup, elixir or any other dosage form suitable for administration.

A subject compound may be administered to the host using any convenient means capable of resulting in the desired reduction in disease condition or symptom. Thus, a subject compound can be incorporated into a variety of formulations for therapeutic administration. More particularly, a subject compound can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Formulations for pharmaceutical compositions are well known in the art. For example, Remington's Pharmaceutical Sciences, by E. W. Martin, Mack Publishing Co., Easton, Pa., 19th Edition, 1995, describes exemplary formulations (and components thereof) suitable for pharmaceutical delivery of disclosed compounds. Pharmaceutical compositions comprising at least one of the subject compounds can be formulated for use in human or veterinary medicine. Particular formulations of a disclosed pharmaceutical composition may depend, for example, on the mode of administration and/or on the location of the infection to be treated. In some embodiments, formulations include a pharmaceutically acceptable carrier in addition to at least one active ingredient, such as a subject compound. In other embodiments, other medicinal or pharmaceutical agents, for example, with similar, related or complementary effects on the affliction being treated can also be included as active ingredients in a pharmaceutical composition.

Pharmaceutically acceptable carriers useful for the disclosed methods and compositions are conventional in the art. The nature of a pharmaceutical carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances (e.g., excipients), such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin or plasma preparations.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The disclosed pharmaceutical compositions may be formulated as a pharmaceutically acceptable salt of a disclosed compound. Pharmaceutically acceptable salts are non-toxic salts of a free base form of a compound that possesses the desired pharmacological activity of the free base. These salts may be derived from inorganic or organic acids. Non-limiting examples of suitable inorganic acids are hydrochloric acid, nitric acid, hydrobromic acid, sulfuric acid, hydroiodic acid, and phosphoric acid. Non-limiting examples of suitable organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, methyl sulfonic acid, salicylic acid, formic acid, trichloroacetic acid, trifluoroacetic acid, gluconic acid, asparagic acid, aspartic acid, benzenesulfonic acid, para-toluenesulfonic acid, naphthalenesulfonic acid, and the like. Lists of other suitable pharmaceutically acceptable salts are found in Remington's Pharmaceutical Sciences, 17th Edition, Mack Publishing Company, Easton, Pa., 1985. A pharmaceutically acceptable salt may also serve to adjust the osmotic pressure of the composition.

A subject compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Such preparations can be used for oral administration.

A subject compound can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. The preparation may also be emulsified or the active ingredient encapsulated in liposome vehicles. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

In some embodiments, a subject compound can be delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

A subject compound can be utilized in aerosol formulation to be administered via inhalation. A subject compound can be formulated into pressurized acceptable propellants such as dichlorodifluoromethane, propane, nitrogen and the like.

Furthermore, a subject compound can be made into suppositories by mixing with a variety of bases such as emulsifying bases or water-soluble bases. A subject compound can be administered rectally via a suppository. The suppository can include vehicles such as cocoa butter, carbowaxes and polyethylene glycols, which melt at body temperature, yet are solidified at room temperature.

The term "unit dosage form," as used herein, refers to physically discrete units suitable as unitary dosages for human and animal subjects, each unit containing a predetermined quantity of a subject compound calculated in an amount sufficient to produce the desired effect in association with a pharmaceutically acceptable diluent, carrier or vehicle. The specifications for a subject compound depend on the particular compound employed and the effect to be achieved, and the pharmacodynamics associated with each compound in the host.

The dosage form of a disclosed pharmaceutical composition will be determined by the mode of administration chosen. For example, in addition to injectable fluids, topical or oral dosage forms may be employed. Topical preparations may include eye drops, ointments, sprays and the like. Oral formulations may be liquid (e.g., syrups, solutions or suspensions), or solid (e.g., powders, pills, tablets, or capsules). Methods of preparing such dosage forms are known, or will be apparent, to those skilled in the art.

Certain embodiments of the pharmaceutical compositions comprising a subject compound may be formulated in unit dosage form suitable for individual administration of precise dosages. The amount of active ingredient administered will depend on the subject being treated, the severity of the affliction, and the manner of administration, and is known to those skilled in the art. Within these bounds, the formulation to be administered will contain a quantity of the extracts or compounds disclosed herein in an amount effective to achieve the desired effect in the subject being treated.

Each therapeutic compound can independently be in any dosage form, such as those described herein, and can also be administered in various ways, as described herein. For example, the compounds may be formulated together, in a single dosage unit (that is, combined together in one form such as capsule, tablet, powder, or liquid, etc.) as a combination product. Alternatively, when not formulated together in a single dosage unit, an individual subject compound may be administered at the same time as another therapeutic compound or sequentially, in any order thereof.

Methods of Administration

The subject compounds can inhibit a protein kinase C activity. Accordingly, the subject compounds are useful for treating a disease or disorder that is mediated through the activity of a PKC activity in a subject. Accordingly, the subject compounds are useful for treating a disease or disorder that is associated with the activation of T-cells in a subject.

The route of administration will be selected according to a variety of factors including, but not necessarily limited to, the condition to be treated, the formulation and/or device used, the patient to be treated, and the like. Routes of administration useful in the disclosed methods include but are not limited to oral and parenteral routes, such as intravenous (iv), intraperitoneal (ip), rectal, topical, ophthalmic, nasal, and transdermal. Formulations for these dosage forms are described herein.

An effective amount of a subject compound will depend, at least, on the particular method of use, the subject being treated, the severity of the affliction, and the manner of administration of the therapeutic composition. A "therapeutically effective amount" of a composition is a quantity of a specified compound sufficient to achieve a desired effect in a subject (host) being treated. For example, this may be the amount of a subject compound necessary to prevent, inhibit, reduce or relieve a disease or disorder that is mediated through the activity of a PKC activity in a subject. Ideally, a therapeutically effective amount of a compound is an amount sufficient to prevent, inhibit, reduce or relieve a disease or disorder that is mediated through the activity of a PKC activity in a subject without causing a substantial cytotoxic effect on host cells.

Therapeutically effective doses (or growth inhibitory amounts) of a subject compound or pharmaceutical composition can be determined by one of skill in the art, with a goal of achieving local (e.g., tissue) concentrations that are at least as high as the $IC_{50}$ of an applicable compound disclosed herein.

An example of a dosage range is from about 0.1 to about 200 mg/kg body weight orally in single or divided doses. In particular examples, a dosage range is from about 1.0 to about 100 mg/kg body weight orally in single or divided doses, including from about 1.0 to about 50 mg/kg body weight, from about 1.0 to about 25 mg/kg body weight, from about 1.0 to about 10 mg/kg body weight (assuming an average body weight of approximately 70 kg; values adjusted accordingly for persons weighing more or less than average). For oral administration, the compositions are, for example, provided in the form of a tablet containing from about 50 to about 1000 mg of the active ingredient, particularly about 75 mg, about 100 mg, about 200 mg, about 400 mg, about 500 mg, about 600 mg, about 750 mg, or about 1000 mg of the active ingredient for the symptomatic adjustment of the dosage to the subject being treated. In one exemplary oral dosage regimen, a tablet containing from about 500 mg to about 1000 mg active ingredient is administered once (e.g., a loading dose) followed by administration of ½ dosage tablets (e.g., from about 250 to about 500 mg) each 6 to 24 hours for at least 3 days.

The specific dose level and frequency of dosage for any particular subject may be varied and will depend upon a variety of factors, including the activity of the subject compound, the metabolic stability and length of action of that compound, the age, body weight, general health, sex and diet of the subject, mode and time of administration, rate of excretion, drug combination, and severity of the condition of the host undergoing therapy.

The present disclosure also contemplates combinations of one or more disclosed compounds with one or more other agents or therapies useful in the treatment of a disease or disorder. In certain instances, the disease or disorder is mediated through the activity of a PKC activity in a subject. In certain instances, the disease or disorder is cell proliferative disorder. For example, one or more disclosed compounds may be administered in combination with effective doses of other medicinal and pharmaceutical agents, or in combination other non-medicinal therapies, such as hormone or radiation therapy. The term "administration in combination with" refers to both concurrent and sequential administration of the active agents.

Protein Kinase C

Protein Kinase C

PKC is a family of enzymes that function as serine/threonine kinases. The isoenzymes of PKC differ in their tissue distribution, enzymatic selectivity, requirement for $Ca^{2+}$, and regulation. PKCs play an important role in cell-cell signaling, gene expression and in the control of cell differentiation and growth.

The subject compound can be a selective inhibitor of PKC, e.g. an inhibitor selective for PKC over one or more other protein kinases, e.g. over one or more tyrosine kinases, for instance, over one or more non-receptor or receptor tyrosine kinases, e.g. over one or more of PKA, PKB, Abl Met, Src, Ins-R, Flt-3, JAK-2, KDR and/or Ret proteins. The selective PKC inhibitors may optionally be selective over one or more serine/threonine kinases, e.g. one or more serine/threonine kinases which do not belong to the CDK family. The subject compounds can exhibit a selectivity of at least 10 fold, or 20 fold, or 100 fold for the PKC over one or more other protein kinases, e.g. over one or more tyrosine kinases, e.g. over Flt-3, JAK-2, KDR and/or Ret proteins, or over one or more serine/threonine kinases which do not belong to the CDK family.

The selectivity of a selective inhibitor of PKC over other protein kinases may be calculated as the ratio of the $IC_{50}$ measured for PKC in an assay described herein over the $IC_{50}$ determined for another kinase. In a certain instance, there is provided a PKC inhibitor for which the ratio of the $IC_{50}$ value as determined in an Allogeneic Mixed Lymphocyte Reaction (MLR) assay to the $IC_{50}$ value as determined in a BM assay is higher than 5, 10, 20, or 30. MLR and BM assays can be done according to known methods, e.g. mouse or human MLR and BM assays, such as disclosed herein.

The disclosure provides an inhibitor of PKC, which can be an isozyme-selective PKC inhibitor, wherein the subject compound possesses selectivity for the isoforms θ and a of PKC over one or more of the other PKC isoforms. In a certain instance, the subject compound possesses selectivity for the isoform θ of PKC over one or more of the other PKC isoforms. In a certain instance, the subject compound possesses selectivity for the isoform α of PKC over one or more of the other PKC isoforms. In one embodiment, the disclosed compounds exhibit selectivity for PKC θ and PKC α over at least one PKC isoform.

A subject compound can show a selectivity of at least 10 fold, or 20 fold, or 100 fold for the isoforms θ or α of PKC over one or more of the other PKC isoforms. Selectivity for the isoforms θ or α of PKC over one or more of the other PKC isoforms can be measured by comparing the $IC_{50}$ of the subject compound for the isoforms θ or α of PKC to the $IC_{50}$ of the subject compound for the other PKC isoforms. In a certain instance, the selectivity can be determined by calculating the ratio of $IC_{50}$ of the subject compound for the other isoforms of PKC to the $IC_{50}$ of the subject compound for θ or α isoforms of PKC. In certain examples subject compounds exhibit a selectivity for PKC θ, α or both over another PKC isoform of at least about 2-fold, such as from about 3-fold to about 300-fold, from about 10-fold to about 100-fold or from about 5-fold to 50-fold. $IC_{50}$ values are obtained, for example, according to PKC assays described herein. The subject compounds can show an $IC_{50}$ value for the isoforms θ or α of PKC of 1 μM or less, such as less than about 300 nM, such as from about 1 nM to about 250 nM, less than 100 nM or even less than 10 nM in the assays disclosed herein.

The subject compounds can show a selectivity of the isoforms θ or μ of PKC over other isoforms of PKC, as well as a selectivity over one or more of the other protein kinases, e.g. over one or more tyrosine kinases, or over one or more serine/threonine kinases which do not belong to the CDK-family, e.g. over one or more of PKA, PKB, Abl, Met, Src, Ins-it, Flt-3, JAK-2, KDR and Ret proteins, e.g. over one or more of Flt-3, JAK-2, KDR and Ret proteins.

Certain isozymes of PKC have been implicated in the mechanisms of various disease states, including, but not necessarily limited to, the following: cancer (PKC α, βI, βII, and δ); cardiac hypertrophy and heart failure (PKC βI and PKC βII) nociception (PKC γ and ε); ischemia including myocardial infarction (PKC ε and δ); immune response, particularly T-cell mediated (PKC θ and α); and fibroblast growth and memory (PKC δ and ζ). The role of PKC ε is also implicated in pain perception. PKC inhibitors can also be used for treating an ocular disease or disorder involving inflammatory and/or neovascular events.

The subject compounds can be used in the treatment of mammalian (especially human) disease states characterized by aberrant, elevated activity of a PKC isozyme in a tissue as compared to non-disease tissue of the same origin. PKC isozymes and disease states and/or biological functions amenable to therapy by inhibition of activity of the PKC isozyme include, but are not necessarily limited to: PKC α (hyperproliferative cellular diseases, such as cancer); PKC βI and PKC βII (cardiac hypertrophy and heart failure); PKC γ (pain management); PKC δ (ischemia, hypoxia (e.g., such as in myocardial infarction and in stroke); apoptosis induced by UV irradiation; and aberrant fibroblast growth (e.g., as may occur in wound healing)); PKC ε (pain management, myocardial dysfunction); PKC θ (immune system diseases, particularly those involving T-cell mediated responses); and PKC ζ (memory and fibroblast growth).

PKC theta

PKC θ is expressed predominantly in lymphoid tissue and skeletal muscle. PKC θ is selectively expressed in T-cells and plays a role in mature T-cell activation. It has been shown that PKC θ is involved in T-cell receptor (TCR)-mediated T-cell activation but inessential during TCR-dependent thymocyte development. PKC θ, but not other PKC isoforms, translocates to the site of cell contact between antigen-specific T-cells and antigen presenting cells (APC), where it localizes with the TCR in the central core of the T-cell activation. PKC θ, but not the α, ε, or ζ isoenzymes, can selectively activate a FasL promoter-reporter gene and upregulate the mRNA or cell surface expression of endogenous FasL. On the other hand, PKC θ and ε can promote T-cell survival by protecting the cells from Fas-induced apoptosis, and this protective effect was mediated by promoting p90Rsk-dependent phosphorylation of BCL-2 family member BAD. Thus, PKC θ appears to play a dual regulatory role in T-cell apoptosis.

PKC θ inhibitors can find use in the treatment or prevention of disorders or diseases mediated by T lymphocytes, for example, autoimmune disease such as rheumatoid arthritis, psoriasis and lupus erythematosus, and inflammatory disease such as asthma and inflammatory bowel diseases.

PKC θ is a drug target for immunosuppression in transplantation and autoimmune diseases (Isakov et al. (2002) Annual Review of Immunology, 20, 761-794). PCT Publication WO2004/043386 identifies PKC θ as a target for treatment of transplant rejection and multiple sclerosis. PKC θ also plays a role in inflammatory bowel disease (The Journal of Pharmacology and Experimental Therapeutics (2005), 313 (3), 962-982), asthma (WO 2005062918), and lupus (Current Drug Targets: Inflammation & Allergy (2005), 4 (3), 295-298).

In addition, PKC θ is highly expressed in gastrointestinal stromal tumors (Blay, P. et al. (2004) Clinical Cancer Research, 10, 12, Pt. 1), it has been suggested that PKC θ is a molecular target for treatment of gastrointestinal cancer (Wiedmann, M. et al. (2005) Current Cancer Drug Targets 5(3), 171).

Experiments induced in PKC θ knock-out mice led to the conclusion that PKC θ inactivation prevented fat-induced defects in insulin signalling and glucose transport in skeletal muscle (Kim J. et al, 2004, The J. of Clinical Investigation 114 (6), 823). This data indicates PKC θ is a therapeutic target for the treatment of type 2 diabetes, and hence PKC θ inhibitors can be useful for treating such disease.

Therapeutic Applications

The subject compounds are useful for treating a disease or disorder that is mediated through, or exacerbated by, the activity of a PKC in a subject in need of treatment. Also, the compounds are useful for treating a disease or disorder that is associated with aberrant or otherwise undesirable T cell activation in a subject.

Accordingly, the present disclosure provides methods of treating an inflammatory disease in a subject by administering an effective amount of a subject compound, including a salt or solvate or stereoisomer thereof, so as to treat inflammation. Inflammatory diseases contemplated for therapy include acute and chronic inflammation mediated or exacerbated by PKC activity The present disclosure also provides methods of treating an autoimmune disease in a subject by administering to the subject an effective amount of a subject compound, including a salt or solvate or stereoisomer thereof, so as to treat the autoimmune disease.

The present disclosure also provides methods of treating an ocular disease or disorder involving inflammatory and/or neovascular events by administration of a subject compound, including a salt or solvate or stereoisomer thereof, in an effective amount.

Diseases or conditions of interest for treatment according to the present disclosure include, but are not limited to, atherosclerosis, vascular occlusion due to vascular injury such as angioplasty, restenosis, obesity, syndrome X, impaired glucose tolerance, polycystic ovary syndrome, hypertension, heart failure, chronic obstructive pulmonary disease, CNS diseases such as Alzheimer disease or amyotrophic lateral sclerosis, cancer, infectious diseases such as: AIDS, septic shock or adult respiratory distress syndrome, ischemia/reperfusion injury, e.g.: myocardial infarction, stroke, gut ischemia, renal failure or hemorrhage shock, and traumatic shock, e.g. traumatic brain injury.

Further diseases or conditions of interest for treatment according to the present disclosure include, but are not limited to, T-cell mediated acute or chronic inflammatory diseases or disorders or autoimmune diseases, rheumatoid arthritis, osteoarthritis, systemic lupus erythematosus, Hashimoto's thyroiditis, multiple sclerosis, myasthenia gravis, diabetes type I or II and the disorders associated therewith, transplant rejection, graft versus host disease, respiratory diseases, asthma, inflammatory lung injury, inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitises, seborrhoeic dermatitis), inflammatory eye diseases (such as Sjoegren's syndrome, keratoconjunctivitis, uveitis) inflammatory bowel disease, Crohn's disease or ulcerative colitis, Guillain-Barre syndrome, and allergies.

The subject compounds can also be used for preventing or treating or delaying ocular diseases and disorders involving inflammation and/or neovascularization. Ocular diseases or disorders involving inflammatory and/or neovascular events include, but are not limited to, macular degeneration (AMD), diabetic ocular diseases or disorders, uveitis, optic neuritis, ocular edema, ocular angiogenesis, ischemic retinopathy, anterior ischemic optic neuropathy, optic neuropathy and neuritis, macular edema, cystoid macular edema (CME), retinal disease or disorder, such as retinal detachment, retinitis pigmentosa (RP), Stargart's disease, Best's vitelliform retinal degeneration, Leber's congenital amaurosis and other hereditary retinal degenerations, Sorsby's fundus dystrophy, pathologic myopia, retinopathy of prematurity (ROP), Leber's hereditary optic neuropathy, corneal transplantation or refractive corneal surgery, keratoconjunctivitis, or dry eye.

Generally, cell proliferative disorders treatable with the subject compound disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, among others, breast cancer, ovarian cancer, renal cancer, gastrointestinal cancer, kidney cancer, bladder cancer, pancreatic cancer, lung squamous carcinoma, and adenocarcinoma.

In some embodiments, the cell proliferative disorder treated is a hematopoietic neoplasm, which is aberrant growth of cells of the hematopoietic system. Hematopoietic malignancies can have its origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. For instance, cells capable of developing specific subtypes of acute myeloid leukemia (AML) upon transplantation display the cell surface markers of hematopoietic stem cells, implicating hematopoietic stem cells as the source of leukemic cells. Blast cells that do not have a cell marker characteristic of hematopoietic stem cells appear to be incapable of establishing tumors upon transplantation (Blaire et al., 1997, Blood 89:3104-3112). The stem cell origin of certain hematological malignancies also finds support in the observation that specific chromosomal abnormalities associated with particular types of leukemia can be found in normal cells of hematopoietic lineage as well as leukemic blast cells. For instance, the reciprocal translocation t(9q34;22q11) associated with approximately 95% of chronic myelogenous leukemia appears to be present in cells of the myeloid, erythroid, and lymphoid lineage, suggesting that the chromosomal aberration originates in hematopoietic stem cells. A subgroup of cells in certain types of CML displays the cell marker phenotype of hematopoietic stem cells.

Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition. Moreover, some chromosomal aberrations associated with subtypes of leukemia are not found in the cell population with a marker phenotype of hematopoietic stem cells, but are found in a cell population displaying markers of a more differentiated state of the hematopoietic pathway (Turhan et al., 1995, Blood 85:2154-2161). Thus, while committed progenitor cells and other differentiated cells may have only a limited potential for cell division, leukemic cells may have acquired the ability to grow unregulated, in some instances mimicking the self-renewal characteristics of hematopoietic stem cells (Passegue et al., Proc. Natl. Acad. Sci. USA, 2003, 100:11842-9).

In some embodiments, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms are further subdivided into precursor T-cell neoplasm and mature (peripheral) T-cell neoplasms. Exemplary precursor T-cell neoplasm is precursor T-lymphoblastic lymphomalleukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphomalleukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma.

In some embodiments, the hematopoietic neoplasm treated is a myeloid neoplasm. This group comprises a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9;22)(qq34;q11)), chronic neutrophilic leukemia, chronic eosinophilic leukemialhypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome with t(9;12)(q22;p12) (TEL-Syk fusion; see, e.g., Kuno et al., 2001, Blood 97:1050).

In some embodiments, the composition can be used to treat acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8;21)(q22;q22), AML1(CBF-alpha)/ETO, Acute promyelocytic leukemia (AML with t(15;17)(q22;q11-12) and variants, PML/RAR-alpha), AML with abnormal bone marrow eosinophils (inv(16)(p13q22) or t(16;16)(p13;q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

In other aspects, cell proliferative disorders comprise virally mediated tumors. These can arise from infection of cells by an oncogenic virus that has the capability of transforming a normal cell into a tumor cell. Because rates of viral infection far exceed the number of actual incidence of cell transformation, viral mediated transformation generally act together with other cellular factors to generate a transformed tumor cell. Thus, a virally mediated tumor does not require the virus to be the sole causative agent of the cell proliferative disorder, but rather that the viral infection or persistent presence of virus is associated with the generation of the tumor. Generally, tumors where the causative agent is a virus typically has continual expression of a limited number of viral genes and that viral these oncogenes, expressed as part of the viral infection or through persistence of the virus, disrupts the normal cellular gene expression and signal transduction pathways. Without being bound by theory, viral oncogenes involved in cell transformation appear to disrupt four main cellular processes: cell surface receptors that interact with growth factors and extracellular matrix, transmembrane signaling networks, cytosolic elements such as soluble proteins and second messengers, and nuclear proteins including DNA binding proteins and factors which function directly and indirectly in gene regulation and replication.

Characterization of Functional Properties

The following are exemplary assays useful in characterizing activities of a compound of interest.

A. In Vitro

1. Protein Kinase C assay

The inhibition of PKC activity is measured by monitoring the production of phosphorylated peptide by fluorescence polarization at different concentrations of the inhibitor. Reactions are carried out in 96-well plate format with a total volume of 20 µL containing 20 mM HEPES, pH 7.4, 5 mM $MgCl_2$, 0.2 mM $CaCl_2$, 1 mM DTT, 0.02% Brij-35, 0.1 mg/mL phosphatidylserine, 0.02 mg/mL dioleoyl-sn-glycerol and 5 µM each of ATP and the peptide substrate. Compounds are first diluted serially in DMSO and then transferred to a solution containing the above concentrations of HEPES, $MgCl_2$, $CaCl_2$, DTT, and Brij-35 to yield 5×compound solutions in 2% DMSO, which is then added to the reaction solution. Reactions are initiated by the addition of PKC at a typical concentration as described in the table below, and then allowed to incubate at room temperature for 20 minutes. At the end of this time, a combination of quench (EDTA) and detection (peptide tracer and antibody) reagents is added using the protocol of Invitrogen P2748 (Carlsbad, Calif.), a Protein Kinase C Fluorescence polarization Assay Kit. After a 30 minute period of incubation, the amount of phosphorylated peptide generated is measured by fluorescence polarization (Ex=485 nm, Em=535 nm) using a Tecan Polarian instrument (Switzerland).

TABLE 2

| Peptide substrate | | SEQ ID | Enzyme source | enzyme concentration |
|---|---|---|---|---|
| PKC theta | RFARKGSLRQKNV | Seq ID No. 1 | Upstate Biotechnologies, Temecula, CA, cat. #14-444 | 40 ng/mL |
| PKC epsilon | RFARKGSLRQKNV | Seq ID No. 1 | Upstate Biotechnologies, Temecula, CA, cat. #14-518 | 50 ng/mL |

2. IL-2 ELISA, Human Primary T Cell, Anti-CD3+CD28+ Assays

Human Primary T Cell Isolation and Culture:

Human primary T cells were prepared as follows. Fresh PBMC's from All Cells (Cat # PB002) were re-suspended in RPMI (RPMI-1640 with L-Glutamine; Mediatech, Inc., Herndon Va., cat. #10-040-CM) with 10% FBS and seeded into flasks and incubated at 37° C. for 2 hours to allow the monocytes to adhere. The non-adherent cells were then centrifuged and re-suspended in RPMI medium containing 40 U/ml IL2 and seeded into a flask pre-coated with 1 µg/ml aCD3 and 5 ug/ml aCD28 (Anti-Human CD3, BD Pharmingen Catalog #555336, Anti-Human CD28, Beckman Coulter Catalog #IM1376). The cells were stimulated for 3-4 days, then transferred to a fresh flask and maintained in RPMI (RPMI-1640 with L-Glutamine; Mediatech, Inc., Herndon Va., cat. #10-040-CM) with 10% FBS and 40 U/mL IL-2.

Primary T Cell Stimulation and IL2 ELISA:

Human primary T cells (100,000 cells per well) were pre-incubated with or without test compound in RPMI-1640 with L-Glutamine and 10% FBS for 1 hour at 37° C. Cells were then stimulated by transferring them to round-bottom 96-well plates pre-coated with 1 µg/ml αCD3 and 5 µg/ml αCD28. For counter assay, cells were instead stimulated by adding 8× stock solutions of PMA and ionomycin in RPMI-1640 with L-Glutamine and 10% FBS (for final concentrations of 0.5 ng/ml PMA and 0.1 µM ionomycin, both from Calbiochem). Cells were incubated at 37° C. for 24 hours before 100 µL supernatants were harvested for quantification of IL-2 by ELISA using Human IL-2 Duoset ELISA Kit from R and D Systems, Cat. # DY202E.

3. Protein Kinase C Assay

The subject compounds can be tested for activity on different PKC isoforms according to the following method. Assay is performed in a white with clear bottom 384-well microtiterplate with non-binding surface. The reaction mixture (25 µl) contains 1.5 µM of a tridecapeptide acceptor substrate that mimics the pseudo substrate sequence of PKC α with the Ala-Ser replacement, 10 µM $^{33}$P-ATP, 10 mM Mg(NO$_3$)$_2$, 0.2 mM CaCl$_2$, PKG at a protein concentration varying from 25 to 400 ng/ml (depending on the isotype used), lipid vesicles (containing 30 mol % phosphatidylserine, 5 mol % DAG and 65 mol % phosphatidylcholine) at a final lipid concentration of 0.5 mM, in 20 mM Tris-HCl buffer pH 7.4+0.1% BSA. Incubation is performed for 60 minutes at room temperature. Reaction is stopped by adding 50 µl of stop mix (100 mM EDTA, 200 µM ATP, 0.1% Triton X-100, 0.375 mg/well streptavidin-coated SPA beads in phosphate buffered saline w/o Ca, Mg. After 10 minutes incubation at room temperature, the suspension is spun down for 10 minutes at 300 g. Incorporated radioactivity is measured in a Trilux counter for 1 minute. IC$_{50}$ measurement is performed on a routine basis by incubating a serial dilution of inhibitor at concentrations ranging between 1-1000 µM. IC$_{50}$ values are calculated from the graph by curve fitting with XL Fit® software.

4. Protein Kinase C α Assay

Human recombinant PKC α is obtained from Oxford Biomedical Research and is used under the assay conditions as described under Section A.1 above.

5. Protein Kinase β1 Assay

Human recombinant PKC β1 is obtained from Oxford Biomedical Research and is used under the assay conditions as described under Section A.1 above.

6. Protein Kinase C δ Assay

Human recombinant PKC δ is obtained from Oxford Biomedical Research and is used under the assay conditions as described under Section A.1 above.

7. Protein Kinase C ε Assay

Human recombinant PKC E is obtained from Oxford Biomedical Research and is used under the assay conditions as described under Section A.1 above.

8. Protein Kinase C η Assay

Human recombinant PKC η is obtained from PanVera and is used under the assay conditions as described under Section A.1 above.

9. Protein Kinase C θ Assay

Human recombinant PKC θ is used under the assay conditions as described above.

10. CD28 Costimulation Assay

The assay is performed with Jurkat cells transfected with a human interleukin-2 promoter/reporter gene construct as described by Baumann G et al. in Transplant. Proc. 1992; 24:43-8, the β-galactosidase reporter gene being replaced by the luciferase gene (de Wet J., et al., Mol. Cell. Biol. 1987, 7(2), 725-737). Cells are stimulated by solid phase-coupled antibodies or phorbol myristate acetate (PMA) and the Ca$^{++}$ ionophore ionomycin as follows. For antibody-mediated stimulation Microlite TM1 microtiter plates (Dynatech) are coated with 3 µg/ml goat anti-mouse IgG Fc antibodies (Jackson) in 55 µl phosphate-buffered saline (PBS) per well for three hours at room temperature. Plates are blocked after removing the antibodies by incubation with 2% bovine serum albumin (BSA) in PBS (300 µl per well) for 2 hours at room temperature. After washing three times with 300 µl PBS per well, 10 ng/ml anti-T cell receptor antibodies (WT31, Becton & Dickinson) and 300 ng/ml anti-CD28 antibodies (15E8) in 50 µl 2% BSA/PBS are added as stimulating antibodies and incubated overnight at 4° C. Finally the plates are washed three times with 300 µl PBS per well. Seven three-fold serial dilutions of test compounds in duplicates in assay medium (RPMI 1640/10% fetal calf serum (FCS) containing 50 µM 2-mercaptoethanol, 100 units/ml penicillin and 100 µg/ml streptomycin) are prepared in separate plates, mixed with transfected Jurkat cells (clone K22 290_H23) and incubated for 30 minutes at 37° C. in 5% CO$_2$ 100 µl of this mixture containing 1×10$^5$ cells are then transferred to the antibody-coated assay plates. In parallel 100 µl are incubated with 40 ng/ml PMA and 2 µM ionomycin. After incubation for 5.5 hours at 37° C. in 5% CO$_2$, the level of luciferase is determined by bioluminescence measurement. The plates are centrifuged for 10 minutes at 500 g and the supernatant is removed by flicking. Lysis buffer containing 25 mM Tris-phosphate, pH 7.8, 2 mM DTT, 2 mM 1,2-diaminocyclohexane-N,N,N',N-tetraacetic acid, 10% (v/v) glycerol and 1% (v/v) Triton X-100 is added (20 µl per well). The plates are incubated at room temperature for 10 minutes under constant shaking. Luciferase activity is assessed with a bioluminescence reader (Labsystem, Helsinki, Finland) after automatic addition of 50 µl per well luciferase reaction buffer containing 20 mM Tricine, 1.07 mM $(MgCO_3)_4Mg(OH)_2 \times 5H_2O$, 2.67 mM $MgSO_4$, 0.1 mM EDTA, 33.3 mM DTT, 270 μM coenzyme A, 470 μM luciferin (Chemie Brunschwig AG), 530 μM ATP, pH 7.8. Lag time is 0.5 seconds, total measuring time is 1 or 2 seconds. Low control values are light units from anti-T cell receptor- or PMA-stimulated cells, high controls are from anti-T cell receptor/anti-CD28- or PMA/ionomycin-stimulated cells without any test sample. Low controls are subtracted from all values. The inhibition obtained in the presence of a test compound is calculated as percent inhibition of the high control. The concentration of test compounds resulting in 50% inhibition ($IC_{50}$) is determined from the dose-response curves.

11. Bone Marrow Proliferation (BM) Assay

Bone marrow cells from CBA mice (2.5×104 cells per well in flat bottom tissue culture microtiter plates) are incubated in 100 μl RPMI medium containing 10% FCS, 100 U/ml penicillin, 100 μg/ml streptomycin (Gibco BRL, Basel, Switzerland), 50 tJM 2-mercaptoethanol (Fluke, Buchs, Switzerland), WEHI-3 conditioned medium (7.5% v/v) and L929 conditioned medium (3% v/v) as a source of growth factors and serially diluted compounds. Seven three-fold dilution steps in duplicates per test compound are performed. After four days of incubation 1 μCi $^3$H-thymidine is added. Cells are harvested after an additional five-hour incubation period, and incorporated $^3$H-thymidine is determined according to standard procedures. Conditioned media are prepared as follows. WEHI-3 cells 1 (ATCC TIB68) and L929 cells (ATCC CCL 1) are grown in RPMI medium until confluence for 4 days and one week, respectively. Cells are harvested, resuspended in the same culture flasks in medium C containing 1% FCS (Schreier and Tees 1981) for WEHI-3 cells and RPMI medium for L929 cells and incubated for 2 days (WEHI-3) or one week (L929). The supernatant is collected, filtered through 0.2 μm and stored in aliquots at −80° C. Cultures without test compounds and without WEHI-3 and L929 supernatants are used as low control values. Low control values are subtracted from all values. High controls without any sample are taken as 100% proliferation. Percent inhibition by the samples is calculated and the concentrations required for 50% inhibition ($IC_{50}$ values) are determined.

12. Allogeneic Mixed Lymphocyte Reaction (MLR)

The two-way MLR is performed according to standard procedures (J. Immunol. Methods, 1973, 2, 279 and Meo T. et al., Immunological Methods, New York, Academic Press, 1979, 227-39). Briefly, spleen cells from CBA and BALB/c mice (1.6×10$^5$ cells from each strain per well in flat bottom tissue culture microtiter plates, 3.2×10$^5$ in total) are incubated in RPMI medium containing 10% FCS, 100 U/ml penicillin, 100 μg/ml streptomycin (Gibco BRL, Basel, Switzerland), 50 μM 2-mercaptoethanol (Fluka, Buchs, Switzerland) and serially diluted compounds. Seven three-fold dilution steps in duplicates per test compound are performed. After four days of incubation 1 μCi $^3$H-thymidine is added. Cells are harvested after an additional five-hour incubation period, and incorporated $^3$H-thymidine is determined according to standard procedures. Background values (low control) of the MLR are the proliferation of BALB/c cells alone. Low controls are subtracted from all values. High controls without any sample are taken as 100% proliferation. Percent inhibition by the samples is calculated, and the concentrations required for 50% inhibition ($IC_{50}$ values) are determined.

B. In vivo

Heart Transplantation Model

The strain combination used: Male Lewis ($RT^1$ haplotype) and BN ($RT^1$ haplotype). The animals are anaesthetised using inhalational isofluorane. Following heparinisation of the donor rat through the abdominal inferior vena cava with simultaneous exsanguination via the aorta, the chest is opened and the heart rapidly cooled. The aorta is ligated and divided distal to the first branch and the brachiocephalic trunk is divided at the first bifurcation. The left pulmonary artery is ligated and divided and the right side divided but left open. All other vessels are dissected free, ligated and divided and the donor heart is removed into iced saline.

The recipient is prepared by dissection and cross-clamping of the infra-renal abdominal aorta and vena cava. The graft is implanted with end-to-side anastomoses, using 1010 monofilament suture, between the donor brachiocephalic trunk and the recipient aorta and the donor right pulmonary artery to the recipient vena cava. The clamps are removed, the graft tethered retroabdominally, the abdominal contents washed with warm saline and the animal is closed and allowed to recover under a heating lamp. Graft survival is monitored by daily palpation of the beating donor heart through the abdominal wall. Rejection is considered to be complete when-heart beat stops. Graft survival is monitored in animals treated with compounds.

Graft v. Host Model

Spleen cells (2×10$^7$) from Wistar/F rats are injected subcutaneously into the right hind footpad of (Wistar/F x Fischer 344)$F_1$ hybrid rats. The left footpad is left untreated. The animals are treated with the test compounds on 4 consecutive days (0-3). The popliteal lymph nodes are removed on day 7, and the weight differences between two corresponding lymph nodes are determined. The results are expressed as the inhibition of lymph node enlargement (given in percent) comparing the lymph node weight differences in the experimental groups to the weight difference between the corresponding lymph nodes from a group of animals left untreated with a test compound. In certain instances the test compound is a selective PKC inhibitor. For example, disclosed compounds that are particularly useful for treating graft versus host disease and related disorders are selective PKC α and θ inhibitors.

Rat Collagen-Induced Arthritis Model

Rheumatoid arthritis (RA) is characterized by chronic joint inflammation eventually leading to irreversible cartilage destruction. IgG-containing IC are abundant in the synovial tissue of patients with RA. While it is still debated what role these complexes play in the etiology and pathology of the disease, IC communicate with the hematopoetic cells via the FcγR.

CIA is a widely accepted animal model of RA that results in chronic inflammatory synovitis characterized by pannus formation and joint degradation. In this model, intradermal immunization with native type II collagen, emulsified with incomplete Freund's adjuvant, results in an inflammatory polyarthritis within 10 or 11 days and subsequent joint destruction in 3 to 4 weeks.

Study Protocol

Syngeneic LOU rats are immunized with native type II collagen on Day 0, and efficacy of a test compound is evaluated in a prevention regimen and a treatment regimen. In the prevention protocol, either vehicle or various doses of a test compound are administered via oral gavage starting on day of immunization (Day 0). In the treatment protocol, after clinical signs of arthritis develop on Day 10, treatment with a test compound is initiated (e.g., 300 mg/kg by oral gavage, qd) and continued until sacrifice on Day 28. In both protocols, clinical scores are obtained daily, and body weights are measured twice weekly. At Day 28, radiographic scores are obtained, and serum levels of collagen II antibody are measured by ELISA.

Determination of Results

By 10 days after immunization, rats can develop clinical CIA, as determined by an increase in their arthritis scores. The mean arthritic score gradually increases in the rats treated with vehicle alone after Day 10, and by Day 28 the mean clinical score can reach about 6.75. Mean clinical scores in animals treated from the day of immunization (Day 0) with a test compound can be significantly reduced on Days 10-28 compared with vehicle controls. In the rats treated with a test compound at disease onset, there can be a significantly lower arthritis score beginning around Day 16, and this difference can be observed until the end of the study on Day 28.

Blinded radiographic scores (scale 0-6) can be obtained on Day 28 of CIA and compared between the animals in the vehicle group, animals in the prevention group, and animals in the treatment group.

The groups administered with a test compound, either prophylactically (at immunization) or after disease onset can preclude the development of erosions and reduced soft tissue swelling. Similarly, the groups administered with a test compound can result in reduction of serum anti-collagen II antibody.

Mouse Experimental Autoimmune Encephalomyelitis

The in vivo efficacy of a test compound towards autoimmune diseases can be demonstrated in a mouse model of experimental autoimmune encephalomyelitis (EAE).

Model Description

EAE is a useful model for multiple sclerosis (MS), an autoimmune disease of the CNS that is caused by immune-cell infiltration of the CNS white matter. Inflammation and subsequent destruction of myelin cause progressive paralysis. Like the human disease, EAE is associated with peripheral activation of T cells autoreactive with myelin proteins, such as myelin basic protein (MBP), proteolipid protein (PLP), or myelin oligodendrocyte protein (MOG). Activated neuroantigen-specific T cells pass the blood-brain barrier, leading to focal mononuclear cell infiltration and demyelination. EAE can be induced in susceptible mouse strains by immunization with myelin-specific proteins in combination with adjuvant. In the SJL mouse model used in these studies, hind limb and tail paralysis is apparent by Day 10 after immunization, the peak of disease severity can be observed between Days 10 and 14, and a cycle of partial spontaneous remission followed by relapse can be observed up to Day 35. The results can demonstrate the potential of the test compound to suppress disease severity and prevent relapse of disease symptoms that may be the result of FcγR-mediated cytokine release from immune cells.

Study Protocol

In the SJL murine model of EAE, each mouse is sensitized with PLP/CFA. (150 µg PLP139-151 with 200 µg CFA in 0.05 ml of homogenate on four sites of hind flank for a total of 0.2 ml emulsion is used to induce EAE). In a suppression protocol, either vehicle or various doses of a test compound are administered via oral gavage starting on the day of immunization (Day 0). In a treatment protocol, at onset of disease, animals are separated to achieve groups with a similar mean clinical score at onset and administered vehicle or various dose frequencies of test compounds via oral gavage. In both protocols, clinical scores are monitored daily, and body weights are measured twice weekly.

Determination of Results

By 10 days after PLP immunization, SJL mice can develop clinical EAE, as evidenced by an increase in their mean clinical scores. The paralytic score can gradually increase in the animals treated with vehicle only from the day of immunization (Day 0), and by Day 14 the mean score can reach a peak of about 5.1. At disease peak (e.g., Day 14), the mean clinical score in animals treated with either daily or twice daily can be significantly reduced. By Day 16, animals can exhibit a partial remission of mean clinical severity, which is a characteristic of the SJL model. The lower clinical scores in animals treated twice daily with a test compound can remain significant throughout the experiment until the animals are sacrificed on Day 30. These lower scores throughout the treatment period are reflected in the significantly lower cumulative disease index (CDI) and increase in cumulative weight index (CWI).

SJL mice treated with a test compound at disease onset (e.g., Day 11) can show a significant decrease in CDI. Further, there can be a decrease in the number of relapses in animals treated with a test compound compared with the number of relapses in animals treated with vehicle.

Research Applications

Since subject compounds can inhibit a PKC activity, such compounds are also useful as research tools. The present disclosure also provides a method for using subject compounds as a research tool for studying a biological system or sample, or for discovering new chemical compounds that can inhibit a PKC activity.

The disclosure provides for a method of studying a biological system or sample known to comprise PKC, the method comprising: (a) contacting the biological sample with a compound of formula I-VIII or a salt or solvate or stereoisomer thereof; and (b) determining the inhibiting effects caused by the compound on the biological sample.

Any suitable biological sample having PKC can be employed in such studies which can be conducted either in vitro or in vivo. Representative biological samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest.

When used as a research tool, a biological sample comprising PKC is typically contacted with a PKC activity-inhibiting amount of a subject compound. After the biological sample is exposed to the compound, the effects of inhibition of a PKC activity are determined using conventional procedures and equipment, such as the assays disclosed herein. Exposure encompasses contacting the biological sample with the compound or administering the compound to a subject. The determining step can involve measuring a response (a quantitative analysis) or can involve making an observation (a qualitative analysis). Measuring a response involves, for example, determining the effects of the compound on the biological sample using conventional procedures and equipment, such as radioligand binding assays and measuring ligand-mediated changes in functional assays. The assay results can be used to determine the activity level as well as the amount of compound necessary to achieve the desired result, that is, a PKC activity-inhibiting amount.

Additionally, subject compounds can be used as research tools for evaluating other chemical compounds, and thus are also useful in screening assays to discover, for example, new compounds having a PKC inhibiting activity. In this manner, a subject compound can be used as a standard in an assay to allow comparison of the results obtained with a test compound and with the subject compounds to identify those test compounds that have about equal or superior activity, if any. For example, $IC_{50}$ data for a test compound or a group of test compounds is compared to the $IC_{50}$ data for a subject compound to identify those test compounds that have the desired properties, for example, test compounds having an $IC_{50}$ about equal or superior to a subject compound, if any.

This aspect includes, as separate embodiments, both the generation of comparison data (using the appropriate assays) and the analysis of test data to identify test compounds of interest. Thus, a test compound can be evaluated in a biological assay, by a method comprising the steps of: (a) conducting a biological assay with a test compound to provide a first assay value; (b) conducting the biological assay with a subject compound to provide a second assay value; wherein step (a) is conducted either before, after or concurrently with step (b); and (c) comparing the first assay value from step (a) with the second assay value from step (b). The assays that can be used for generation of comparison data are disclosed herein, such as the PKC assays.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. As will be understood, by those of skill in the art of organic synthesis and medicinal chemistry the specific conditions set forth below are exemplary and can be varied or adapted to other reagents and products in routine fashion. Unless indicated otherwise, parts are parts by weight, molecular weight is weight average molecular weight, temperature is in degrees Celsius, and pressure is at or near atmospheric. Standard abbreviations may be used.

Example 1

5-fluoro-n2-[4-(4-methylpiperazino)-3-trifluoromethyl]phenyl-n4-(1,2,2,6,6-pentamethylpiperidin-4-yl)-2,4-pyrimidinediamine 2-Fluoro-5-nitrobenzotrifluoride (2 g) and 1-methylpiperazine (2 mL) were dissolved in methanol (5 mL). The yellow solution was stirred at room temperature overnight. The reaction mixture was diluted with water (100 mL) and extracted with ethyl acetate (2×100 mL). The organic solutions were evaporated to give 2-(4-methylpiperazino)-5-nitrobenzotrifluoride.

2-(4-Methylpiperazino)-5-nitrobenzotrifluoride was dissolved in methanol (100 mL) and to the solution was added 10% Pd—C. The reaction mixture was reacted under hydrogen atmosphere (~40 psi) for 1 hour. The catalyst was filtered off over cellite and washed with methanol. The filtrate was evaporated to give [4-(4-methylpiperazino)-3-trifluoromethyl]aniline (2.25 g, 91% in two steps). $^1$H NMR (DMSO-d6): δ 2.19 (s, 3H), 2.38 (br, 4H), 2.70 (t, J=4.5 Hz, 4H), 5.31 (br, 2H), 6.73 (dd, J=2.4, 8.7 Hz, 1H), 6.78 (d, J=2.7 Hz, 1H), 7.20 (d, J=8.1 Hz, 1H).

4-Amino-1,2,2,6,6-pentamethylpiperidine (1 g) and 2,6-dichloro-5-fluoropyrimidine (1.5 g) were dissolved in methanol (10 mL). The reaction solution was stirred at room temperature overnight. The reaction solution was evaporated and crystallized from ethyl acetate and hexanes to give 2-chloro-5-fluoro-N4-(1,2,2,6,6-pentamethylpiperidin-4-yl)-4-pyrimidineamine HCl salt (1.65 g, 93%). $^1$H NMR (DMSO-d6): δ 1.38 (s, 6H), 1.48 (s, 6H), 2.02 (m, 4H), 2.68 (d, J=4.8 Hz, 3H), 4.33 (br, 1H), 8.10 (d, J=3.3 Hz, 1H), 8.32 (d, J=6.9 Hz, 1H), 9.66 (br, 1H).

2-Chloro-5-fluoro-N4-(1,2,2,6,6-pentamethylpiperidin-4-yl)-4-pyrimidineamine (300 mg) and [4-(4-methylpiperazino)-3-trifluoromethyl]aniline (300 mg) were suspended in isopropanol (1 mL) and TFA (5 drops). The solution was heated at 100° C. overnight, then cooled to room temperature. The solution was evaporated and purified by flash column chromatography (2.0 M NH$_3$/MeOH in dichloromethane=2, 4, 6, 10%) to give 5-fluoro-N2-[4-(4-methylpiperazino)-3-trifluoromethyl]phenyl-N4-(1,2,2,6,6-pentamethylpiperidin-4-yl)-2,4-pyrimidinediamine (440 mg, 84%). $^1$H NMR (DMSO-d6): δ 1.04 (s, 6H), 1.07 (s, 6H), 1.44 (t, J=11.7 Hz, 2H), 1.68 (d, J=9.9 Hz, 2H), 2.18 (s, 3H), 2.20 (s, 3H), 2.41 (br, 4H), 2.76 (t, J=4.2 Hz, 4H), 4.29 (br, 1H), 7.16 (d, J=8.4 Hz, 1H), 7.32 (d, J=8.4 Hz, 1H), 7.75 (d, J=2.1 Hz, 1H), 7.84 (d, J=3.6 Hz, 1H), 8.07 (d, J=8.7 Hz, 1H), 9.13 (s, 1H); $^{19}$F NMR (282 MHz, DMSO-d6): δ −165.87, −59.89; LCMS: purity: 100%; MS (m/e): 524.43 (MH+).

The following compounds were made in a similar fashion to the Example 1 or by methods described herein or known to skilled artisans.

Example 2

I-1: 5-fluoro-n2-{4-fluoro-[3-(4-h)-1,2,3,4-tetrazol-5-one-1-yl]}phenyl-n4-(1,2,2,6,6-pentamethylpiperidin-4-yl)-2,4-pyrimidinediamine $^1$H NMR (DMSO d$_6$, 300 MHz): δ 9.21 (s, 1H), 7.88 (m, 2H), 7.63 (bs, 1H), 7.35 (d, J=8.1 Hz, 1H), 7.19 (t, J=9.6 Hz, 1H), 4.48 (bs, 1H), 1.86 (d, J=11.4 Hz, 2H), 1.65 (bs, 2H), 1.22 (s, 6H), 1.15 (s 6H); LCMS (m/z): 460.07 (MH$^+$).

Example 3

I-2: 5-fluoro-n2-{4-fluoro-[3-(4-h)-1,2,3,4-tetrazol-5-one-1-yl]}phenyl-n4-(2,2,6,6-tetramethylpiperidin-4-yl)-2,4-pyrimidinediamine $^1$H NMR (DMSO d$_6$, 300 MHz): δ 9.19 (s, 1H), 7.90 (m, 2H), 7.48-7.34 (m, 2H), 7.15 (t, J=9.9 Hz, 1H), 4.44 (s, 1H), 1.90 (d, J=10.5 Hz, 2H), 1.51 (t, J=12 Hz, 2H), 1.29 (d, J=7.5 Hz, 12H); LCMS (m/z): 446.10 (MH$^+$).

Example 4

I-3: 5-fluoro-n2-{4-fluoro-[3-(4-methyl)-1,2,3,4-tetrazol-5-one-1-yl]}phenyl-n4-(1,2,2,6,6-pentamethylpiperidin-4-yl)-2,4-pyrimidinediamine $^1$H NMR (DMSO d$_6$, 300 MHz): δ 9.37 (s, 1H), 9.09 (s, 1H), 8.02-7.71 (m, 3H), 7.65 (d, J=7.5 Hz, 1H), 7.36 (t, J=9.9 Hz, 1H), 4.38 (bs, 1H), 3.62 (s, 3H), 2.68 (d, J=3.9 Hz, 3H), 2.05-2.00 (m, 2H), 1.87 (m, 2H), 1.41 (s, 6H), 1.31 (s, 6H); LCMS (m/z): 474.11 (MH+).

Example 5

I-4: 5-fluoro-n2-{4-fluoro-[3-(4-isopropyl)-1,2,3,4-tetrazol-5-one-1-yl]}phenyl-n4-(2,2,6,6-tetramethyl-piperidin-4-yl)-2,4-pyrimidinediamine $^1$H NMR (DMSO d$_6$, 300 MHz): δ 9.37 (s, 1H), 8.02 (d, J=6.6 Hz, 1H), 7.87 (d, J=3.6 Hz, 1H), 7.77 (m, 1H), 7.32 (t, J=9.6 Hz, 1H), 7.23 (d, J=7.8 Hz, 1H), 4.45 (bs, 1H), 3.6 (s, 3H), 1.65 (d, J=9 Hz, 2H), 1.14 (t, J=11.4 Hz, 2H), 1.04 (s, 6H), 0.99 (s, 6H); LCMS (m/z): 460.15 (MH+).

Example 6

I-5: 5-fluoro-n2-{4-fluoro-[3-(4-isopropyl)-1,2,3,4-tetrazol-5-one-1-yl]}phenyl-n4-(1,2,2,6,6-pentamethylpiperidin-4-yl)-2,4-pyrimidinediamine $^1$H NMR (DMSO d$_6$, 300 MHz): δ 9.34 (s, 1H), 7.98 (m, 1H), 7.86 (m, 2H), 7.32 (m, 2H), 4.44 (m, 1H), 4.29 (bs, 1H), 2.14 (bs, 3H), 1.67 (m, 2H), 1.46 (s, 6H), 1.43 (s, 6H), 1.52 (m, 2H), 1.05 (m, 12H); LCMS (m/z): 502.19 (MH+).

Example 7

I-6: 5-fluoro-n2-{4-fluoro-3-[4-(2-fluoroethyl)-1,2,3,4-tetrazol-5-one-1-yl]}phenyl-n4-(2,2,6,6-tetramethylpiperidin-4-yl)-2,4-pyrimidinediamine $^1$H NMR (DMSO d$_6$, 300 MHz): δ 9.34 (s, 1H), 7.98 (m, 1H), 7.88 (d, J=3.6 Hz, 1H), 7.8 (m, 1H), 7.29 (m, 2H), 4.44 (m, 1H), 4.29 (bs, 1H), 1.67 (m, 2H), 1.46 (s, 6H), 1.43 (s, 6H), 1.52 (m, 2H), 1.05 (m, 12H); LCMS (m/z): 488.28 (MH+).

Example 8

I-7: 5-fluoro-n2-{4-fluoro-3-[4-(2-fluoroethyl)-1,2,3,4-tetrazol-5-one-1-yl]}phenyl-n4-(2,2,6,6-tetramethylpiperidin-4-yl)-2,4-pyrimidinediamine $^1$H NMR (DMSO d$_6$, 300 MHz): δ 9.35 (s, 1H), 8.25 (s, 1H), 7.91 (d, J=6.9 Hz, 1H), 7.88 (m, 1H), 7.34 (m, 2H), 4.87 (m, 1H), 4.71 (m, 1H), 4.36 (m, 2H), 4.28 (m, 1H), 1.74 (d, J=11.4 Hz, 2H), 1.26 (t, J=12.9 Hz, 2H), 1.15 (s, 6H), 1.09 (s, 6H); LCMS (m/z): 492.12 (MH+).

Example 9

I-8: 5-fluoro-n2-{4-methyl-[3-(4-methyl)-1,2,3,4-tetrazol-5-one-1-yl]}phenyl-n4-(1,2,2,6,6-pentamethylpiperidin-4-yl)-2,4-pyrimidinediamine $^1$H NMR (DMSO d$_6$, 300 MHz): δ 9.25 (s, 1H), 8.15 (s, 1H), 7.86 (d, J=3.9 Hz, 1H), 7.78-7.74 (m, 2H), 7.22 (m, 2H), 4.26 (s, 1H), 3.60 (s, 3H), 2.19 (s, 3H), 2.05 (s, 3H), 1.68 (d, J=11.4 Hz, 2H), 1.45 (t, J=12 Hz, 2H), 1.07 (s, 6H), 0.96 (s, 6H); LCMS (m/z): 470.14 (MH+).

Example 10

I-9: 5-fluoro-n2-{4-methyl-[3-(4-methyl)-1,2,3,4-tetrazol-5-one-1-yl]}phenyl-n4-(2,2,6,6-tetramethyl-piperidin-4-yl)-2,4-pyrimidinediamine $^1$H NMR (DMSO d$_6$, 300 MHz): δ 9.26 (s, 1H), 8.29 (s, 1H), 7.88 (d, J=3.7 Hz, 1H), 7.74 (s, 1H), 7.35 (d, J=7.8 Hz, 2H), 7.22 (d, J=9.3 Hz, 1H), 4.39 (s, 1H), 3.60 (s, 3H), 2.05 (s, 3H), 1.77 (d, J=12.9 Hz, 2H), 1.33 (t, J=12.9 Hz, 2H), 1.17 (m, 12H); LCMS (m/z): 456.16 (MH+).

Example 11

I-10: 5-fluoro-n2-{4-isopropoxy-[3-(4-methyl)-1,2,3,4-tetrazol-5-one-1-yl]}phenyl-n4-(1,2,2,6,6-pentamethylpiperidin-4-yl)-2,4-pyrimidinediamine $^1$H NMR (DMSO d$_6$, 300 MHz): δ 9.10 (s, 1H), 8.16 (s, 3H), 7.83 (d, J=3.6 Hz, 1H), 7.79 (s, 1H), 7.71 (d, J=9 Hz, 1H), 7.17 (d, J=8.1 Hz 1H), 7.1 (d, 9 Hz, 1H), 4.46 (m, 1H), 4.25 (s, 1H), 3.59 (s, 3H), 2.18 (s, 3H), 1.66 (d, J=10.2 Hz, 2H), 1.45 (t, J=12.1 Hz, 9H), 1.12 (d, J=6 Hz, 6H), 1.06 (s, 6H), 0.93 (s, 6H); LCMS (m/z): 514.17 (MH+).

Example 12

I-11: 5-fluoro-n2-{4-isopropoxy-[3-(4-methyl)-1,2,3,4-tetrazol-5-one-1-yl]}phenyl-n4-(2,2,6,6-tetramethylpiperidin-4-yl)-2,4-pyrimidinediamine $^1$H NMR (DMSO d$_6$, 300 MHz): δ 9.12 (s, 1H), 8.30 (s, 1H), 7.85 (d, J=3.6 Hz, 1H), 7.8 (s, 1H), 7.69 (d, J=9.0 Hz, 1H), 7.28 (d, J=8.1 Hz, 1H), 7.12 (d, J=9 Hz, 1H), 4.46 (m, 1H), 4.35 (s, 1H), 3.58 (s, 3H), 1.74 (d, J=12 Hz, 10H), 1.31 (t, J=12.3 Hz, 2H), 1.12 (m, 12H); LCMS (m/z): 500.16 (MH+).

Example 13

I-12: 5-fluoro-n2-[3-(4-methyl)-1,2,3,4-tetrazol-5-one-1-yl]phenyl-n4-(1,2,2,6,6-pentamethylpiperidin-4-yl)-2,4-pyrimidinediamine $^1$H NMR (DMSO d$_6$, 300 MHz): δ 9.33 (s, 1H), 8.08 (s, 1H), 7.84 (dd, J=3.9 Hz, 1H), 7.8 (d, J=7.5 Hz, 1H), 7.29 (m, 3H), 4.33 (m, 1H), 3.59 (s, 3H), 2.22 (s, 3H), 1.72 (d, J=11.7 Hz, 2H), 1.47 (t, J=12.0 Hz, 2H), 1.08 (s, 6H), 0.99 (s, 6H); LCMS (m/z): 456.17 (MH+).

Example 14

I-13: 5-fluoro-n2-[3-(4-methyl)-1,2,3,4-tetrazol-5-one-1-yl]phenyl-n4-2,2,6,6-tetramethylpiperidin-4-yl)-2,4-pyrimidinediamine $^1$H NMR (DMSO d$_6$, 300 MHz): δ 9.38 (s, 1H), 8.72 (s, 1H), 8.07 (s, 1H), 7.86 (dd, J=3.6 Hz, 1H), 7.77 (d, J=7.8 Hz, 1H), 7.55 (bs, 1H), 7.39-7.3 (m, 2H), 4.43 (s, 1H), 3.59 (s, 3H), 1.93 (bs, 2H), 1.53 (bs, 2H), 1.33 (s, 12H); LCMS (m/z): 442.17 (MH+).

Example 15

Synthesis of 2-chloro-5-fluoro-N4-(1,2,2,6,6-pentamethylpiperdin-4-yl)-4-pyrimidineamine, HCL Salt

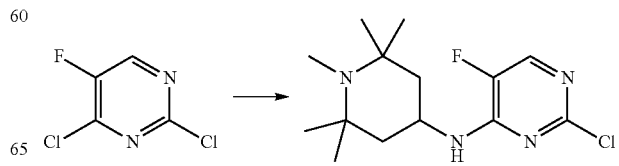

4-Amino-1,2,2,6,6-pentamethylpiperidine (1 g) and 2,6-dichloro-5-fluoropyrimidine (1.5 g) were dissolved in methanol (10 mL). The reaction solution was stirred at room temperature overnight. The reaction solution was evaporated and crystallized from ethyl acetate and hexanes to give 2-chloro-5-fluoro-N4-(1,2,2,6,6-pentamethylpiperidin-4-yl)-4-pyrimidineamine HCl salt (1.65 g, 93%). See also Example 1 for this synthesis.

$^1$H NMR (DMSO-$d_6$): δ 9.66 (br. s, 1H), 8.32 (d, J=6.9 Hz, 1H), 8.10 (d, J=3.3 Hz, 1H), 4.33 (br. s, 1H), 2.68 (d, J=4.8 Hz, 3H), 2.02 (m, 4H), 1.48 (s, 6H), 1.38 (s, 6H).

Example 16

Synthesis of 2-chloro-5-fluro-n4-(2,2,6,6-tetramethylpiperidin-4-yl)-4-pyrimidineamine, HCL Salt

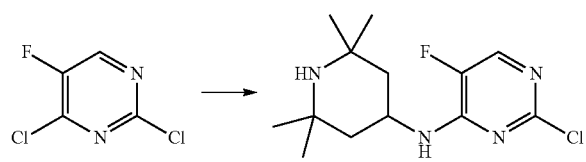 [SMILES: Fc1cnc(Cl)nc1Cl ; CC1(C)CC(Nc2nc(Cl)ncc2F)CC(C)(C)N1]

2,4-Dichloro-5-fluoropyrimidine (21.7 g) was dissolved in methanol (400 mL) and cooled to 0° C. 4-Amino-2,2,6,6-tetramethylpiperidine (19.2 mL) was added dropwise. The resulting mixture was slowly warmed to room temperature and stirred overnight. The reaction solution was evaporated and triturated with ethyl to 2-chloro-5-fluoro-N-(2,2,6,6-tetramethylpiperidin-4-yl)-4-pyrimidineamine, HCl salt (36.2 g, 93%).

$^1$H NMR (DMSO-$d_6$): δ 8.24 (d, 1H), 8.16 (d, 1H), 4.38 (m, 1H), 1.92 (d, 2H), 1.63 (t, 2H), 1.39 (d, 12H); m/z=287 (M+H)$^+$.

Example 17

Synthesis of 5-carboxyamide-2,4-dichloropyrimidine

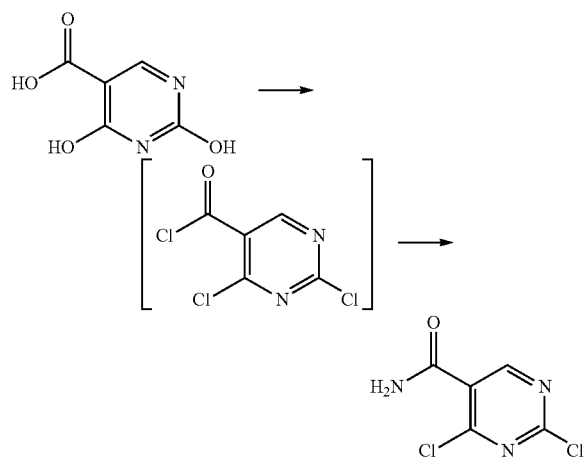

To a 2 L round bottom flask equipped with water condenser and a CaCl$_2$ drying tube, 2,4-dihydroxypyrimidine (25 g, 0.16 mole) was added to PCl$_5$ (117 g, 0.56 mole), and POCl$_3$ ml, 2.6 mole). The mixture was heated at 115° C. overnight to give a clear, slightly light yellow solution. The mixture was cooled to room temperature, and was concentrated under reduced pressure to give pale yellowish oil.

To this oil, anhydrous 1,4-dioxane (300 ml) was added and the mixture was cooled to 0° C. in an ice/water bath. 35 ml of NH$_3$ in water (28%) was added dropwise to the mixture with stirring, temperature was kept below 5° C. The mixture changed from clear to white with precipitate forming, and was stirred for 1 hour at 0° C., reaction was followed by TLC (1:1 Hexanes:Ethyl Acetate). Ethyl acetate (700 ml) and water (500 ml) were added to the mixture, the 2 layers were separated. The organic layer was dried with Na$_2$SO$_4$, and filtered. The solution was concentrated under reduced pressure to give a light yellow solid. This light yellow solid was sonicated with methylene chloride (200 ml), and filtered to give a pale yellow solid (1.6 g). This pale yellow solid was dissolved into ethyl acetate (1.5 L) and washed with saturated NaHCO$_3$ (500 ml). The organic layer was dried with Na$_2$SO$_4$, filtered, and concentrated under reduced pressure to give 13.1 g of product as a white solid (44% yield).

$^1$H NMR (DMSO-$d_6$, 300 MHz): δ 8.86 (s, 1H), 8.14 (bs, 1H), 8.02 (bs, 1H).

Example 18

Synthesis of 5-carboxyamide-2,4-dichloropyrimidine

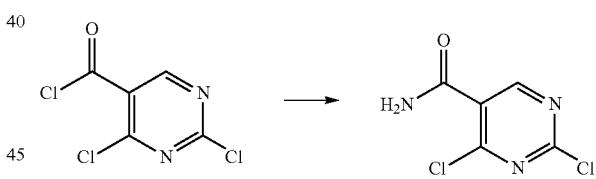

Concentrated ammonium hydroxide solution in H$_2$O (assumed to be 8.5M; 14.1 mL; 120 mmol) was added over 15-20 minutes to a stirred solution of 2,4-dichloropyrimidine-5-carbonyl chloride (12.5 g; 60 mmol; Manchester Organics, Sutton Weaver, England) in CH$_2$Cl$_2$ (300 mL) at −15 to −20° C. (internal temperature) [n.b.: a precipitate is formed during the addition]. After complete addition, the mixture was filtered (the filter cake comprises desired product and an impurity—for purification see below). H$_2$O (50 mL) was added to the filtrate, which was partitioned. The organic layer was dried (NaSO$_4$), filtered and the solvent removed under vacuum to give the title compound (1.1 g) as a solid. The filter cake from above was triturated with hot (ca. 50° C.) EtOAc (300 mL) and the mixture filtered—this was repeated another 2 times. The combined filtrates from the trituration were concentrated under vacuum to give another 9.1 g of the title compound. The total yield from the reaction is 10.2 g (88%). Data identical to those of Example 17.

Example 19

Synthesis of 5-carboxyamide-2-chloro-N4-1,2,2,6,6-pentamethylpiperidin-4-yl)-4-pyrimidineamine, HCL Salt

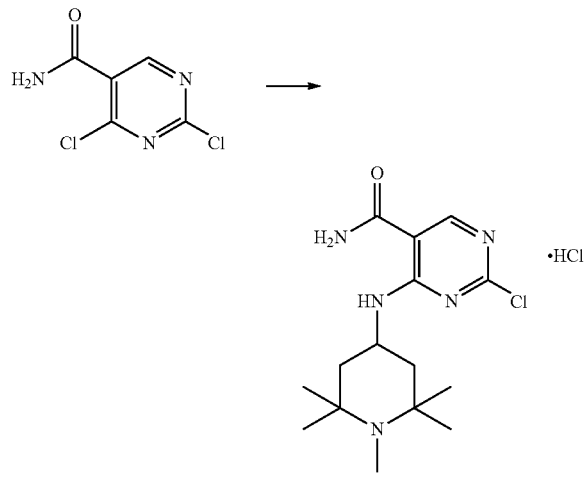

5-Carboxyamide-2,4-dichloropyrimidine (7.5 g, 0.04 mole) was dissolved into MeOH (300 ml)/H$_2$O (30 ml). The solution was cooled to 0° C. in a ice/water bath, 4-amino-1,2,2,6,6-pentamethylpiperidine (6.65 g, 0.04 mole) was added dropwise. The mixture was stirred at 0° C. and let warmed up to room temperature over 2 days. Solution was concentrated under reduced pressure to give a light yellow slush. Ethyl acetate (250 ml×2) was added and then concentrated under reduced pressure to remove the remaining traces of methanol and water to give a light yellowish solid. This solid was then sonicated with methylene chloride (100 ml), and filtered using a Buchner funnel, to give 9.5 g of pale yellow solid (75% yield) of the title compound as a HCl salt.

$^1$H NMR (DMSO d$_6$, 300 MHz): δ 9.74 (s, 1H), 9.23 (s, 1H), 8.6 (bs, 1H), 8.39 (bs, 1H), 7.76 (s, 1H), 4.36 (bs, 1H), 2.68 (s, 3H), 2.14 (d, 2H), 1.88 (t, 2H), 1.48 (s, 6H), 1.39 (s, 6H).

Example 20

Synthesis of 5-carboxyamide-2-chloro-N4-(1,2,2,6,6-pentamethylpiperidin-4-yl)-4-pyrimidineamine Free Base

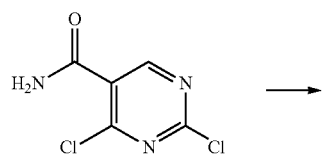

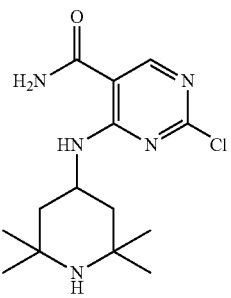

5-Carboxyamide-2,4-dichloropyrimidine (7.5 g, 0.04 mol) was dissolved into MeOH (300 ml)/H$_2$O (30 ml). The solution was cooled to 0° C. in a ice/water bath, 4-amino-2,2,6,6-tetramethylpiperidine (6.8 ml, 0.04 mole) was added dropwise. The mixture was stirred at 0° C. and let warmed up to room temperature over 2 days. Solution was concentrated under reduced pressure to give a light yellow slush. Ethyl acetate (250 ml×2) was added and then concentrated under reduced pressure to remove the remaining traces of methanol and water to give a light yellowish solid. This solid was then sonicated with methylene chloride (100 ml), and filtered using a Buchner funnel, to give a pale yellow solid.

This solid was treated with ethyl acetate (2 L), and saturated NaHCO$_3$, the 2 layers were separated, and the organic layer was dried with Na$_2$SO$_4$. The drying agent was filtered off and the solution was concentrated under reduced pressure to give a white solid (5 g, 41% yield). Additional product can be retrieved from the aqueous layer by back extracting it with additional ethyl acetate.

$^1$H NMR (DMSO-d$_6$, 300 MHz): δ 9.14 (d, 1H), 8.54 (s, 1H), 8.18 (bs, 1H), 7.68 (s, 1H), 4.30 (bs, 1H), 1.79 (d, 2H), 1.15 (s, 6H), 1.02 (s, 6H); m/z=312.2 (M+H)$^+$.

Example 21

Synthesis of 5-cyano-2-chloro-N4-(2,2,6,6-tetramethylpiperidin-4-yl)-4-pyrimidineamine

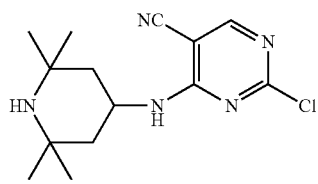 [SMILES: CC1(C)CC(Nc2nc(Cl)ncc2C#N)CC(C)(C)N1]

Burgess reagent—methyl (N-triethylammoniumsulfonyl)carbamate—(238 mg; 1.0 mmol) was added in one portion to a stirred solution of 5-carboxamide-2-chloro-N4-(2,2,6,6-tetramethylpiperidin-4-yl)-4-pyrimidineamine (156 mg; 0.5 mmol) in 1,2-dichloroethane (3 mL) at room temperature. The mixture was heated to 70° C. and stirred for 2 hours. After allowing to cool to room temperature the mixture was diluted with further 1,2-dichloroethane (20 mL) and H$_2$O (30 mL). The aqueous and organic layers were partitioned and the organic layer washed with saturated NaHCO$_3$ then dried (Na$_2$SO$_4$), filtered and the solvent removed under vacuum to leave a crude viscous oil (NMR shows this to be product and unreacted Burgess reagent). The crude oil was purified by column chromatography on silica gel using EtOAc:MeOH (9:1) then EtOAc:MeOH:

Et₃N (90:8:2) as eluent to give the title compound (75 mg, 51%) as a foam solid. This solid was suitable for use without further purification.

Example 22

Synthesis of 5-cyano-2-chloro-N4-(2,2,6,6-tetramethylpiperidin-4-yl)-4-pyrimidineamine

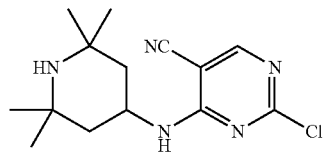 [SMILES: CC1(C)CC(Nc2nc(Cl)ncc2C#N)CC(C)(C)N1]

Trifluoroacetic anhydride (9.4 mL; 67.3 mmol) was added dropwise over 30-45 minutes to a stirred solution of 5-carboxyamide-2-chloro-N4-(2,2,6,6-tetramethylpiperidin-4-yl)-4-pyrimidineamine (2.1 g, 6.7 mmol) and Et₃N (11.3 mL; 80.8 mmol) in THF (40 mL) at −78° C. under nitrogen. After complete addition, the mixture was stirred at −78° C. for a further 60 minutes, then a saturated solution of NaHCO₃ (30 mL) was added dropwise keeping the internal temperature below −30° C. After complete addition of the NaHCO₃, EtOAc (150 mL) and H₂O (100 mL) was added and the mixture was stirred for 10 minutes. Further H₂O (200 mL) was added and the organic and aqueous layers were partitioned. The aqueous layer was extracted with EtOAc (4×150 mL)—until substantially all precipitated material had gone in to solution. The combined organic extracts were washed with brine (1×50 mL), dried (Na₂SO₄), filtered and the solvent removed under vacuum to leave a crude solid with TFAA and Et₃N residues. The solid was triturated with Et₂O (50 mL) and filtered to give the product (2.1 g) as a TFA salt.

Example 23

Formation of Free Base of 5-cyano-2-chloro-n4-(2,2,6,6-tetramethylpiperidin-4-yl)-4-pyrimidineamine 5-Cyano-2-chloro-N4-(2,2,6,6-tetramethylpiperidin-4-yl)-4-pyrimidineamine TFA salt (2.1 g) was partitioned between EtOAc (100 mL) and 0.2 M NaOH (50 mL). The organic layer was washed with brine (1×50 mL), dried (Na₂SO₄), filtered and the solvent removed under vacuum to leave the product (1.35 g, 68%) as a solid.

¹H NMR (DMSO-d₆, 300 MHz): δ 8.51 (s, 1H), 8.34 (br. S, 1H), 4.42 (t, 1H), 1.61 (br. d, 2H), 1.23 (t, 2H), 1.14 (s, 6H), 1.02 (s, 6H); m/z=294.1 (M+H)⁺ for ³⁵Cl.

Example 24

Synthesis of 5-cyano-2-chloro-N4-(1,2,2,6,6-pentamethylpiperidin-4-yl)-4-pyrimidineamine

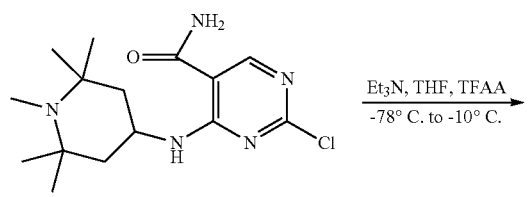

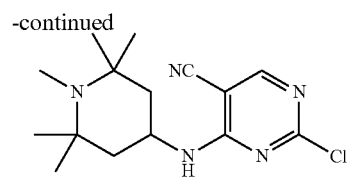

Trifluoroacetic anhydride (9.35 mL; 67.3 mmol, 10 eq) was added dropwise over 30-45 minutes to a stirred solution of 5-carboxyamide-2-chloro-N4-(1,2,2,6,6-pentamethylpiperidin-4-yl)-4-pyrimidineamine hydrochloride (2.19 g, 6.73 mmol, 1 eq) and Et₃N (11.26 mL; 80.76 mmol, 12 eq) in THF (45 mL) at −78° C. under nitrogen. After complete addition, the mixture was stirred at −78° C. for a further 60 minutes, then a saturated solution of NaHCO₃ (30 mL) was added dropwise keeping the internal temperature below −30° C. After complete addition of the NaHCO₃, EtOAc (100 mL) and H₂O (100 mL) was added and the mixture was stirred for 10 minutes. Further H₂O (100 mL) was added and the organic and aqueous layers were partitioned. The aqueous layer was extracted with EtOAc (4×100 mL) —until all precipitated material had gone in to solution. The combined organic extracts were washed with brine (1×50 mL), dried (Na₂SO₄), filtered and the solvent removed under vacuum to leave a crude solid with TFAA and Et₃N residues. The crude solid was dissolved in 100 mL of EtOAc and partitioned with 1 N aqueous NaOH (50 mL). The ethyl acetate layer was extracted with 2×50 mL aqueous 1N NaOH. The combined organic extracts were washed with brine (1×50 mL), dried (Na₂SO₄), filtered and the solvent removed under vacuum to give light yellow solid (1.80 g, 87%).

¹H NMR (DMSO-d₆, 300 MHz): δ 8.51 (s, 1H), 8.37 (d, 1H), 4.31 (bm, 1H), 2.15 (s, 3H), 1.47-1.66 (m, 4H), 1.06 (s, 6H), 1.00 (s, 6H); m/z=309 (M+H)⁺.

Example 25

Synthesis of 2-bromo-4-fluoro-5-nitroaniline

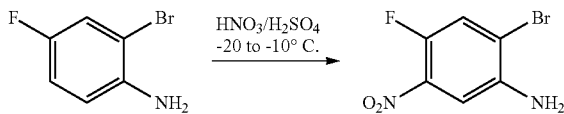 [SMILES: Nc1ccc(F)cc1Br ; Nc1cc([N+](=O)[O-])c(F)cc1Br]

2-Bromo-4-fluoroaniline (47.5 g, 250 mmol) was added to a solution of concentrated H₂SO₄ (300 mL) keeping the internal temperature below 30° C. The mixture was aged for ca. 30-60 minutes then cooled to −20° C. 90% HNO₃ (35 g) was added dropwise over ca. 60 minutes keeping the internal temperature between −15 to −20° C.. TLC indicated a slight amount of starting material, so a further aliquot of 90% HNO₃ (3 g) was added over 5 minutes at −15 to −20° C. The cold mixture was then poured on to ice H₂O (ca. 1 L ice+500 mL H₂O) and EtOAc (1 L). The aqueous and organic layers were partitioned and the organic layer was washed with saturated NaHCO₃ (2×500 mL), dried (Na₂SO₄), filtered and the solvent removed under vacuum to leave a dark solid (35 g, 60%).

¹H NMR (DMSO-d₆, 300 MHz): δ 8.27 (br. S, 2H), 7.70 (d 1H), 7.47 (d, 1H); m/z=275.9 (M+MeCN+H)⁺ for ⁷⁹Br.

Example 26

Synthesis of 1-(2-bromo-4-fluoro-5-nitrophenyl)-1H-tetrazol-5(4H)-one

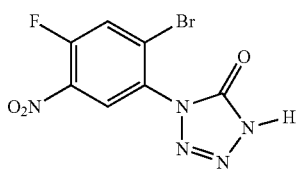 [SMILES: O=c1[nH]nnn1-c1cc([N+](=O)[O-])c(F)cc1Br]

2-Bromo-4-fluoro-5-nitrobenzenamine (2.4 g, 10.2 mmol) was added to phosgene (20% weight in toluene, 25 mL, excess) in a 100 mL single neck round bottom flask equipped with a water condenser. The mixture was heated to 80° C. and stirred for 2.5 hours under $N_2$. The mixture was cooled to room temperature and was concentrated under reduced pressure to give a dark residue. To this residue, azidotrimethylsilane (20 mL, excess) was added and the mixture was heated at 80° C. overnight under $N_2$. The mixture was cooled to room temperature, then concentrated under reduced pressure. Ethyl acetate was added to the residue and the product was extracted with saturated $NaHCO_3$ (×2—until substantially all product had gone in to the aqueous layer). The aqueous layers were combined and washed with a small amount of ethyl acetate, then the aqueous layer was acidified with 2N HCl. The emerging precipitate from the acidic aqueous layer was extracted with ethyl acetate, and the organic layer was washed with brine and dried ($Na_2SO_4$), filtered and concentrated under vacuum to give the title compound (1.35 g, 44%) as a light brown solid.

$^1$H NMR (300 MHz, DMSO) δ 8.66 (d, J=7.5 Hz, 1H), 8.37 (d, J=10.8 Hz, 1H); m/z=303.9 (M−H)$^+$.

Example 27

Synthesis of 1-(2-borom-4-fluoro-5-nitrophenyl)-4-methyl-1H-tetrazol-5(4H)-one

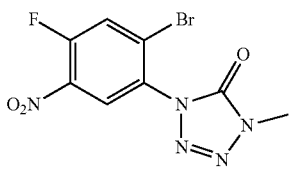 [SMILES: Cn1nnn(-c2cc([N+](=O)[O-])c(F)cc2Br)c1=O]

1-(2-Bromo-4-fluoro-5-nitrophenyl)-4-methyl-1H-tetrazol-5(4H)-one (1.4 g, 4.6 mmol) was added to anhydrous DMF (45 mL) in a single neck round bottom flask followed by $K_2CO_3$ (1.8 g, 13.8 mmol) and chilled to −40° C. in an acetone/dry ice bath. Iodomethane (0.35 mL, 6.9 mmol) was added, and the mixture was further chilled to −78° C. The mixture was stirred under $N_2$ and allowed to warm up to room temperature overnight. Ethyl acetate (300 mL) was added and the mixture was washed with brine (2×200 mL). The organic and aqueous layers were separated and the organic layer was dried ($Na_2SO_4$), filtered and concentrated under vacuum. Dichloromethane (300 mL) was added to the residue and the organic layer was washed with brine (×2) dried ($Na_2SO_4$), filtered and the solvent concentrated under vacuum. To the residue, EtOAc was added, and the mixture was sonicated and filtered. The mother liquor was concentrated under reduced pressure to give the title compound (1.4 g) as a yellowish brown solid.

$^1$H NMR (300 MHz, DMSO) δ 8.64 (d, J=7.2 Hz, 1H), 8.38 (d, J=10.8 Hz, 1H), 3.63 (s, 3H); m/z=317.95 (M+H)$^+$.

Example 28

Alternative Synthesis of 1-(2-bromo-4-fluoro-5-nitrophenyl)-1H-tetrazol-5(4H)-one

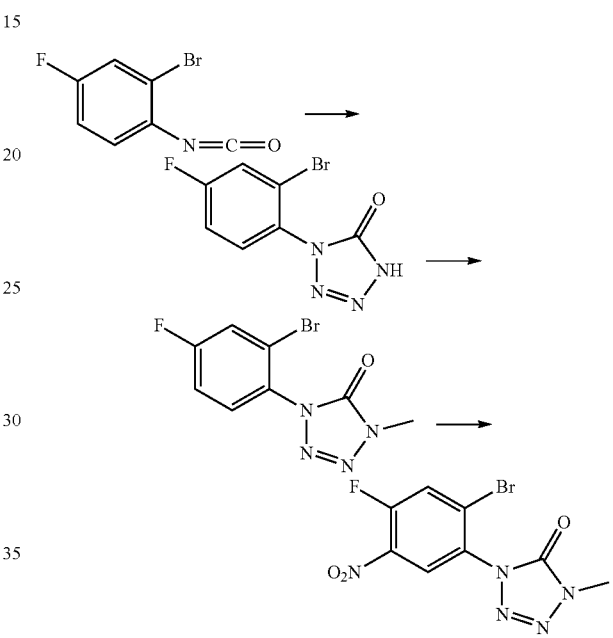

Step 1: Preparation of 1-(2-Bromo-4-fluorophenyl)-1H-tetrazol-5(4H)-one

A mixture of 2-bromo-4-fluoro-1-isocyanatobenzene (20 g, 92.6 mmol; UkrOrgSynthesis, Kiev, Ukraine) and trimethylsilyazide (50 mL) was heated to reflux under $N_2$ and stirred overnight. After allowing to cool to room temperature the mixture was concentrated under vacuum and the residue partitioned between EtOAc (300 mL) and saturated $NaHCO_3$ (300 mL). The organic layer was then extracted with saturated $NaHCO_3$ (200 mL portions) until TLC indicated all the product had been removed from the organic layer (ca. 5 extractions). EtOAc (500 mL) was added to the combined aqueous layers and the mixture was acidified using 6N HCl (to pH<3). The aqueous and organic layers were partitioned and the organic layer was washed with brine (300 mL), dried ($Na_2SO_4$), filtered and the solvent removed under vacuum to leave the product (20.1 g, 84%) as a solid.

$^1$H NMR (DMSO-$d_6$, 300 MHz): δ 7.91 (dt, 1H), 7.79-7.74 (m, 1H), 7.52-7.45 (m, 1H); $^{19}$F NMR (DMSO-$d_6$, 282 MHz): 108.0 (dd); m/z=258.9 (M+H)$^+$ for $^{79}$Br.

Step 2: 1-(2-bromo-4-fluorophenyl)-4-methyl-1H-tetrazol-5(4H)-one

K$_2$CO$_3$ (26.8 g, 194 mmol) and MeI (9.7 mL, 155 mmol) were added at −78° C. to a solution of 1-(2-bromo-4-fluorophenyl)-1H-tetrazol-5(4H)-one (20.1 g, 77.6 mmol) in DMF (150 mL) under N$_2$. The mixture was stirred from −78° C. to room temperature over 2 days. The mixture was poured

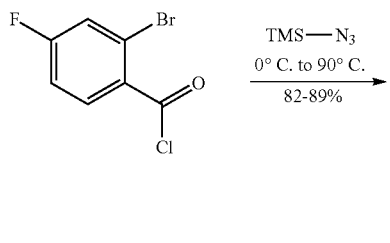

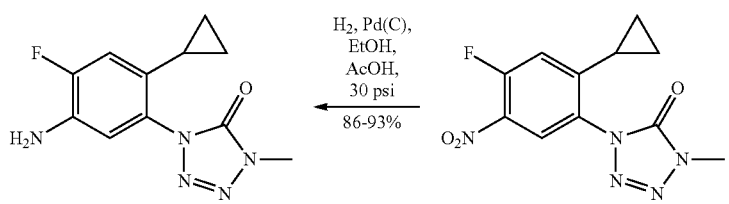

in to EtOAc (300 mL) and H$_2$O (500 mL) and the aqueous and organic layers were partitioned. The organic layer was washed with H$_2$O (3×500 mL) then brine (300 mL), dried (Na$_2$SO$_4$), filtered and the solvent removed under vacuum to leave the product (20.3 g, 96%) as a solid. This methylation reaction can be conducted at room temperature with similar results.

$^1$H NMR (DMSO-d$_6$, 300 MHz): δ 7.93 (dd, 1H), 7.77 (dd, 1H), 7.51 (dt, 1H); $^{19}$F NMR (DMSO-d$_6$, 282 MHz): 107.7 (dd); m/z=274.9 (M+H)$^+$ for 81Br.

Step 3: 1-(2-bromo-4-fluoro-5-nitrophenyl)-4-methyl-1H-tetrazol-5(4H)-one

HNO$_3$ (25 g) was added dropwise over ca. 30 minutes to a solution of 1-(2-bromo-4-fluorophenyl)-4-methyl-1H-tetrazol-5(4H)-one (23 g, 84.2 mmol) in H$_2$SO$_4$ (250 mL) at 0 to −10° C. After complete addition of the HNO$_3$, TLC indicated some unreacted starting material so a further aliquot of HNO$_3$ (5 g) was added dropwise over ca. 10 minutes TLC indicated complete reaction so the mixture was poured in to a mixture of ice/H$_2$O (750 g ice:500 mL H$_2$O) and EtOAc (500 mL). The aqueous ad organic layers were partitioned and the aqueous layer was washed with saturated NaHCO$_3$ (300 mL; with care: acid residues present). The organic layer was dried (Na$_2$SO$_4$), filtered and the solvent removed under vacuum to leave a crude residue. The crude residue was triturated with EtOAc and filtered. The filtrate was concentrated under vacuum and the trituration procedure repeated. The solid collected in the triturations above were combined to give the title compound (20.1 g, 75%) as a solid [note: the filtrate still contains some desired product which can be purified by column chromatography on silica gel if need be]. Data for this product identical to 1-(2-Bromo-4-fluoro-5-nitrophenyl)-4-methyl-1H-tetrazol-5(4H)-one produced above.

Example 29

Synthesis of 1-(5-amino-2-cyclopropyl-4-fluorophenyl)-4-methyl-1H-tetrazol-5(4H)-one

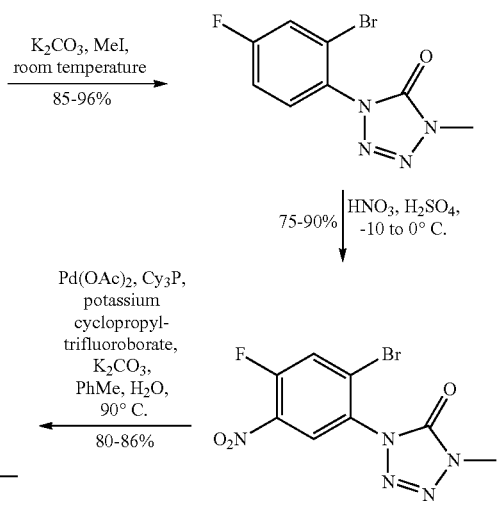

Step 1: Preparation of 1-(2-bromo-4-fluorophenyl)-1H-tetrazol-5-(4H)-one

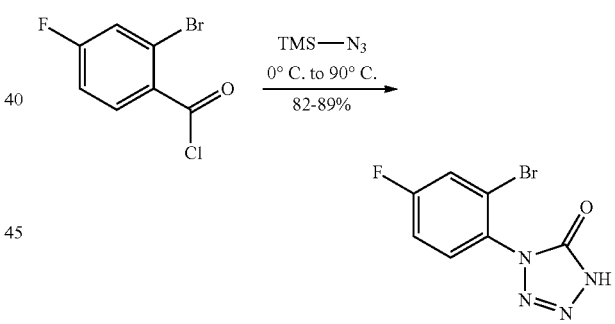

Trimethylsilyl azide (65 mL, 494 mmol; ca. 6 equiv.) was added to a stirred mixture of 2-bromo-4-fluorobenzoyl chloride (20.4 g, 86 mmol; Apollo Scientific Ltd) under N$_2$ at 0 to 10° C. The mixture was then heated slowly to 50-70° C. (gas evolution starts at approximately 50-60° C. and becomes vigorous after ca. 65° C.). The mixture was briefly removed from the heat until nitrogen evolution was more controlled, then the mixture returned to the heat. The mixture was then heated to 90° C. under nitrogen overnight.

A safety notice for the procedure: The reaction was performed behind a blast shield in a 250 mL round-bottom flask. A nitrogen balloon and vent (needle vent) was used in the set-up, especially the first part of the reaction in which nitrogen gas is evolved.

After allowing to cool to room temperature, the mixture was concentrated under vacuum and the residue partitioned between EtOAc (200 mL) and saturated NaHCO$_3$ (100 mL).

The organic layer was then extracted with saturated NaHCO₃ (150 mL portions) until TLC indicated the desired product had been removed from the organic layer (ca. 5 extractions). EtOAc (300 mL) was added to the combined aqueous layers and the mixture was acidified using 6N HCl (to pH<3). The aqueous and organic layers were partitioned and the aqueous layer was extracted with EtOAc (1×150 mL). The combined organic extracts were dried (MgSO₄), filtered and the solvent removed under vacuum to leave the product (19.9 g, 89%) as a solid.

¹H NMR (DMSO-d₆, 300 MHz): δ 7.91 (dt, 1H), 7.79-7.74 (m, 1H), 7.52-7.45 (m, 1H) 19F NMR (DMSO-d₆, 282 MHz): −107.6 (dd). m/z=301.95 (M⁺MeCN+H)⁺ for 81Br.

The other steps in the scheme of Example 29 are disclosed the examples herein.

Example 30

Synthesis of 1-(2-cyclopropyl-4-fluoro-5-nitrophenyl)-4-methyl-1H-tetrazol-4(4H)-one

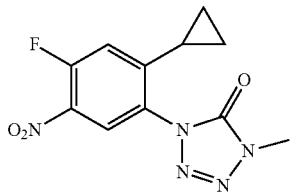

1-(2-Bromo-4-fluoro-5-nitrophenyl)-4-methyl-1H-tetrazol-5(4H)-one (350 mg, 1.1 mmol) was added to toluene/water (4.6 mL:0.9 mL), in a 60 ml round bottom flask fitted with a water condenser. To this solution was added tricyclohexylphosphine (92 mg, 0.3 mmol), Cs₂CO₃ (2.14 g, 6.6 mmol) and cyclopropylboronic acid MIDA ester (303 mg, 1.5 mmol). This mixture was degassed by bubbling N₂ into the solution for 15 minutes. Pd(OAc)₂ (37 mg, 0.2 mmol) was added, and the mixture was heated to 100° C. under N₂ and stirred overnight. After allowing to cool to room temperature, EtOAc and saturated K₂CO₃ were added, and the organic and aqueous layers were partitioned. The organic layer was dried (Na₂SO₄), filtered and the solvent was concentrated under vacuum to leave a crude residue. The residue was purified by column chromatography on silica gel using EtOAc/hexanes (1:3 to 1:2.5) as an eluent to give the title compound as a yellow solid (200 mg).

¹H NMR (300 MHz, DMSO) δ 8.37 (d, J=7.5 Hz, 1H), 7.32 (d, J=12.6 Hz, 1H), 3.61 (s, 3H), 1.87 (m, 1H), 1.08-1.04 (m, 2H), 0.97-0.93 (m, 2H); m/z=279.95 (M+H)⁺.

Alternative Suzuki Conditions for Synthesis of 1-(2-Cyclopropyl-4-Fluoro-5-Nitrophenyl)-4-Methyl-1H-Tetrazol-5(4H)-One Toluene (140 mL) then H₂O (50 mL) was added to a mixture of 1-(2-bromo-4-fluoro-5-nitrophenyl)-4-methyl-1H-tetrazol-5(4H)-one (14.5 g, 45.6 mmol), potassium cyclopropyltrifluoroborate (7.42 g, 50.1 mmol), palladium (II) acetate (205 mg, 0.91 mmol), tricyclohexylphosphine (511 mg, 1.82 mmol) and K₂CO₃ (12.6 g, 91.1 mmol) under N₂. The mixture was sparged with N₂ for 10 mins then heated to 90° C. and stirred overnight. TLC did not indicate complete reaction, so more palladium(II) acetate (103 mg, 0.45 mmol), tricyclohexylphosphine (255 mg, 0.91 mmol) and potassium cyclopropyltrifluoroborate (3.7 g, 25.5 mmol) were added. The mixture was sparged with N₂ once again and heated to 90° C. under N₂ overnight. TLC only indicated a little further reaction, so after allowing to cool to room temperature, the mixture was filtered through a small plug of celite and the filter cake washed with EtOAc (5×50 mL). The filtrate was partitioned and the organic layer was dried (MgSO₄), filtered and the solvent removed under vacuum to leave a solid residue. To the solid residue was added potassium cyclopropyltrifluoroborate (3.7 g, 25.5 mmol), palladium(II) acetate (103 mg, 0.45 mmol), tricyclohexylphosphine (255 mg, 0.91 mmol) and K₂CO₃ (6.3 g, 91.1 mmol). The mixture was placed under N₂ and toluene (140 mL) and H₂O (50 mL) were added. The mixture was sparged with N₂ for 10 min then the mixture heated to 90° C. under N₂ overnight. TLC indicated complete reaction. After allowing to cool to room temperature, the mixture was partitioned and the organic layer dried (MgSO₄), filtered and the solvent removed under vacuum. The mixture was purified by filtration through a 4-to-5 inch plug of silica (the residue was dry-loaded on to silica) eluting with EtOAc/hexane (3:7 to 4:6; fractions collected in conical flasks) to give the product (11.0 g, 86%) as a solid.

Example 31

Alternative Synthesis of 1-(2-cyclopropyl-4-fluoro-5-nitrophenyl)-4-methyl-1H-tetrazol-5(4h)-one

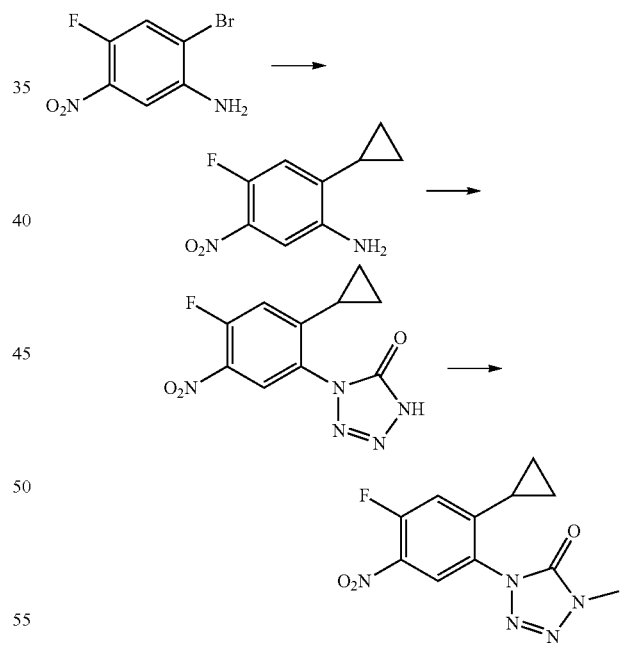

Step 1: 2-cyclopropyl-4-fluoro-5-nitroaniline

A mixture of 2-bromo-4-fluoro-5-nitroaniline (12 g, 51 mmol), cyclopropylboronic acid MIDA ester (Aldrich; 20.1 g, 102 mmol), Pd(OAc)₂ (1.72 g, 7.7 mmol), Cy₃P (4.3 g, 15.3 mmol) and Cs₂CO₃ (98.8 g, 306 mmol) in toluene (120 mL) and H₂O (40 mL) was de-gassed with N₂ for 15 minutes. The mixture was then heated at 100° C. (oil bath temperature) overnight (the reaction mixture can also be heated to reflux). After allowing to cool to room temperature, the mixture was diluted with EtOAc (200 mL) and H$_2$O (100 mL) and the mixture filtered through Celite. The filter cake was washed with EtOAc (2×100 mL) and the filtrate partitioned. The organic layer was dried (Na$_2$SO$_4$), filtered and the solvent removed under vacuum to leave a crude residue. The residue was purified by column chromatography on silica gel (residue dry-loaded on to silica gel) using EtOAc/hexanes (1:4 to 3:7) as eluent to give the product (8.1 g, 81%) as a dark solid.

$^1$H NMR (DMSO-d$_6$, 300 MHz): δ 7.27 (d 1H), 6.84 (d, 1H), 5.52 (br. s, 2H), 1.74-1.83 (m, 1H), 0.92-0.98 (m, 2H), 0.62-0.73 (m, 2H); m/z=238.0 (M$^+$MeCN+H)$^+$.

Alternative Step 1:
2-cyclopropyl-4-fluoro-5-nitroaniline Using Potassium Cyclopropyltrifluoroborate A mixture of 2-bromo-4-fluoro-5-nitroaniline (13.1 g, 56 mmol), potassium cyclopropyltrifluoroborate (16.5 g, 112 mmol), Pd(OAc)$_2$ (1.89 g, 8.4 mmol), Cy$_3$P (4.7 g, 16.8 mmol) and Cs$_2$CO$_3$ (109.5 g, 336 mmol) in toluene (150 mL) and H$_2$O (60 mL) was de-gassed with N$_2$ for 15 minutes. The mixture was then heated at reflux overnight (120° C. oil bath temperature). After allowing to cool to room temperature, the mixture was diluted with EtOAc (200 mL) and H$_2$O (200 mL) and the mixture filtered through Celite. The filter cake was washed with EtOAc (3×100 mL) and the filtrate transferred to a separating funnel. Brine (200 mL) was added and the aqueous and organic layers partitioned. The organic layer was dried (Na$_2$SO$_4$), filtered and the solvent removed under vacuum to leave a crude residue. The residue was purified by column chromatography on silica gel (residue dry-loaded on to silica gel) using EtOAc/hexanes (1:9 to 1:4) as eluent to give the product (8.3 g, 76%) as a dark solid. Data same as above.

Step 2: 1-(2-cyclopropyl-4-fluoro-5-nitrophenyl)-1h-tetrazol-5(4h)-one

2-Cyclopropyl-4-fluoro-5-nitroaniline (10.2 g, 52 mmol) was added over 5 minutes to a stirred solution of phosgene in toluene (20% wt./vol; 100 mL) at ca. −10° C. under N$_2$. Residual aniline from the flask was washed in to the mixture by rinsing with toluene (10 mL). The mixture was stirred at −10° C. for 10 minutes then heated to 80° C. and stirred for 3 hours. After allowing to cool to room temperature, the mixture was concentrated under vacuum to leave a crude residue. The residue was suspended in EtOAc (150 mL) and then concentrated under vacuum. The residue was placed under N$_2$ and trimethylsilylazide (50 g) was added. A reflux condenser was added to the apparatus and the mixture was heated to 80° C. under N$_2$ with stirring overnight (note: the mixture does not reflux, but condenser used to minimize any loss of trimethylsilylazide). After allowing to cool to room temperature, the mixture was concentrated under vacuum and the residue partitioned between EtOAc (200 mL) and H$_2$O (60 mL). The organic layer was washed with H$_2$O (60 mL) and then extracted with saturated NaHCO$_3$ (7×100 mL—until TLC indicated all product had been removed from the EtOAc layer). EtOAc (500 mL) was added to the combined aqueous extracts, and the pH was adjusted to <3 using 2N HCl. The aqueous and organic layers were partitioned and the aqueous layer was extracted with EtOAc (2×200 mL). The combined organic layers were dried (Na$_2$SO$_4$), filtered and the solvent removed under vacuum to leave the product (10.3 g, 75%) as a solid.

$^1$H NMR (300 MHz, DMSO) δ 8.38 (d, 1H), 7.3 (d, 1H), 1.82-1.78 (m, 1H), 1.09-1.04 (m, 2H), 0.92-0.91 (m, 2H); 19F NMR (DMSO-d$_6$, 282 MHz): 115.7 (dd).

Step 3: 1-(2-cyclopropyl-4-fluoro-5-nitrophenyl)-4-methyl-1h-tetrazol-5(4h)-one

K$_2$CO$_3$ (13.4 g, 97.1 mmol) and MeI (4.8 mL, 77.7 mmol) were added sequentially to a stirred solution of 1-(2-cyclopropyl-4-fluoro-5-nitrophenyl)-1H-tetrazol-5(4H)-one (10.3 g, 38.8 mmol) in DMF (100 mL) at −78° C. under N$_2$. The mixture was allowed to warm to room temperature over 3 hours. TLC indicated complete reaction, so poured mixture into H$_2$O (1 L) and EtOAc (500 mL). The aqueous and organic layers were partitioned and the organic layer was washed with H$_2$O (2×300 mL), brine (300 mL), then dried (Na$_2$SO$_4$), filtered and the solvent removed under vacuum to leave the product (10.2 g, 94%) as a solid. Data identical to preparation of 1-(2-cyclopropyl-4-fluoro-5-nitrophenyl)-4-methyl-1H-tetrazol-5 (4H)-one described above.

Example 32

Synthesis of 1-(5-amino-2-chclopropyl-4-fluorophenyl)-4-methyl-1H-tetrazol-5(4H)-one

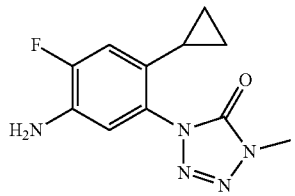

1-(2-Cyclopropyl-4-fluoro-5-nitrophenyl)-4-methyl-1H-tetrazol-5(4H)-one (170 mg, 0.6 mmol) was added to a Radley's Carousel reactor tube, ethanol (18 ml) was added to the solid, followed by SnCl$_2$.2H$_2$O (460 mg, 2.4 mmol) and concentrated HCl (0.6 ml). The mixture was heated at 80° C., reaction followed by thin layer chromatography. Once the reaction was determined to be completed, the reaction mixture was allowed to cool down to room temperature and concentrated under reduced pressure. Ethyl acetate was added to the residue, the solution was washed with saturated K$_2$CO$_3$. The layers were separated, and the organic layer was washed with brine, dried with Na$_2$SO$_4$, and the solid was filtered off. The mother liquor was then concentrated under reduced pressure, and the title compound was obtained as light brown oil (125 mg).

$^1$H NMR (300 MHz, DMSO) δ 6.79 (d, J=12.3 Hz, 1H), 6.72 (d, J=8.4 Hz, 1H), 5.36 (s, 2H), 3.59 (s, 3H), 1.56 (m, 1H), 0.68 (d, J=8.7 Hz, 2H), 0.46 (d, J=5.1 Hz, 2H); m/z=250.09 (M+H)+.

Example 33

Alternative Synthesis of 1-(5-amino-2-cyclopropyl-4-fluorophenyl)-4-methyl-1H-tetrazol-5(4H)-one

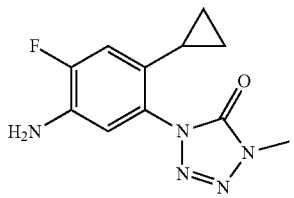 [SMILES: Cn1nnn(-c2cc([N+](=O)[O-])c(F)cc2C2CC2)c1=O]

Palladium on carbon (2.0 g, 20% by wt.) was added to a suspension of 1-(2-cyclopropyl-4-fluoro-5-nitrophenyl)-4-methyl-1H-tetrazol-5(4H)-one (10.2 g, 36.5 mmol) in EtOH (150 mL) and AcOH (5.1 mL) under $N_2$ in a 1 L Parr hydrogenation flask. The mixture was evacuated then filled with $H_2$ on a Parr hydrogenation apparatus. The mixture was hydrogenated at 25-30 psi for ca. 5 hours until LC/MS indicated completion of the reaction (note: the hydrogen pressure decreases rapidly in the first 15 minutes and is replenished to 25-30 psi). After completion of the reaction the mixture is filtered through a small layer of Celite and the filter cake is washed with EtOH (4×50 mL). The filtrate was concentrated under vacuum to leave a crude solid that was dissolved in EtOAc (250 mL) and washed with saturated $NaHCO_3$ (150 mL), then dried ($Na_2SO_4$), filtered and the solvent removed under vacuum to leave a crude solid. The solid was purified by column chromatography on silica gel (dry-loaded solid on silica gel) using EtOAc/hexanes (3:7 to 6:4) as an eluent to give the product (8.6 g, 86%) as a solid. Data identical to preparation of 1-(5-amino-2-cyclopropyl-4-fluorophenyl)-4-methyl-1H-tetrazol-5(4H)-one described above. Also collected from the column were some less pure fractions (0.3 g) that were kept separate from the 8.6 g lot of product. The less pure fractions contained ca. 93% of the title compound and ca. 4% of 1-(5-amino-2-isopropyl-4-fluorophenyl)-4-methyl-1H-tetrazol-5(4H)-one, together with ca. 3% of other impurities by LC/MS analysis.

Example 34

Synthesis of N2-{4-chloropropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidineamine (I-14)

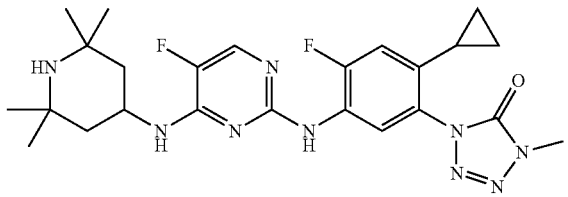

2-Chloro-5-fluoro-N-(2,2,6,6-tetramethylpiperidin-4-yl)pyrimidin-4-amine hydrochloride (72 mg, 0.3 mmol) and 1-(5-amino-2-cyclopropyl-4-fluorophenyl)-4-methyl-H-tetrazol-5(4H)-one (62.5 mg, 0.3 mmol) were added to a Radley's Carousel reactor tube. Isopropyl alcohol (2 mL) was added, followed by para-toluenesulfonic acid monohydrate (48 mg, 0.3 mmol). The mixture was heated at 100° C. under $N_2$ overnight and the progress of the reaction was followed by LCMS. Upon completion of the reaction, the mixture was cooled, then neutralized by adding 2N $NH_3$ in MeOH. The mixture was concentrated under vacuum and the residue was purified by column chromatography on silica gel using EtOAc:2N $NH_3$ in MeOH (100:0 to 90:10) as an eluent to give the title compound as an off-white solid.

$^1$H NMR (300 MHz, DMSO) δ 8.47 (s, 1H), 7.82-7.76 (m, 2H), 7.17 (d, J=8.1 Hz, 1H), 6.95 (d, J=12.0 Hz, 1H), 4.22 (bs, 1H), 3.59 (s, 3H), 1.64-1.55 (m, 3H), 1.07 (t, J=12.0 Hz, 2H), 0.97 (s, 12H), 1.56 (m, 1H), 0.79 (d, J=8.1 Hz, 2H), 0.58 (d, J=5.1 Hz, 2H); m/z=500.20 (M+H)$^+$.

Example 35

Synthesis of 5-cyano-N2-{4-cyclopropyl-6-fluoro[3-(4-methyl)-1,2,3,4-tetrazol-5-one-1-yl]}phenyl-N4-(2,2,6,6-tetramethylpiperidin-4-yl)-2,4-pyrimidineamine

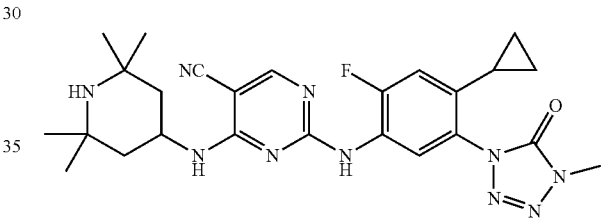

5-Carboxyamide-2-chloro-N-(2,2,6,6-tetramethylpiperidin-4-yl)pyrimidin-4-amine hydrochloride (78 mg, 0.3 mmol) and 1-(5-amino-2-cyclopropyl-4-fluorophenyl)-4-methyl-H-tetrazol-5(4H)-one (62.5 mg, 0.3 mmol) were added to a Radley's Carousel reactor tube. Isopropyl alcohol (1.25 mL) was added, followed by para-toluenesulfonic acid monohydrate (48 mg, 0.3 mmol). The mixture was heated at 100° C. under $N_2$ overnight and the progress of the reaction was followed by LCMS. Upon completion of the reaction, the mixture was cooled, then neutralized by adding 2N $NH_3$ in MeOH. The mixture was concentrated under vacuum to leave a crude residue. Anhydrous THF (2 mL) was added to the residue, and the mixture cooled to 0° C. in an ice/water bath. $Et_3N$ (0.07 mL, 0.6 mmol) was added, followed by the addition of TFAA (0.05 mL, 0.45 mmol) dropwise. The progress of the reaction was followed by LCMS, additional $Et_3N$ (2×0.07 mL) and TFAA (2×0.05 mL) being added to push the reaction to completion. The mixture was concentrated under vacuum and the residue was purified by column chromatography on silica gel using EtOAc:2N $NH_3$ in MeOH (100:0 to 90:10) as an eluent to give the title compound as an off-white solid.

$^1$H NMR (300 MHz, DMSO) δ 9.56 (bs, 1H), 8.52 (bs, 1H), 8.33 (s, 1H), 7.74 (m, 2H), 7.48 (s, 1H), 7.03 (d, J=11.4 Hz, 1H), 4.27 (bs, 1H), 3.59 (s, 3H), 1.73-1.69 (m, 3H), 1.52 (m, 2H), 1.27 (bs, 6H), 1.08 (bs, 6H), 0.86 (d, J=8.1 Hz, 2H), 0.64 (bs, 2H); m/z=506.58 (M+H)+.

Example 36

Synthesis of N2-{4-cyclopropyl-6-fluoro-[3-(4-methyl)-1,2,3,4-tetrazol-5-one-1-yl]}phenyl-5-fluoro-N4-(1,2,2,6,6-pentamethylpiperidin-4-yl)-2,4-pyrimidineamine (I-16)

Synthesis of N2-{4-cyclopropyl-6-fluoro-[3-(4-methyl)-1,2,3,4-tetrazol-5-one-1-yl]}phenyl-5-fluoro-N4-(1,23,2,6,k6-pentamethylpiperidin-4-yl)-2,3-pyrimidineamine (I-16)

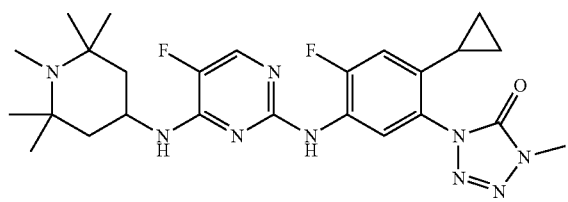

A mixture of 1-(5-amino-2-cyclopropyl-4-fluorophenyl)-4-methyl-1H-tetrazol-5(4H)-one (200 mg, 0.8 mmol), 2-chloro-5-fluoro-N4-(1,2,2,6,6-pentamethylpiperidin-4-yl)-4-pyrimidineamine, HCl salt (246 mg, 0.73 mmol) and para-toluenesulfonic acid monohydrate (139 mg, 0.73 mmol) in isopropanol (2 mL) was heated at 110° C. in a sealed vial and stirred for 2 days. After 2 days, the mixture was cooled and 3-amino benzoic acid (excess) was added. The mixture was re-heated to 110° C. and stirred for 1 day (to ensure reaction of all 2-chloro-5-fluoro-N4-(1,2,2,6,6-pentamethylpiperidin-4-yl)-4-pyrimidineamine). After allowing to cool the solvent was concentrated under vacuum to leave a crude residue. The residue was partitioned between EtOAc (50 L) and 1N NaOH (50 mL). The organic layer was washed with 1N NaOH (20 mL) and brine (20 mL), then dried (Na$_2$SO$_4$), filtered and the solvent removed under vacuum to leave a crude solid. The solid was triturated with Et$_2$O and filtered. The filter cake was re-triturated with Et$_2$O and filtered to give the title compound (30 mg) as a solid [note: the filtrates from the triturations were also kept and contain desired product].

$^1$H NMR (300 MHz, d$_6$-DMSO) δ 8.53 (s, 1H), 7.84 (d, 1H), 7.80 (d, 1H), 7.24 (d, 1H), 7.00 (d, 1H), 4.21-4.07 (m, 1H), 3.62 (s, 3H), 2.14 (s, 3H), 1.66-1.58 (m, 3H), 1.38 (t, 2H), 1.03 (s, 6H), 0.84 (br. s, 8H), 0.62-0.60 (m, 2H); m/z=514.45 (M+H)+.

Example 37

Synthesis of 5-cyano-N2-{4-cyclopropyl-6-fluoro-[3-(4-methyl)-1,2,3,4-tetrazol-5-one-1-yl]}phenyl-N4-(1,2,2,6,6-pentamethylpiperidin-4-yl)-2,4-pyrimidinediamine (I-17)

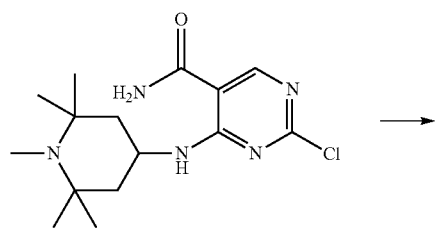

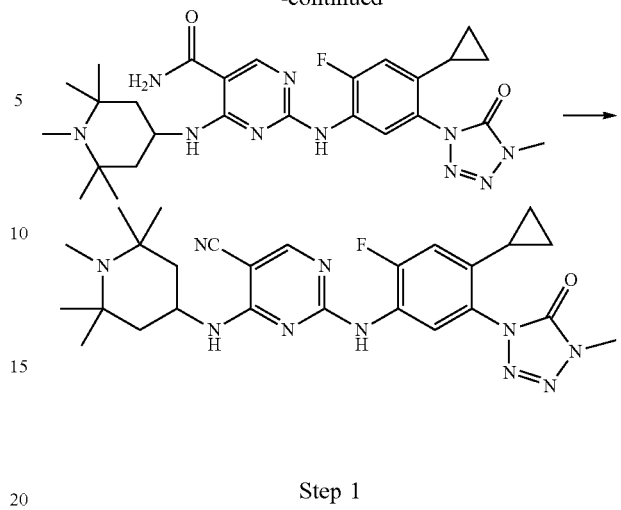

Step 1

A mixture of 5-carboxamide-2-chloro-N4-(1,2,2,6,6,-pentamethylpiperidin-4-yl)-4-pyrimidineamine, HCl salt (326 mg, 1.0 mmol), 1-(5-amino-2-cyclopropyl-4-fluorophenyl)-4-methyl-1H-tetrazol-5(4H)-one (250 mg, 1.0 mmol) and para-toluenesulfonic acid monohydrate (190 mg, 1.0 mmol) in isopropanol (5 mL) was heated in a sealed vial at 100° C. overnight. After allowing to cool to room temperature the mixture was concentrated under vacuum. The residue was partitioned between 1N NaOH (50 mL) and EtOAc (50 mL) and the organic layer was washed with 1N NaOH (25 mL), brine (25 mL), then dried (Na$_2$SO$_4$), filtered and the solvent removed under vacuum to leave a crude solid. The solid was triturated with Et$_2$O and filtered to give the product (285 mg, 53%) that was used directly in the next step.

Step 2

TFAA (1.4 mL, 5.0 mmol) was added over 10 minutes to a stirred suspension of the amide product from step 1 above (270 mg, 0.5 mmol) and Et$_3$N (1.67 mL, 6.0 mmol) in THF (5 mL) at −50° C. under N$_2$. The mixture was stirred at −50° C. for 20 minutes then allowed to warm to 0° C. over 1 hour and stirred for another 2 hours at 0° C. (LC/MS indicated complete reaction). The mixture was quenched by pouring in to saturated NaHCO$_3$ (50 mL) and EtOAc (100 mL). The aqueous and organic layers were partitioned and the organic layer was washed with brine (50 mL), dried (Na$_2$SO$_4$), filtered and the solvent removed under vacuum to leave a crude solid. The solid was triturated with Et$_2$O and filtered and the filter cake was then recrystallized from EtOAc/MeOH. $^1$H NMR indicated the recrystallized product to be a trifluoroacetate salt, so partitioned recrystallized solid between 0.5N NaOH (30 mL) and EtOAc (50 mL). The organic layer was washed with brine (30 mL), dried (Na$_2$SO$_4$), filtered and the solvent removed under vacuum to leave a solid (65 mg, 25%) as a solid [note: much product in Et$_2$O filtrate and EtOAc/MeOH filtrate].

$^1$H NMR (300 MHz, d$_6$-DMSO) δ 9.44 (s, 1H), 8.28 (s, 1H), 7.49 (d, 1H), 7.39 (d, 1H), 6.99 (d, 1H), 4.16 (m, 1H), 3.59 (s, 3H), 2.08 (s, 3H), 1.69 (m, 1H), 1.43-1.33 (m, 4H), 0.98 (s, 6H), 0.88-0.83 (m, 2H), 0.73 (s, 6H), 0.62-0.60 (m, 2H); m/z=521.37 (M+H)$^+$.

Example 38

Step 1: Preparation of 1-(2-(1,1,1-trifluoro-2-methylpropan-2-yloxy)-5-nitrophenyl)-4-methyl-1H-tetrazol-5(4H)-one

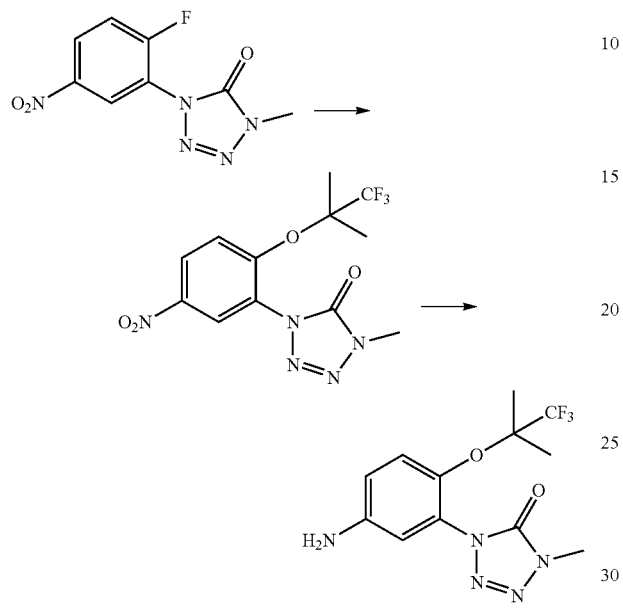

KH (35% wt. in mineral oil; 126 mg, 1.1 mmol of KH) was washed with hexanes and the solvent removed with a pipette. The solid KH remaining (about 44 mg, 1.1 mmol) was cooled to 0° C. under an atmosphere of nitrogen and THF (2 mL) was added. A solution of 2-trifluoromethyl-2-propanol (116 mg, 1.0 mmol) in THF (1 mL) was slowly added (after complete addition, the vial containing 2-trifluoromethyl-2-propanol was rinsed with an additional 0.5 mL of THF). The mixture was stirred at 0° C. for 20 minutes then 1-(2-fluoro-5-nitrophenyl)-4-methyl-1H-tetrazol-5 (4H)-one (120 mg, 0.5 mmol) was added in one portion. The mixture was stirred at 0° C. for 5 minutes then allowed to warm to room temperature and stirred for 2 hours. The solvent was removed under vacuum and the residue was partitioned between $CH_2Cl_2$ (30 mL) and $H_2O$ (20 mL). The aqueous layer was extracted with $CH_2Cl_2$ (10 mL) and the combined organic extracts were dried ($Na_2SO_4$), filtered and the solvent removed under vacuum to leave a residue (150 mg) that crystallized on standing.

$^1$H NMR (300 MHz; $d_6$-DMSO) δ 8.60 (m, 1H), 8.40 (m, 1H), 7.75 (d, 1H), 3.60 (s, 3H), 1.5 (s, 6H); 19F NMR (282 MHz; $d_6$-DMSO) δ −83.0; m/z=348.2 $(M+H)^+$.

Step 2: Preparation of 1-(2-(1,1,1,-trifluoro-2-methylpropan-2-yloxy)-5-aminophenyl)-4-methyl-1h-tetrazol-5(4h)-one Pd(C), 10% w/w Pd, wet Degussa grade E101 (30 mg) was added to a stirred mixture of 1-(2-(1,1,1,-trifluoro-2-methylpropan-2-yloxy)-5-nitrophenyl)-4-methyl-1H-tetrazol-5(4H)-one (150 mg) in MeOH (10 mL) under nitrogen. The mixture was evacuated and placed under an atmosphere of hydrogen (balloon of $H_2$ used). The evacuation and hydrogen-fill procedure was repeated twice, then the mixture was placed under an atmosphere of $H_2$ and stirred for 1 hour. After completion of the reaction, the mixture was filtered through Celite and the filter cake was washed with MeOH (3×10 mL). The solvent was removed under vacuum to leave a crude residue (112 mg, 70% over 2 steps) that crystallized on standing. r/z=318.2 $(M+H)^+$.

Example 39

Preparation of 1-(2-(1,1,1-trifluoro-2-methylpropan-2-yloxy)-5-(4-(1,2,2,6,6-pentamethylpiperidin-4-ylamino)-5-fluoropyrimidin-2-ylamino)phenyl)-4-methyl-1H-tetrazol-5(4H)-one (I-18)

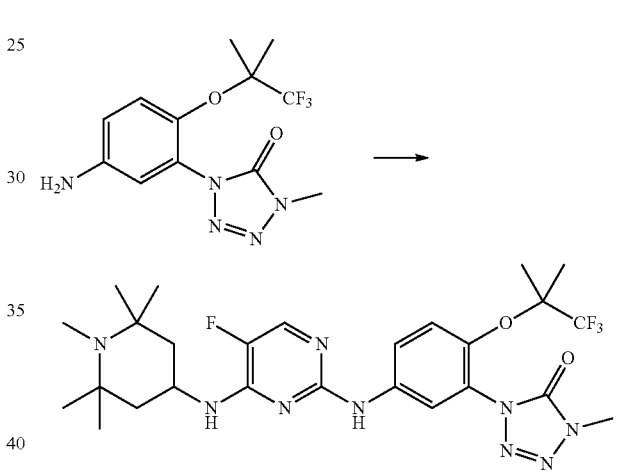

A mixture of 2-chloro-5-fluoro-N4-(1,2,2,6,6-pentamethylpiperidin-4-yl)-4-pyrimidineamine (56 mg, 0.19 mmol), 1-(2-(1,1,1,-trifluoro-2-methylpropan-2-yloxy)-5-aminophenyl)-4-methyl-1H-tetrazol-5(4H)-one (56 mg, 0.18 mmol) and para-toluenesulfonic acid monohydrate (17 mg, 0.09 mmol) in isopropanol (2 mL) was heated to reflux and stirred overnight. After allowing to cool to room temperature, the mixture was dry-loaded on to silica gel and then purified by column chromatography on silica gel using $CH_2Cl_2/2N$ $NH_3$ in MeOH (1:0 too 95:5) to give a solid. The solid was triturated with $Et_2O$ and filtered—the filter cake comprised the desired product and p-TsOH. The filter cake was suspended in $CH_2Cl_2$ and washed with 0.5 N NaOH. The organic layer was dried ($Na_2SO_4$), filtered and the solvent removed under vacuum to leave the product as a solid.

$^1$H NMR (300 MHz; $d_6$-DMSO) δ 9.44 (s, 1H), 7.87-7.78 (m, 3H), 7.24-7.19 (m, 2H), 4.28-4.25 (m, 1H), 3.58 (s, 3H), 2.14 (s, 3H), 1.66-1.63 (m, 2H), 1.43 (app. t, 2H), 1.25 (s, 6H), 1.04 (s, 6H), 0.91 (s, 6H); m/z=580.3 $(M-H)^+$.

Example 40

Preparation of 1-(2-(1,1,1-trifluoro-2-methylpropan-2-yloxy)-5-(4-(2,2,6,6-tetramethylpiperidin-4-ylamino)-5-fluoropyrimidin-2-ylamino)phenyl)-4-methyl-1H-tetrazol-5(4H)-one (I-19)

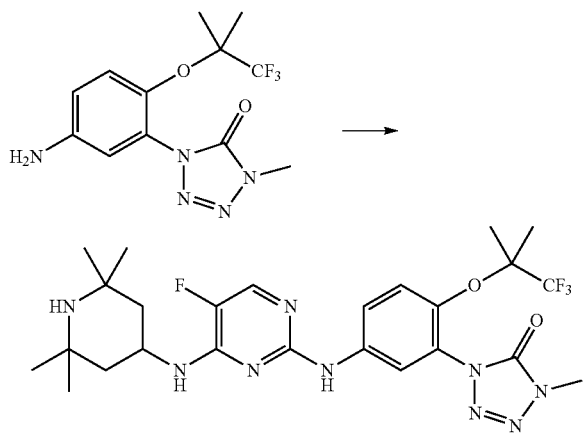

Reaction performed in a manner similar to that described for Example 39, to give the product as a solid.
$^1$H NMR (300 MHz; d$_6$-DMSO) δ 9.35 (s, 1H), 7.79-7.87 (m, 3H), 7.19-7.22 (m, 2H), 4.37-4.35 (m, 1H), 3.57 (s, 3H), 1.62-1.66 (m, 2H), 1.24 (s, 6H), 1.14 (app. t, 2H), 1.05 (s, 6H), 1.00 (s, 6H); m/z=568.4 (M+H)$^+$.

Example 41

Step 1: Preparation of 1-methyl-4-(5-nitro-2-(oxetan-3-yloxy)phenyl)-1H-tetrazol-5-(4H)-one

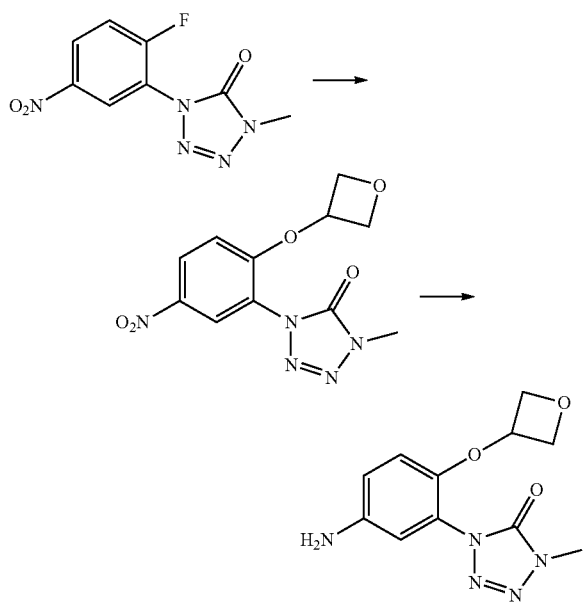

tert-BuOK (123 mg, 1.1 mmol) was added to a stirred solution of oxetan-3-ol (74 mg, 1.0 mmol) in THF (3 mL) at 0° C. under nitrogen. The mixture was stirred at 0° C. for 20 minutes then 1-(2-fluoro-5-nitrophenyl)-4-methyl-1H-tetrazol-5(4H)-one (120 mg, 9.5 mmol) was added in one portion. The mixture was stirred at 0° C. for 10 minutes, then allowed to warm to room temperature and stirred for 2 hours. The solvent was removed under vacuum and the residue was partitioned between CH$_2$Cl$_2$ (30 mL) and H$_2$O (20 mL). The aqueous layer was extracted with CH$_2$Cl$_2$ (1×20 mL) and the combined organic extracts were dried (Na$_2$SO$_4$), filtered and the solvent removed under vacuum to leave a residue (150 mg; theoretical=147 mg) that crystallized on standing.
$^1$H NMR (300 MHz; d$_6$-DMSO) δ 8.51-8.50 (m, 1H), 8.41-8.36 (m, 1H), 7.18-7.15 (m, 1H), 5.58-5.41 (m, 1H), 4.92 (t, 2H), 4.47 (t, 2H), 3.63 (s, 3H).

Step 2: Preparation of 1-(5-amino-2-(oxetan-3-yloxy)phenyl)-4-methyl-1h-tetrazol-5-(4h)-one Pd(C), 10% w/w Pd, wet Degussa grade E101 (30 mg) was added to a stirred mixture of 1-methyl-4-(5-nitro-2-(oxetan-3-yloxy)phenyl)-1H-tetrazol-5-(4H)-one (147 mg, 0.5 mmol) in MeOH (10 mL) under nitrogen. The mixture was evacuated and placed under an atmosphere of hydrogen (balloon of H$_2$ used). The evacuation and hydrogen-fill procedure was repeated twice, then the mixture was placed under an atmosphere of H$_2$ and stirred for 1 hour. After completion of the reaction, the mixture was filtered through Celite and the filter cake was washed with MeOH (3×10 mL). The solvent was removed under vacuum to leave a crude residue that crystallized on standing (119 mg, 90% over 2 steps). The compound was used directly in the next step.

Example 42

Preparation of 1-(5-(4-(1,2,2,6,6-pentamethylpiperidin-4-ylamino)-5fluoropyrimidine-2-ylamino)-2-(oxetan-3-yloxy)phenyl)-4-methyl-1H-tetrazol-5(4H)-one (I-20)

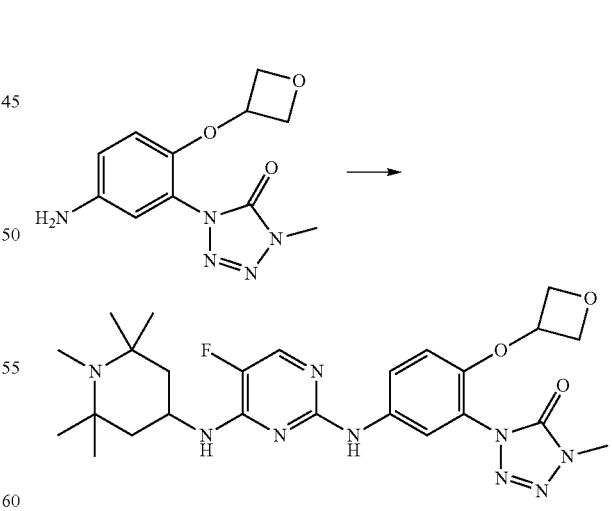

A mixture of 2-chloro-5-fluoro-N4-(1,2,2,6,6-pentamethylpiperidin-4-yl)-4-pyrimidineamine (72 mg, 0.24 mmol), 1-(5-amino-2-(oxetan-3-yloxy)phenyl)-4-methyl-1H-tetrazol-5-(4H)-one (60 mg, 0.23 mmol), Pd(OAc)$_2$ (5.1 mg, 0.02 mmol), BINAP (28.4 mg, 0.05 mmol) and Cs$_2$CO$_3$ (223 mg, 0.68 mmol) were combined in a 10 mL CEM microwave vial. 1,4-Dioxane (3 mL) was added and the mixture was degassed with nitrogen for 5-10 minutes. The mixture was sealed and then heated to 120° C. under microwave irradiation for 60 minutes. After completion of the first microwave heating cycle, the mixture was then heated under microwave irradiation for a further 60 minutes. After allowing to cool to room temperature, the mixture was filtered through Celite and the filter cake was washed with 1,4-dioxane (3×5 mL). The filtrate was concentrated under vacuum and purified by column chromatography on silica gel using $CH_2Cl_2$:2N $NH_3$ in MeOH (1:0 to 95:5) to give a solid. The solid was triturated with $Et_2O$ and filtered to give the title compound (50 mg, 42%) as a solid.

$^1$H NMR (300 MHz; $d_6$-DMSO) δ 9.15 (s, 1H), 7.85 (m, 2H), 7.67 (d, 1H), 7.18 (br. d, 1H), 6.77 (d, 1H), 5.26 (m, 1H), 4.81 (t, 2H), 4.36 (t, 2H), 3.61 (s, 3H), 2.17 (s, 3H), 1.67-1.63 (m, 2H), 1.44 (app. t, 2H), 1.05 (s, 6H), 0.92 (s, 6H); m/z=528.6 (M+H)$^+$.

Example 43

Preparation of 1-(5-(4-(2,2,6,6-gtetramethylpiperidin-4-ylamino)-5-fluoropyrimidin-2-ylamino)-2-(oxetan-3-yloxy)phenyl)-4-methyl-1H-tetrazol-5(4H)-one (I-21)

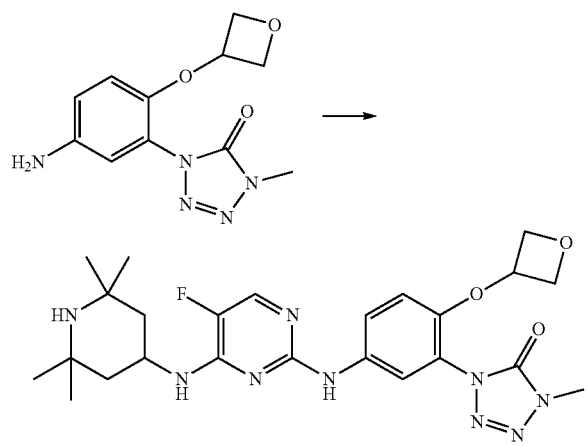

Reaction performed in a manner similar to that described for Example 42, to give the product (60 mg, 56%) as a solid.

$^1$H NMR (300 MHz; $d_6$-DMSO) δ 9.15 (s, 1H), 7.90 (d, 1H), 7.65-7.68 (m, 1H), 7.14 (br. d, 1H), 6.75 (d, 1H), 5.22-5.27 (m, 1H), 4.80 (t, 2H), 4.40 (t, 2H), 4.26-4.40 (m, 1H), 3.60 (s, 3H), 1.61-1.64 (m, 2H), 1.07-1.24 (m, 2H), 1.03 (s, 6H), 0.99 (s, 6H); m/z=514.3 (M+H)$^+$.

Example 44

Step 1: Preparation of 1-(3-fluoro-5-nitrophenyl)-1H-tetrazol-5(4H)-one

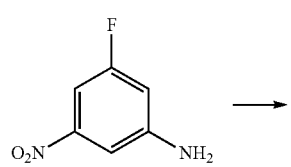

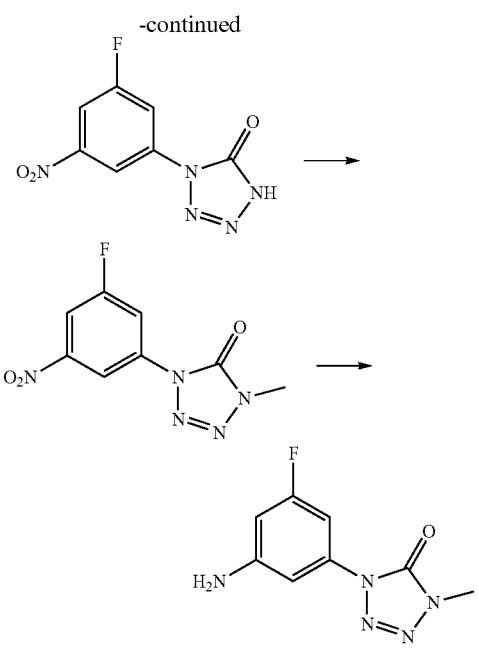

A mixture of 5-fluoro-3-nitroaniline (1.56 g, 10.0 mmol) and phosgene in toluene (20% wt./vol; 25 mL) was heated to reflux and stirred for 3 hours. After allowing to cool to room temperature, the solvent was removed under vacuum and the residue was suspended in trimethylsilyl azide (25 mL) and the contents transferred to a sealed tube. The mixture was heated at 105° C. overnight. After allowing to cool to room temperature, the mixture was concentrated under vacuum and the residue partitioned between EtOAc (40 mL) and saturated $NaHCO_3$ (40 mL). The organic layer was extracted with further saturated $NaHCO_3$ (3×40 mL —TLC being used to monitor the removal of the tetrazolone product from the EtOAc layer). The combined aqueous layers were acidified using 6N HCl and the emerging solid was extracted with EtOAc (4×40 mL). The combined organic extracts were dried ($Na_2SO_4$), filtered and the solvent removed under vacuum to leave the product (1.16 g, 52%) as a solid.

$^1$H NMR (300 MHz; $d_6$-DMSO) δ 8.59-8.58 (m, 1H), 8.20-8.16 (m, 2H); m/z=224.1 (M–H)$^+$.

Step 2: Preparation of 1-(3-fluoro-5-nitrophenyl)-4-methyl-1h-tetrazol-5(4h)-one A mixture of 1-(3-fluoro-5-nitrophenyl)-1H-tetrazol-5 (4H)-one (1.12 g, 5.0 mmol), $K_2CO_3$ (1.73 g, 12.5 mmol) and iodomethane (1.42 g, 10.0 mmol) in DMF (20 mL) was stirred at room temperature overnight. $H_2O$ (100 mL) and EtOAc (50 mL) were then added, and the aqueous and organic layers were partitioned. The organic layer was washed with $H_2O$ (3×75 mL), brine (1×50 mL), then dried ($Na_2SO_4$), filtered and the solvent removed under vacuum to leave the product (1.18 g, 98%) as a solid.

$^1$H NMR (300 MHz; $d_6$-DMSO) δ 8.58 (s, 1H), 8.22-8.18 (m, 2H), 3.63 (s, 3H).

Step 3: Preparation of 1-(3-amino-5-fluorophenyl)-4-methyl-1h-tetrazol-5(4h)-one Pd(C), 10% w/w Pd, wet Degussa grade E101 (90 mg) was added to a stirred suspension of 1-(3-fluoro-5-nitrophenyl)-4-methyl-H-tetrazol-5(4H)-one (500 mg, 2.1 mmol) in MeOH (20 mL) under nitrogen. The mixture was evacuated and placed under an atmosphere of hydrogen (balloon of H$_2$ used). The evacuation and hydrogen-fill procedure was repeated twice, then the mixture was placed under an atmosphere of H$_2$ and stirred for 3 hours. After completion of the reaction, the mixture was filtered through Celite and the filter cake was washed with MeOH (4×10 mL). The solvent was removed under vacuum. The crude residue was purified by column chromatography on silica gel using EtOAc/hexane (4:6) as eluent to give the product (396 mg, 91%) as a solid.

$^1$H NMR (300 MHz; d$_6$-DMSO) δ 6.95 (t, 1H), 6.79 (dt, 1H), 6.31 (dt, 1H), 5.85 (br. s, 2H), 3.57 (s, 3H); m/z=210.2 (M−H)$^+$.

Example 45

Preparation of 1-(3-(4-(1,2,2,6,6-pentamethylpiperidin-4-ylamion)-5fluoropyrimidin-2-ylamino)-5-fluorophenyl)-4-methyl-1H-tetrazol-5(4H)-one (I-22)

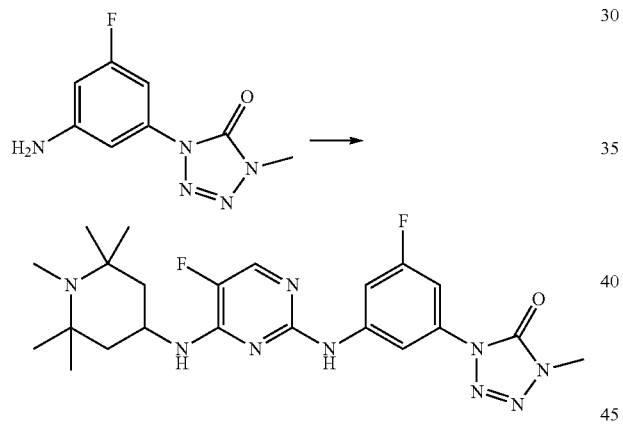

A mixture of 2-chloro-5-fluoro-N4-(1,2,2,6,6-pentamethylpiperidin-4-yl)-4-pyrimidineamine hydrochloride (202 mg, 0.6 mmol), 1-(3-amino-5-fluorophenyl)-4-methyl-1H-tetrazol-5(4H)-one (190 mg, 0.9 mmol) and TFA (186 μL, 2.4 mmol) in isopropanol (6 mL) was heated at 100° C. overnight in a sealed vial. Additional TFA (186 μL, 2.4 mmol) was added and the mixture was heated at 100° C. over 2 days. After allowing to cool to room temperature, the solvent was removed under vacuum and the residue purified by column chromatography on silica gel using CH$_2$Cl$_2$/2N NH$_3$ in MeOH (1:0 to 95:5) as eluent to give the product as a solid.

$^1$H NMR (300 MHz; d$_6$-DMSO) δ 9.58 (s, 1H), 7.90-7.92 (m, 1H), 7.85 (br. s, 1H), 7.30 (d, 1H), 7.16-7.19 (m, 1H), 4.31-4.34 (m, 1H), 3.59 (s, 3H), 2.15 (s, 3H), 1.66-1.69 (m, 2H), 1.44 (t, 2H), 1.05 (s, 6H), 0.99 (s, 6H); $^{19}$F NMR (282 MHz; d$_6$-DMSO) δ −110.6 (t), −165.3 (s); m/z=474.3 (M+H)+; m/z=472.3 (M−H)$^+$.

Example 46

Preparation of 1-(3-(4-(2,2,6,6-tetramethylpiperidin-4-ylamino)-5-fluoropyrimidin-2-ylamino)-5-fluorophenyl)-4-methyl-1H-tetrazol-5(4H)-one (I-23)

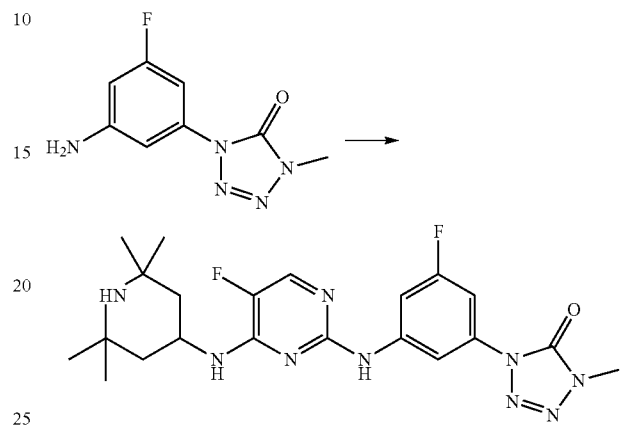

Reaction performed in a manner similar to that described for Example 45, to give the product as a solid.

$^1$H NMR (300 MHz; d$_6$-DMSO) δ 9.58 (s, 1H), 7.87 (d, 1H), 7.85 (d, 1H), 7.29 (br. d, 1H), 7.15-7.18 (m, 1H), 4.39-4.42 (m, 1H), 3.58 (s, 3H), 1.66-1.69 (m, 2H), 1.19-1.12 (m, 2H), 1.12 (s, 6H), 1.00 (s, 6H); $^{19}$F NMR (282 MHz; d$_6$-DMSO) δ −110.6 (t), −165.2 (s); m/z=460.4 (M+H)$^+$.

Example 47

Step 1: Preparation of 1-methyl-4-(3-nitro-5-(oxetan-3-yloxy)phenyl)-1H-tetrazol-5-(5H)-one

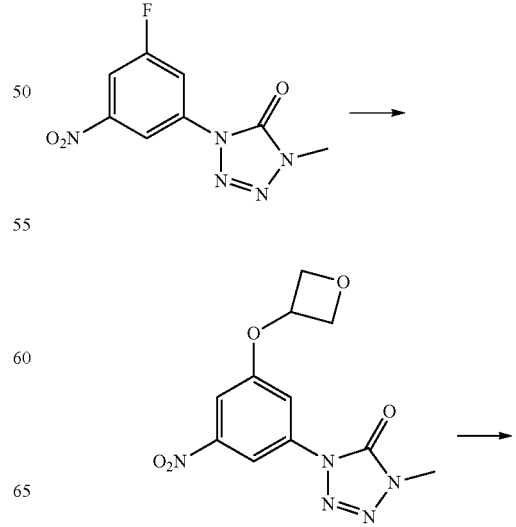

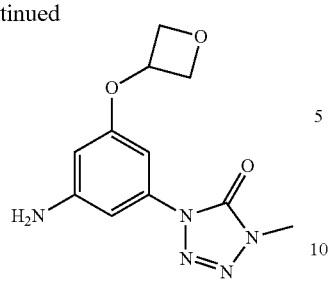

tert-BuOK (123 mg, 1.1 mmol) was added to a stirred solution of oxetan-3-ol (74 mg, 1.0 mmol) in THF (3 mL) at 0° C. under nitrogen. The mixture was stirred at 0° C. for 30 minutes then 1-(3-fluoro-5-nitrophenyl)-1H-tetrazol-5(4H)-one (120 mg, 9.5 mmol) was added in THF (1 mL). The mixture was allowed to warm to room temperature and then stirred overnight. The solvent was removed under vacuum and the residue was partitioned between EtOAc (20 mL) and H$_2$O/brine (40 mL). The aqueous layer was extracted with EtOAc (2×20 mL) and the combined organic extracts were washed with brine (1×20 mL), dried (Na$_2$SO$_4$), filtered and the solvent removed under vacuum to leave a crude residue. The residue was purified by column chromatography on silica gel using EtOAc/hexane (3:7 to 1:1) as eluent to give the product (70 mg, 48%) as a solid.

$^1$H NMR (300 MHz; CDCl$_3$) δ 8.52 (m, 1H), 7.84 (m, 1H), 7.53 (m, 1H), 5.36 (app. q, 1H), 5.06 (dd, 2H), 4.81 (dd, 2H), 3.74 (s, 3H).

Note: the reaction was repeated starting with 500 mg of 1-(3-fluoro-5-nitrophenyl)-1H-tetrazol-5(4H)-one to give the product (249 mg, 41%).

Step 2: Preparation of 1-(3-amino-5-(oxetan-3-yloxy)phenyl)-4-methyl-1h-tetrazol-5(4h)-one Pd(C), 10% w/w Pd, wet Degussa grade E101 (50 mg) was added to a stirred suspension of 1-methyl-4-(3-nitro-5-(oxetan-3-yloxy)phenyl)-1H-tetrazol-5(4H)-one (320 mg, 1.1 mmol) in MeOH (25 mL) under nitrogen. The mixture was evacuated and placed under an atmosphere of hydrogen (balloon of H$_2$ used). The evacuation and hydrogen-fill procedure was repeated twice, then the mixture was placed under an atmosphere of H$_2$ and stirred for 6 hours. Additional Pd(C) (40 mg) was added under an atmosphere of nitrogen, and the mixture was hydrogenated for a further 3 hours. After completion of the reaction, the mixture was filtered through Celite and the filter cake was washed with MeOH (3×15 mL). The solvent was removed under vacuum and the crude residue was purified by column chromatography on silica gel using EtOAc/hexane (3:7 to 6:4) as eluent to give the product (225 mg, 79%) as a solid.

$^1$H NMR (300 MHz; CDCl$_3$) δ 6.98 (t, 1H), 6.70 (t, 1H), 6.05 (t, 1H), 5.21 (app. q, 1H), 4.97 (t, 2H), 4.76 (t, 2H), 3.89 (br. s, 2H), 3.69 (s, 3H).

Example 48

Preparation of 1-(3-(4-(1,2,2,6,6-pentamethylpiperidin-4-ylamino)-5-fluoropyrimidin-2-ylamino)-5-(oxetan-3-yloxy)phenyl)-4-methyl-1H-tetrazol-5(4H)-one (I-24)

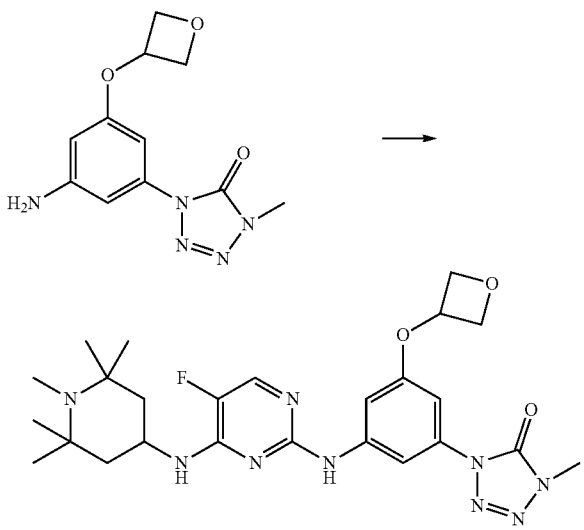

Reaction performed in a similar manner to that described for Example 42, except using 1-(3-amino-5-(oxetan-3-yloxy)phenyl)-4-methyl-1H-tetrazol-5(4H)-one as a starting material, and a reaction temperature of 160° C. for 1 hour. Purification by column chromatography on silica gel using CH$_2$Cl$_2$/2N NH$_3$ in MeOH (1:0 to 95:5), then by preparative thin-layer chromatography using CH$_2$Cl$_2$/2N NH$_3$ in MeOH (92.5:7.5) gave the product as a solid.

$^1$H NMR (300 MHz; d$_6$-DMSO) δ 9.32 (s, 1H), 7.89 (d, 1H), 7.72 (s, 1H), 7.40 (s, 1H), 7.24 (br. d, 1H), 6.68 (s, 1H), 5.22-5.25 (m, 1H), 4.89 (t, 2H), 4.53 (dd, 2H), 4.30 (m, 1H), 3.58 (s, 3H), 2.14 (s, 3H), 1.64-1.68 (m, 2H), 1.42 (t, 2H), 1.04 (s, 6H), 0.98 (s, 6H); m/z=528.4 (M+H)$^+$.

Example 49

Preparation of 1-(3-(4-(2,2,6,6-tetramethylpiperidin-4-ylamino)-5-fluoropyrimidin-2-ylamino)-5-(oxetan-3-yloxy)phenyl)-4-methyl-1H-tetrazol-5(4H)-one (I-25)

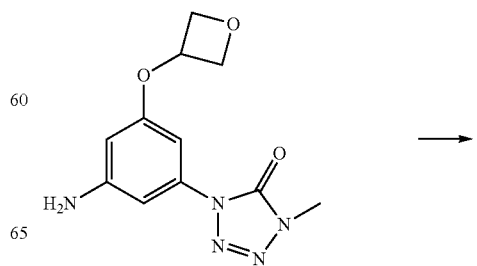

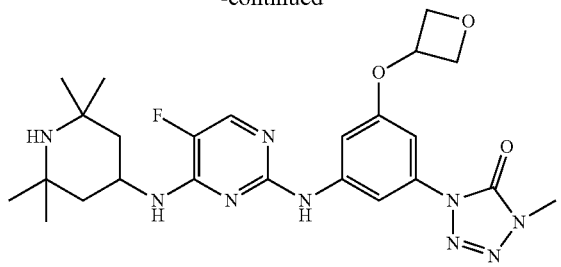

Reaction performed in a manner similar to that described for Example 42, except a temperature of 160° C. for 1 hour was used for the reaction. Purification by column chromatography on silica gel using $CH_2Cl_2/2N\ NH_3$ in MeOH (1:0 to 95:5) gave the product (30 mg, 27%) as a solid.

$^1$H NMR (300 MHz; $d_6$-DMSO) δ 9.31 (s, 1H), 7.88-7.89 (m, 1H), 7.72 (m, 1H), 7.41 (m, 1H), 7.22 (br. d, 1H), 6.70 (m, 1H), 5.21-5.23 (m, 1H), 4.88 (t, 2H), 4.52 (t, 2H), 4.41 (m, 1H), 3.56 (s, 3H), 1.65-1.68 (m, 4H), 1.26-1.11 (m, 4H), 1.11 (s, 6H), 1.00 (s, 6H); m/z=514.5 (M+H)$^+$.

Example 50

1-(2-fluoro-5-nitrophenyl)-1H-tetrazol-5(4H)-one

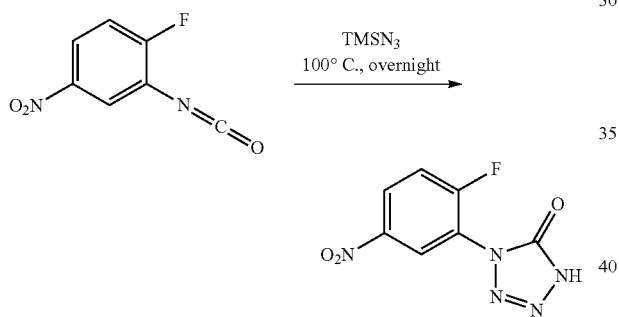

To 2-Fluoro-5-nitrobenzoisocyanate (1.86 g, 10.2 mmol), azidotrimethylsilane (3.36 ml, 2.5 eq) was added and the mixture was heated at 100° C. overnight. The mixture was cooled to room temperature, concentrated under reduced pressure. The title compound (1.8 g, 78%) was obtained by column chromatography using ethyl acetate and hexanes as an eluent (40:60).

$^1$H NMR (300 MHz, DMSO) δ 8.66 (m, 1H), 8.46 (m, 1H), 7.82 (t, J=9.6 Hz, 1H).

Example 51

1-(5-amino-2-fluorophenyl)-1H-tetrazol-5(4H)-one

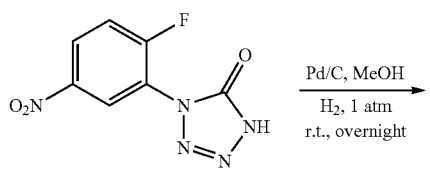

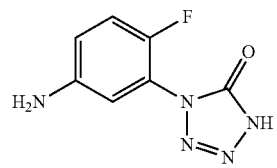

1-(2-Fluoro-5-nitrophenyl)-1H-tetrazol-5(4H)-one (240 mg, 1.1 mmol) was dissolved into MeOH (5 ml), Pd/C (36 mg, 10% weight) was added to the solution. The mixture was degassed and stirred under 1 atmosphere of $H_2$ via a balloon at room temperature overnight. After filtering off Pd/C first through fluted filter paper and then again through a bed of Celite, the solution was concentrated under reduced pressure to give the title compound (150 mg, 72% yield) as an off-colored solid.

$^1$H NMR (300 MHz, DMSO) δ 7.10 (m, 1H), 6.67 (m, 2H), 5.38 (bs, 2H); LCMS (m/z): 196.01 (MH$^+$).

Example 52

1-(2-fluoro-5-nitrophenyl)-4-methyl-1H-tetrazol-5(4H)-one

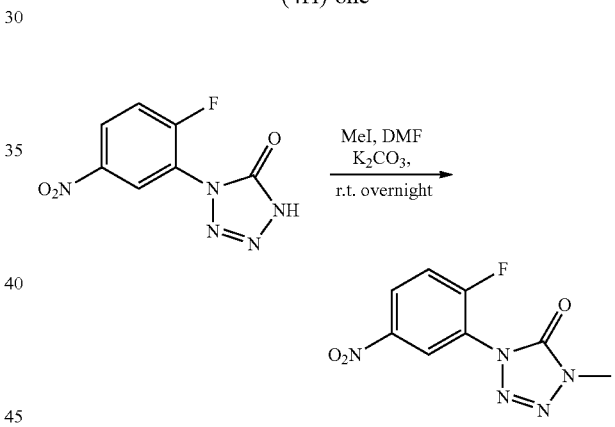

1-(2-Fluoro-5-nitrophenyl)-1H-tetrazol-5(4H)-one (500 mg, 2.2 mmol) was dissolved into DMF (5 ml), $K_2CO_3$ (1 g, 7.2 mmol) was added to this solution and followed by MeI (0.15 ml, 2.4 mmol). The mixture was stirred at room temperature overnight. Ethyl acetate (15 ml) and water (15 ml) was added to this mixture, the 2 layers were separated. Aqueous layer was extracted with ethyl acetate (15 ml), the organic layers were combined and concentrated under reduced pressure. DCM (40 ml) was added to the residue and washed twice with brine ml). The layers were separated and the organic layer was dried with $Na_2SO_4$. After filtering off the solid, the solution was concentrated under reduced pressure and the residue was purified by flash column chromatography (1:1 Ethyl Acetate:Hexanes) to give the title compound as a white solid (400 mg, 75% yield).

$^1$H NMR (300 MHz, DMSO) δ 8.64 (m, 1H), 8.48 (m, 1H), 7.85 (t, J=9.3 Hz, 1H), 3.63 (s, 3H); LCMS (m/z): 239.99 (MH$^+$).

Example 53

1-(5-amino-2-fluorophenyl)-4-methyl-1H-tetrazol-5(4H)-one

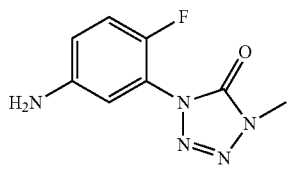

1-(2-Fluoro-5-nitrophenyl)-4-methyl-1H-tetrazol-5(4H)-one (360 mg, 1.5 mmol) was suspended in MeOH (8 ml) and ethyl acetate (3 ml) mixture, Pd/C (50 mg, 10% weight) was added to the solution. The mixture was degassed and stirred under 1 atmosphere of $H_2$ via a balloon at room temperature overnight. After filtering off Pd/C first through fluted filter paper and then again through a bed of Celite, the solution was concentrated under reduced pressure to give the title compound (200 mg, 63% yield) as an off-colored solid.

$^1$H NMR (300 MHz, DMSO) δ 7.11 (t, J=9.9 Hz, 1H), 6.68 (m, 2H), 5.38 (s, 2H), 3.58 (s, 3H); LCMS (m/z): 210.02 (MH$^+$).

Example 54

1-(2-fluoro-5-nitrophenyl)-4-isopropyl-1H-tetrazol-4(4H)-one

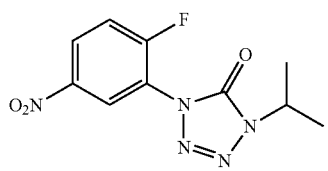 [SMILES: CC(C)n1nnn(-c2cc([N+](=O)[O-])ccc2F)c1=O]

1-(2-Fluoro-5-nitrophenyl)-1H-tetrazol-5(4H)-one (500 mg, 2.2 mmol) was dissolved into DMF (5 ml), $K_2CO_3$ (1 g, 7.2 mmol) was added to this solution and followed by 2-iodopropane (0.25 ml, 2.4 mmol). The mixture was stirred at room temperature overnight. Ethyl acetate (15 ml) and water (15 ml) was added to this mixture, the 2 layers were separated. Aqueous layer was extracted with ethyl acetate (15 ml), the organic layers were combined and concentrated under reduced pressure. DCM (40 ml) was added to the residue and washed twice with brine (20 ml). The layers were separated and the organic layer was dried with $Na_2SO_4$. After filtering off the solid, the solution was concentrated under reduced pressure and the residue was purified by flash column chromatography (1:2 Ethyl acetate:Hexanes) to give the title compound as a white solid (200 mg, 75% pure).

$^1$H NMR (300 MHz, DMSO) δ 8.68 (m, 1H), 8.48 (m, 1H), 7.84 (t, J=9.6 Hz, 1H), 4.47 (m, 1H), 1.45 (d, J=3.3 Hz, 6H); LCMS (m/z): 268.01 (MH$^+$).

Example 55

1-(5-amino-2-fluoropheenyl-4-isopropyl-1H-tetrazol-5(4H)-one

1-(2-Fluoro-5-nitrophenyl)-4-isopropyl-1H-tetrazol-5(4H)-one (200 mg, 0.75 mmol) was suspended in MeOH (10 ml), Pd/C (20 mg, 10% weight) was added to the solution. The mixture was degassed and stirred under 1 atmosphere of $H_2$ via a balloon at room temperature overnight. Pd/C was removed by using 2 layers of fluted filter paper and the mother liquor was concentrated under reduced pressure. Dichloromethane (20 ml) was added and the solution was filtered through another 2 layers of fluted filter paper, thereafter the mother liquor was concentrated under reduced pressure to give the title compound (130 mg, 73% yield) as an off-white solid.

$^1$H NMR (300 MHz, DMSO) δ 7.12 (t, J=9.3 Hz, 1H), 6.69 (m, 2H), 5.38 (s, 2H), 3.57 (s, 3H), 4.43 (m, 1H), 1.43 (d, J=3.4 Hz, 6H); LCMS (m/z): 238.05 (MH$^+$).

Example 56

1-(2-fluoro-5-nitrophenyl)-4-(2-fluoroethyl)-1H-tetrazol-5(4H)-one

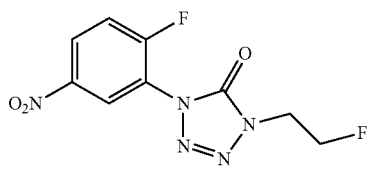 [SMILES: O=c1n(CCF)nnn1-c1cc([N+](=O)[O-])ccc1F]

1-(2-Fluoro-5-nitrophenyl)-1H-tetrazol-5(4H)-one (500 mg, 2.2 mmol) was dissolved into DMF (5 ml), $K_2CO_3$ (1 g, 7.2 mmol) was added to this solution and followed by 1-bromo-2-fluoroethane (0.31 g, 2.4 mmol). The mixture was stirred at room temperature overnight. Ethyl acetate (15 ml) and water (15 ml) was added to this mixture, the 2 layers were separated. Aqueous layer was extracted with ethyl acetate (15 ml), the organic layers were combined and concentrated under reduced pressure. DCM (40 ml) was added to the residue and washed twice with brine (20 ml). The layers were separated and the organic layer was dried with $Na_2SO_4$. After filtering off the solid, the solution was concentrated under reduced pressure and the residue was purified by flash column chromatography (1:2 Ethyl acetate:Hexanes) to give the title compound as a white solid (70 mg, 11.6% yield).

$^1$H NMR (300 MHz, DMSO) δ 8.69-8.67 (m, 1H), 8.51-8.47 (m, 1H), 7.86 (t, J=9.3 Hz, 1H), 4.87 (t, J=4.5 Hz, 1H), 4.72 (t, J=4.2 Hz, 1H), 4.39 (t, J=4.5 Hz, 1H), 4.3 (t, J=4.8 Hz, 1H); LCMS (m/z): 271.05 (MH$^+$).

Example 57

1-(5-amino-2-fluorophenyl)-4-(2-fluoroethyl)-1H-tetrazol-5(4H)-one

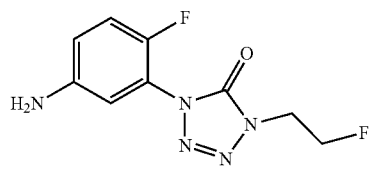

1-(2-Fluoro-5-nitrophenyl)-4-(2-fluoroethyl)-1H-tetrazol-5(4H)-one (70 mg, 0.2 mmol) was dissolved into MeOH (1 ml), Pd/C (10 mg, 10% weight) was added to the solution. The mixture was degassed and stirred under 1 atmosphere of $H_2$ via a balloon at room temperature overnight. Pd/C was removed by using 2 layers of fluted filter paper and the mother liquor was concentrated under reduced pressure. Dichloromethane (10 ml) was added and the solution was filtered through another 2 layers of fluted filter paper, thereafter the mother liquor was concentrated under reduced pressure to give the title compound (36 mg, 58% yield).

$^1$H NMR (300 MHz, DMSO) δ 7.13 (t, J=9.3 Hz, 1H), 6.69 (m, 2H), 5.38 (s, 2H), 4.85 (t, J=4.8 Hz, 1H), 4.7 (t, J=4.5 Hz, 1H), 4.35 (t, J=4.8 Hz, 1H), 4.26 (t, J=4.8 Hz, 1H); LCMS (m/z): 242.02 (MH$^+$).

Example 58

1-(2-methyl-5-nitrophenyl)-1H-tetrazol-5(4H)-one

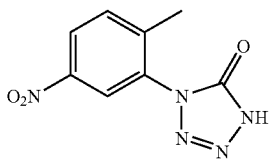 [SMILES: Cc1ccc([N+](=O)[O-])cc1-n1nn[nH]c1=O]

To 2-methyl-5-nitrobenzoisocyanate (2 g, 11.2 mmol), azidotrimethylsilane (3.7 ml, 2.5 eq) was added and the mixture was heated at 100° C. overnight. The mixture was cooled to room temperature, concentrated under reduced pressure. Traces of azidotrimethylsilane were removed by co-evaporating with ethyl acetate under reduced pressure. To this residue, dichloromethane was added and the mixture was sonicated, the title compound (1.9 g, 80% yield) was obtained as a fluffy white solid after filtering through the Buchner funnel fitted with filter paper.

$^1$H NMR (300 MHz, DMSO) δ 8.38 (s, 1H), 8.3 (d, J=8.4 Hz, 1H), 7.74 (d, J=8.7 Hz, 1H), 2.35 (s, 3H); LCMS (m/z): 211.01 (MH$^+$).

Example 59

1-(2-methyl-5-nitrophenyl)-4-methyl-1H-tetrazol-5(4H)-one

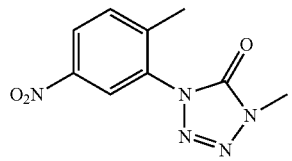 [SMILES: Cc1ccc([N+](=O)[O-])cc1-n1nnn(C)c1=O]

1-(2-Methyl-5-nitrophenyl)-1H-tetrazol-5(4H)-one (900 mg, 4.3 mmol) was dissolved into DMF (13 ml), $K_2CO_3$ (1.95 g, 14.1 mmol) was added to this solution and followed by iodomethane (0.32 ml, 5.1 mmol). The mixture was stirred at room temperature overnight. Ethyl acetate (20 ml) and water (20 ml) was added to this mixture, the 2 layers were separated and the organic layer was dried with $Na_2SO_4$. After filtering off the solid, the solution was concentrated under reduced pressure and the residue was sonicated with ether and then filtered off mother liquor to give the title compound as a white solid (700 mg, 73% yield).

$^1$H NMR (300 MHz, DMSO) δ 8.36 (s, 1H), 8.31 (d, J=8.1 Hz, 1H), 7.75 (d, J=8.7 Hz, 1H), 3.62 (s, 3H), 2.36 (s, 3H); LCMS (m/z): 236.05 (MH$^+$).

Example 60

1-(5-amino-2-methylphenyl)-4-methyl-1H-tetrazol-5(4H)-one

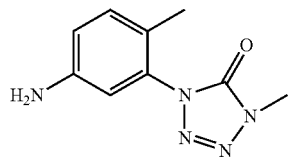

1-(2-Methyl-5-nitrophenyl)-4-methyl-H-tetrazol-5(4H)-one (300 mg, 0.75 mmol) was suspended in MeOH (10 ml), Pd/C (30 mg, 10% weight) was added to the solution. The mixture was degassed and stirred under 1 atmosphere of $H_2$ via a balloon at room temperature for 4 hours. Pd/C was removed by using 2 layers of fluted filter paper and the mother liquor was concentrated under reduced pressure to give the title compound (140 mg, 54% yield) as brown oil.

$^1$H NMR (300 MHz, DMSO) δ 7.02 (d, J=8.1 Hz, 1H), 6.63 (d, J=8.4 Hz, 1H), 6.52 (s, 1H), 5.26 (s, 2H), 3.58 (s, 3H), 1.96 (s, 3H); LCMS (m/z): 206.07 (MH$^+$).

Example 61

1-(2-isopropoxy-5-nitrophenyl)-4-methyl-1H-tetrazol-5(4H)-one

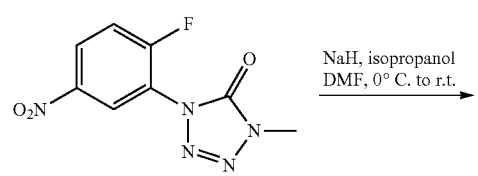

-continued

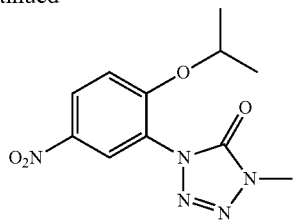

Isopropanol (0.04 ml, 0.5 mmol) was dissolved into DMF (1 ml), the solution was chilled to 0° C. in a ice/water bath. NaH (15 mg, 0.62 mmol) was added and the mixture was stirred at 0° C. for 10 minutes. 1-(2-Fluoro-5-nitrophenyl)-4-methyl-1H-tetrazol-5(4H)-one (100 mg, 0.4 mmol) in DMF (1 ml) was added into the mixture dropwise, and the solution was allowed to warm up to room temperature, progress of reaction followed by thin layer chromatography. Additional isopropanol (0.04 ml) and NaH (15 mg) were added to the again chilled solution, and warmed to room temperature. Ethyl acetate (5 ml) and water (5 ml) were added to the mixture, the 2 layers were separated, and the organic layer was dried with $Na_2SO_4$. The organic layer was concentrated under reduced pressure and purified by flash column chromatrography (2:1 Hexanes:Ethyl acetate) to give the title compound (56 mg, 48% yield) as a light yellow solid.

$^1$H NMR (300 MHz, DMSO) δ 8.45-8.39 (m, 2H), 7.52 (d, J=9.3 Hz, 1H), 4.93-4.89 (m, 1H), 3.60 (s, 3H), 1.24 (d, J=6.0 Hz, 6H); LCMS (m/z): 280.05 (MH$^+$).

Example 62

1-(5-amino-2-isopropoxyphenyl)4-methyl-1H-tetrazol-5(4H)-one

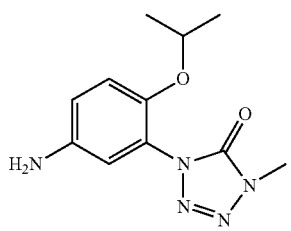 [SMILES: CC(C)Oc1ccc(N)cc1-n1nnn(C)c1=O]

1-(2-Isopropxy-5-nitrophenyl)-4-methyl-1H-tetrazol-5 (4H)-one (356 mg, 1.27 mmol) was suspended in MeOH (10 ml), Pd/C (40 mg, 10% weight) was added to the solution. The mixture was degassed and stirred under 1 atmosphere of $H_2$ via a balloon at room temperature for 6 hours. Another 15 mg of Pd/C was added to the solution and stirred under 1 atmosphere of hydrogen until TLC (1:1 Hexanes:Ethyl Acetate) indicated the completion of reaction. Pd/C was removed by using 2 layers of fluted filter paper and the mother liquor was concentrated under reduced pressure. Dichloromethane (5 ml) was added to the residue and it was filtered through another double layers of fluted filter paper again. The mother liquor was concentrated under reduced pressure to give the title compound (200 mg, 63% yield) as an off white solid.

$^1$H NMR (300 MHz, DMSO) δ 6.95 (d, J=8.7 Hz, 1H), 6.69 (d, J=8.7 Hz, 1H), 6.55 (s, 1H), 5.03 (s, 2H), 4.25 (m, 1H), 3.57 (s, 3H), 1.07 (d, J=6.0 Hz, 6H); LCMS (m/z): 250.08 (MH$^+$).

Example 63

1-(3-nitrophenyl)-1H-tetrazol-5(4H)-one

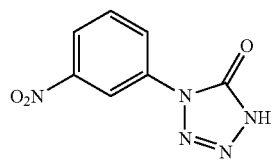 [SMILES: O=c1[nH]nnn1-c1cccc([N+](=O)[O-])c1]

To 3-nitrobenzoisocyanate (2 g, 12.2 mmol), azidotrimethylsilane (3.2 ml, 24.4 mmol) was added and the mixture was heated at 100° C. overnight. The mixture was cooled to room temperature, concentrated under reduced pressure. Residue was sonicated with hexanes (100 ml), and filtered to give a pale yellow solid (2.3 g). This solid was further purified by flash column chromatography (2:1 Hexanes: Ethyl Acetate to 4:1 Ethyl Acetate:Hexanes) to give 1.8 g of the title compound (75% pure). This solid was dissolved into ethyl acetate (100 ml) and washed with saturated $NaHCO_3$, the layers were separated. The aqueous layer was acidified with 1N HCl, and extracted with ethyl acetate (100 ml). The organic layer was dried with $Na_2SO_4$, the solid was filtered off and mother liquor was concentrated under reduced pressure to give the title compound (1.6 g, 64% yield).

$^1$H NMR (300 MHz, DMSO) δ 8.73 (s, 1H), 8.3-8.23 (m, 2H), 7.85 (t, J=8.1 Hz, 1H); LCMS (m/z): 208.13 (MH$^+$).

Example 64

1-(3-nitrophenyl)-4-methyl-1H-tetrazol-5(4H)-one

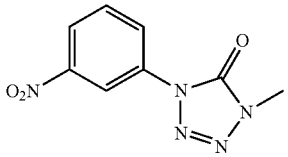 [SMILES: Cn1nnn(-c2cccc([N+](=O)[O-])c2)c1=O]

1-(3-Nitrophenyl)-1H-tetrazol-5(4H)-one (500 mg, 2.4 mmol) was dissolved into DMF (5 ml), $K_2CO_3$ (1.1 g, 6.0 mmol) was added to this solution and followed by iodomethane (0.17 ml, 2.7 mmol). The mixture was stirred at room temperature over 2 days. Ethyl acetate (20 ml) was added to this mixture, after filtering off solid, the solution was concentrated under reduced pressure. Dichloromethane was added and the solution was washed with saturated $NaHCO_3$, brine (4×50 ml) and dried with $Na_2SO_4$. The solid was filtered off and mother liquor was concentrated under reduced pressure to give the title compound as a white solid (360 mg, 67% yield).

$^1$H NMR (300 MHz, DMSO) δ 8.71 (s, 1H), 8.32-8.25 (m, 2H), 7.87 (t, J=8.1 Hz, 1H), 3.62 (s, 3H); LCMS (m/z): 222.16 (MH$^+$).

Example 65

1-(3-aminophenyl)-4-methyl-1H-tetrazol-5(4H)-one

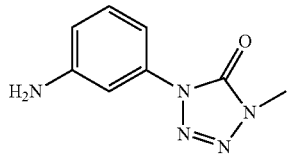

1-(3-Nitrophenyl)-4-methyl-1H-tetrazol-5(4H)-one (360 mg, 1.6 mmol) was suspended in MeOH (10 ml), Pd/C (40 mg, 10% weight) was added to the solution. The mixture was degassed and stirred under 1 atmosphere of $H_2$ via a balloon at room temperature for 2 hours. Reaction was monitored by TLC (2:1 Ethyl Acetate:Hexanes) and an addition of 25 mg of Pd/C was added to the mixture and left stirred at room temperature overnight. Pd/C was removed by using 2 layers of fluted filter paper and the mother liquor was concentrated under reduced pressure. To this residue, dichloromethane was added and the solution was filtered again through double layer of fluted filter paper. Mother liquor was concentrated under reduced pressure to give the title compound (200 mg, 64% yield) as light grey solid.

$^1$H NMR (300 MHz, DMSO) δ 7.13 (t, J=8.1 Hz, 1H), 7.04 (s, 1H), 6.94 (d, J=7.8 Hz, 1H), 6.56 (d, J=8.1 Hz, 1H), 5.48 (s, 2H), 3.57 (s, 3H); LCMS (m/z): 192.19 (MH$^+$).

Example 66

1-[5-nitro-2-(4-tetrahydropyran-4-yloxy)phenyl]-4-methyl-1H-tetrazol-5(4H)-one

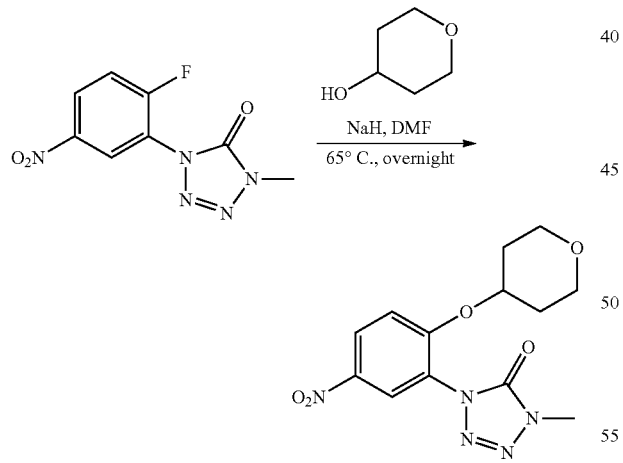

Oxan-4-ol (0.28 ml, 3 mmol) was dissolved into DMF (5 ml), the solution was chilled to 0° C. in a ice/water bath. NaH (90 mg, 3.7 mmol) was added and the mixture was stirred at 0° C. for 10 minutes. 1-(2-Fluoro-5-nitrophenyl)-4-methyl-1H-tetrazol-5(4H)-one (600 mg, 2.5 mmol) in DMF (5 ml) was added into the mixture dropwise, and the solution was allowed to warm up to room temperature, progress of reaction followed by thin layer chromatography. The mixture was first warmed to 45° C., then increased to 65° C. and left at that temperature overnight. Ethyl acetate (20 ml) and water (20 ml) were added to the mixture, the 2 layers were separated, and the organic layer was dried with $Na_2SO_4$. The organic layer was concentrated under reduced pressure and purified by flash column chromatrography (2:1 Hexanes:Ethyl acetate) to give the title compound (600 mg, 75% yield).

$^1$H NMR (300 MHz, DMSO) δ 8.47 (s, 1H), 8.4 (d, J=9.3 Hz, 1H), 7.59 (d, J=9.3 Hz, 1H), 4.37 (1, 1H), 3.68 (bs, 2H), 3.62 (s, 3H), 3.47 (bs, 2H), 1.9 (bs, 2H), 1.58 (bs, 2H); LCMS (m/z): 322.12 (MH$^+$).

Example 67

1-[5-amino-2-(4-tetrahydropyran-4-yloxy)phenyl]-4-methyl-1H-tetrazol-5(4H)-one

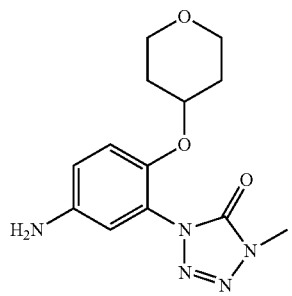 [SMILES: Cn1nnn(-c2cc(N)ccc2OC2CCOCC2)c1=O]

1-[5-Nitro-2-(4-tetrahydropyran-4-yloxy)phenyl]-4-methyl-1H-tetrazol-5(4H)-one (260 mg, 0.8 mmol) was suspended in MeOH (5 ml), Pd/C (30 mg, 10% weight) was added to the solution. The mixture was degassed and stirred under 1 atmosphere of $H_2$ via a balloon at room temperature overnight. Pd/C was removed by using 2 layers of fluted filter paper and the mother liquor was concentrated under reduced pressure. To this residue, dichloromethane was added and the solution was filtered again through double layer of fluted filter paper. Mother liquor was concentrated under reduced pressure to give the title compound (100 mg, 43% yield) as light grey solid.

$^1$H NMR (300 MHz, DMSO) δ 6.99 (d, J=9.0 Hz, 1H), 6.7 (d, J=9.0 Hz, 1H), 6.57 (s, 1H), 5.06 (s, 2H), 4.3 (m, 1H), 3.6 (m, 2H), 3.58 (s, 3H), 3.35 (m, 2H), 1.78 (m, 2H), 1.45 (m, 2H); LCMS (m/z): 292.28 (MH$^+$).

Example 68

N2-{[3-(4-methyl)-1,2,3,4-tetrazol-5-one-1-yl](tetrahydropyran-4-yloxy}phenyl-5-fluoro-N4-(1,2,2,6,6-pentamethylpiperidin-4-yl)-2,4-pyrimidinediame
(I-26)

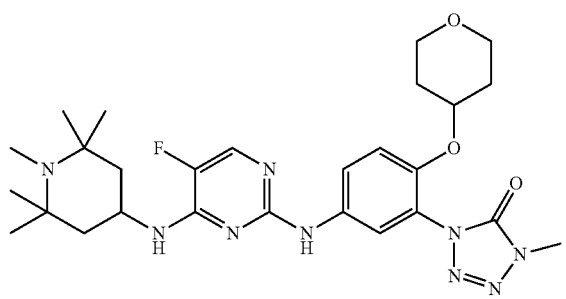

¹H NMR (300 MHz, DMSO) δ 9.12 (s, 1H), 7.88-7.83 (m, 2H), 7.69 (d, J=2.4 Hz, 1H), 7.17-7.14 (m, 2H), 4.51 (m, 1H), 4.23 (m, 1H), 3.67-3.6 (m, 5H), 3.41 (m, 2H), 2.13 (s, 3H), 1.79 (m, 2H), 1.61 (m, 2H), 1.44 (m, 4H), 1.03 (s, 6H), 0.89 (s, 6H); LCMS (m/z): 556.60 (MH⁺).

Example 69

N2-{4-(tetrahydropyran-4-yloxy)-[3-(4-methyl)-1,2,3,4-tetrazol-5-one-1-yl]}phenyl-5-fluoro-N4-(2,2,6,6-tetramethylpyridin-4-yl)-2,4-pyrimidinediamine (I-27)

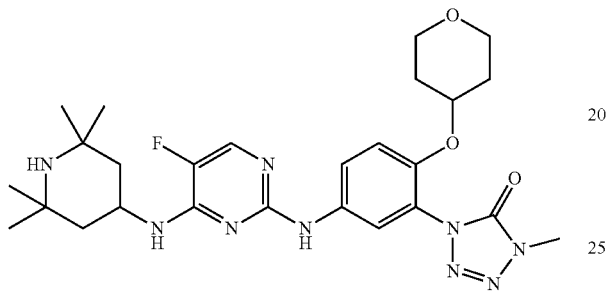

¹H NMR (300 MHz, DMSO) δ 9.13 (s, 1H), 7.89 (d, J=3 Hz, 1H), 7.83 (d, J=3.6 Hz, 1H), 7.67 (d, J=9 Hz, 1H), 7.17 (m, 2H), 4.51 (m, 1H), 4.33 (m, 1H), 3.66-3.59 (m, 5H), 3.36 (m, 2H), 1.78 (m, 2H), 1.64 (d, J=9.6 Hz, 2H), 1.44 (m, 2H), 1.15 (t, J=11.7 Hz, 2H), 1.03 (s, 6H), 1.0 (s, 6H); LCMS (m/z): 542.58 (MH⁺).

Example 70

1-{2-[(3-methylozetan-3-yl)methody]-5-nitrophenyl}-4-methyl-1H-tetrazol-5(4H)-one

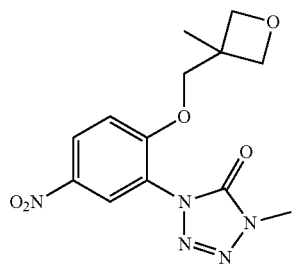 [SMILES: Cn1nnn(-c2cc([N+](=O)[O-])ccc2OCC2(C)COC2)c1=O]

(3-Methyloxetan-3-yl)methanol (0.3 ml, 3 mmol) was dissolved into DMF (4 ml), the solution was chilled to 0° C. in a ice/water bath. NaH (90 mg, 3.7 mmol) was added and the mixture was stirred at 0° C. for 10 minutes. 1-(2-Fluoro-5-nitrophenyl)-4-methyl-1H-tetrazol-5(4H)-one (600 mg, 2.5 mmol) in DMF (5 ml) was added into the mixture dropwise, and the solution was allowed to warm up to room temperature, progress of reaction followed by thin layer chromatography. The mixture was first warmed to 45° C., then increased to 60° C. and left at that temperature overnight. Additional 0.3 ml of (3-methyloxetan-3-yl)methanol and 100 mg of NaH were added to the mixture and left for another day. Ethyl acetate (20 ml) and water (20 ml) were added to the mixture, the 2 layers were separated, and the organic layer was dried with Na₂SO₄. The organic layer was concentrated under reduced pressure and purified by flash column chromatrography (2:1 Hexanes:Ethyl acetate) to give the title compound (466 mg, 58% yield).

¹H NMR (300 MHz, DMSO) δ 8.51-8.45 (m, 2H), 7.53 (d, J=9.3 Hz, 1H), 4.36 (d, J=5.7 Hz, 2H), 4.25 (s, 2H), 4.19 (d, J=5.7 Hz, 2H), 3.58 (s, 3H), 1.23 (s, 3H); LCMS (m/z): 322.11 (MH⁺).

Example 71

1-{5-amino-2-[(3-methyloxetan-3-yl)methody]-phenyl}-4-methyl-1H-tetrazol-5(4H)-one

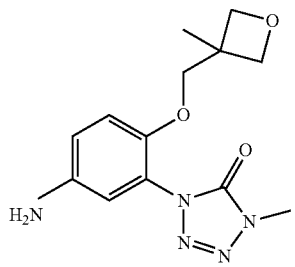 [SMILES: Cn1nnn(-c2cc(N)ccc2OCC2(C)COC2)c1=O]

1-{2-[(3-Methyloxetan-3-yl)methoxy]-5-nitrophenyl}-4-methyl-1H-tetrazol-5(4H)-one (466 mg, 1.45 mmol) was suspended in MeOH (8 ml), Pd/C (50 mg, 10% weight) was added to the solution. The mixture was degassed and stirred under 1 atmosphere of H₂ via a balloon at room temperature overnight. Pd/C was removed by using 2 layers of fluted filter paper and the mother liquor was concentrated under reduced pressure. To this residue, dichloromethane was added and the solution was filtered again through double layer of fluted filter paper. Mother liquor was concentrated under reduced pressure to give the title compound (300 mg, 71% yield) as light grey solid.

¹H NMR (300 MHz, DMSO) δ 7.0 (d, J=9 Hz, 1H), 6.72 (d, J=8.7 Hz, 1H), 6.62 (d, J=2.7 Hz, 1H), 5.05 (s, 2H), 4.30 (d, J=5.7 Hz, 2H), 4.14 (d, J=5.4 Hz, 2H), 3.87 (s, 2H), 3.55 (s, 3H), 1.16 (s, 3H); LCMS (m/z): 292.24 (MH⁺).

Example 72

5-fluoro-N2-{4-(3-methyloxetan-3-yl)methody-3-[(4-methyl)-1,2,3,4-tetrazol-5-one-1-yl]}phenyl-N4-(2,2,6,6-tetramethylpiperidin-4-yl)-2,4pyrimidinediamine (I-28)

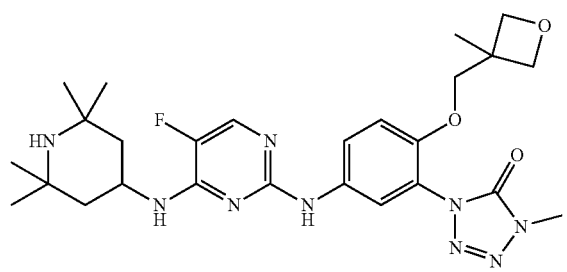

¹H NMR (300 MHz, DMSO) δ 9.15 (s, 1H), 7.98 (s, 1H), 7.84 (m, 1H), 7.68 (d, J=9.3 Hz, 1H), 7.17 (m, 2H), 4.32 (m,

3H), 4.15 (d, J=5.4 Hz, 1H), 3.96 (s, 2H), 3.55 (s, 3H), 1.63 (d, J=9.6 Hz, 2H), 1.18 (s, 3H), 1.09 (m, 2H), 1.03 (s, 6H), 0.99 (s, 6H); LCMS (m/z): 542.52 (MH⁺).

Example 73

1-(2-chloro-5-nitrophenyl)-1H-tetrazol-5(4H)-one

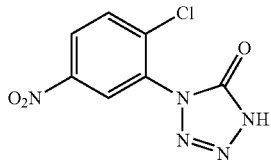 [SMILES: O=c1[nH]nnn1-c1cc([N+](=O)[O-])ccc1Cl]

To 2-chloro-5-nitrobenzoisocyanate (2 g, 10.1 mmol), azidotrimethylsilane (3.3 ml, 25.2 mmol) was added and the mixture was heated at 100° C. overnight. The mixture was cooled to room temperature, concentrated under reduced pressure. Residue was dissolved into ethyl acetate (100 ml) and washed with saturated NaHCO₃ (100 ml), the layers were separated. The aqueous layer was acidified with 2N HCl, and extracted with ethyl acetate (100 ml). The organic layer was dried with Na₂SO₄, the solid was filtered off and mother liquor was concentrated under reduced pressure to give the title compound (1.0 g, 41% yield).

¹H NMR (300 MHz, DMSO) δ 8.67 (s, 1H), 8.43 (d, J=9.0 Hz, 1H), 8.05 (d, J=8.7 Hz, 1H); LCMS (m/z): 241.99 (MH⁺).

Example 74

1-(2-chloro-5-nitrophenyl)-4-methyl-1H-tetrazol-5(4H)-one

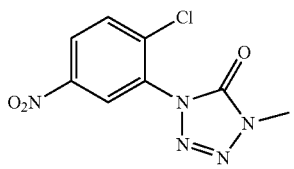 [SMILES: Cn1nnn(-c2cc([N+](=O)[O-])ccc2Cl)c1=O]

1-(2-Chloro-5-nitrophenyl)-1H-tetrazol-5(4H)-one (1 g, 4.1 mmol) was dissolved into DMF (20 ml), K₂CO₃ (1.9 g, 10.25 mmol) was added to this solution and followed by iodomethane (0.32 ml, 4.92 mmol). The mixture was stirred at room temperature over 2 days. Ethyl acetate (20 ml) was added to this mixture, after filtering off solid, the solution was concentrated under reduced pressure. Dichloromethane was added and the solution was washed with saturated NaHCO₃, brine (4×50 ml) and dried with Na₂SO₄. The solid was filtered off and mother liquor was concentrated under reduced pressure to give the title compound as a white solid (950 mg, 89.6% yield).

¹H NMR (300 MHz, DMSO) δ 8.65 (s, 1H), 8.44 (d, J=9 Hz, 1H), 8.07 (d, J=9 Hz, 1H), 3.63 (s, 3H); LCMS (m/z): 256.00 (MH+).

Example 75

1-(5-amino-2-chlorophenyl)-4-methyl-1H-tetrazol-5(4H)-one

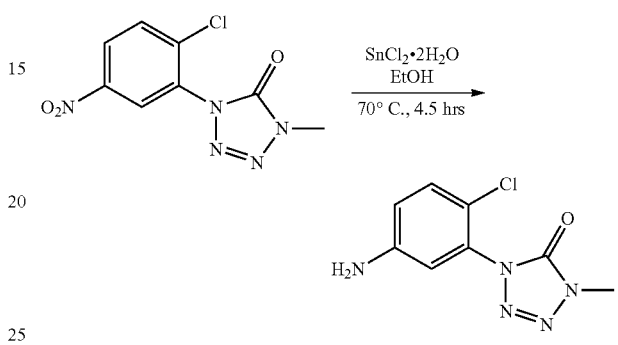

1-(2-Chloro-5-nitrophenyl)-4-methyl-1H-tetrazol-5(4H)-one (500 mg, 1.96 mmol) was added to EtOH (15 ml), followed by SnCl₂.2H₂O (1.1 g, 5.88 mmol) and heated at 75° C. for 4.5 hours. The solution was allowed to cool to room temperature and concentrated under reduced pressure. To this residue, ethyl acetate (50 ml) was added and washed with aqueous K₂CO₃ (50 ml). The 2 layers were separated, the organic layer was washed with brine (50 ml) and dried with Na₂SO₄. The solid was filtered off and the solution was concentrated under reduced pressure to give the title compound (300 mg, 68% yield).

¹H NMR (300 MHz, DMSO) δ 7.27 (d, J=8.4 Hz, 1H), 6.75-6.7 (m, 2H), 5.69 (s, 2H), 3.59 (s, 3H); LCMS (m/z): 226.08 (MH⁺).

Example 76

N2-{4-chloro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine (I-30)

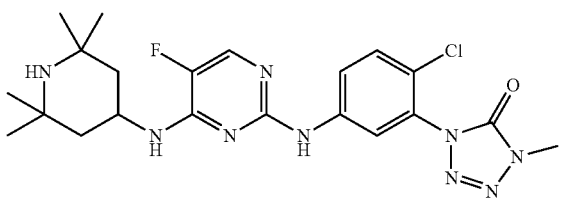

¹H NMR (300 MHz, DMSO) δ 9.53 (s, 1H), 8.05 (s, 1H), 7.85 (m, 2H), 7.49 (d, J=8.7 Hz, 1H), 7.29 (d, J=7.2 Hz, 1H), 4.33 (m, 1H), 3.61 (s, 3H), 1.65 (d, J=10.2 Hz, 2H), 1.15 (m, 2H), 1.06 (s, 6H), 0.99 (s, 6H); LCMS (m/z): 476.32 (MH⁺).

Example 77

N2-{4-chloro-[3-(4-methyl)-1,2,3,4-tetrazol-5-one-1-yl]}phenyl-5-fluoro-N4-(1,2,2,6,6-pentamethylpiperidin-4-yl)-2,4-pyrimidinediamine (I-29)

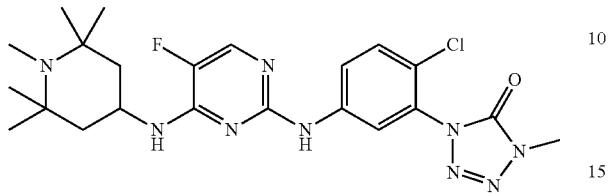

¹H NMR (300 MHz, DMSO) δ 9.53 (s, 1H), 8.03 (s, 1H), 7.88 (m, 2H), 7.49 (d, J=8.7 Hz, 1H), 7.3 (d, J=8.1 Hz, 1H), 4.24 (m, 1H), 3.62 (s, 3H), 2.15 (s, 3H), 1.65 (d, J=11.1 Hz, 2H), 1.43 (t, J=12.3 Hz, 2H), 1.05 (s, 6H), 0.93 (s, 6H); LCMS (m/z): 490.40 (MH⁺).

Example 78

1-(3-methoxy-5-nitrophenyl)-1H-tetrazol-5(4H)-one

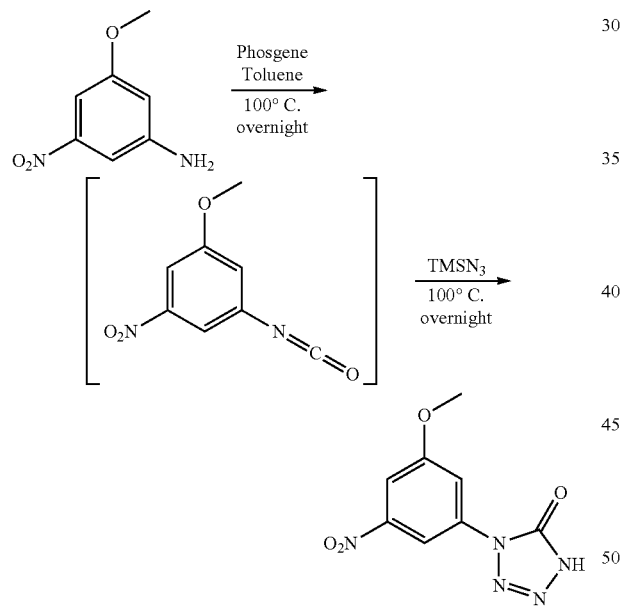

3-Methoxy-5-nitroaniline (2 g, 11.9 mmol) was added to 32 ml of phosgene (20% in toluene), the mixture was heated at 100° C. The reaction mixture was cooled to room temperature and concentrated under reduced pressure. To this residue, azidotrimethylsilane (6 ml, 47.6 mmol) was added and the solution was heated at 100° C. overnight. After cooled to room temperature, TMSN₃ was removed under reduced pressure. Ethyl Acetate (50 ml) was added to this residue and treated with saturated NaHCO₃ (50 ml). The aqueous layer was separated and acidified with 2N HCl, extracted with ethyl acetate (150 ml). The organic layer was washed with brine, dried with Na₂SO₄, filtered off solid, and concentrated under reduced pressure to give the title compound (2 g, 71.2% yield).

¹H NMR (300 MHz, DMSO) δ 8.35 (s, 1H), 7.87 (s, 1H), 7.78 (s, 1H), 3.96 (s, 3H); LCMS (m/z): 237.00 (MH⁺).

Example 79

1-(3-methoxy-5-nitrophenyl)-4-methyl-1H-tetrazol-5(4H)-one

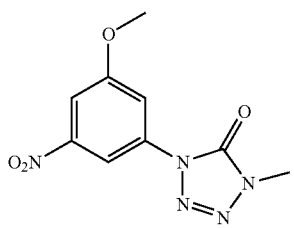 [SMILES: COc1cc(-n2nnn(C)c2=O)cc([N+](=O)[O-])c1]

1-(3-Methoxy-5-nitrophenyl)-1H-tetrazol-5(4H)-one (1 g, 4.2 mmol) was dissolved into DMF (20 ml), K₂CO₃ (1.9 g, 10.25 mmol) was added to this solution and followed by iodomethane (0.4 ml, 6.3 mmol). The mixture was stirred at room temperature overnight. Dichloromethane (100 ml) and water (100 ml) were added to the mixture, and the layers were separated. The organic layer was washed with brine (3×50 ml) and dried with Na₂SO₄. The solid was filtered off and mother liquor was concentrated under reduced pressure to give the title compound as a white solid (800 mg, 74% yield).

¹H NMR (300 MHz, DMSO) δ 8.32 (s, 1H), 7.84 (s, 1H), 7.78 (s, 1H), 3.95 (s, 3H), 3.63 (s, 3H); LCMS (m/z): 256.00 (MH⁺).

Example 80

1-(5-amino-3-methoxyphenyl)-4-methyl-1H-tetrazol-5(4H)-one

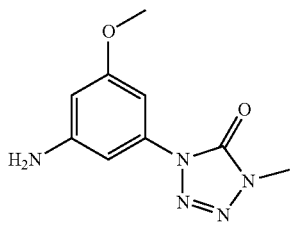

1-(3-Methoxy-5-nitrophenyl)-4-methyl-H-tetrazol-5(4H)-one (600 mg, 2.3 mmol) was suspended in MeOH (10 ml), Pd/C (80 mg, 10% weight) was added to the solution. The mixture was degassed and stirred under 1 atmosphere of H₂ via a balloon at room temperature overnight. Pd/C was removed by using 2 layers of fluted filter paper and the mother liquor was concentrated under reduced pressure. To this residue, dichloromethane was added and the solution was filtered again through double layers of fluted filter paper. Mother liquor was concentrated under reduced pressure to give the title compound (450 mg, 86% yield) as light grey solid.

¹H NMR (300 MHz, DMSO) δ 6.7 (s, 1H), 6.58 (s, 1H), 6.14 (s, 1H), 5.52 (s, 2H), 3.68 (s, 3H), 3.57 (s, 3H); LCMS (m/z): 222.19 (MH⁺).

Example 81

N2-{5-methody-[3-(4-methyl)-1,2,3,4-tetrazol-5-one-1-yl]}phenyl-5-fluoro-N4-(2,2,6,6-tetramethyl-piperidin-4-yl)-2,5-pyrimidinediamine (I-32)

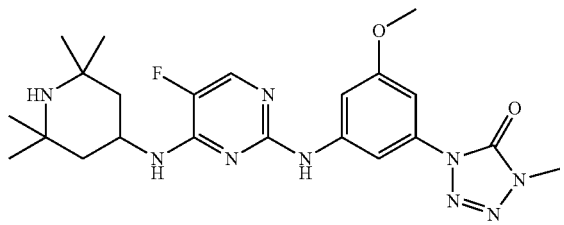

$^1$H NMR (300 MHz, DMSO) δ 9.23 (s, 1H), 7.87 (d, J=3.6 Hz, 1H), 7.78 (s, 1H), 7.37 (s, 1H), 7.18 (d, J=7.2 Hz, 1H), 6.89 (s, 1H), 4.38 (m, 1H), 3.72 (s, 3H), 3.57 (s, 3H), 1.66 (d, J=9.9 Hz, 2H), 1.15 (m, 2H), 1.06 (s, 6H), 0.99 (s, 6H); LCMS (m/z): 472.45 (MH$^+$).

Example 82

N2-{5-methody-[3-(4-methyl)-1,2,3,4-tetrazol-5-one-1-yl]}phenyl-5-fluoro-N4-(1,2,2,6,6-pentamethylpiperidin-4-yl)-2,4-pyrimidinediamine (I-31)

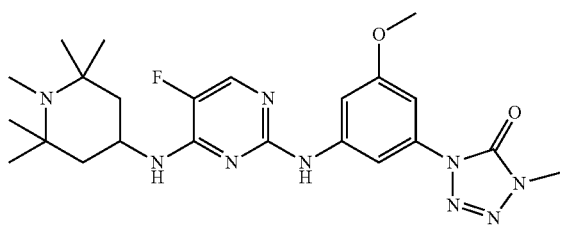

$^1$H NMR (300 MHz, DMSO) δ 9.25 (s, 1H), 7.88 (d, J=3.9 Hz, 1H), 7.78 (s, 1H), 7.38 (s, 1H), 7.23 (d, J=8.1 Hz, 1H), 6.9 (s, 1H), 4.29 (m, 1H), 3.73 (s, 3H), 3.58 (s, 3H), 2.17 (s, 3H), 1.68 (d, J=9.6 Hz, 2H), 1.43 (t, J=11.7 Hz, 2H), 1.05 (s, 6H), 0.95 (s, 6H); LCMS (m/z): 486.56 (MH$^+$).

Example 83

1-(2-cyclopropyl-5-nitrophenyl)-4-methyl-1H-tetrazol-5(4H)-one

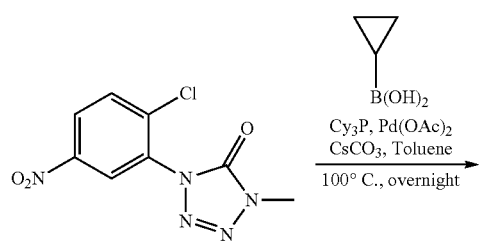

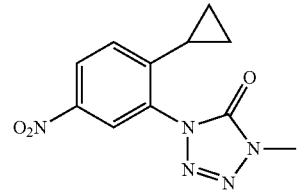

1-(2-Chloro-5-nitrophenyl)-4-methyl-1H-tetrazol-5(4H)-one (500 mg, 1.96 mmol) was added to toluene (10 ml), followed by cyclopropyl boronic acid (250 mg, 2.9 mmol), tricyclohexylphosphine (55 mg, 0.2 mmol), cesium carbonate (1.9 g, 5.9 mmol). The mixture was degassed by bubbling N$_2$ into it for 15 minutes, and Pd(OAc)$_2$ (22 mg, 0.1 mmol) was added. The mixture was heated at 100° C. for 4 hours, followed by thin layer chromatography (1:1 Hexanes:Ethyl Acetate). Additional cyclopropyl boronic acid (125 mg, 1.45 mmol), tricyclohexylphosphine (25 mg, 0.09 mmol), cesium carbonate (1 g, 3. mmol) and Pd(OAc)$_2$ (10 mg, 0.045 mmol) were added to the mixture and left heated at 100° C. overnight. The solution was cooled to room temperature, ethyl acetate (50 ml) and water (50 ml) were added to the mixture. The 2 layers were separated and the organic layer was dried with Na$_2$SO$_4$, filtered and concentrated under reduced pressure. The title compound (230 mg, 45% yield) was obtained after purifying residue using flash column chromatography (2:1 Hexanes:Ethyl Acetate).

$^1$H NMR (300 MHz, DMSO) δ 8.37 (s, 1H), 8.28 (d, J=9 Hz, 1H), 7.34 (d, J=8.7 Hz, 1H), 3.62 (s, 3H), 1.91 (m, 1H), 1.05 (m, 2H), 0.87 (m, 2H); LCMS (m/z): 262.26 (MH$^+$).

Example 84

1-(5-amino-2-cyclopropylophenyl)-4-methyl-1H-tetrazol-5(4H)-one

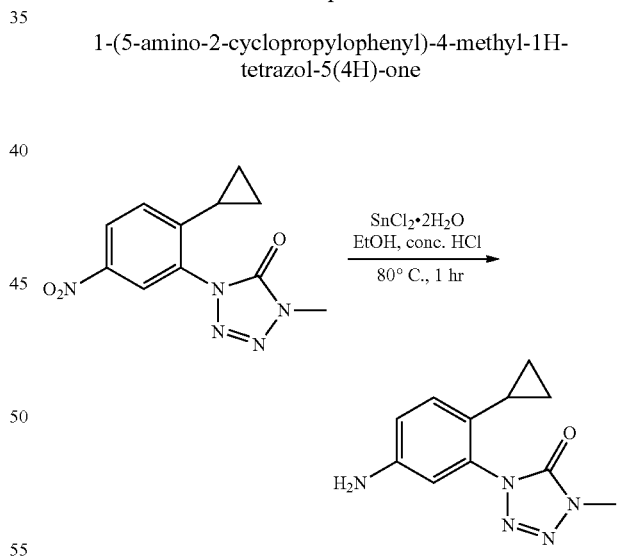

1-(2-Cyclopropyl-5-nitrophenyl)-4-methyl-1H-tetrazol-5(4H)-one (200 mg, 0.77 mmol) was added to EtOH (18 ml), followed by SnCl$_2$.2H$_2$O (581 mg, 3.1 mmol), concentrated HCl (0.72 ml) and heated at 80° C. for 1 hour. The solution was allowed to cool to room temperature and concentrated under reduced pressure. To this residue, ethyl acetate (20 ml) was added and washed with aqueous K$_2$CO$_3$ (20 ml). The 2 layers were separated, the organic layer was washed with brine (20 ml) and dried with Na$_2$SO$_4$. The solid was filtered off and the solution was concentrated under reduced pressure to give the title compound (~180 mg, 100% yield).

¹H NMR (300 MHz, DMSO) δ 6.84 (d, J=8.4 Hz, 1H), 6.63 (d, J=8.7 Hz, 1H), 6.5 (s, 1H), 5.32 (s, 2H), 3.59 (s, 3H), 1.56 (m, 1H), 0.64 (d, J=8.7 Hz, 2H), 0.38 (d, J=3.9 Hz, 2H); LCMS (m/z): 232.21 (MH⁺).

Example 85

N2-{4-cyclopropyl-[3-(4-methyl)-1,2,3,4-tetrazol-5-one-1-yl]}phenyl-5-fluoro-N4-(2,2,6,6-tetramethyl-piperidin-4-yl)-2,4-pyrimidinediamine (I-33)

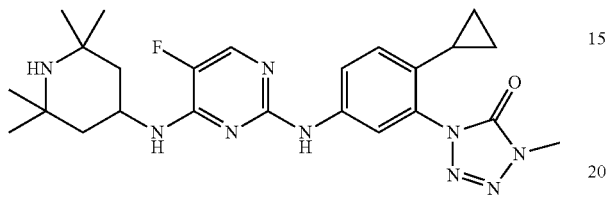

¹H NMR (300 MHz, DMSO) δ 9.25 (s, 1H), 7.85 (d, J=3.9 Hz, 1H), 7.78 (s, 1H), 7.72 (d, J=8.4 Hz, 1H), 7.2 (d, J=8.4 Hz, 1H), 6.98 (d, J=8.4 Hz, 1H), 4.34 (m, 1H), 3.6 (s, 3H), 1.63 (m, 3H), 1.14 (t, J=12 Hz, 2H), 1.05 (s, 6H), 0.99 (s, 6H), 0.72 (d, J=8.7 Hz, 2H), 0.46 (d, J=4.8 Hz, 2H); LCMS (m/z): 482.47 (MH⁺).

Example 86

N2-{4-cyclopropyl-[3-(4-methyl)-1,2,3,4-tetrazol-5-one-1-yl]}phenyl-5-fluoro-N4-(1,2,2,6,6-pentamethylpiperidin-4-yl)-2,4-pyrimidinediamine (I-34)

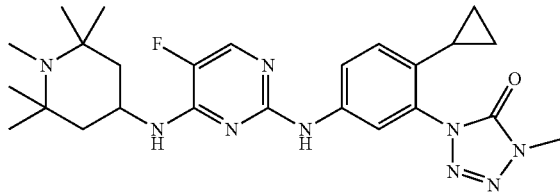

¹H NMR (300 MHz, DMSO) δ 9.25 (s, 1H), 7.85 (d, J=3.9 Hz, 1H), 7.75-7.71 (m, 2H), 7.2 (d, J=8.1 Hz, 1H), 6.98 (d, J=8.4 Hz, 1H), 4.26 (m, 1H), 3.61 (s, 3H), 2.15 (s, 3H), 1.62 (m, 3H), 1.42 (t, J=12 Hz, 2H), 1.04 (s, 6H), 0.92 (s, 6H), 0.73 (d, J=7.2 Hz, 2H), 0.46 (d, J=4.8 Hz, 2H); LCMS (m/z): 496.35 (MH⁺).

Example 87

1-chloro-3,5-dinitrobenzene

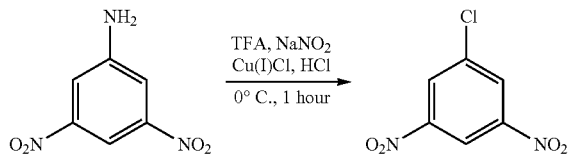 [SMILES: Nc1cc([N+](=O)[O-])cc([N+](=O)[O-])c1 ; O=[N+]([O-])c1cc(Cl)cc([N+](=O)[O-])c1]

3,5-Dinitroaniline (3 g, 16.4 mmol), was added to trifluoroacetic acid (60 ml, excess), followed by NaNO₂ (2.26 g, 32.8 mmol), and the mixture was cooled to 0° C. Cu(I)Cl (6 g, 60 mmol) in concentrated HCl (60 ml) was added dropwise to the mixture and stirred at 0° C. for 1 hour. It was poured onto ice/water and extracted with ethyl acetate, the 2 layers were separated and the organic layer was washed with saturated NaHCO₃, followed with brine and dried with Na₂SO₄. The solid was filtered off and concentrated under reduced pressure, and purified by flash column chromatography (3:1 Hexanes:Ethyl Acetate) to give the title compound (2.5 g, 76% yield) as a light yellow solid.

¹H NMR (300 MHz, DMSO) δ 8.75 (s, 3H), ¹H NMR (300 MHz, CDCl₃) δ 8.97 (s, 1H), 8.57 (s, 2H); LCMS (m/z): 201.90 (MH⁺).

Example 88

3-chloro-5-nitroaniline

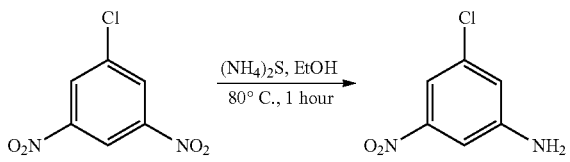 [SMILES: O=[N+]([O-])c1cc(Cl)cc([N+](=O)[O-])c1 ; Nc1cc(Cl)cc([N+](=O)[O-])c1]

1-Chloro-3,5-dinitrobenzene (512 mg, 2.5 mmol) was dissolved into EtOH (8 ml) with the aid of sonication. (NH₄)₂S (3 ml, 20% in H₂O) was added to the solution and heated at 80° C. for 1 hour, followed by thin layer chromatography (3:1 Hexanes:Ethyl Acetate). After the completion of reaction, the solution was allowed to cool to room temperature, ethyl acetate (75 ml) was added and washed with brine (30 ml). The 2 layers were separated, the organic layer was dried with Na₂SO₄ and concentrated under reduced pressure after filtering off solid. The title compound (225 mg, 53% yield) was obtained by purifying the residue with flash column chromatography (3:1 Hexanes:Ethyl Acetate) as an orange solid.

¹H NMR (300 MHz, DMSO) δ 7.32 (s, 1H), 7.24 (s, 1H), 6.94 (s, 1H), 6.14 (s, 2H); LCMS (m/z): 173.04 (MH⁺).

Example 89

1-(3-chloro-5-nitrophenyl)-1H-tetrazol-5(4H)-one

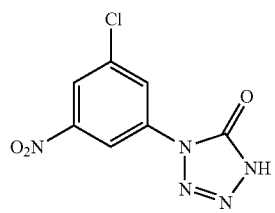 [SMILES: O=c1[nH]nnn1-c1cc(Cl)cc([N+](=O)[O-])c1]

To 3-chloro-5-nitroaniline (138 mg, 0.8 mmol), was added to 6 ml of phosgene (20% in toluene), the mixture was heated at 100° C. The reaction mixture was cooled to room temperature and concentrated under reduced pressure. To this residue, azidotrimethylsilane (5 ml, excess) was added and the solution was heated at 100° C. overnight. Cooled to room temperature, TMSN₃ was removed under reduced pressure. Ethyl acetate (10 ml) was added to this residue and treated with saturated NaHCO₃ (10 ml). The aqueous layer was separated and acidified with 2N HCl, extracted with ethyl acetate (50 ml). The organic layer was washed with brine, dried with Na₂SO₄, filtered off solid, and concentrated under reduced pressure to give the title compound (118 mg, 61% yield).

$^1$H NMR (300 MHz, DMSO) δ 8.66 (s, 1H), 8.36 (s, 1H), 8.32 (s, 1H), 3.95 (s, 3H), 3.63 (s, 3H); LCMS (m/z): 240.07 (MH−).

Example 90

1-(3-chloro-5-nitrophenyl)-4-methyl-1H-tetrazol-5(4H)-one

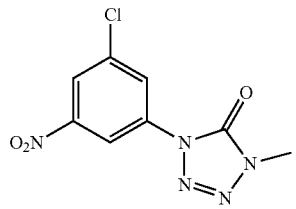 [SMILES: Cn1nnn(-c2cc(Cl)cc([N+](=O)[O-])c2)c1=O]

1-(3-Chloro-5-nitrophenyl)-1H-tetrazol-5(4H)-one (118 mg, 0.49 mmol) was dissolved into DMF (1.5 ml), K₂CO₃ (224 mg, 1.6 mmol) was added to this solution and followed by iodomethane (0.05 ml, 0.73 mmol). The mixture was stirred at room temperature overnight. Dichloromethane (10 ml) and water (10 ml) were added to the mixture, and the layers were separated. The organic layer was washed with brine (3×5 ml) and dried with Na₂SO₄. The solid was filtered off and mother liquor was concentrated under reduced pressure to give the title compound (86 mg, 69% yield).

$^1$H NMR (300 MHz, DMSO) δ 8.64 (s, 1H), 8.36 (s, 2H), 3.63 (s, 3H); LCMS (m/z): 255.13 (MH+).

Example 91

1-(5-amino-3-chlorophenyl)-4-methyl-1H-tetrazol-5(4H)-one

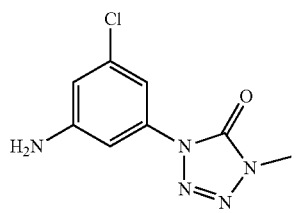

1-(3-Chloro-5-nitrophenyl)-4-methyl-1H-tetrazol-5(4H)-one (86 mg, 0.34 mmol) was added to EtOH (5.1 ml), followed by SnCl₂.2H₂O (228 mg, 1 mmol), and heated at 70° C. for 4.5 hours. The solution was allowed to cool to room temperature and concentrated under reduced pressure. To this residue, ethyl acetate (50 ml) was added and washed with aqueous K₂CO₃ (50 ml). The 2 layers were separated, the organic layer was washed with brine (50 ml) and dried with Na₂SO₄. The solid was filtered off and the solution was concentrated under reduced pressure to give the title compound (42 mg, 72% in purity).

$^1$H NMR (300 MHz, DMSO) δ 7.04 (s, 1H), 7.00 (s, 1H), 6.58 (s, 1H), 5.87 (s, 2H), 3.58 (s, 3H); LCMS (m/z): 226.11 (MH+).

Example 92

N2-{5-chloro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine (I-37)

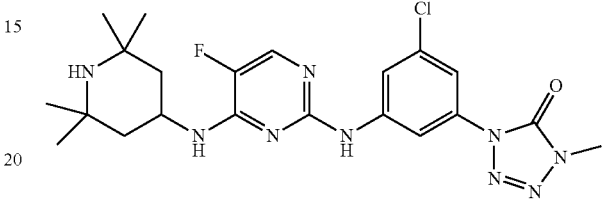

$^1$H NMR (300 MHz, DMSO) δ 9.54 (s, 1H), 8.05 (s, 1H), 7.99 (s, 1H), 7.93 (bs, 1H), 7.65 (bs, 1H), 7.42 (s, 1H), 4.43 (m, 1H), 3.59 (s, 3H), 1.93 (m, 2H), 1.56 (m, 2H), 1.36 (bs, 12H); LCMS (m/z): 476.30 (MH+).

Example 93

1-cyclopropyl-3,6-dinitrobenzene

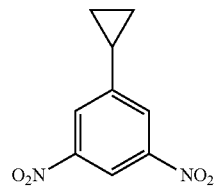

3,5-Dinitrobromobenzene (600 mg, 2.4 mmol) was added to toluene/water (10:2 ml), in a 60 ml round bottom flask fitted with a water condenser. To this solution, tricyclohexylphosphine (200 mg, 0.7 mmol), cesium carbonate (4.74 g, 14.5 mmol), cyclopropylboronic acid MIDA ester (670 mg, 3.4 mmol) were added subsequently. This mixture was degassed by bubbling N₂ into the solution for 15 minutes, and finally palladium acetate (82 mg, 0.36 mmol) was added to the mixture and was heated at 100° C. with stirring under N₂ overnight. The solution was cooled to room temperature. Ethyl acetate and saturated K₂CO₃ was added to the mixture, and the two layers were separated. Organic layer was dried with Na₂SO₄, after filtering off the solid, the mother liquor was concentrated under reduced pressure. The residue was purified with chromatography using ethyl acetate and hexanes (1:4) as an eluent to give the title compound as a yellow solid (350 mg, 69% yield).

$^1$H NMR (300 MHz, DMSO) δ 8.57 (s, 1H), 8.31 (s, 2H), 2.33 (m, 1H), 1.14 (d, J=6 Hz, 2H), 0.95 (m, 2H).

Example 94

3-cyclopropyl-5-nitroaniline

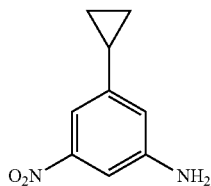 [SMILES: O=[N+]([O-])c1cc(C2CC2)cc([N+](=O)[O-])c1]

1-Chloro-3,5-dinitrobenzene (570 mg, 2.7 mmol) was dissolved into EtOH (14 ml) with the aid of sonication. $(NH_4)_2S$ (3.6 ml, 20% in $H_2O$) was added to the solution and heated at 80° C. for 1 hour. Upon completion of reaction, the solution was cooled to room temperature and concentrated under reduced pressure. Hexanes was added to the residue, sonicated and filtered to give ~600 mg of dark red solid. The title compound (270 mg, 55% yield) was obtained by purifying the filtrate with flash column chromatography (4:1 Hexanes:Ethyl Acetate) as an orange solid.

$^1$H NMR (300 MHz, DMSO) δ 7.13 (s, 1H), 7.01 (s, 1H), 6.63 (s, 1H), 5.68 (s, 2H), 1.89 (m, 1H), 0.94 (d, J=6.6 Hz, 2H), 0.64 (d, J=4.8 Hz, 2H).

Example 95

1-(3-cyclopropyl-5-nitrophenyl)-1H-tetrazol-5(4H)-one

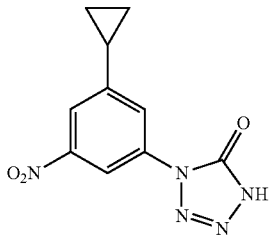 [SMILES: O=c1[nH]nnn1-c1cc(C2CC2)cc([N+](=O)[O-])c1]

To 3-cyclopropyl-5-nitroaniline (270 mg, 2.25 mmol), was added 6 ml of phosgene (20% in toluene), the mixture was heated at 100° C. for 2 hours. The reaction mixture was cooled to room temperature and concentrated under reduced pressure. To this residue, azidotrimethylsilane (11 ml, excess) was added and the solution was heated at 100° C. overnight. Cooled to room temperature, $TMSN_3$ was removed under reduced pressure. Ethyl Acetate (20 ml) was added to this residue and treated with saturated $NaHCO_3$ (20 ml). The aqueous layer was separated and acidified with 2N HCl, extracted with ethyl acetate (50 ml). The organic layer was washed with brine, dried with $Na_2SO_4$, filtered off solid, and concentrated under reduced pressure to give the title compound (200 mg, 54% yield).

$^1$H NMR (300 MHz, DMSO) δ 8.47 (s, 1H), 7.97 (s, 1H), 7.93 (s, 1H), 2.24 (m, 1H), 1.1 (d, J=8.4 Hz, 2H), 0.84 (d, J=4.5 Hz, 2H); LCMS (m/z): 246.12 (MH–).

Example 96

1-(3-cyclopropyl-5-nitrophenyl)-4-methyl-1H-tetrazol-5(4H)-one

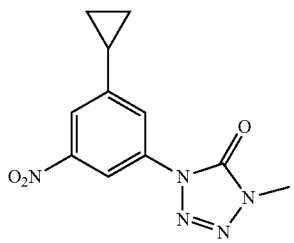 [SMILES: Cn1nnn(-c2cc(C3CC3)cc([N+](=O)[O-])c2)c1=O]

1-(3-Cyclopropyl-5-nitrophenyl)-1H-tetrazol-5(4H)-one (200 mg, 0.8 mmol) was dissolved into DMF (3 ml), $K_2CO_3$ (370 mg, 2.64 mmol) was added to this solution and followed by iodomethane (0.78 ml, 1.2 mmol). The mixture was stirred at room temperature overnight. Dichloromethane (50 ml) and water (2×25 ml) were added to the mixture, and the layers were separated. The organic layer was washed with brine (2×50 ml) and dried with $Na_2SO_4$. The solid was filtered off and mother liquor was concentrated under reduced pressure to give the title compound as a white solid (150 mg, 71% yield).

$^1$H NMR (300 MHz, DMSO) δ 8.46 (s, 1H), 7.97 (s, 1H), 7.95 (s, 1H), 3.62 (s, 3H), 2.45 (m, 1H), 1.11 (d, J=8.4 Hz, 2H), 0.85 (m, 2H); LCMS (m/z): 262.21 (MH–).

Example 97

1-(5-amino-3-cyclopropylphenyl)-4-methyl-1H-tetrazol-5(4H)-one

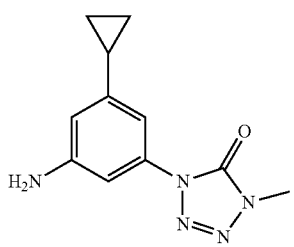

1-(3-Cyclopropyl-5-nitrophenyl)-4-methyl-1H-tetrazol-5(4H)-one (150 mg, 0.57 mmol) was added to EtOH (16 ml), followed by $SnCl_2.2H_2O$ (436 mg, 2.3 mmol), conc. HCl (0.6 ml) and heated at 80° C. for 1 hours. The solution was allowed to cool to room temperature and concentrated under reduced pressure. To this residue, ethyl acetate (20 ml) was added and washed with aqueous $K_2CO_3$ (20 ml). The 2 layers were separated, the organic layer was washed with brine (20 ml) and dried with $Na_2SO_4$. The solid was filtered off and the solution was concentrated under reduced pressure to give the title compound (140 mg, 100% yield).

$^1$H NMR (300 MHz, DMSO) δ 6.83 (s, 1H), 6.68 (s, 1H), 6.28 (s, 1H), 5.38 (s, 2H), 3.57 (s, 3H), 1.8 (m, 1H), 0.89 (d, J=7.8 Hz, 2H), 0.57 (d, J=6.3 Hz, 2H); LCMS (m/z): 232.13 (MH$^+$).

Example 98

N2-{5-cyclopropyl-[3-(4-methyl)-1,2,3,4-tetrazol-5-one-1-yl]}phenyl-5-fluoro-N4-(2,2,6,6-tetramethyl-piperidin-4-yl)-2,4-pyrimidinediamine (I-35)

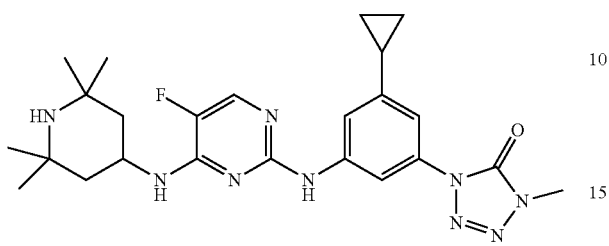

$^1$H NMR (300 MHz, DMSO) δ 9.11 (s, 1H), 8.09 (s, 1H), 7.86 (d, J=3.6 Hz, 1H), 7.22 (s, 1H), 7.14 (d, J=8.1 Hz, 1H), 6.94 (s, 1H), 4.3 (m, 1H), 3.56 (s, 3H), 1.9 (m, 1H), 1.65 (d, J=9.9 Hz, 2H), 1.1 (t, J=12 Hz, 2H), 0.97 (m, 14H), 0.64 (d, J=6.3 Hz, 2H); LCMS (m/z): 482.43 (MH$^+$).

Example 99

N2-{5-cyclopropyl-[3-(4-methyl)-1,2,3,4-tetrazol-5-one-1-yl]}phenyl-5-fluoro-N4-(1,2,2,6,6-pentamethylpiperidin-4-yl)-2,4-pyrimidinediamine (I-36)

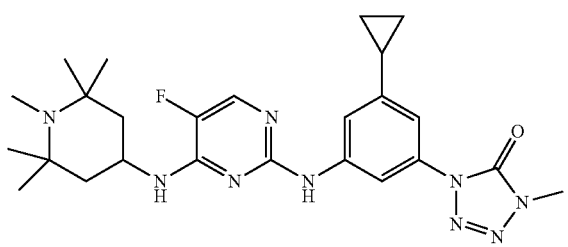

$^1$H NMR (300 MHz, DMSO) δ 9.11 (s, 1H), 8.08 (s, 1H), 7.86 (d, J=3.9 Hz, 1H), 7.24 (s, 1H), 7.15 (d, J=8.4 Hz, 1H), 6.95 (s, 1H), 4.23 (m, 1H), 3.57 (s, 3H), 2.11 (s, 3H), 1.9 (m, 1H), 1.65 (d, J=11.1 Hz, 2H), 1.38 (t, J=12 Hz, 2H), 1.01 (s, 6H), 0.95 (d, J=6 Hz, 2H), 0.86 (s, 6H), 0.64 (d, J=6.3 Hz, 2H); LCMS (m/z): 496.37 (MH$^+$).

Example 100

1-(2-chloro-5-nitro-3-trifluoromethylphenyl)-1H-tetrazol-5(4H)-one

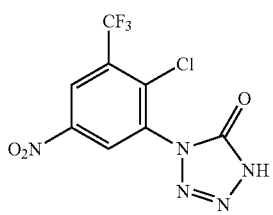 [SMILES: O=c1[nH]nnn1-c1cc([N+](=O)[O-])cc(C(F)(F)F)c1Cl]

To 2-chloro-3-trifluoromethyl-5-nitroaniline (500 mg, 2.1 mmol), was added to 20 ml of phosgene (20% in toluene), the mixture was heated at 100° C. for 2 hours. The reaction mixture was cooled to room temperature and concentrated under reduced pressure. To this residue, azidotrimethylsilane (20 ml, excess) was added and the solution was heated at 100° C. overnight. Cooled to room temperature, TMSN$_3$ was removed under reduced pressure. Ethyl acetate (50 ml) was added to this residue and treated with saturated NaHCO$_3$ (50 ml). The aqueous layer was separated and acidified with 2N HCl, extracted with ethyl acetate (50 ml). The organic layer was washed with brine, dried with Na$_2$SO$_4$, filtered off solid, and concentrated under reduced pressure to give the title compound (42 mg, 6.5% yield).
$^1$H NMR (300 MHz, DMSO) δ 9.01 (d, J=2.7 Hz, 1H), 8.7 (d, J=2.7 Hz, 1H); LCMS (m/z): 308.07 (MH–).

Example 101

1-(2-chloro-5-nitro-3-trifluoromethylphenyl)-4-methyl-1H-tetrazol-5(4H)-one

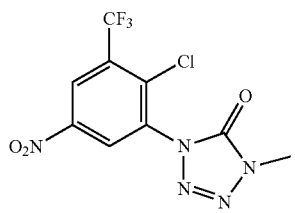 [SMILES: Cn1nnn(-c2cc([N+](=O)[O-])cc(C(F)(F)F)c2Cl)c1=O]

1-(2-Chloro-5-nitro-3-trifluoromethyl-phenyl)-1H-tetrazol-5(4H)-one (42 mg, 0.13 mmol) was dissolved into DMF (1 ml), K$_2$CO$_3$ (62 mg, 0.43 mmol) was added to this solution and followed by iodomethane (0.013 ml, 0.195 mmol). The mixture was stirred at room temperature overnight. Ethyl acetate (10 ml), was added to the mixture and was washed water (2×25 ml), with brine (2×50 ml) and dried with Na$_2$SO$_4$. The solid was filtered off and mother liquor was concentrated under reduced pressure to give the title compound as a white solid (33 mg, 75% yield).
$^1$H NMR (300 MHz, DMSO) δ 8.97 (d, J=2.7 Hz, 1H), 8.71 (d, J=2.4 Hz, 1H), 3.65 (s, 3H).

Example 102

1-(5-amino-2-chloro-3-trifluoromethylphenyl)-4-methyl-1H-tetrazol-5(4H)-one

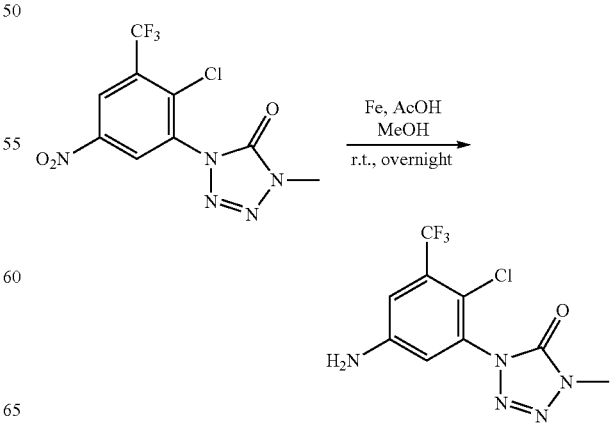

1-(2-Chloro-3-trifluoro-5-nitrophenyl)-4-methyl-1H-tetrazol-5 (4H)-one (33 mg, 0.1 mmol) was added to MeOH (1 ml), followed by Fe (33 mg, 0.6 mmol), acetic acid (2 drops) and stirred at room temperature overnight. Fe was filtered off, and ethyl acetate (5 ml) was added to the mother liquor. The solution was concentrated under reduced pressure to give the title compound (26.9 mg, 75% in purity).

$^1$H NMR (300 MHz, DMSO) δ 7.29 (s, 1H), 7.20 (s, 1H), 6.22 (s, 2H), 3.62 (s, 3H); LCMS (m/z): 293.13 (MH$^+$).

Example 103

N2-{4-chloro-5-trifluoromethyl-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine
(I-38)

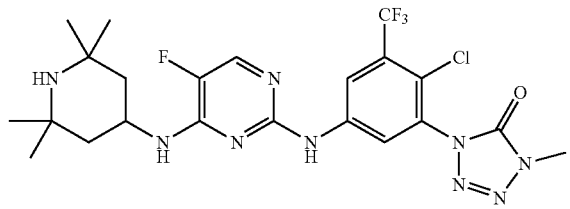

$^1$H NMR (300 MHz, DMSO) δ 9.77 (s, 1H), 8.47 (s, 1H), 8.26 (s, 1H), 7.94 (d, J=3.6 Hz, 1H), 7.4 (bs, 1H), 4.34 (m, 1H), 3.63 (s, 3H), 1.66 (d, J=12.6 Hz, 1H), 1.21 (m, 2H), 1.06 (s, 6H), 1.02 (s, 6H); LCMS (m/z): 544.37 (MH$^+$).

Example 104

2-cyclopropyl-1-trifluoromethyl-3,5-dinitrobenzene

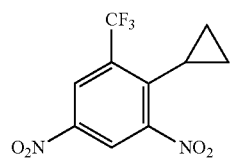

2-Chloro-1-(trifluoromethyl)-3,5-dinitrobenzene (5 g, 18.5 mmol) was added to toluene (91.6 ml) and water (18 ml), followed by cyclopropylboronic acid MIDA ester (5.1 g, 25.9 mmol), tricyclohexylphosphine (1.55 g, 5.5 mmol), cesium carbonate (36 g, 0.11 mol). The mixture was degassed by bubbling N$_2$ into it for 30 minutes, and Pd(OAc)$_2$ (620 mg, 2.76 mmol) was added. The mixture was heated at 100° C. overnight, followed by thin layer chromatography (9.75:0.25 Hexanes:Ethyl Acetate). The solution was cooled to room temperature, ethyl acetate (250 ml) and saturated NaHCO$_3$ (250 ml) were added to the mixture. The 2 layers were separated, the organic layer washed with brine (250 ml) and dried with Na$_2$SO$_4$, filtered and concentrated under reduced pressure. The title compound (3 g, 59% yield) was obtained after purifying residue using flash column chromatography (9.75:0.25 Hexanes:Ethyl Acetate).

$^1$H NMR (300 MHz, DMSO) δ 8.94 (d, J=2.4 Hz, 1H), 8.62 (d, J=2.1 Hz, 1H), 2.25 (m, 1H), 1.05 (m, 2H), 0.61 (m, 2H); LCMS (m/z): 277.14 (MH$^+$).

Example 105

4-cyclopropyl-3-trifluoromethyl-5-nitroaniline

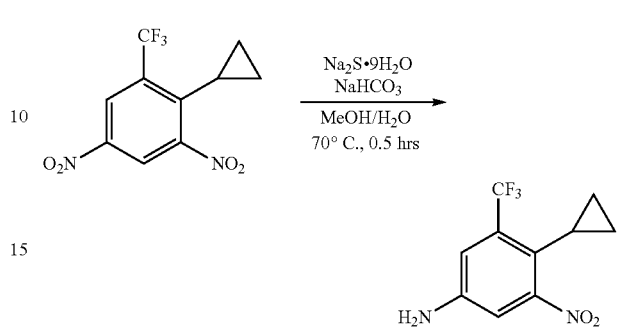

Na$_2$S.9H2O (2.5 g, 10.4 mmol) and NaHCO3 (0.88 g, 10.4 mmol) was mixed together in MeOH (30 ml) and water (20 ml). This mixture, was added to 2-cyclopropyl-1-trifluoromethyl-3,5-dinitrobenzene (1.44 g, 5.2 mmol) in MeOH (20 ml) and it was heated at 70° C. for 0.5 hour. The reaction was followed by thin layer chromatography (4:1 Hexanes:Ethyl Acetate), upon completion, it was cooled to room temperature. The solution was concentrated under reduced pressure. Dichloromethane (125 ml) was added to the residue and washed twice with water (150 ml). The 2 layers were separated, organic layer was dried with Na$_2$SO$_4$, filtered and concentrated under reduced pressure. The residue was purified by flash column chromatography (4:1 Hexanes:Ethyl Acetate) to give the title compound (640 mg, 50% yield).

$^1$H NMR (300 MHz, DMSO) δ 7.1 (s, 1H), 7.01 (s, 1H), 6.08 (s, 2H), 1.87 (m, 1H), 0.815 (m, 2H), 0.34 (d, J=5.1 Hz, 2H); LCMS (m/z): 247.15 (MH$^+$).

Example 106

2-(4-chclopropyl-3-trifluoromethyl-6-nitrophenyl)isoindole-1,3-dione

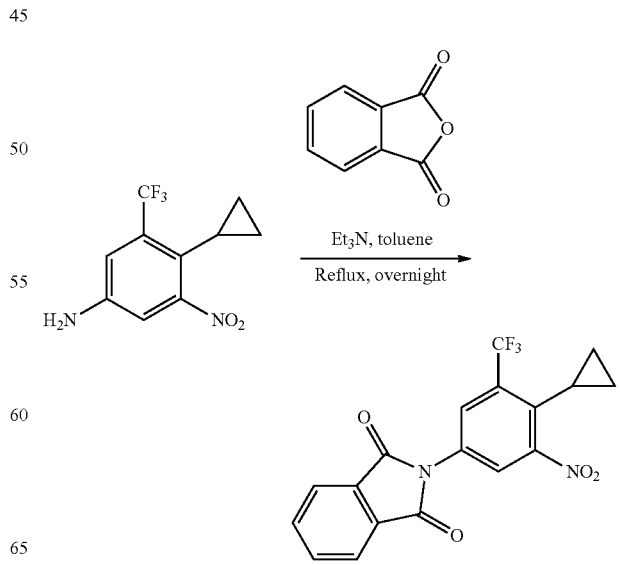

4-Cyclopropyl-3-trifluoromethyl-5-nitroaniline (140 mg, 0.57 mmol), 2-benzofuran-1,3-dione (92 mg, 0.6 mmol), triethylamine were added to toluene, and the mixture was refluxed overnight. The reaction mixture was cooled to room temperature and concentrated under reduced pressure. To this residue, dichloromethane (10 ml) was added, it was washed with 1N HCl, followed by washing with brine and organic layer was dried with $Na_2SO_4$. The solid was filtered off and the solution was concentrated under reduced pressure. The residue was purified by flash column chromatography (4:1 Hexanes:Ethyl Acetate) as an eluent, to give the title compound (100 mg, 47% yield).

$^1$H NMR (300 MHz, DMSO) δ 8.23 (s, 1H), 8.2 (s, 1H), 8.0-7.92 (m, 4H), 2.2 (m, 1H), 1.0 (m, 2H), 0.61 (d, J=5.4 Hz, 2H); LCMS (m/z): 377.11 (MH$^+$).

Example 107

2-(3-amino-4-cyclopropyl-5-trifluoromethylphenyl)isoindole-1,3-dione

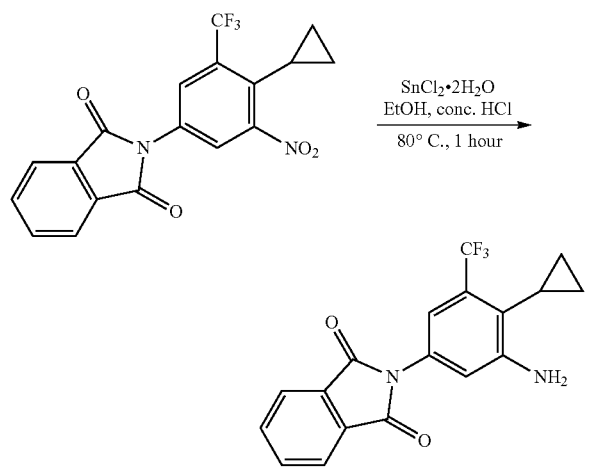

2-(4-Cyclopropyl-3-trifluoromethyl-5-nitrophenyl)isoindole-1,3-dione (110 mg, 0.3 mmol) was added to EtOH (15 ml), followed by $SnCl_2 \cdot 2H_2O$ (264 mg, 1.2 mmol), conc. HCl (0.5 ml) and heated at 80° C. for 1 hour. The solution was allowed to cool to room temperature and concentrated under reduced pressure. To this residue, ethyl acetate (10 ml) was added and washed with aqueous $K_2CO_3$ (10 ml). The 2 layers were separated, the organic layer was washed with brine (20 ml) and dried with $Na_2SO_4$. The solid was filtered off and the solution was concentrated under reduced pressure. The residue was purified by flash column chromatography (4:1 Hexanes:Ethyl Acetate) to give the title compound (40 mg, 40% yield).

$^1$H NMR (300 MHz, DMSO) δ 7.95-7.86 (m, 4H), 6.92 (s, 2H), 5.63 (s, 2H), 1.59 (m, 1H), 1.06 (m, 2H), 0.57 (d, J=5.1 Hz, 2H); LCMS (m/z): 347.14 (MH$^+$).

Example 108

2-[4-cyclopripyl-3-trifluoromethyl-5-(4,5-dihydro-4-methyl-5-oxotetrazol-1-yl)phenyl]isoindole-1,3-dione

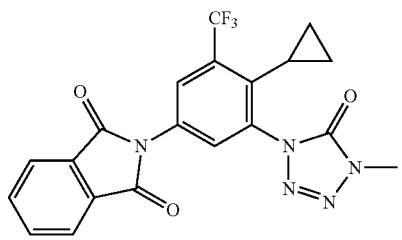 [SMILES: Cn1nnn(-c2cc(N3C(=O)c4ccccc4C3=O)cc(C(F)(F)F)c2C2CC2)c1=O]

2-(3-Amino-4-cyclopropyl-5-trifluoromethylphenyl)isoindole-1,3-dione (1.06 g, 3.1 mmol), was added to 22.8 ml of phosgene (20% in toluene), the mixture was heated at 100° C. for 1.5 hours. The reaction mixture was cooled to room temperature and concentrated under reduced pressure. To this residue, azidotrimethylsilane (42 ml, excess) was added and the solution was heated at 100° C. overnight. Cooled to room temperature, TMSN$_3$ was removed under reduced pressure. Ethyl acetate (10 ml) was added to this residue and concentrated under reduced pressure to give 2-[4-cyclopropyl-3-trifluoromethyl-5-(4,5-dihydro-4-H-5-oxotetrazol-1-yl)phenyl]isoindole-1,3-dione (1.28 g, 50% in purity) as a white solid. This solid was added to DMF (18 ml), followed by $K_2CO_3$ (1.24 g), and iodomethane (0.1 ml). The mixture was stirred under N$_2$, at room temperature overnight. Ethyl acetate (100 ml) and water (100 ml) was added to the mixture, the 2 layers were separated, the organic layer was washed with brine, dried with $Na_2SO_4$. The solid was filtered off, and the mother liquor was concentrated under reduced pressure. The title compound (500 mg, 38%) was obtained after purified through flash column chromatography (2:1 Hexanes:Ethyl Acetate).

$^1$H NMR (300 MHz, DMSO) δ 8.12 (s, 2H), 8.0-7.9 (m, 4H), 3.65 (s, 3H), 2.01 (m, 1H), 0.86 (m, 2H), 0.35 (d, J=5.4 Hz, 2H); LCMS (m/z): 430.22 (MH$^+$).

Example 109

1-(5-amino-2-cyclopropyl-3-trifluoromethylphenyl)-4-methyl-1H-tetrazol-5(4H)-one

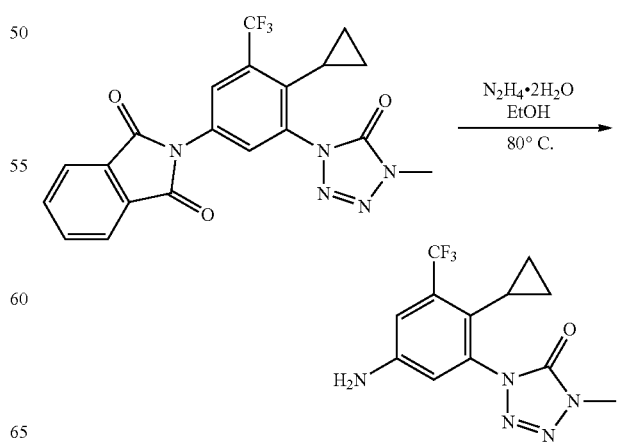

2-[4-Cyclopropyl-3-trifluoromethyl-5-(4,5-dihydro-4-methyl-5-oxotetrazol-1-yl)phenyl]isoindole-1,3-dione (500 mg, 1.16 mmol) was suspended in EtOH (10 ml), N$_2$H$_4$.2H$_2$O was added and the mixture was heated at 80° C. Solution turned from turbid to clear, then white solid crashed out, additional EtOH (1 ml) was added, and the solution was heated at 80° C. for 15 minutes. The solution was concentrated under reduced pressure and was sonicated with ethyl acetate (10 ml). The title compound (265 mg, 76% yield) as a white solid was obtained by filtering solution through a Buchner funnel fitted with a filter paper.

$^1$H NMR (300 MHz, DMSO) δ 7.05 (s, 1H), 7.78 (s, 1H), 5.89 (s, 2H), 3.61 (s, 3H), 1.7 (m, 1H), 0.65 (m, 2H), 0.12 (d, J=5.1 Hz, 2H); LCMS (m/z): 300.23 (MH$^+$).

Example 110

N2-{4-cyclopropyl-5-trifluoromethyl-[3-(4-methyl)-1,2,3,4-tetrazol-5-one-1-yl]}phenyl-5-fluoro-N4-(2,2,6,6-tetramethylpiperidin-4-yl)2,5-pyrimidinediamine (I-39)

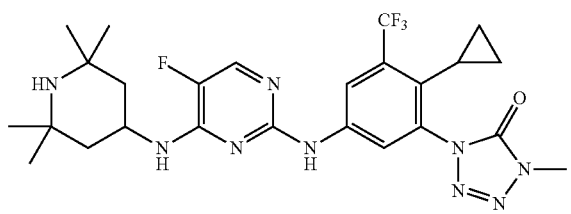

$^1$H NMR (300 MHz, DMSO) δ 9.54 (s, 1H), 8.26 (s, 1H), 8.04 (s, 1H), 7.91 (d, J=3.6 Hz, 1H), 7.29 (d, J=9.0 Hz, 1H), 4.25 (m, 1H), 3.63 (s, 3H), 1.81 (m, 1H), 1.64 (d, J=9.6 Hz, 2H), 1.24 (m, 2H), 1.02 (s, 6H), 0.99 (s, 6H), 0.72 (d, J=8.1 Hz, 2H), 0.16 (d, J=4.8 Hz, 2H); LCMS (m/z): 550.45 (MH$^+$).

Example 111

N2-{4-cyclopropyl-5-trifluoromethyl-[3-(4-methyl)-1,2,3,4-tetrazol-5-one-1-yl]}phenyl-5-fluoro-N4-(1,2,2,6,6-pentamethylpiperidin-4-yl)-2,4-pyrimidinediamine (I-40)

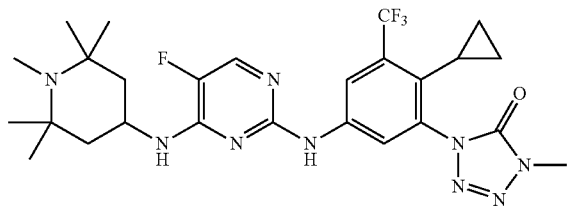

$^1$H NMR (300 MHz, DMSO) δ 9.54 (s, 1H), 8.25 (s, 1H), 8.05 (s, 1H), 7.91 (d, J=3.6 Hz, 1H), 7.29 (d, J=8.1 Hz, 1H), 4.21 (m, 1H), 3.64 (s, 3H), 2.13 (s, 3H), 1.8 (m, 1H), 1.64 (d, J=8.7 Hz, 2H), 1.4 (t, J=12.3 Hz, 2H), 1.03 (s, 6H), 0.88 (s, 6H), 0.72 (d, J=7.8 Hz, 2H), 0.17 (d, J=5.4 Hz, 2H); LCMS (m/z): 564.59 (MH$^+$).

Example 112

5-cyano-N2-{4-cyclopropyl-5-trifluoromethyl-[3-(4-methyl)-1,2,3,4-tetrazol-5-one-1-yl]}phenyl-N4-(2,2,6,6-tetramethylpiperidin-4-yl)-2,4-pyrimidinediamine (I-41)

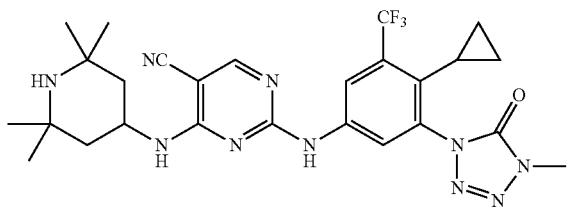

$^1$H NMR (300 MHz, DMSO) δ 8.57 (bs, 1H), 8.44 (s, 1H), 8.1 (bs, 2H), 7.85-7.75 (m, 2H), 4.42 (m, 1H), 3.64 (s, 3H), 1.87 (d, J=10.8 Hz, 2H), 1.6 (m, 2H), 1.32 (m, 12H), 0.77 (d, J=8.4 Hz, 2H), 0.18 (s, 2H); LCMS (m/z): 557.48 (MH$^+$).

Example 113

5-cyano-N2-{4-cyclopropyl-5-trifluoromethyl-[3-(4-methyl)-1,2,3,4-tetrazol-5-one-1-yl]}phenyl-N4-(1,2,2,6,6-pentamethylpiperidin-4-yl)-2,4-pyrimidinediamine (I-42)

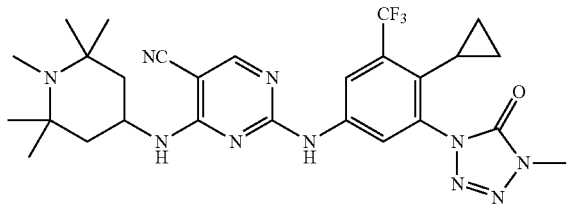

$^1$H NMR (300 MHz, DMSO) δ 8.54 (bs, 1H), 8.44 (s, 1H), 8.07 (bs, 2H), 7.87 (d, J=7.8 Hz, 1H), 4.42 (m, 1H), 3.65 (s, 3H), 2.69 (s, 3H), 2.05 (m, 1H), 1.98 (bs, 2H), 1.82 (m, 2H), 1.36 (m, 12H), 0.77 (d, J=8.4 Hz, 2H), 0.19 (s, 2H); LCMS (m/z): 571.47 (MH$^+$).

Example 114

1-(3-bromo-2-fluoro-5-nitrophenyl)-1H-tetrazol-5(4H)-one

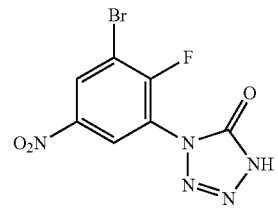 [SMILES: O=c1[nH]nnn1-c1cc([N+](=O)[O-])cc(Br)c1F]

To 3-bromo-2-fluoro-5-nitroaniline (400 mg, 1.7 mmol), was added to 4.23 ml of phosgene (20% in toluene), the mixture was heated at 100° C. for 1 hour. The reaction mixture was cooled to room temperature and concentrated under reduced pressure. To this residue, azidotrimethylsilane (16 ml, excess) was added and the solution was heated at 100° C. overnight. Cooled to room temperature, TMSN$_3$ was removed under reduced pressure. Ethyl Acetate (50 ml) was added to this residue and treated with saturated NaHCO$_3$ (50 ml). The aqueous layer was separated and acidified with 2N HCl, extracted with ethyl acetate (70 ml). The organic layer was washed with brine, dried with Na$_2$SO$_4$, filtered off solid, and concentrated under reduced pressure to give the title compound (210 mg, 42% yield).

$^1$H NMR (300 MHz, DMSO) δ 8.77-8.75 (m, 1H), 8.67-8.64 (m, 1H); LCMS (m/z): 303.88 (MH−).

Example 115

1-(3-bromo-2-fluoro-5-nitrophenyl)-4-methyl-1H-tetrazol-5(4H)-one

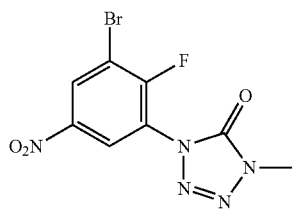 [SMILES: Cn1nnn(-c2cc([N+](=O)[O-])cc(Br)c2F)c1=O]

1-(3-Bromo-2-fluoro-5-nitrophenyl)-1H-tetrazol-5(4H)-one (210 mg, 0.7 mmol) was dissolved into DMF (3.5 ml), K$_2$CO$_3$ (286 mg, 2.1 mmol) was added to this solution and followed by iodomethane (0.064 ml, 1.03 mmol). The mixture was stirred at room temperature overnight. Ethyl acetate (10 ml) and brine (10 ml) were added to the mixture, and the layers were separated. The aqueous layer was extracted with ethyl acetate (2×10 ml), the organic layers were combined and dried with Na$_2$SO$_4$. The solid was filtered off and mother liquor was concentrated under reduced pressure. This residue was purified by flash column chromatography (3:1 Hexanes: Ethyl Acetate) to give the title compound as a white solid (120 mg, 55% yield).

$^1$H NMR (300 MHz, DMSO) δ 8.8-8.77 (m, 1H), 8.64-8.61 (m, 1H), 3.65 (s, 3H); LCMS (m/z): 315.90 (MH−).

Example 116

1-(3-cyclopropyl-2-fluoro-5-nitrophenyl)-4-methyl-1H-tetrazol-5(4H)-one

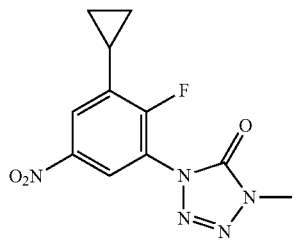

1-(3-Bromo-2-fluoro-5-nitrophenyl)-4-methyl-1H-tetrazol-5(4H)-one (120 mg, 0.38 mmol) was added to toluene/water (1.5 ml:0.3 ml), in a carousel reaction tube. To this solution, tricyclohexylphosphine (35 mg, 0.11 mmol), cesium carbonate (750 mg, 2.3 mmol), cyclopropylboronic acid MIDA ester (104 mg, 0.53 mmol) were added subsequently. This mixture was degassed by bubbling N$_2$ into the solution for 15 minutes, and finally palladium acetate (13 mg, 0.057 mmol) was added to the mixture and was heated at 100° C. with stirring under N$_2$ overnight. The solution was cooled to room temperature. Ethyl acetate and saturated K$_2$CO$_3$ was added to the mixture, and the two layers were separated. Organic layer was dried with Na$_2$SO$_4$, after filtering off the solid, the mother liquor was concentrated under reduced pressure. The residue was purified with chromatography using ethyl acetate and hexanes (1:4) as an eluent to give the title compound (80 mg, 76% yield).

$^1$H NMR (300 MHz, DMSO) δ 8.4-8.38 (m, 1H), 7.99-7.96 (m, 1H), 3.62 (s, 3H), 2.21 (m, 1H), 1.12 (m, 2H), 0.96 (m, 2H).

Example 117

1-(5-amino-3-cyclopropyl-2-fluorophenyl)-4-methyl-1H-tetrazol-5(4H)-one

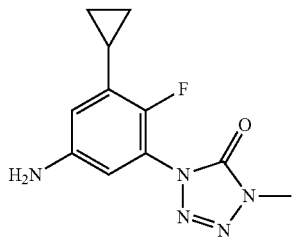 [SMILES: Cn1nnn(-c2cc([N+](=O)[O-])cc(C3CC3)c2F)c1=O]

1-(3-Cyclopropyl-2-fluoro-5-nitrophenyl)-4-methyl-1H-tetrazol-5(4H)-one (80 mg, 0.29 mmol) was added to EtOH (2 ml), followed by SnCl$_2$.2H$_2$O (217 mg, 1.16 mmol), concentrated HCl (0.6 ml) and heated at 80° C. for 0.5 hour. The solution was allowed to cool to room temperature and concentrated under reduced pressure. To this residue, ethyl acetate (5 ml) was added and washed with aqueous K$_2$CO$_3$ (5 ml). The 2 layers were separated and the aqueous layer was extracted with ethyl acetate (5 ml). The combined organic layers were dried with Na$_2$SO$_4$. The solid was filtered off and the solution was concentrated under reduced pressure to give the title compound (60 mg, 84% yield).

$^1$H NMR (300 MHz, DMSO) δ 6.48-6.45 (m, 1H), 6.29-6.26 (m, 1H), 5.23 (s, 2H), 3.59 (s, 3H), 1.97 (m, 1H), 0.96 (m, 2H), 0.64 (m, 2H); LCMS (m/z): 250.18 (MH$^+$).

Example 118

N2-{5-cyclopropyl-4-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine (I-43)

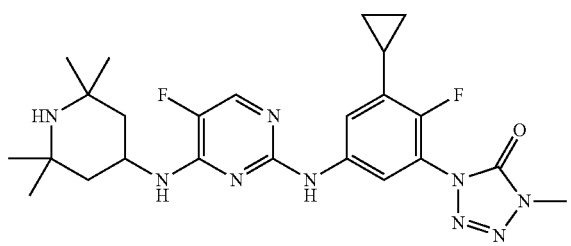

¹H NMR (300 MHz, DMSO) δ 9.1 (s, 1H), 8.07 (d, J=6.0 Hz, 1H), 7.85 (d, J=3.9 Hz, 1H), 7.2 (d, J=8.7 Hz, 1H), 7.11 (d, J=3.6 Hz, 1H), 4.28 (m, 1H), 3.6 (s, 3H), 2.45 (m, 1H), 1.62 (d, J=9.9 Hz, 2H), 1.12 (m, 4H), 0.98 (m, 12H), 0.7 (m, 2H); LCMS (m/z): 500.47 (MH⁺).

Example 119

5-cyano-N2-{5-cyclopropyl-4-fluoro-[3-(4-methyl)-1,2,3,4-tetrazol-5-one-1-yl]}phenyl-N4-(2,2,6,6-tetramethylpiperidin-4-yl)-2,4-pyrimidinediamine (I-44)

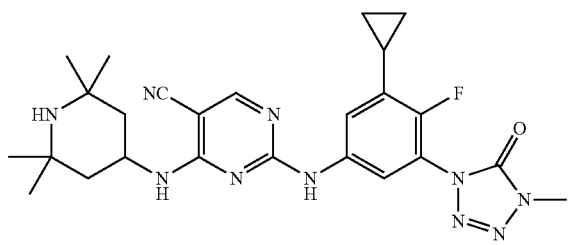

¹H NMR (300 MHz, DMSO) δ 9.84 (bs, 1H), 8.33 (s, 1H), 7.82 (bs, 1H), 7.45 (bs, 1H), 7.14 (bs, 1H), 4.26 (m, 1H), 3.59 (s, 3H), 2.05 (m, 1H), 1.58 (bs, 2H), 1.26 (m, 4H), 1.01 (m, 12H), 0.73 (m, 2H); LCMS (m/z): 507.41 (MH⁺).

Example 120

2,3-dimethyl-5-nitrophenylisocyanate

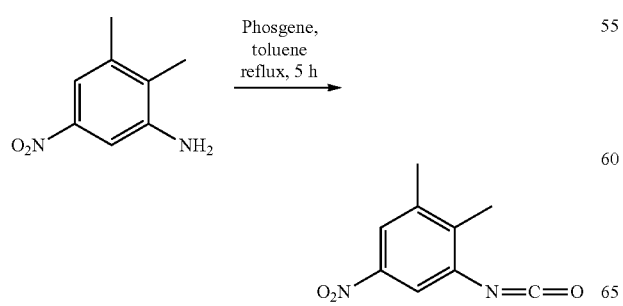

A solution of 2,3-dimethyl-5-nitroaniline (1.0 g, 6.02 mmol, 1 equiv) in 20% of phosgene in toluene (9.5 mL, 18.06 mmol, 3 equiv) was refluxed for 5 hours. The reaction mixture was then concentrated and the resulting residue was directly used in the next step.

¹H NMR (CDCl₃, 300 MHz): δ 7.88 (s, 1H), 7.83 (s, 1H), 2.39 (s, 3H), 2.33 (s, 3H).

Example 121

1-(2,3-dimethyl-5-nitrophenyl)-4,5-dihydro-5H-tetrazol-5-one

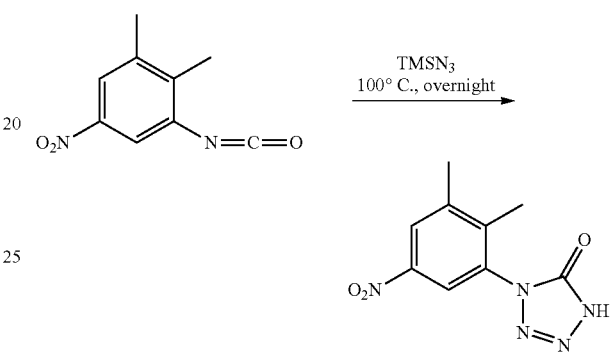

To the above residue of Example 120, 3.2 mL of TMSN₃ (24.08 mmol, 4 equiv) was added and then the resulting mixture was heated at 100° C. overnight. After being cooled to room temperature, the reaction mixture was concentrated. The residue was diluted with EtOAc (50 mL) and saturated aqueous NaHCO₃ (50 mL). The aqueous layer was separated, neutralized with 2 N HCl to pH 4~5 and extracted with EtOAc (2×50 mL). The organic layers were combined, dried over MgSO₄ and concentrated to give a beige solid (1.0 g, 71% two steps) which was directly used in the next step.

¹H NMR (DMSO-d₆, 300 MHz): δ 8.26 (s, 1H), 8.22 (s, 1H), 2.45 (s, 3H), 2.17 (s, 3H); m/z=236 (M)⁺.

Example 122

1-(2,3-dimethyl-5-nitrophenyl)-4-methyl-5H-tetrazol-5-one

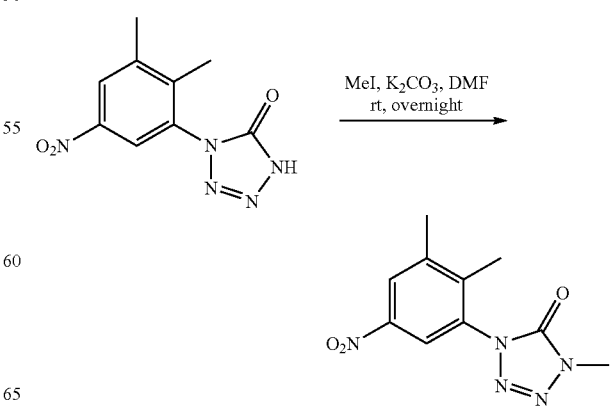

To a mixture of 1-(2,3-dimethyl-5-nitrophenyl)-4,5-dihydr-5H-tetrazol-5-one (1.0 g, 4.26 mmol, 1 equiv) and K₂CO₃ (1.76 g, 12.76 mmol, 3 equiv) in 8 mL of DMF was added MeI (0.8 mL, 12.76 mmol, 3 equiv) and the resulting mixture was stirred at room temperature overnight. A pale yellow solid crashed out, filtered, washed with water and dried to give 1.0 g of product (94%). m/z=250 (M)⁺.

Example 123

1-(5-amino-2,3-dimethylphenyl)-4-methyl-5H-tetrazol-5-one

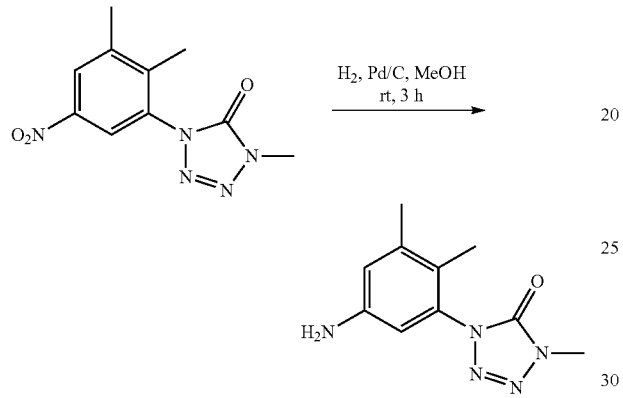

A solution of 1-(2,3-dimethyl-5-nitrophenyl)-4-methyl-5H-tetrazol-5-one (1.0 g, 4.01 mmol, 1 equiv) in 20 mL of MeOH in the presence of 50 mg of 10% Pd/C was hydrogenated at room temperature for 3 hours. The reaction mixture was then filtered over a pad of Celite and washed with MeOH. The solvent was concentrated to give the product in quantitative yield.

¹H NMR (CDCl₃, 300 MHz): δ 6.91 (s, 1H), 6.85 (s, 1H), 6.75 (br. s, 1H), 5.22 (br. s, 1H), 2.31 (s, 3H), 2.05 (s, 3H); m/z=220 (M+H)⁺.

Example 124

N2-(4,5-dimethyl-3-(4-methyl-4,5-dihydro-5-oxo-1H-tetrazol-1-yl)phenyl)-5-fluoro-N4-(1,2,2,6,6-pentamethylpiperidin-4-yl)pyrimidine-2,4-diamine
(I-45)

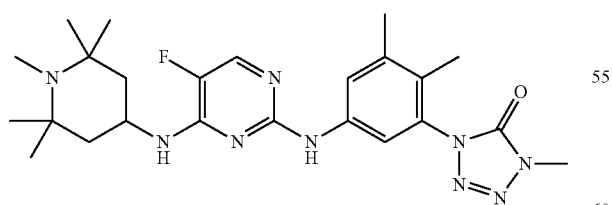

¹H NMR (DMSO-d₆, 300 MHz): δ 9.11 (s, 1H), 7.85 (d, J=3.6 Hz, 1H), 7.76 (s, 1H), 7.45 (s, 1H), 7.38 (d, J=8.4 Hz, 1H), 4.28-4.18 (m, 1H), 3.60 (s, 3H), 2.24 (s, 3H), 2.13 (s, 3H), 1.88 (s, 3H), 1.62 (dm, J=11.4 Hz, 2H), 1.40 (tm, J=12.9, 12.0 Hz, 2H), 1.03 (s, 6H), 0.86 (s, 6H); m/z=484 (M+H)⁺.

Example 125

N2-(4,5-dimethyl-3-(4-methyl-4,5-dihydro-5-oxo-1H-tetrazol-1-yl)phenyl)-5-fluoro-N4 -(2,2,6,6-tetramethylpiperidin-4-yl)pyrimidine-2,4-diamine
(I-46)

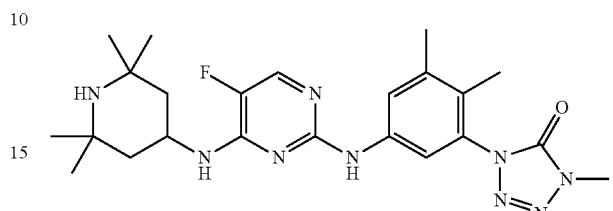

¹H NMR (DMSO-d₆, 300 MHz): δ9.11 (s, 1H), 7.85 (d, J=3.9 Hz, 1H), 7.78 (s, 1H), 7.44 (s, 1H), 7.14 (d, J=8.7 Hz, 1H), 4.35-4.25 (m, 1H), 3.59 (s, 3H), 2.24 (s, 3H), 1.88 (s, 3H), 1.62 (dm, J=10.8 Hz, 2H), 1.14-1.08 (m, 2H), 0.99 (s, 6H), 0.98 (s, 6H); m/z=470 (M+H)⁺.

Example 126

5-nitro-3-trifluoromethylphenylisocyanate

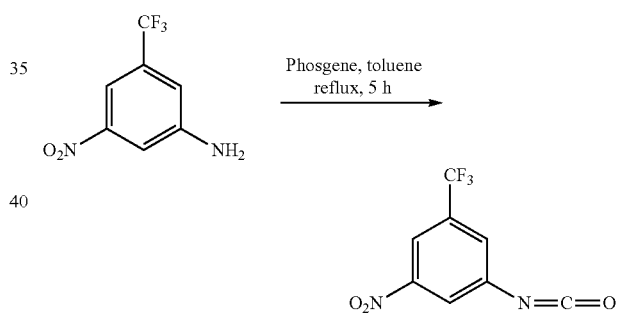

A solution of 3-amino-5-nitrobenzotrifluoride (3.3 g, 16.01 mmol, 1 equiv) in 20% of phosgene in toluene (16.85 mL, 32.02 mmol, 2 equiv) was refluxed for 5 hours. The reaction mixture was then concentrated and the resulting residue was directly used in the next step.

Example 127

1-(5-nitro-3-trifluoromethylphenyl)-4,5-dihydro-5H-tetrazol-5-one

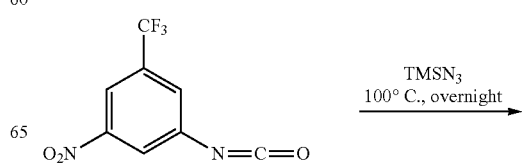

-continued

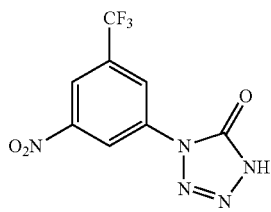

To the above residue 4.3 mL of TMSN₃ (32.02 mmol, 2 equiv) was added and then the resulting mixture was heated at 100° C. overnight. After being cooled to room temperature, the reaction mixture was concentrated. The residue was diluted with EtOAc (100 mL) and saturated aqueous NaHCO₃ (50 mL). The organic layer was separated and concentrated. The residue was purified by column chromatography on silica gel using EtOAc/hexanes/HOAc (6:4:0.05) as eluent to give 1.42 g of product (32% two steps). m/z=276 (M+H)⁺.

Example 128

1-(5-nitro-3-trifluoromethylphenyl)-4-methyl-5h-tetrazol-5-one

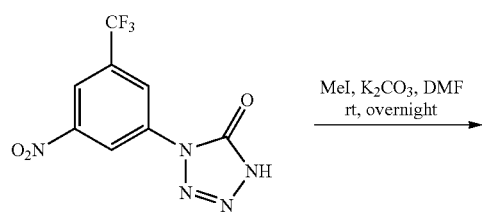

To a mixture of 1-(5-nitro-3-trifluoromethylphenyl)-4,5-dihydro-5H-tetrazol-5-one (1.42 g, 5.16 mmol, 1 equiv) and K₂CO₃ (2.14 g, 15.49 mmol, 3 equiv) in 25 mL of DMF was added MeI (1.0 mL, 15.49 mmol, 3 equiv) and the resulting mixture was stirred at room temperature overnight. The reaction mixture was diluted with water and extracted with EtOAc. The organic layer was separated and concentrated. The residue was triturated in water to give 1.41 g of product (95%) as a yellow solid. m/z=289 (M).

Example 129

1-(5-amino-3-trifluoromethylphenyl)-4-methyl-5H-tetrazol-5-one

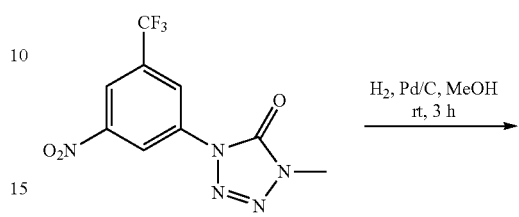

A solution of 1-(5-nitro-3-trifluoromethylphenyl)-4-methyl-5H-tetrazol-5-one (0.7 g, 2.42 mmol, 1 equiv) in 10 mL of MeOH in the presence of 50 mg of 10% Pd/C was hydrogenated at room temperature for 3 hours. The reaction mixture was then filtered over a pad of Celite and washed with MeOH. The solvent was concentrated to give the product in quantitative yield. m/z=259 (M)⁺.

Example 130

N2-(3-(4-methyl-4,5-dihydro-5-oxo-1H-tetrazol-1-yl)-5-trifluoromethylphenyl)-5-fluoro-N4-(1,2,2,6,6-pentamethylpiperidin-4-yl)pyrimidine-2,4-diamine (I-47)

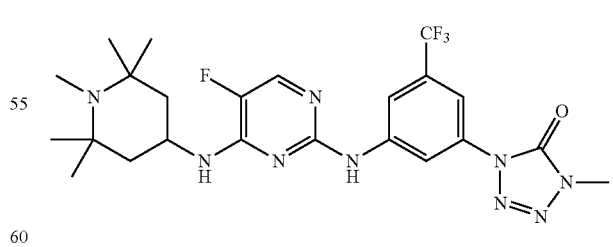

¹H NMR (DMSO-d₆, 300 MHz): δ 9.58 (s, 1H), 8.55 (s, 1H), 8.03 (s, 1H), 7.94 (d, J=3.9 Hz, 1H), 7.64 (s, 1H), 7.29 (d, J=7.2 Hz, 1H), 4.28-4.18 (m, 1H), 3.60 (s, 3H), 2.13 (s, 3H), 1.66 (dm, J=8.7 Hz, 2H), 1.40 (tm, J=13.8, 10.2 Hz, 2H), 1.03 (s, 6H), 0.92 (s, 6H); m/z=524 (M+H)⁺.

Example 131

N2-(3-(4-methyl-4,5-dihydro-5-oso-1H-tetrazol-1-yl)-5-trifluoromethylphenyl)-5-fluoro-N4-(2,2,6,6-tetramethylpiperidin-4-yl)pyrimidine-2,5-diamine (I-48)

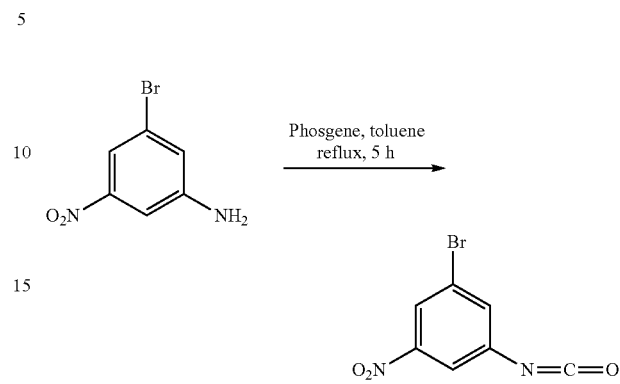

$^1$H NMR (DMSO-d$_6$, 300 MHz): δ 9.58 (s, 1H), 8.56 (s, 1H), 8.03 (s, 1H), 7.94 (d, J=3.9 Hz, 1H), 7.64 (s, 1H), 7.45 (s, 1H), 7.30 (d, J=7.2 Hz, 1H), 4.45-4.35 (m, 1H), 3.59 (s, 3H), 1.69 (dm, J=10.8 Hz, 2H), 1.15-1.10 (m, 2H), 1.08 (s, 6H), 1.02 (s, 6H); m/z=510 (M+H)$^+$.

Example 132

3-bromo-5-nitroaniline

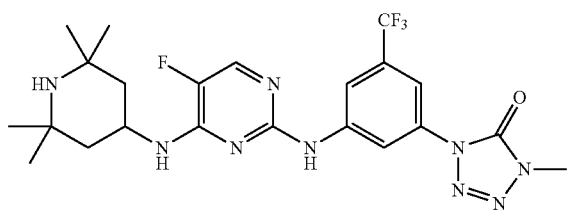

To a solution of 1-bromo-3,5-dinitrobenzene (3.0 g, 12 mmol, 1 equiv) in EtOH (15 mL) at room temperature was added 20% of (NH$_4$)$_2$S in water (9.0 mL, 26 mmol, 2.2 equiv). The mixture was then refluxed for 2 hours. After being cooled to room temperature, the reaction mixture was diluted with EtOAc and water. The organic layer was separated, washed with brine and concentrated. The residue was purified by column chromatography on silica gel using EtOAc/hexanes (1:4) as eluent to give 2.2 g of 3-bromo-5-nitroaniline (84%) as an orange solid.

$^1$H NMR (CDCl$_3$, 300 MHz): δ 7.70 (s, 1H), 7.41 (d, J=1.8 Hz, 1H), 7.08 (d, J=1.5 Hz, 1H), 4.07 (br. s, 2H); m/z=217 (M)$^+$.

Example 133

3-bromo-5-nitrophenylisocyanate

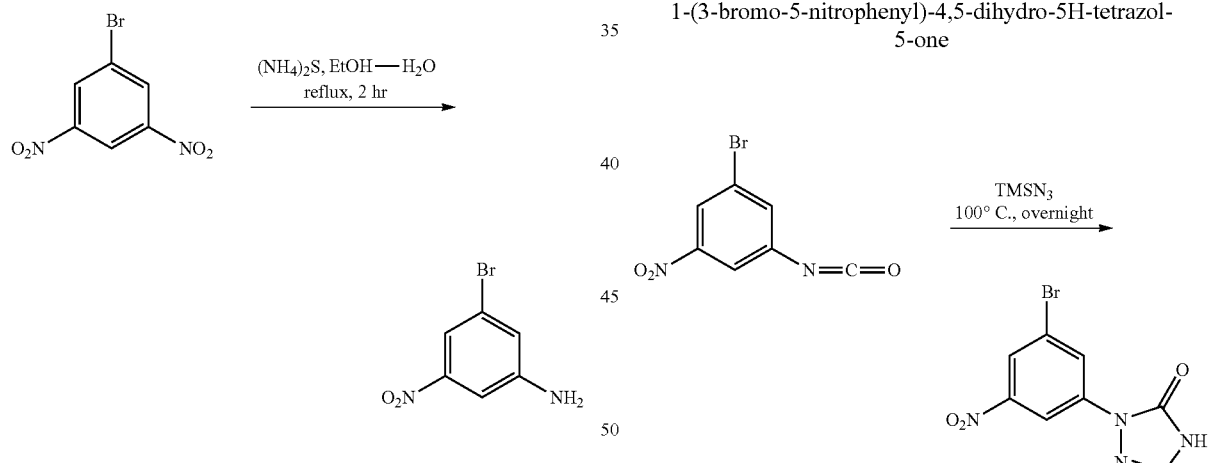

A solution of 3-bromo-5-nitroaniline (500 mg, 2.3 mmol, 1 equiv) in 20% of phosgene in toluene (2.5 mL, 4.6 mmol, 2 equiv) was refluxed for 5 hours. The reaction mixture was then concentrated and the resulting residue was directly used in the next step.

$^1$H NMR (CDCl$_3$, 300 MHz): δ 8.21 (s, 1H), 7.90 (s, 1H), 7.58 (s, 1H).

Example 134

1-(3-bromo-5-nitrophenyl)-4,5-dihydro-5H-tetrazol-5-one

To the above residue 1.2 mL of TMSN$_3$ (9.2 mmol, 4 equiv) was added and then the resulting mixture was heated at 100° C. overnight. After being cooled to room temperature, the reaction mixture was concentrated. The residue was diluted with EtOAc (20 mL) and saturated aqueous NaHCO$_3$ (20 mL). The aqueous layer was separated, neutralized with 2 N HCl to pH 4-5 and extracted with EtOAc (2×30 mL). The organic layers were combined, dried over MgSO$_4$ and concentrated to give the product (370 mg, 56% two steps) which was directly used in the next step. m/z=283.97 (M−H)$^+$ for $^{79}$Br.

Example 135

1-(3-bromo-5-nitrophenyl)-4-methyl-5H-tetrazol-5-one

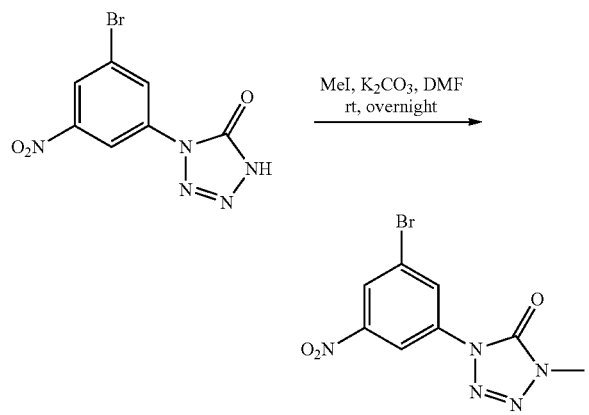

To a mixture of 1-(3-bromo-5-nitrophenyl)-4,5-dihydro-5H-tetrazol-5-one (200 mg, 0.7 mmol, 1 equiv) and K$_2$CO$_3$ (290 mg, 2.1 mmol, 3 equiv) in 5 mL of DMF was added MeI
mL, 2.1 mmol, 3 equiv) and the resulting mixture was stirred at room temperature overnight. The reaction mixture was diluted with water and extracted with EtOAc. The organic layer was separated and concentrated. The residue was triturated in water to give 150 mg of product (74%) as a pale yellow solid.

$^1$H NMR (DMSO-d$_6$, 300 MHz): δ 8.66 (d, J=0.9 Hz, 1H), 8.47 (d, J=1.8 Hz, 1H), 8.44 (t, J=2.1, 1.5 Hz, 1H), 3.62 (s, 3H); m/z=300.0 (M+H)$^+$ for $^{79}$Br.

Example 136

3-(4,5-dihydro-4-methyl-5-oxotetrazol-1-yl)-5-nitrobenzene

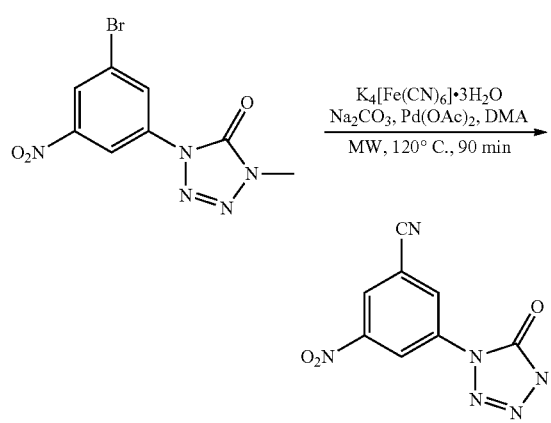

A mixture of 1-(3-bromo-5-nitrophenyl)-4-methyl-5H-tetrazol-5-one (100 mg, 0.34 mmol, 1 equiv), K$_4$[Fe(CN)$_6$]·3H$_2$O (215 mg, 0.51 mmol, 1.5 equiv), Pd(OAc)$_2$ (8 mg, 0.034 mmol, 0.1 equiv) and Na$_2$CO$_3$ (54 mg, 0.51 mmol, 1.5 equiv) in 3 mL of DMA was degassed under N$_2$ for 1 minute and then irridated under MW at 120° C. for 90 minutes. The reaction mixture was directly purified by column chromatography on silica gel using EtOAc/hexanes (3:7) as eluent to give 47 mg of product (56%).

$^1$H NMR (CDCl$_3$, 300 MHz): δ 9.15 (dd, J=1.8, 1.2 Hz, 1H), 8.76 (dd, J=1.5, 1.2 Hz, 1H), 8.48 (dd, J=1.5, 1.2 Hz, 1H), 3.76 (s, 3H);

Example 137

Alternative Preparation of 3-(4,5-dihydro-4-methyl-5-oxotetrazol-1-yl)-5-nitrobenzonitrile

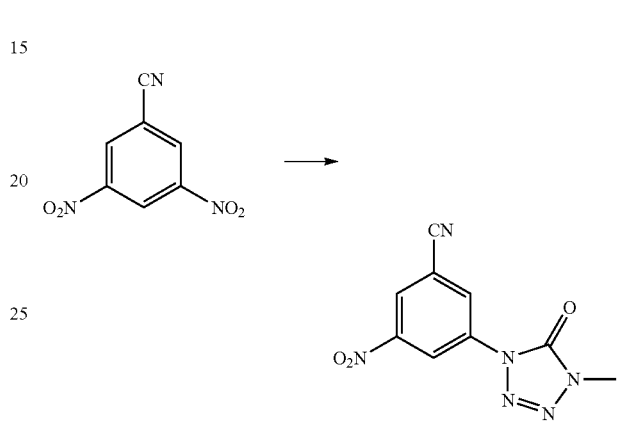

A mixture of 3,5-dinitrobenzonitrile (386 mg, 2.0 mmol), 1-methyl-1H-tetrazol-5(4H)-one (400 mg, 4.0 mmol) and K$_2$CO$_3$ (552 mg, 4.0 mmol) in NMP (6 mL) was heated to 110° C. and stirred overnight. After allowing to cool, the mixture was poured in to H$_2$O (75 mL) and EtOAc (40 mL). The aqueous and organic layers were partitioned and the aqueous layer was extracted with EtOAc (2×30 mL). The combined organic extracts were washed with brine (1×20 mL), dried (Na$_2$SO$_4$), filtered and the solvent removed under vacuum to leave a crude residue. The residue was purified by column chromatography on silica gel using EtOAc/hexane (3:7 to 4:6) as eluent to give the product (182 mg, 37%) as a solid.

Data identical to previously synthesized material. (Example 136)

Note: 1-methyl-1H-tetrazol-5(4H)-one was prepared according to procedure detailed in EP643049 (1995); Preparation of 1-substituted-5(4H)-tetrazolinones by desulfurization of tetrazolinethiones, which is hereby incorporated by reference.

Example 138

5-amino-3-(4,5-dihydro-4-methyl-5-oxotetrazol-1-yl)benzonitrile

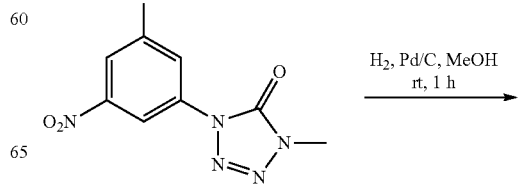

-continued

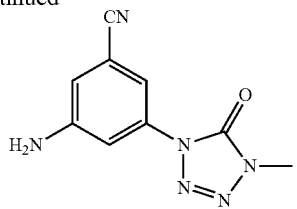

A solution of 1-(3-cyano-5-nitrophenyl)-4-methyl-5H-tetrazol-5-one (200 mg, 0.81 mmol, 1 equiv) in 10 mL of MeOH in the presence of 20 mg of 10% Pd/C was hydrogenated at room temperature for 1 hour. The reaction mixture was then filtered over a pad of Celite and washed with MeOH. The solvent was concentrated to give the product in quantitative yield. m/z=217.2 (M+H)$^+$.

Example 139

N3-(5-cyano-3-(4-methyl-4,5-dihysro-5-oxo-1H-tetrazol-1-yl)phenyl)-5-fluoro-N4-(2,3,3,6,6-pentamethylpiperidin-4-yl)pyridimine-2,4-diamine (I-49)

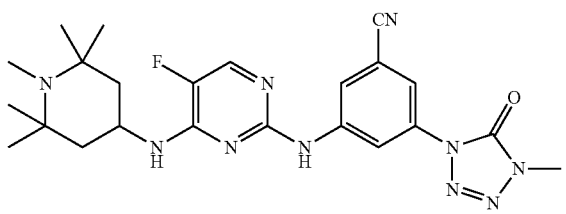

$^1$H NMR (DMSO-d$_6$, 300 MHz): δ 9.66 (s, 1H), 8.40 (s, 1H), 8.20 (s, 1H), 7.94 (d, J=3.6 Hz, 1H), 7.72 (s, 1H), 7.34 (d, J=7.2 Hz, 1H), 4.35-4.25 (m, 1H), 3.60 (s, 3H), 1.97 (s, 3H), 1.66 (dm, J=10.8 Hz, 2H), 1.41 (tm, J=12.3, 12.0 Hz, 2H), 1.04 (s, 6H), 0.97 (s, 6H); m/z=481.4 (M+H)$^+$.

Example 140

N2-(5-cyano-3-(4-methyl-4,5-dihysro-5-oxo-1H-tetrazol-1-yl)phenyl)-5-fluoro-N4-(2,2,6,6-tetramethylpiperidin-4-yl)pyrimidine-2,4-diamine (I-50)

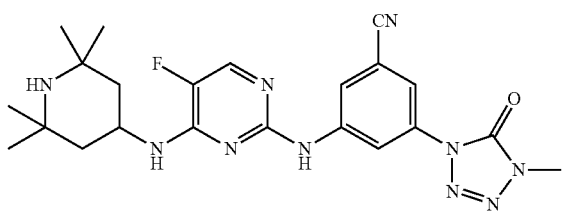

$^1$H NMR (DMSO-d$_6$, 300 MHz): δ 9.66 (s, 1H), 8.41 (s, 1H), 8.19 (s, 1H), 7.94 (d, J=3.6 Hz, 1H), 7.72 (s, 1H), 7.34 (d, J=8.1 Hz, 1H), 4.40-4.30 (m, 1H), 3.59 (s, 3H), 1.68 (dm, J=9.6 Hz, 2H), 1.14 (tm, J=12.0 Hz, 2H), 1.11 (s, 6H), 1.00 (s, 6H); m/z=467.4 (M+H)$^+$.

Example 141

3,5-dinitro-2-isopropoxybenzotrifluoride

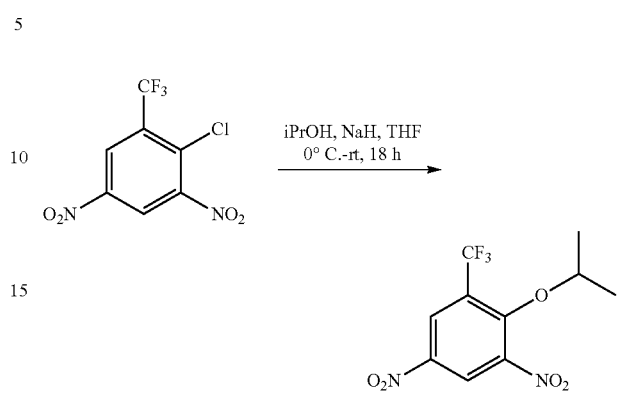

iPrOH (4.3 mL, 55.44 mmol, 3 equiv) was added to a suspension of NaH (1.11 g, 27.72 mmol, 1.5 equiv, 60%) in 20 mL of THF at 0° C. and stirred for 30 minutes. A solution of 2-chloro-3,5-dinitrobenzotrifluoride (5.0 g, 18.48 mmol, 1 equiv) in 10 mL of THF was then added dropwise. The reaction was left to reach room temperature overnight. THF was evaporated and water was added to the residue. The aqueous phase was extracted with a mixture of hexanes/EtOAc (4/1, 2×100 mL). The organic layers were combined and concentrated. The residue was purified by column chromatography on silica gel using EtOAc/hexanes (1:9) as eluent to give 3.3 g of product (60%) as a dark yellow oil.

$^1$H NMR (CDCl$_3$, 300 MHz): δ 8.82 (s, 1H), 8.70 (s, 1H), 4.59 (sept, J=6.0 Hz, 1H), 1.36 (d, J=6.0 Hz, 6H).

Example 142

3-hydroxyamino-2-isopropoxy-5-nitrobenzotrifluoride

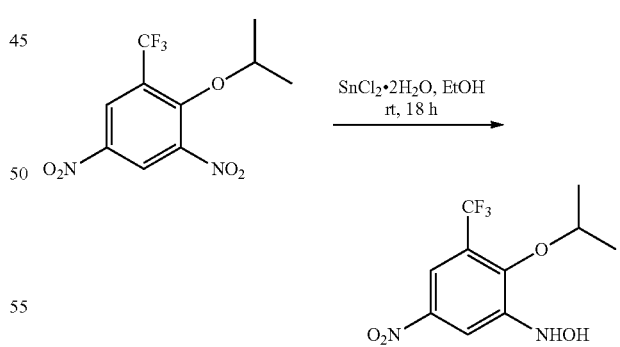

A mixture of 2.2 g of 3,5-dinitro-2-isopropoxybenzotrifluoride (7.5 mmol, 1 equiv) and 5.0 g of SnCl$_2$·2H$_2$O (22.5 mmol, 3 equiv) in 50 mL of EtOH was stirred at room temperature for 3 hours. The solvent was evaporated and the residue was diluted with 2N NaOH and EtOAc. The organic layer was separated and concentrated. The residue was purified by column chromatography on silica gel using EtOAc/hexanes (1:4) as eluent to give 1.1 g of product (52%).

¹H NMR (CDCl₃, 300 MHz): δ 8.30 (d, J=2.1 Hz, 1H), 8.08 (d, J=2.4 Hz, 1H), 7.19 (br. s, 1H), 5.56 (br. s, 1H), 4.67 (sept, J=6.3 Hz, 1H), 1.31 (d, J=6.0 Hz, 6H). m/z=279.2 (M−H)⁺.

Example 143

3-amino-2-isopropoxy-5-nitrobenzotrifluoride

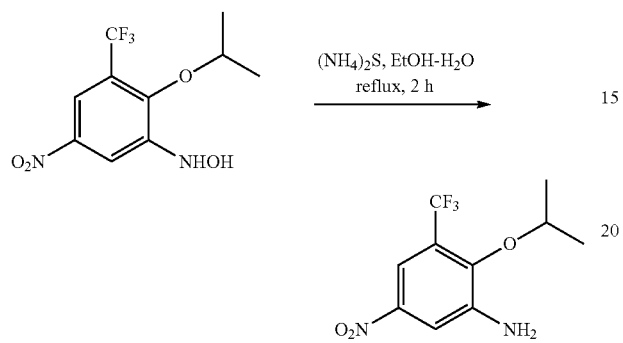

To a solution of 3-hydroxyamino-2-isopropoxy-5-nitrobenzotrifluoride (32 mg, 0.11 mmol, 1 equiv) in EtOH (1 mL) at room temperature was added 20% of (NH₄)₂S in water (0.04 mL, 0.11 mmol, 1.0 equiv). The mixture was then refluxed for 2 hours. After being cooled to rt, the reaction mixture was diluted with EtOAc and water. The organic layer was separated, washed with brine and concentrated. The residue was purified by column chromatography on silica gel using EtOAc/hexanes (1:4) as eluent to give 16 mg of product (55%) as a yellow solid. ¹H NMR (CDCl₃, 300 MHz): δ 7.86 (s, 1H), 7.73 (s, 1H), 4.66 (sept, J=6.0 Hz, 1H), 1.34 (d, J=6.3 Hz, 6H). m/z=263.1 (M−H)⁺.

Example 144

2-isopropoxy-5-nitro-3-trifluoromethylphenylisocyanate

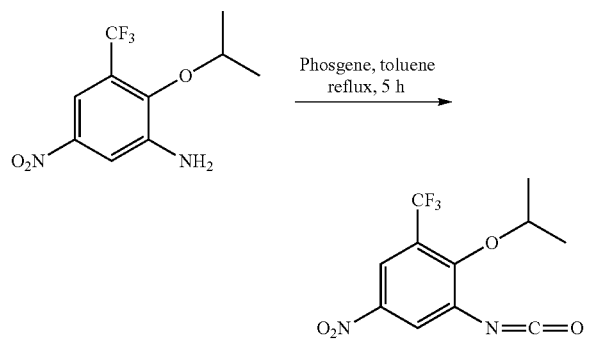

A solution of 3-amino-2-isopropoxy-5-nitrobenzotrifluoride (520 mg, 1.97 mmol, 1 equiv) in 20% of phosgene in toluene (6.0 mL, 11.82 mmol, 6 equiv) was refluxed for 5 hours. The reaction mixture was then concentrated and the resulting residue was directly used in the next step.

¹H NMR (CDCl₃, 300 MHz): δ 8.34 (s, 1H), 8.12 (s, 1H), 4.89 (m, 1H), 1.40 (d, J=6.3 Hz, 6H).

Example 145

1-(2-isopropoxy-5-nitro-3-trifluoromethylphenyl)-4,5-dihysro-5H-tetrazol-5-one

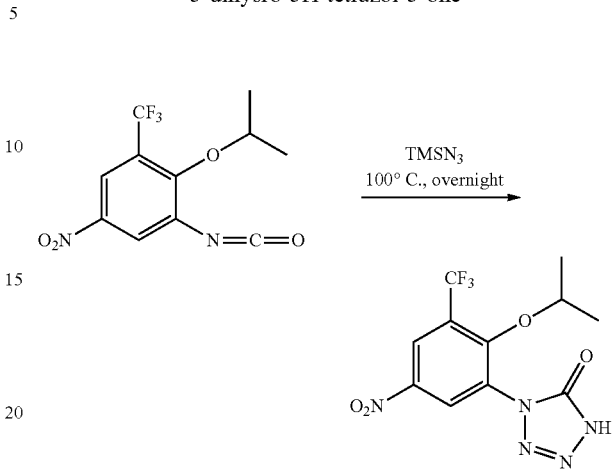

To the above residue 1.1 mL of TMSN₃ (7.88 mmol, 4 equiv) was added and then the resulting mixture was heated at 100° C. overnight. After being cooled to room temperature, the reaction mixture was concentrated. The residue was diluted with EtOAc (20 mL) and saturated aqueous NaHCO₃ (20 mL). The aqueous layer was separated, neutralized with 2 N HCl to pH 4~5 and extracted with EtOAc (2×20 mL). The organic layers were combined, dried over MgSO₄ and concentrated to give a yellow solid (270 mg, 41% two steps) which was directly used in the next step. m/z=332.2 (M)⁺.

Example 146

1-(2-isopropoxy-5-nitro-3-trifluoromethylphenyl)-4-methyl-5H-tetrazol-5-one

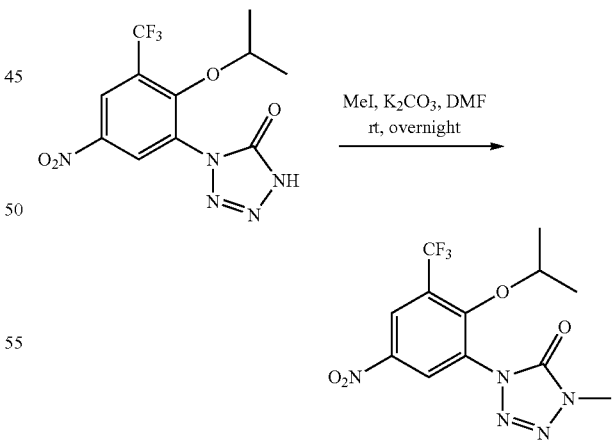

To a mixture of 1-(2-isopropoxy-5-nitro-3-trifluoromethylphenyl)-4,5-dihydro-5H-tetrazol-5-one (270 mg, 0.81 mmol, 1 equiv) and K₂CO₃ (335 mg, 2.43 mmol, 3 equiv) in 5 mL of DMF was added MeI (0.15 mL, 2.43 mmol, 3 equiv) and the resulting mixture was stirred at room temperature overnight. The reaction mixture was diluted with water and extracted with EtOAc. The organic layer was separated and concentrated. The residue was triturated in water to give 200 mg of product (71%). m/z=347 (M)+.

Example 147

1-(5-amino-2-isopropoxy-3-trifluoromethylphenyl)-4-methyl-5H-tetrazol-5-one

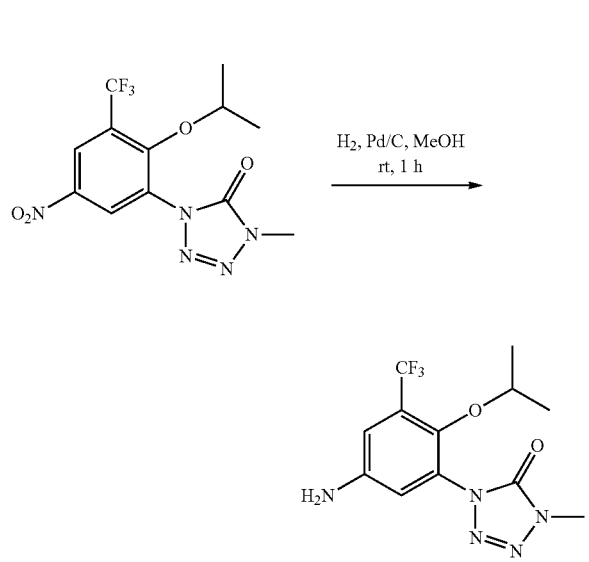

A solution of 1-(2-isopropoxy-5-nitro-3-trifluoromethylphenyl)-4-methyl-5H-tetrazol-5-one (200 mg, 0.58 mmol, 1 equiv) in 10 mL of MeOH in the presence of 20 mg of 10% Pd/C was hydrogenated at room temperature for 1 hour. The reaction mixture was then filtered over a pad of Celite and washed with MeOH. The solvent was concentrated to give the product in quantitative yield. m/z=318.3 (M+H)+.

Example 148

N2-(4-isopropoxy-3-(4-methyl-4,5-dihysro-5-oxo-1H-tetrazol-1-yl)-5-trifluoromethylphenyl)-5-fluoro-N4-(2,2,6,6-tetramethylpiperidin-4-yl)pyrimidine-2,4-diamine (I-51)

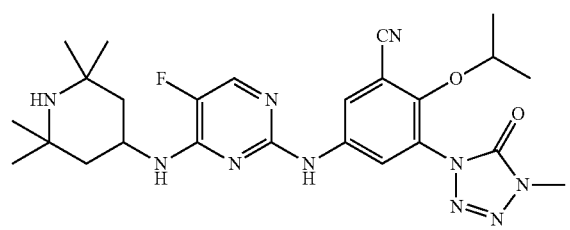

$^1$H NMR (DMSO-d$_6$, 300 MHz): δ 9.42 (s, 1H), 8.17 (s, 1H), 8.02 (s, 1H), 7.89 (d, J=3.6 Hz, 1H), 7.25 (d, J=9.3 Hz, 1H), 4.30-4.20 (m, 1H), 3.82 (sept. J=6.9 Hz, 1H), 3.62 (s, 3H), 1.63 (dm, J=11.7 Hz, 2H), 1.13 (dm, J=10.8 Hz, 2H), 1.01 (s, 6H), 0.99 (d, J=7.8 Hz, 6H), 0.98 (s, 6H); m/z=568 (M+H)+.

Example 149

N2-(4-isopropoxy-3-(4-methyl-4,5-dihysro-5-oxo-1H-tetrazol-1-yl)-5-trifluoromethylphenyl)-5-fluoro-N4-(1,2,2,6,6-pentamethylpiperidin-4-yl)pyrimidine-2,4-diamine (I-52)

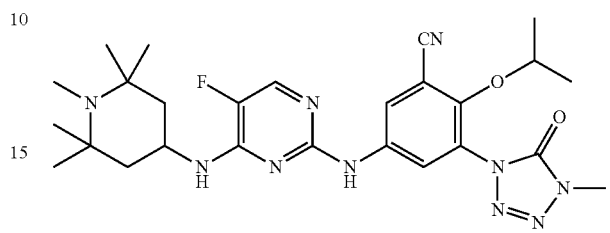

$^1$H NMR (DMSO-d$_6$, 300 MHz): δ 9.42 (s, 1H), 8.15 (s, 1H), 8.03 (s, 1H), 7.89 (d, J=3.6 Hz, 1H), 7.26 (d, J=7.8 Hz, 1H), 4.25-4.15 (m, 1H), 3.82 (sept. J=6.9 Hz, 1H), 3.62 (s, 3H), 2.13 (s, 3H), 1.64 (dm, J=10.8 Hz, 2H), 1.40 (dm, J=11.4 Hz, 2H), 1.03 (s, 6H), 0.99 (d, J=6.3 Hz, 6H), 0.89 (s, 6H); m/z=582.4 (M+H)+.

Example 150

3-amino-2-methyl-5-nitrobenzotrifluoride

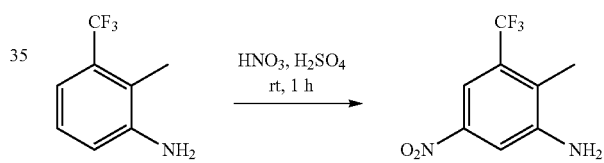

70% HNO$_3$ (1.96 mL, 32.6 mmol, 1.1 equiv) was added dropwise to a mixture of 3-amino-2-methylbenzotrifluoride (5.0 g, 28.55 mmol, 1 equiv) in 30 mL of fuming H$_2$SO$_4$ at 0° C. Then the mixture was left to reach room temperature and stirred for 1 hour. Poured into ice and the aqueous phase was extracted with EtOAc. The organic layer was separated, washed with saturated NaHCO$_3$ and concentrated. The residue was purified by column chromatography on silica gel using EtOAc/hexanes (3:7) as eluent to give 1.6 g of product (25%) as a yellow solid.

$^1$H NMR (CDCl$_3$, 300 MHz): δ 7.91 (s, 1H), 7.67 (s, 1H), 4.13 (br. s, 2H), 2.31 (s, 3H). m/z=221.1 (M+H)+.

Example 151

2-methyl-5-nitro-3-trifluoromethylphenylisocyanate

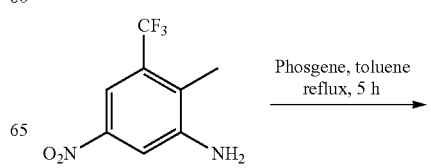

-continued

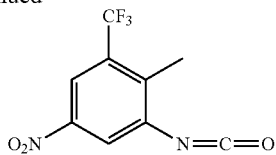

A solution of 3-amino-2-methyl-5-nitrobenzotrifluoride (700 mg, 3.2 mmol, 1 equiv) in 20% of phosgene in toluene (3.4 mL, 6.4 mmol, 2 equiv) was refluxed for 5 hours. The reaction mixture was then concentrated and the resulting residue was directly used in the next step.

$^1$H NMR (CDCl$_3$, 300 MHz): δ 8.36 (s, 1H), 8.17 (s, 1H), 2.55 (s, 3H).

Example 152

1-(2-methyl-5-nitro-3-trifluoromethylphenyl)-4,5-dihysro-5H-tetrazol-5-one

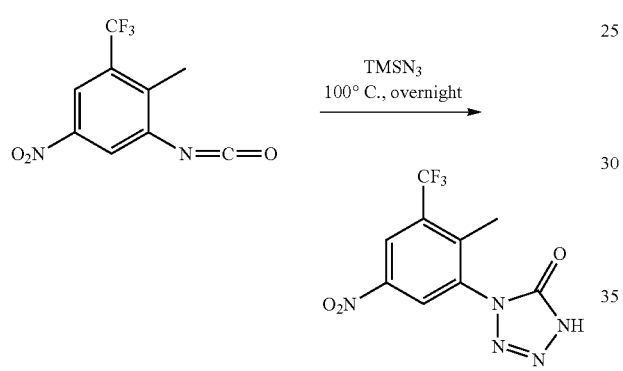

To the above residue of Example 151, 1.7 mL of TMSN$_3$ (12.8 mmol, 4 equiv) was added and then the resulting mixture was heated at 100° C. overnight. After being cooled to room temperature, the reaction mixture was concentrated. The residue was diluted with EtOAc (30 mL) and saturated aqueous NaHCO$_3$ (30 mL). The aqueous layer was separated, neutralized with 2 N HCl to pH 4~5 and extracted with EtOAc (2×20 mL). The organic layers were combined, dried over MgSO$_4$ and concentrated to give a yellow solid (560 mg, 60% two steps) which was directly used in the next step. m/z=289 (M)$^+$.

Example 153

1-(2-methyl-5-nitro-3-trifluoromethylphenyl)-4-methyl-5H-tetrazol-5-one

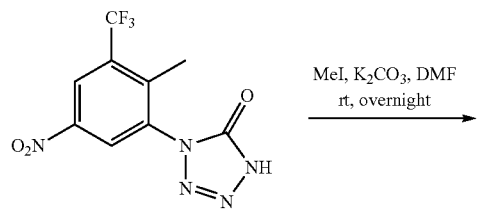

-continued

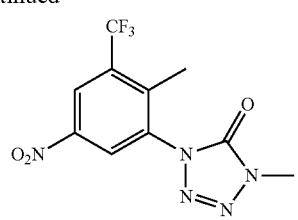

To a mixture of 1-(2-methyl-5-nitro-3-trifluoromethylphenyl)-4,5-dihydro-5H-tetrazol-5-one (560 mg, 1.94 mmol, 1 equiv) and K$_2$CO$_3$ (802 mg, 5.81 mmol, 3 equiv) in 10 mL of DMF was added MeI (0.36 mL, 5.81 mmol, 3 equiv) and the resulting mixture was stirred at room temperature overnight. The reaction mixture was diluted with water and extracted with EtOAc. The organic layer was separated and concentrated. The residue was triturated in water to give 520 mg of product (88%) as a yellow solid. $^1$H NMR (CDCl$_3$, 300 MHz): δ 8.66 (d, J=2.1 Hz, 1H), 8.45 (d, J=2.4 Hz, 1H), 3.74 (s, 3H), 2.51 (s, 3H). m/z=304.1 (M+H)$^+$.

Example 154

1-(5-amino-2-methyl-3-trifluoromethylphenyl)-4-methyl-5H-tetrazol-5-one

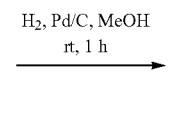

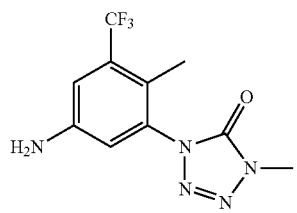

A solution of 1-(2-methyl-5-nitro-3-trifluoromethylphenyl)-4-methyl-5H-tetrazol-5-one (520 mg, 1.72 mmol, 1 equiv) in 10 mL of MeOH in the presence of 30 mg of 10% Pd/C was hydrogenated at room temperature for 1 hour. The reaction mixture was then filtered over a pad of Celite and washed with MeOH. The solvent was concentrated to give the product in quantitative yield. m/z=274.2 (M+H)$^+$.

Example 155

N2-(4-methyl-3-(4-methyl-4,5-dihydro-5-oxo-1H-tetrazol-1-yl)-5-trifluoromethylphenyl)-5-fluoro-N4-(2,2,6,6-tetramethylpiperidin-4-yl)pyrimidine-2,5-diamine (I-53)

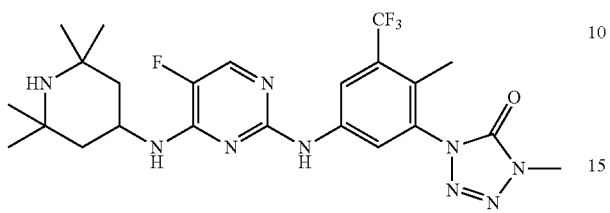

$^1$H NMR (DMSO-d$_6$, 300 MHz): δ 9.50 (s, 1H), 8.21 (s, 1H), 8.09 (s, 1H), 7.90 (d, J=3.6 Hz, 1H), 7.27 (d, J=7.5 Hz, 1H), 4.35-4.25 (m, 1H), 3.61 (s, 3H), 2.11 (s, 3H), 1.64 (dm, J=9.3 Hz, 2H), 1.13 (dm, J=9.3 Hz, 2H), 1.03 (s, 6H), 0.99 (s, 6H); m/z=524 (M+H)$^+$.

Example 156

N2-(4-methyl-3-(4-methyl-4,5-dihysro-5-oxo-1H-tetrazol-1-yl)-5-trifluoromethylphenyl)-5-fluoro-N4-(1,2,2,6,6-pentamethylpiperidin-4-yl)pyrimidine-2,4-diamine (I-54)

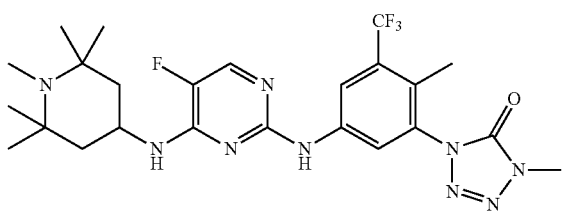

$^1$H NMR (DMSO-d$_6$, 300 MHz): δ 9.51 (s, 1H), 8.20 (s, 1H), 8.10 (s, 1H), 7.90 (d, J=3.6 Hz, 1H), 7.28 (d, J=8.7 Hz, 1H), 4.25-4.15 (m, 1H), 3.62 (s, 3H), 2.14 (s, 3H), 2.11 (s, 3H), 1.64 (dm, J=9.9 Hz, 2H), 1.41 (dm, J=9.3 Hz, 2H), 1.03 (s, 6H), 0.89 (s, 6H); m/z=538.3 (M+H)$^+$.

Example 157

3-chloro-2-methyl-5-nitrophenylisocyanate

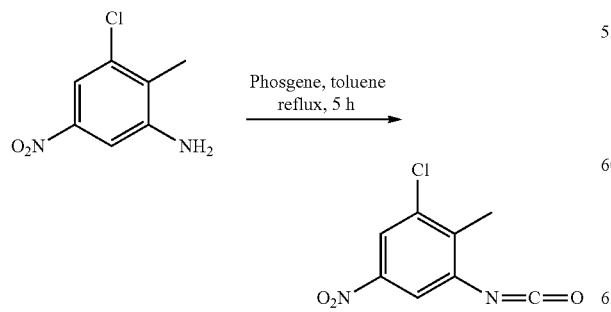

A solution of 3-chloro-2-methyl-5-nitroaniline (1.0 g, 5.36 mmol, 1 equiv) in 20% of phosgene in toluene (17.0 mL, 32.16 mmol, 6 equiv) was refluxed for 5 hours. The reaction mixture was then concentrated and the resulting residue was directly used in the next step.

$^1$H NMR (CDCl$_3$, 300 MHz): δ 8.10 (d, J=1.8 Hz, 1H), 7.89 (d, J=2.4 Hz, 1H), 2.48 (s, 3H).

Example 158

1-(3-chloro-2-methyl-5-nitrophenyl)-4,5-dihysro-5H-tetrazol-5-one

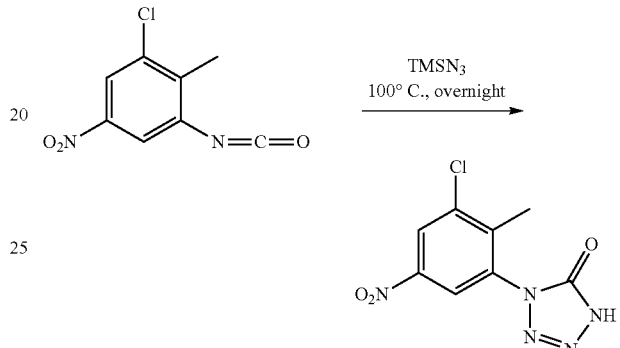

To the above residue 2.8 mL of TMSN$_3$ (21.44 mmol, 4 equiv) was added and then the resulting mixture was heated at 100° C. overnight. After being cooled to room temperature, the reaction mixture was concentrated. The residue was diluted with EtOAc (30 mL) and saturated aqueous NaHCO$_3$ (30 mL). The aqueous layer was separated, neutralized with 2 N HCl to pH 4~5 and extracted with EtOAc (2×20 mL). The organic layers were combined, dried over MgSO$_4$ and concentrated to give a yellow solid (320 mg, 24% two steps) which was directly used in the next step.

Example 159

1-(3-chloro-2-methyl-5-nitrophenyl)-4-methyl-5H-tetrazol-5-one

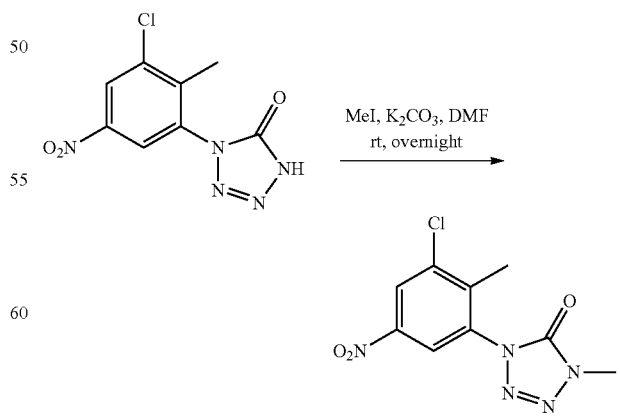

To a mixture of 1-(3-chloro-2-methyl-5-nitrophenyl)-4,5-dihydro-5H-tetrazol-5-one (320 mg, 1.3 mmol, 1 equiv) and K₂CO₃ (538 mg, 3.9 mmol, 3 equiv) in 6 mL of DMF was added MeI (0.24 mL, 3.9 mmol, 3 equiv) and the resulting mixture was stirred at room temperature overnight. The reaction mixture was diluted with water and extracted with EtOAc. The organic layer was separated and concentrated. The residue was triturated in water to give 280 mg of product (80%) as a light yellow solid.

Example 160

1-(5-amino-3-chloro-2-methylphenyl)-4-methyl-5H-tetrazol-5-one

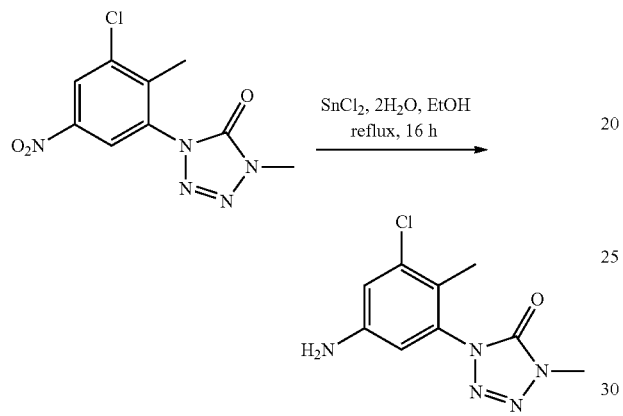

A mixture of 280 mg of 1-(3-chloro-2-methyl-5-nitrophenyl)-4-methyl-5H-tetrazol-5-one (1.04 mmol, 1 equiv) and 704 mg of SnCl₂.2H₂O (3.12 mmol, 3 equiv) in 10 mL of EtOH was refluxed for 16 hours. After being cooled to room temperature, the reaction mixture was diluted with 2N NaOH and EtOAc. The organic layer was separated, dried over MgSO₄ and concentrated to give the product as a yellow solid in quantitative yield.

¹H NMR (CDCl₃, 300 MHz): δ 6.84 (s, 1H), 6.54 (d, J=1.8 Hz, 1H), 3.79 (br. s, 2H), 3.70 (s, 3H), 2.13 (s, 3H). m/z=240.2 (M+H)⁺.

Example 161

N2-(5-chloro-4-methyl-3-(4-methyl-4,5-dihysro-5-oxo-1H-tetrazol-1-yl)phenyl)-5-fluoro-N4-(2,2,6,6-tetramethylpiperidin-4-yl)pyrimidine-2,4-diamine
(I-55)

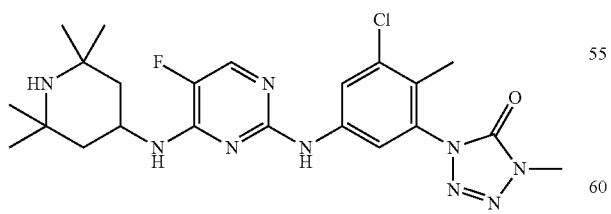

¹H NMR (DMSO-d₆, 300 MHz): δ 9.39 (s, 1H), 7.98 (s, 1H), 7.89 (d, J=3.6 Hz, 1H), 7.78 (d, J=1.5 Hz, 1H), 7.26 (d, J=7.2 Hz, 1H), 4.35-4.25 (m, 1H), 3.60 (s, 3H), 2.05 (s, 3H), 1.64 (dm, J=8.7 Hz, 2H), 1.19-1.13 (m, 2H), 1.06 (s, 6H), 0.99 (s, 6H); m/z=490.3 (M+H)⁺.

Example 162

N2-(5-chloro-4-methyl-3-(4-methyl-4,5-dihydro-5-oxo-1H-tetrazol-1-yl)phenyl)-5-fluoro-N4-(1,2,2,6,6-pentamethylpiperidin-4-yl)pyrimidine-2,4-diamine
(I-56)

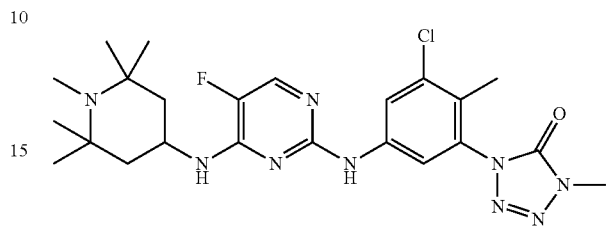

¹H NMR (DMSO-d₆, 300 MHz): δ 9.39 (s, 1H), 7.98 (s, 1H), 7.89 (d, J=3.3 Hz, 1H), 7.75 (s, 1H), 7.27 (d, J=8.4 Hz, 1H), 4.25-4.15 (m, 1H), 3.61 (s, 3H), 2.14 (s, 3H), 2.05 (s, 3H), 1.64 (dm, J=9.9 Hz, 2H), 1.42 (tm, J=12.6 Hz, 2H), 1.04 (s, 6H), 0.93 (s, 6H); m/z=504.4 (M+H)⁺.

Example 163

4,6-dinitro-2-fluorophenol

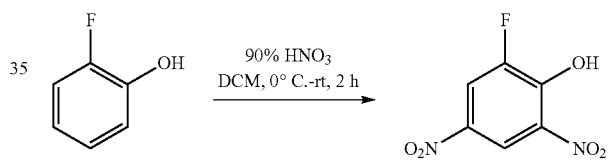

To 2-fluorophenol (10 mL, 12.1 g, 108 mmol, 1 equiv) in anhydrous DCM at 0° C. was added 90% HNO₃ (12.6 mL, 17.0 g, 270 mmol, 2.5 equiv) dropwise. The mixture was warmed to room temperature and stirred for 2 hours, then cooled to 0° C. again and quenched with 2N NaOH solution to pH 5 (ca. 80 mL). The mixture was concentrated, diluted with water and extracted with EtOAc (3×150 mL). The combined organic layers was dried over MgSO₄, filtered and concentrated. The residue was triturated in hexanes to give the product (18 g, 82%) as a yellow solid.

¹H NMR (CDCl₃, 300 MHz): δ 10.97 (br. s, 1H), 8.92-8.90 (m, 1H), 8.32 (dm, J=9.3 Hz, 1H); m/z=201.1 (M−H)⁺.

Example 164

2-bromo-1,5-dinitro-3-fluorobenzene

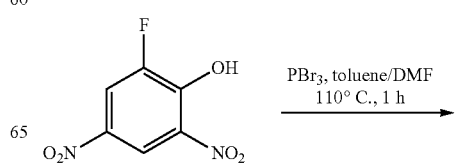

-continued

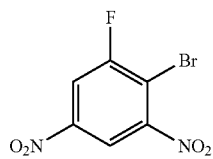

To a solution of 4,6-dinitro-2-fluorophenol (8 g, 39.60 mmol, 1 equiv) in DMF (24 mL) and toluene (160 mL), PBr$_3$ (5.6 mL, 59.40 mmol, 1.5 equiv) was added at room temperature. Then the reaction mixture was heated at 110° C. for 1 hour. After allowing to cool to room temperature, the upper colorless layer was poured into a separate funnel and diluted with hexanes. The organic layer was washed with water, dried over MgSO$_4$ and evaporated to dryness to give the product (10.3 g, 98%) as a yellow solid.

$^1$H NMR (CDCl$_3$, 300 MHz): δ 8.54 (d, J=1.2 Hz, 1H), 8.22 (dd, J=7.5, 0.9 Hz, 1H); m/z=263.0 (M)$^+$.

Example 165

2-bromo-3-fluoro-5-nitroaniline and 4-bromo-3-fluoro-5-nitroaniline

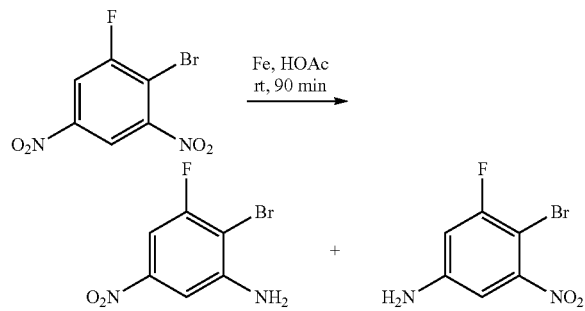

A mixture of 2-bromo-1,5-dinitro-3-fluorobenzene (100 mg, 0.38 mmol, 1 equiv) and iron powder (64 mg, 1.14 mmol, 3 equiv) in 3 mL of HOAc was stirred at room temperature for 90 minutes. The reaction mixture was diluted with EtOAc (20 mL) and saturated NaHCO$_3$ (to ca. pH 7-8). The organic layer was separated and evaporated under vacuum. The crude residue was purified by column chromatography on silica gel using EtOAc/hexanes (1:4) as eluent to give 47 mg of 2-bromo-3-fluoro-5-nitroaniline (52%).

$^1$H NMR (CDCl$_3$, 300 MHz): δ 7.43-7.32 (m, 2H), 4.63 (br. s, 2H), 1.40-1.35 (m, 1H), 1.25-1.20 (m, 2H), 0.85-0.80 (m, 2H); m/z=237.0 (M+H)$^+$ for 81Br.

A later fraction gave 28 mg of 4-Bromo-3-fluoro-5-nitroaniline (31%).

$^1$H NMR (CDCl$_3$, 300 MHz): δ 6.94 (d, J=2.7 Hz, 1H), 6.62 (dd, J=9.6, 2.7 Hz, 1H), 4.15 (br. s, 2H), 1.40-1.35 (m, 1H), 1.28-1.23 (m, 2H), 0.88-0.85 (m, 2H); m/z=237.0 (M+H)$^+$ for 81Br.

Example 166

2-cyclopropyl-3-fluoro-5-nitroaniline

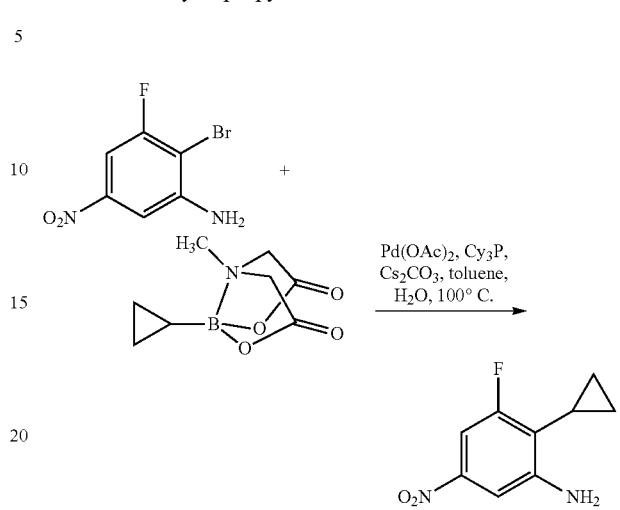

A mixture of 2-bromo-3-fluoro-5-nitroaniline (1.6 g, 6.81 mmol, 1 equiv), cyclopropylboronic acid MIDA ester (Aldrich; 4.0 g, 20.43 mmol, 3 equiv), Pd(OAc)$_2$ (238 mg, 1.06 mmol, 0.15 equiv), Cy$_3$P (578 mg, 2.06 mmol, 0.3 equiv) and Cs$_2$CO$_3$ (13.26 g, 40.8 mmol, 6 equiv) in toluene (70 mL) and H$_2$O (14 mL) was de-gassed with N$_2$ for 5 minutes. The mixture was then heated at 100° C. (oil bath temperature) overnight. After allowing to cool to room temperature, the mixture was diluted with EtOAc (100 mL) and H$_2$O (50 mL) and the mixture filtered through Celite. The filter cake was washed with EtOAc (2×50 mL) and the filtrate partitioned. The organic layer was evaporated under vacuum to leave a crude residue which was purified by column chromatography on silica gel using EtOAc/hexanes (1:4) as eluent to give the product (1.2 g, 90%) as a dark yellow solid.

$^1$H NMR (CDCl$_3$, 300 MHz): δ 7.29-7.21 (m, 2H), 4.44 (br. s, 2H), 1.52-1.42 (m, 1H), 1.11-1.05 (m, 2H), 0.73-0.67 (m, 2H); m/z=197.2 (M+H)$^+$

Example 167

2-cyclopropyl-3-fluoro-5-nitrophenylisocyanate

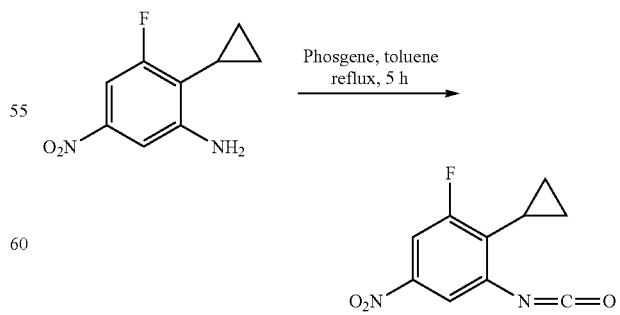

A solution of 2-cyclopropyl-3-fluoro-5-nitroaniline (413 mg, 2.1 mmol, 1 equiv) in 20% of phosgene in toluene (2.1 mL, 4.2 mmol, 2 equiv) was refluxed for 5 hours. The reaction mixture was then concentrated and the resulting residue was directly used in the next step.

Example 168

1-(2-cyclopropyl-3-fluoro-5-nitrophenyl)-4,5-di-hydro-5H-tetrazol-5-one

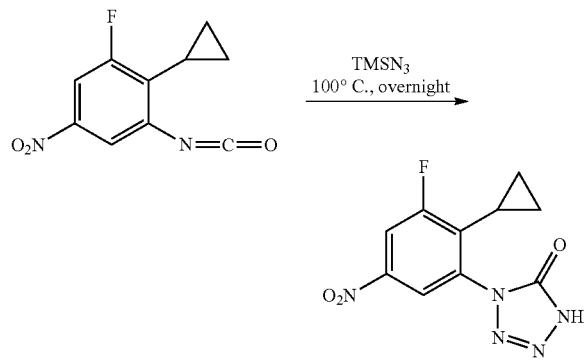

To the above residue of Example 167, 1.1 mL of TMSN$_3$ (8.4 mmol, 4 equiv) was added and then the resulting mixture was heated at 100° C. overnight. After being cooled to room temperature, the reaction mixture was concentrated. The residue was diluted with EtOAc (20 mL) and saturated aqueous NaHCO$_3$ (20 mL). The aqueous layer was separated, neutralized with 2 N HCl to pH 4~5 and extracted with EtOAc (2×20 mL). The organic layers were combined, dried over MgSO$_4$ and concentrated to give a pale yellow solid (300 mg, 54% two steps) which was directly used in the next step. m/z=266.2 (M+H)$^+$.

Example 169

1-(2-cyclopropyl-3-fluoro-5-nitrophenyl)-4-methyl-5H-tetrazol-5-one

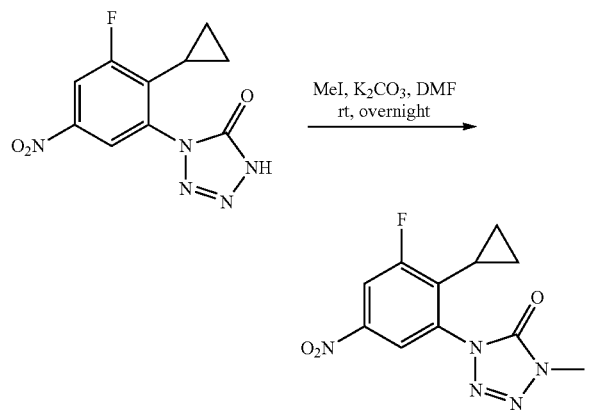

To a mixture of 1-(2-cyclopropyl-3-fluoro-5-nitrophenyl)-4,5-dihydro-5H-tetrazol-5-one (300 mg, 1.13 mmol, 1 equiv) and K$_2$CO$_3$ (470 mg, 3.4 mmol, 3 equiv) in 6 mL of DMF was added MeI (0.22 mL, 3.4 mmol, 3 equiv) and the resulting mixture was stirred at room temperature overnight. The reaction mixture was diluted with water and extracted with EtOAc. The organic layer was separated and concentrated. The residue was triturated in water to give 270 mg of product (86%) as a pale yellow solid. m/z=280.2 (M+H)$^+$.

Example 170

1-(5-amino-2-cyclopropyl-3-fluorophenyl)-4-methyl-5H-tetrazol-5-one

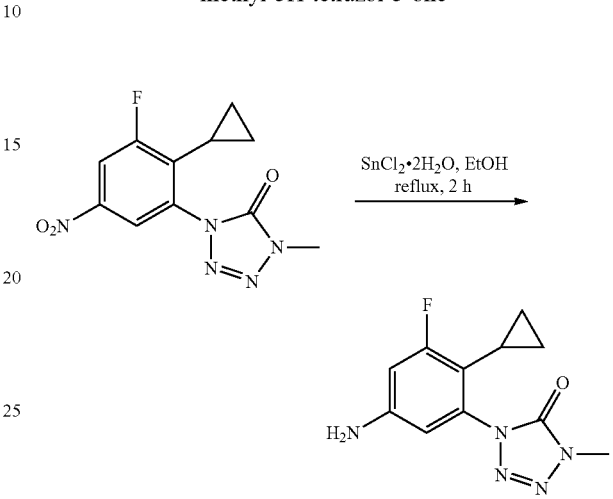

A mixture of 270 mg of 1-(3-chloro-2-methyl-5-nitrophenyl)-4-methyl-5H-tetrazol-5-one (0.97 mmol, 1 equiv) and 655 mg of SnCl$_2$.2H$_2$O (2.9 mmol, 3 equiv) in 8 mL of EtOH was refluxed for 2 hours. After being cooled to room temperature, the reaction mixture was diluted with 2N NaOH and EtOAc. The organic layer was separated, dried over MgSO$_4$ and concentrated to give 230 mg of product (95%). m/z=250.2 (M+H)$^+$.

Example 171

N2-(4-cyclopropyl-5-fluoro-3-(4-methyl-4,5-di-hydro-5-oxo-1H-tetrazol-1-yl)phenyl)-N4-(2,2,6,6-tetramethylpiperidin-4-yl)pyrimidine-2,4-diamino-5-carboxyamide (I-57)

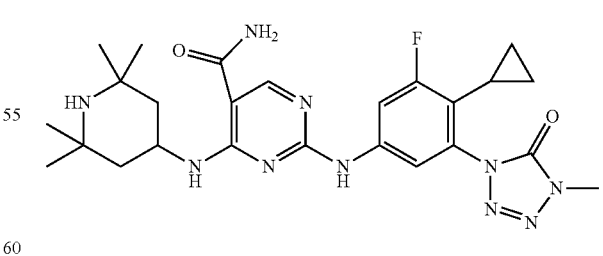

$^1$H NMR (DMSO-d$_6$, 300 MHz): δ 9.91 (s, 1H), 9.25 (br. s, 1H), 8.53 (s, 1H), 7.87 (d, J=12.9 Hz, 1H), 7.85 (br. s, 1H), 7.57 (s, 1H), 7.22 (br. s, 1H), 4.40-4.30 (m, 1H), 3.62 (s, 3H), 1.80-1.70 (m, 2H), 1.60-1.56 (m, 1H), 1.20-1.10 (m, 2H), 1.07 (s, 6H), 1.00 (s, 6H), 0.71-0.68 (m, 2H), 0.26-0.24 (m, 2H); m/z=525.5 (M+H)$^+$.

Example 172

N2-(4-chcloropyl-5-fluoro-3-(4-methyl-4,5-dihydro-5-oxo-1H-tetrazol-1-yl)phenyl)-5-fluoro-N4-(2,2,6,6-tetramethylpiperidin-4-yl)pyrimidine-2,4-diamine

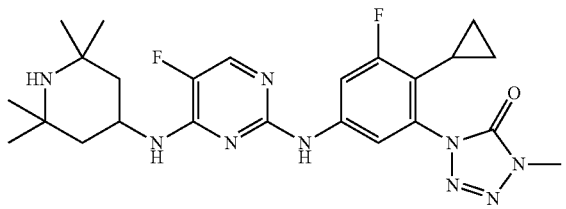

$^1$H NMR (DMSO-d$_6$, 300 MHz): δ 9.50 (s, 1H), 7.89 (d, J=3.6 Hz, 1H), 7.81 (d, J=13.5 Hz, 1H), 7.52 (s, 1H), 7.30 (d, J=7.8 Hz, 1H), 4.40-4.30 (m, 1H), 3.62 (s, 3H), 1.67-1.63 (m, 2H), 1.60-1.50 (m, 1H), 1.20-1.10 (m, 2H), 1.09 (s, 6H), 1.00 (s, 6H), 0.69-0.67 (m, 2H), 0.26-0.24 (m, 2H); m/z=500.3 (M+H)$^+$.

Example 173

N2-(4-cyclopropyl-5-fluoro-3-(4-methyl-4,5-dihydro-5-oxo-1H-tetrazol-1 -yl)phenyl)-N4-(2,2,6,6-tetramethylpiperidin-4-yl)pyrimidine-2,4-diamino-5-carbonitrile (I-62)

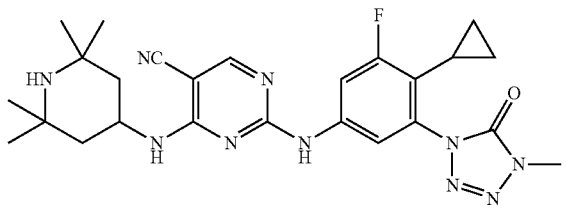

$^1$H NMR (DMSO-d$_6$, 300 MHz): δ 10.16 (s, 1H), 8.36 (s, 1H), 7.84 (d, J=13.2 Hz, 1H), 7.52 (d, J=9.0 Hz, 1H), 7.48 (s, 1H), 4.50-4.40 (m, 1H), 3.62 (s, 3H), 1.61-1.57 (m, 2H), 1.28-1.19 (m, 2H), 1.16-1.13 (m, 1H), 1.05 (s, 6H), 0.99 (s, 6H), 0.72-0.70 (m, 2H), 0.27-0.25 (m, 2H); m/z=507.4 (M+H)$^+$.

Example 174

2-bromo-5-nitrophenylisocyanate

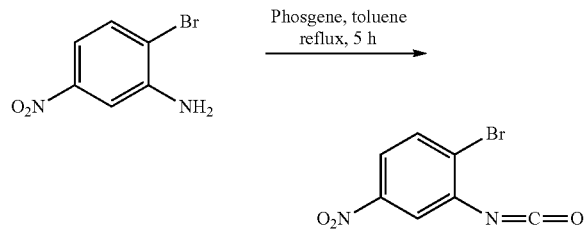

A solution of 2-bromo-5-nitroaniline (1.0 g, 4.61 mmol, 1 equiv) in 20% of phosgene in toluene (4.85 mL, 9.22 mmol, 2 equiv) was refluxed for 5 hours. The reaction mixture was then concentrated and the resulting residue was directly used in the next step.

Example 175

1-(2-bromo-5-nitrophenyl)-4,5-dihydro-5H-tetrazol-5-one

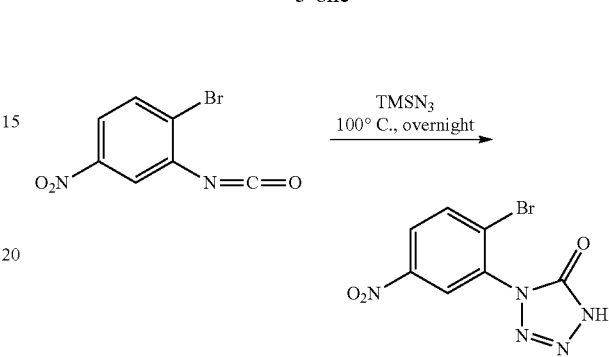

To the above residue 2.4 mL of TMSN$_3$ (18.44 mmol, 4 equiv) was added and then the resulting mixture was heated at 100° C. overnight. After being cooled to room temperature, the reaction mixture was concentrated. The residue was diluted with EtOAc (50 mL) and saturated aqueous NaHCO$_3$ (50 mL). The aqueous layer was separated, neutralized with 2 N HCl to pH 4~5 and extracted with EtOAc (2×50 mL). The organic layers were combined, dried over MgSO$_4$ and concentrated to give a yellow solid (500 mg, 38% two steps) which was directly used in the next step. m/z=288.0 (M+H)$^+$ for 81Br.

Example 176

1-(2-bromo-5-nitrophenyl)-4-methyl-5H-tetrazol-5-one

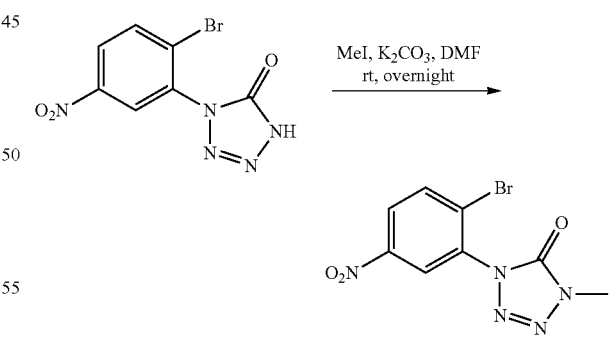

To a mixture of 1-(2-bromo-5-nitrophenyl)-4,5-dihydro-5H-tetrazol-5-one (500 mg, 1.75 mmol, 1 equiv) and K$_2$CO$_3$ (724 g, 5.25 mmol, 3 equiv) in 8 mL of DMF was added MeI (0.33 mL, 5.25 mmol, 3 equiv) and the resulting mixture was stirred at room temperature overnight. The reaction mixture was diluted with water and extracted with EtOAc. The organic layer was separated and concentrated. The residue was triturated in water to give 460 mg of product (88%) as a pale yellow solid. m/z=302.0 (M+H)$^+$ for 81Br.

Example 177

2-(4,5-dihydro-4-methyl-5-oxotetrazol-1-yl)-4-nitrobenzonitrile

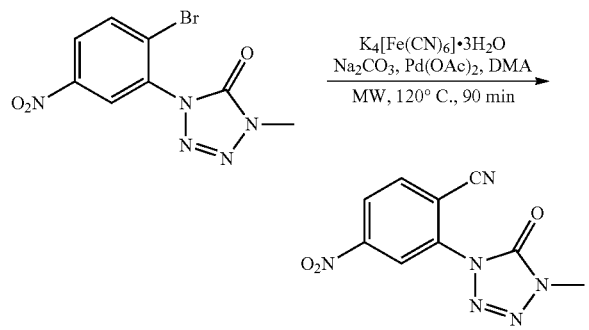

A mixture of 1-(2-bromo-5-nitrophenyl)-4-methyl-5H-tetrazol-5-one (100 mg, 0.34 mmol, 1 equiv), $K_4[Fe(CN)_6]\cdot 3H_2O$ (215 mg, 0.51 mmol, 1.5 equiv), $Pd(OAc)_2$ (8 mg, 0.034 mmol, 0.1 equiv) and $Na_2CO_3$ (54 mg, 0.51 mmol, 1.5 equiv) in 3 mL of DMA was degassed under $N_2$ for 1 minute and then irridated under MW at 120° C. for 90 minutes. The reaction mixture was directly purified by column chromatography on silica gel using EtOAc/hexanes (3:7) as eluent to give 58 mg of product (70%). m/z=247.2 $(M+H)^+$.

Example 178

4-amino-2-(4,5-dihydro-4-methyl-5-oxotetrazol-1-yl)benzonitrile

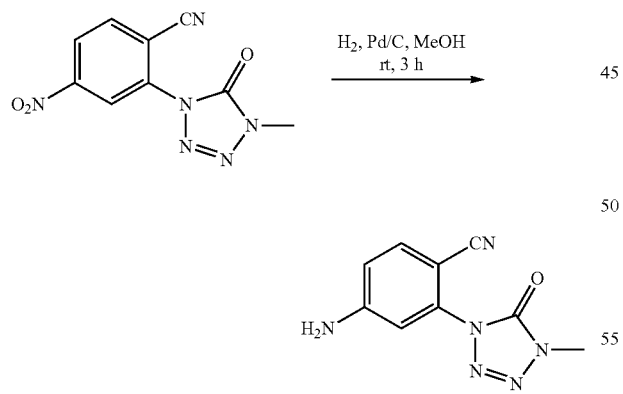

A solution of 2-(4,5-dihydro-4-methyl-5-oxotetrazol-1-yl)-4-nitrobenzonitrile (58 mg, 0.24 mmol, 1 equiv) in 5 mL of MeOH in the presence of 5 mg of 10% Pd/C was hydrogenated at room temperature for 3 hours. The reaction mixture was then filtered over a pad of Celite and washed with MeOH. The solvent was concentrated to give the product in quantitative yield. m/z=217.2 $(M+H)^+$.

Example 179

N2-(4-cyano-3-(4-methyl-4,5-dihydro-5-oxo-1H-tetrazol-1-yl)phenyl)-5-fluoro-N4-(2,2,6,6-tetramethylpiperidin-4-yl)pyrimidine-2,4-diamine (I-58)

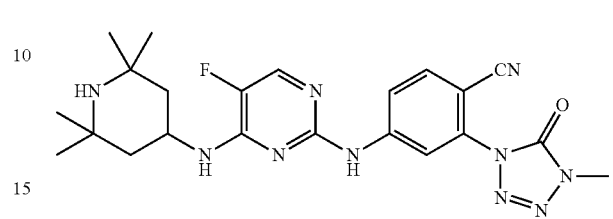

$^1$H NMR (DMSO-$d_6$, 300 MHz): δ 9.99 (s, 1H), 8.15 (s, 1H), 7.95 (d, J=3.6 Hz, 1H), 7.94 (s, 1H), 7.81 (d, J=8.1 Hz, 1H), 7.43 (d, J=7.8 Hz, 1H), 4.28-4.18 (m, 1H), 3.62 (s, 3H), 1.66 (dm, J=9.6 Hz, 2H), 1.14 (tm, J=12.0 Hz, 2H), 1.06 (s, 6H), 1.03 (s, 6H); m/z=467.3 $(M+H)^+$.

Example 180

Methyl 3-isocyanato-2-methyl-5-nitrobenzoate

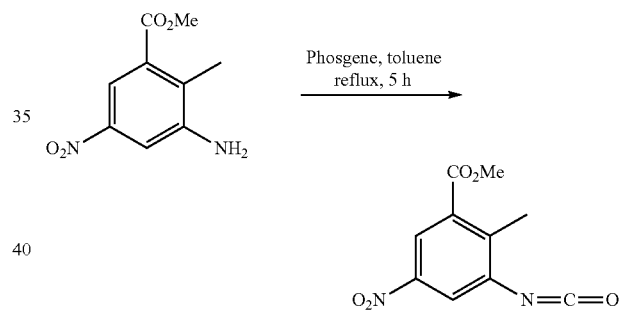

A solution of methyl 3-amino-2-methyl-5-nitrobenzoate (2.0 g, 9.52 mmol, 1 equiv) in 20% of phosgene in toluene (10.0 mL, 19.03 mmol, 2 equiv) was refluxed for 5 hours. The reaction mixture was then concentrated and the resulting residue was directly used in the next step.

$^1$H NMR (CDCl$_3$, 300 MHz): δ 8.54 (s, 1H), 8.10 (s, 1H), 3.96 (s, 3H), 2.66 (s, 3H).

Example 181

Methyl 3-(4,5-dihydro-5-oxotetrazol-1-yl)-2-methyl-5-nitrobenzoate

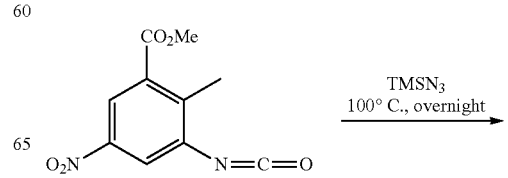

169

-continued

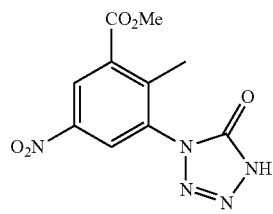

To the above residue 5.0 mL of TMSN₃ (38.06 mmol, 4 equiv) was added and then the resulting mixture was heated at 100° C. overnight. After being cooled to room temperature, the reaction mixture was concentrated. The residue was diluted with EtOAc (50 mL) and saturated aqueous NaHCO₃ (50 mL). The aqueous layer was separated, neutralized with 2 N HCl to pH 4~5 and extracted with EtOAc (2×50 mL). The organic layers were combined, dried over MgSO₄ and concentrated to give a yellow solid (430 mg, 16% two steps) which was directly used in the next step.

Example 182

Methyl 3-(4,5-dihydro-4-methyl-5-oxotetrazol-1-yl)-2-methyl-5-nitrobenzoate

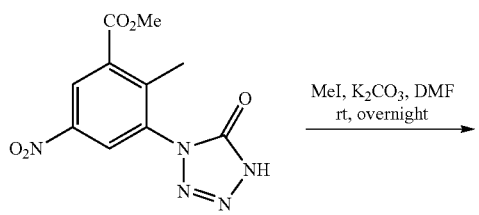

To a mixture of methyl 3-(4,5-dihydro-5-oxotetrazol-1-yl)-2-methyl-5-nitrobenzoate (430 mg, 1.54 mmol, 1 equiv) and K₂CO₃ (640 g, 4.62 mmol, 3 equiv) in 8 mL of DMF was added MeI (0.29 mL, 4.62 mmol, 3 equiv) and the resulting mixture was stirred at room temperature overnight. The reaction mixture was diluted with water and extracted with EtOAc. The organic layer was separated and concentrated. The residue was triturated in water to give 400 mg of product (89%) as a pale yellow solid. m/z=294.2 (M+H)⁺.

170

Example 183

Methyl 5-amino-3-(4,5-dihydro-4-methyl-5-oxotetrazol-1-yl)-2-methylbenzoate

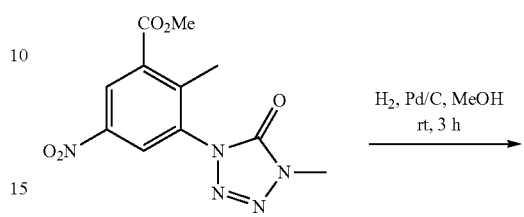

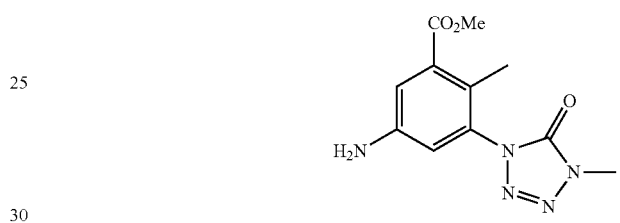

A solution of methyl 3-(4,5-dihydro-4-methyl-5-oxotetrazol-1-yl)-2-methyl-5-nitrobenzoate (400 mg, 1.37 mmol, 1 equiv) in 10 mL of MeOH in the presence of 40 mg of 10% Pd/C was hydrogenated at room temperature for 3 hours. The reaction mixture was then filtered over a pad of Celite and washed with MeOH. The solvent was concentrated to give the product in quantitative yield. m/z=264.2 (M+H)⁺.

Example 184

Methyl 5-((5-fluoro-4-((2,2,6,6-tetramethylpiperidin-4-yl)amino)-2-pyrimidinyl)amino)-2-methyl-3-(4-methyl-4,5-dihysro-5-oxo-1H-tetrazol-1-yl)benzoate (I-60)

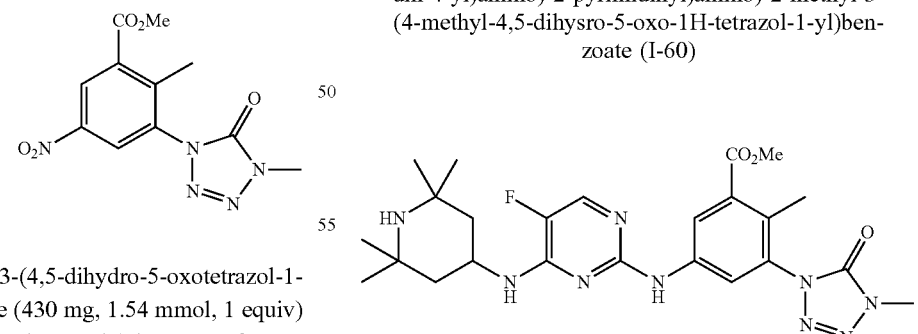

¹H NMR (DMSO-d₆, 300 MHz): δ 9.38 (s, 1H), 8.13 (s, 1H), 8.08 (d, J=2.7 Hz, 1H), 7.88 (d, J=3.0 Hz, 1H), 7.21 (d, J=7.8 Hz, 1H), 4.30-4.20 (m, 1H), 3.83 (s, 3H), 3.60 (s, 3H), 2.12 (s, 3H), 1.64 (dm, J=11.7 Hz, 2H), 1.15-1.11 (m, 2H), 1.02 (s, 6H), 0.98 (s, 6H); m/z=514.3 (M+H)⁺.

Example 185

Methyl 5-((5-fluoro-4-((1,2,2,6,6-pentamethylpiperidin-4-yl)amino)-2-pyrimidinyl)amino)-2-methyl-3-(4-methyl-4,5-dihysro-5-oxo-1H-tetrazol-1-yl)benzoate (I-63)

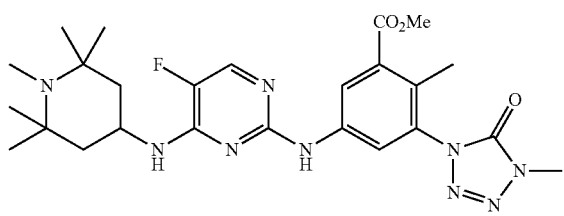

$^1$H NMR (DMSO-$d_6$, 300 MHz): δ 9.35 (s, 1H), 8.13 (s, 1H), 8.05 (s, 1H), 7.96 (d, J=3.0 Hz, 1H), 7.62 (d, J=7.8 Hz, 1H), 4.40-4.30 (m, 1H), 3.85 (s, 3H), 3.63 (s, 3H), 2.71 (s, 3H), 2.16 (s, 3H), 2.05 (dm, J=13.2 Hz, 2H), 1.78 (tm, J=13.2 Hz, 2H), 1.39 (s, 6H), 1.32 (s, 6H); m/z=528.5 (M+H)$^+$.

Example 186

5-((5-fluoro-4-((2,2,6,6-tetramethylpiperidin-4-yl)amino)-2-pyrimidinyl)amino-2-methyl-3-(4-methyl-4,5-dihydro-5-oxo-1H-tetrazol-1-yl)benzoic Acid (I-61)

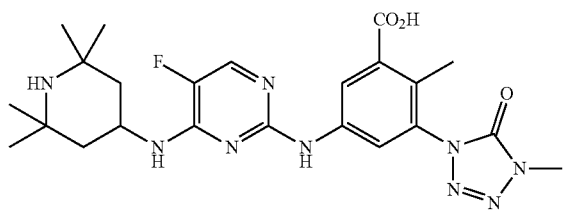

A mixture of 80 mg of methyl 5-((5-fluoro-4-((2,2,6,6-tetramethylpiperidin-4-yl)amino)-2-pyrimidinyl)amino)-2-methyl-3-(4-methyl-4,5-dihydro-5-oxo-1H-tetrazol-1-yl)benzoate (0.16 mmol, 1 equiv) in THF/H$_2$O (1.5 mL/1.5 mL) in the presence of LiOH (37 mg, 1.6 mmol, 10 equiv) was stirred at room temperature for 5 hours. Then the reaction mixture was neutralized with 2N HCl to pH 3. The product crashed out as a white solid which was filtered and dried (77 mg, 90%).

$^1$H NMR (DMSO-$d_6$, 300 MHz): δ 9.37 (s, 1H), 8.72 (br. s, 1H), 8.13 (s, 1H), 7.95 (d, J=4.2 Hz, 1H), 7.78 (br. s, 1H), 7.57 (d, J=7.2 Hz, 1H), 4.40-4.30 (m, 1H), 3.62 (s, 3H), 2.15 (s, 3H), 1.95 (dm, J=11.7 Hz, 2H), 1.60-1.50 (m, 2H), 1.34 (s, 6H), 1.32 (s, 6H); m/z=500.3 (M+H)$^+$.

Example 187

5-((5-fluoro-4-((1,2,2,6,6-pentamethylpiperidin-4-yl)amino)-2-pyrimidinyl)amino)-2-methyl-3-(4-methyl-4,5-dihydro-5-oxo-1H-tetrazol-1-yl)benzoic Acid (I-65)

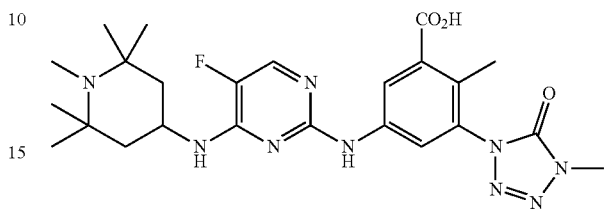

A mixture of 120 mg of methyl 5-((5-fluoro-4-((1,2,2,6,6-pentamethylpiperidin-4-yl)amino)-2-pyrimidinyl)amino)-2-methyl-3-(4-methyl-4,5-dihydro-5-oxo-1H-tetrazol-1-yl)benzoate (0.23 mmol, 1 equiv) in THF/H$_2$O (2.0 mL/2.0 mL) in the presence of LiOH (55 mg, 2.3 mmol, 10 equiv) was stirred at room temperature for 5 hours. Then the reaction mixture was neutralized with 2N HCl to pH 3. The product crashed out as a white solid which was filtered and dried (55 mg, 47%).

$^1$H NMR (DMSO-$d_6$, 300 MHz): δ 9.35 (s, 1H), 8.51 (br. s, 1H), 8.15 (s, 1H), 7.95 (d, J=1.5 Hz, 1H), 7.63 (d, J=8.1 Hz, 1H), 4.40-4.30 (m, 1H), 3.62 (s, 3H), 2.70 (s, 3H), 2.17 (s, 3H), 2.05 (dm, J=12.9 Hz, 2H), 1.74 (tm, J=13.2 Hz, 2H), 1.36 (s, 6H), 1.30 (s, 6H); m/z=514.4 (M+H)$^+$.

Example 188

N-methyl 5-((5-fluoro-4-(1,2,2,6,6-pentamethylpiperidin-4-yl)amino)-2-pyrimidinyl)amino)-2-methyl-3-(4-methyl-4,5-dihydro-5-oxo-1H-tetrazol-1-yl)benzenecarboxyamide (I-67)

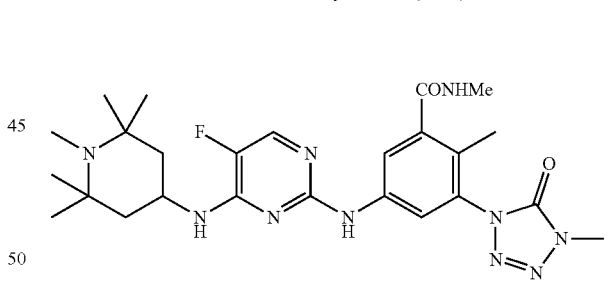

A mixture of 120 mg of methyl 5-((5-fluoro-4-((1,2,2,6,6-pentamethylpiperidin-4-yl)amino)-2-pyrimidinyl)amino)-2-methyl-3-(4-methyl-4,5-dihydro-5-oxo-1H-tetrazol-1-yl)benzoate (0.23 mmol, 1 equiv) in THF/H$_2$O (2.0 mL/2.0 mL) in the presence of LiOH (55 mg, 2.3 mmol, 10 equiv) was stirred at room temperature for 5 hours. Then the reaction mixture was neutralized with 2N HCl to pH 3. The product crashed out as a white solid which was filtered and dried (55 mg, 47%).

$^1$H NMR (DMSO-$d_6$, 300 MHz): δ 9.27 (s, 1H), 8.35-8.30 (m, 1H), 7.96 (s, 1H), 7.87 (d, J=3.9 Hz, 1H), 7.64 (s, 1H), 7.20 (d, J=8.1 Hz, 1H), 4.30-4.20 (m, 1H), 3.61 (s, 3H), 2.73 (d, J=4.8 Hz, 3H), 2.13 (s, 3H), 1.96 (s, 3H), 1.62 (dm, J=10.2 Hz, 2H), 1.41 (tm, J=12.3 Hz, 2H), 1.36 (s, 6H), 1.30 (s, 6H); m/z=527.5 (M+H)$^+$.

Example 189

1-(2,6-difluorophenyl)-4,5-dihydro-5H-tetrazol-5-one

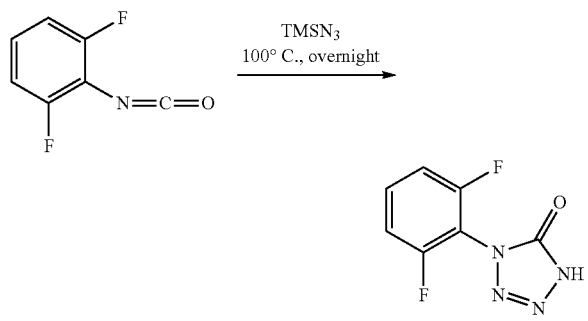

A mixture of 2,6-difluorophenylisocyanate (6.0 g, 38.68 mmol, 1 equiv) in 10.32 mL of TMSN₃ (77.36 mmol, 2 equiv) was heated at 100° C. overnight. After being cooled to room temperature, the reaction mixture was concentrated. The residue was diluted with EtOAc (100 mL) and saturated aqueous NaHCO₃ (100 mL). The aqueous layer was separated, neutralized with 2 N HCl to pH 4~5 and extracted with EtOAc (2×100 mL). The organic layers were combined, dried over MgSO₄ and concentrated to give a white solid (7.1 g, 93%).

$^1$H NMR (CDCl₃, 300 MHz): δ 7.59-7.49 (m, 1H), 7.15 (t, J=9.0, 8.4 Hz, 2H); m/z=199.3 (M+H)$^+$.

Example 190

1-(2,6-difluorophenyl)-4-methyl-5H-tetrazol-5-one

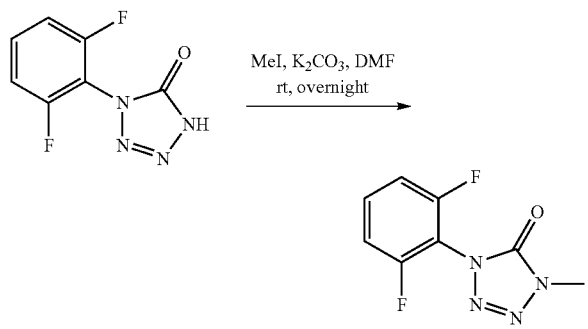

To a mixture of 1-(2,6-difluorophenyl)-4,5-dihydro-5H-tetrazol-5-one (3.55 g, 17.92 mmol, 1 equiv) and K₂CO₃ (7.42 g, 53.75 mmol, 3 equiv) in 60 mL of DMF was added MeI (3.35 mL, 53.75 mmol, 3 equiv) and the resulting mixture was stirred at room temperature overnight. The reaction mixture was diluted with water and extracted with EtOAc. The organic layer was separated and concentrated. The residue was triturated in water to give 3.45 g of product (91%) as a white solid.

$^1$H NMR (CDCl₃, 300 MHz): δ 7.54-7.46 (m, 1H), 7.12 (t, J=8.4, 7.5 Hz, 2H), 3.73 (s, 3H); m/z=213.4 (M+H)$^+$.

Example 191

1-(2,6-difluoro-5-nitrophenyl)-4-methyl-5H-tetrazol-5-one

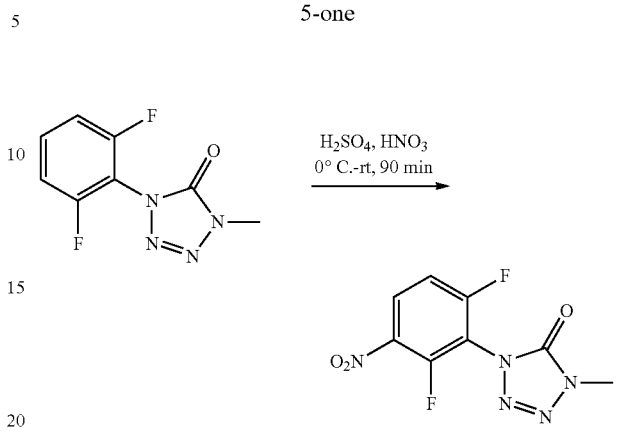

90% HNO₃ (0.37 mL, 8.3 mmol, 1.1 equiv) was added dropwise to a mixture of 1-(2,6-difluorophenyl)-4-methyl-5H-tetrazol-5-one (1.6 g, 7.55 mmol, 1 equiv) in 6 mL of fuming H₂SO₄ at 0° C. Then the mixture was left to room temperature and stirred for 1 hour. Poured into ice and the aqueous phase was extracted with EtOAc. The organic layer was separated, washed with saturated NaHCO₃ and concentrated to give 1.98 g of product (quantitative) as a yellow solid.

$^1$H NMR (CDCl₃, 300 MHz): δ 8.40-8.33 (m, 1H), 7.29 (td, J=8.1, 1.2 Hz, 1H), 3.75 (s, 3H); m/z=258.4 (M+H)$^+$.

Example 192

1-(5-amino-2,6-difluorophenyl)-4-methyl-5H-tetrazol-5-one

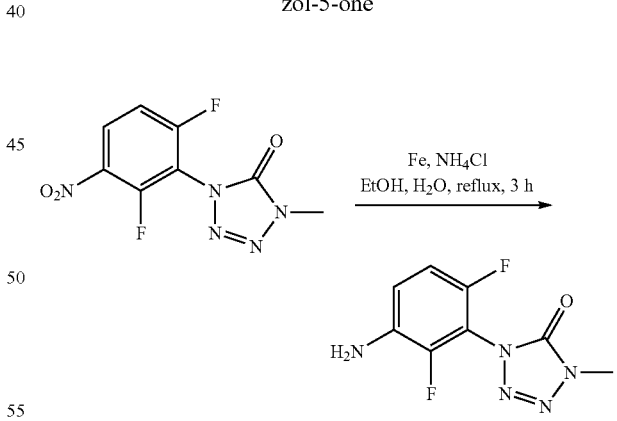

A mixture of 1-(2,6-difluoro-5-nitrophenyl)-4-methyl-5H-tetrazol-5-one (500 mg, 1.95 mmol, 1 equiv), iron powder (543 mg, 9.73 mmol, 5 equiv) and ammonium chloride (520 mg, 9.73 mmol, 5 equiv) in iPrOH (15 mL) and water (3 mL) was refluxed for 3 hours. After cooling to room temperature, the reaction mixture was filtered through a pad of Celite, and the pad of Celite was rinsed with EtOAc (50 mL). The filtrate was washed with water. The organic layer was separated, dried over MgSO₄ and evaporated to give 420 mg of product (95%) as a dark oil. m/z=228.4 (M+H)$^+$.

Example 193

N2-(2,4-difluoro-3-(4-methyl-4,5-dihydro-5-oxo-1H-tetrazol-1-yl)phenyl)-5-fluoro-N4-(1,2,2,6,6-pentamethylpiperidin-4-yl)pyrimidine-2,4-diamine (I-66)

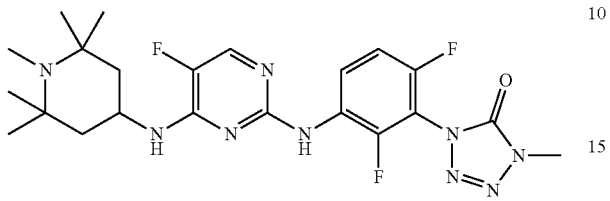

$^1$H NMR (DMSO-d$_6$, 300 MHz): δ 9.01 (s, 1H), 8.53 (br. s, 1H), 7.93 (d, J=3.6 Hz, 1H), 7.75 (d, J=6.9 Hz, 1H), 7.36 (t, J=9.0 Hz, 1H), 4.25-4.15 (m, 1H), 3.64 (s, 3H), 2.67 (d, J=5.1 Hz, 3H), 1.98 (dm, J=12.6 Hz, 2H), 1.71 (tm, J=13.2, 12.6 Hz, 2H), 1.35 (s, 6H), 1.23 (s, 6H); m/z=492.4 (M+H)+.

Example 194

N2-(2,4-difluoro-3-(4-methyl-4,5-dihydro-5-oxo-1H-tetrazol-1-yl)phenyl)-5-fluoro-N4-(2,2,6,6-tetramethylpiperidin-4-yl)pyrimidine-2,4-diamine (I-67)

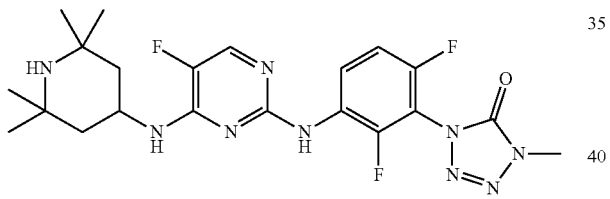

$^1$H NMR (DMSO-d$_6$, 300 MHz): δ 8.99 (s, 1H), 8.57 (br. s, 1H), 7.92 (d, J=3.6 Hz, 1H), 7.71 (d, J=6.9 Hz, 1H), 7.37 (t, J=9.3 Hz, 1H), 4.40-4.30 (m, 1H), 3.64 (s, 3H), 1.88 (dm, J=12.6 Hz, 2H), 1.48 (tm, J=13.2, 12.6 Hz, 2H), 1.32 (s, 6H), 1.26 (s, 6H); m/z=478.4 (M+H)$^+$.

Example 195

2-chloro-4-fluorophenylisocyanate

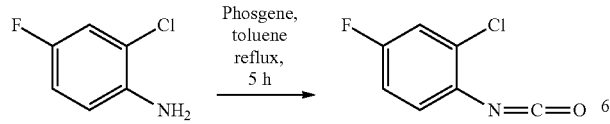

A solution of 2-chloro-4-fluoroaniline (5.0 g, 34.35 mmol, 1 equiv) in 20% of phosgene in toluene (36 mL, 68.7-mmol, 2 equiv) was refluxed for 5 hrs. The reaction mixture was then concentrated and the resulting residue was directly used in the next step.

Example 196

1-(2-chloro-4-fluorophenyl)-4,5-dihydro-5H-tetrazol-5-one

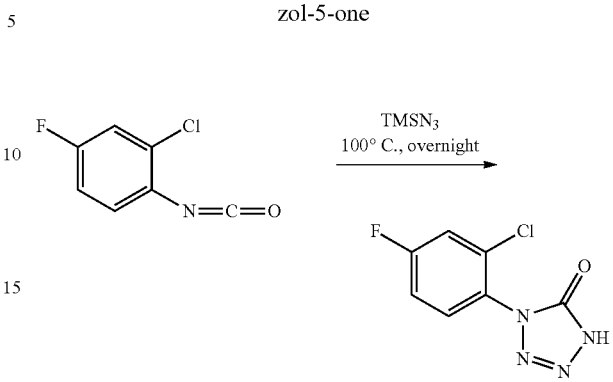

To the above residue of Example 195, 9.12 mL of TMSN$_3$ (68.7 mmol, 2 equiv) was added and then the resulting mixture was heated at 100° C. overnight. After being cooled to room temperature, the reaction mixture was concentrated. The residue was diluted with EtOAc (100 mL) and saturated aqueous NaHCO$_3$ (100 mL). The aqueous layer was separated, neutralized with 2 N HCl to pH 4~5 and extracted with EtOAc (2×100 mL). The organic layers were combined, dried over MgSO$_4$ and concentrated to give a white solid (1.8 g, 24% two steps) which was directly used in the next step. m/z=215.3 (M+H)$^+$.

Example 197

1-(2-chloro-4-fluorophenyl)-4-methyl-5H-tetrazol-5-one

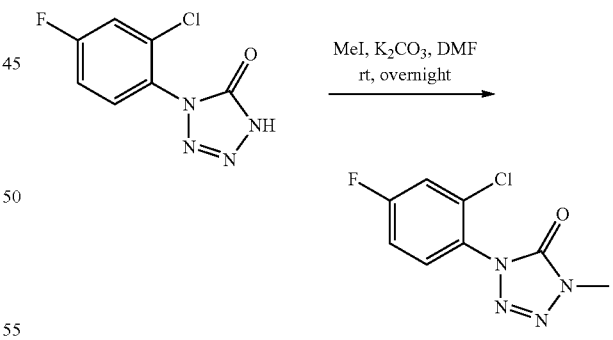

To a mixture of 1-(2-chloro-4-fluorophenyl)-4,5-dihydro-5H-tetrazol-5-one (1.8 g, 8.4 mmol, 1 equiv) and K$_2$CO$_3$ (3.48 g, 25.23 mmol, 3 equiv) in 25 mL of DMF was added MeI (1.57 mL, 25.23 mmol, 3 equiv) and the resulting mixture was stirred at room temperature overnight. The reaction mixture was diluted with water and extracted with EtOAc. The organic layer was separated and concentrated. The residue was triturated in water to give 1.68 g of product (88%) as a white solid. m/z=229.4 (M+H)$^+$.

Example 198

1-(2-chloro-4-fluoro-5-nitrophenyl)-4-methyl-5H-tetrazol-5-one

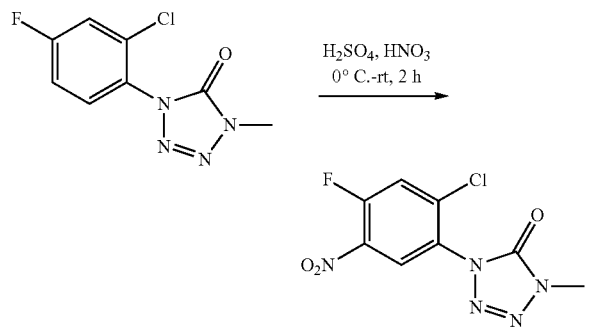

90% HNO₃ (0.19 mL, 3.86 mmol, 1.1 equiv) was added dropwise to a mixture of 1-(2-chloro-4-fluorophenyl)-4-methyl-5H-tetrazol-5-one (800 mg, 3.51 mmol, 1 equiv) in 3 mL of fuming H₂SO₄ at 0° C. Then the mixture was left to room temperature and stirred for 2 hours. Poured into ice and the aqueous phase was extracted with EtOAc. The organic layer was separated, washed with saturated NaHCO₃ and concentrated to give 980 mg of product (quantitative) as a yellow solid.

$^1$H NMR (CDCl$_3$, 300 MHz): δ 8.31 (d, J=7.5 Hz, 1H), 7.61 (d, J=10.2 Hz, 1H), 3.75 (s, 3H); m/z=274.4 (M+H)$^+$.

Example 199

1-(5-amino-2-chloro-4-fluorophenyl)-4-methyl-5H-tetrazol-5-one

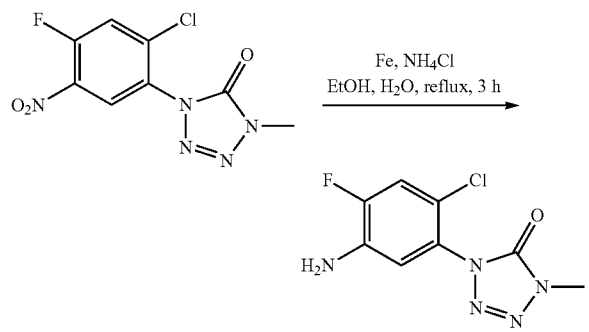

A mixture of 1-(2-chloro-4-fluoro-5-nitrophenyl)-4-methyl-5H-tetrazol-5-one (600 mg, 2.2 mmol, 1 equiv), iron powder (614 mg, 10.99 mmol, 5 equiv) and ammonium chloride (588 mg, 10.99 mmol, 5 equiv) in iPrOH (10 mL) and water (2 mL) was refluxed for 3 hours. After cooling to room temperature, the reaction mixture was filtered through a pad of Celite, and the pad of Celite was rinsed with EtOAc (50 mL). The filtrate was washed with water. The organic layer was separated, dried over MgSO₄ and evaporated to give the product quantitatively. m/z=244.4 (M+H)$^+$.

Example 200

N2-(2-chloro-4-fluoro-3-(4-methyl-4,5-dihydro-5-oxo-1H-tetrazol-1-yl)phenyl)-5-fluoro-N4-(2,2,6,6-tetramethylpiperidin-4-yl)pyrimidine-2,4-diamine (I-68)

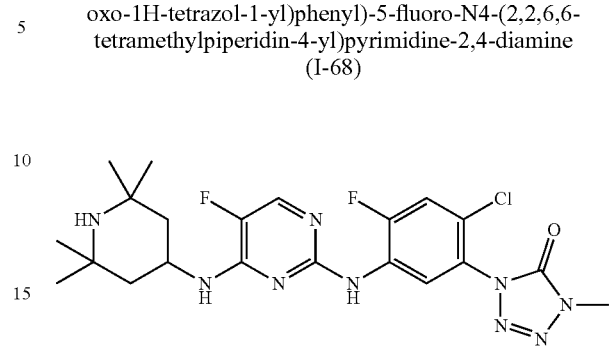

$^1$H NMR (DMSO-d$_6$, 300 MHz): δ 8.75 (br. s, 1H), 8.15 (d, J=7.8 Hz, 1H), 7.87 (d, J=3.6 Hz, 1H), 7.76 (d, J=10.5 Hz, 1H), 7.29 (br. s, 1H), 4.30-4.20 (m, 1H), 3.61 (s, 3H), 1.70-1.60 (m, 2H), 1.40-1.50 (m, 2H), 1.02 (s, 12H); m/z=494.3 (M+H)$^+$.

Example 201

N2-(2-chloro-4-fluoro-3-(4-methyl-4,5-dihydro-5-oxo-1H-tetrazol-1-yl)phenyl)-5-fluoro-N4-(1,2,2,6,6-pentamethylpiperidin-4-yl)pyrimidine-2,4-diamine (I-69)

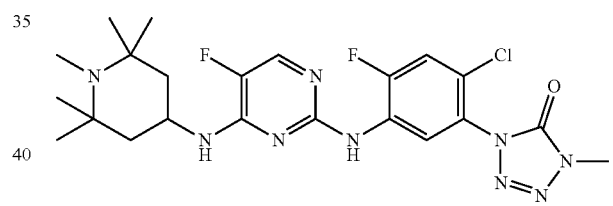

$^1$H NMR (DMSO-d$_6$, 300 MHz): δ 8.73 (br. s, 1H), 8.15 (d, J=6.9 Hz, 1H), 7.86 (br. s, 1H), 7.74 (d, J=10.8 Hz, 1H), 7.28 (s, 1H), 4.20-4.10 (m, 1H), 3.62 (s, 3H), 2.12 (s, 3H), 1.64-1.58 (m, 2H), 1.37 (tm, J=11.7 Hz, 2H), 1.02 (s, 6H), 0.84 (s, 6H); m/z=508.3 (M+H)$^+$.

Synthesis of 1-(4-fluoro-5-(5-fluoro-4-(2,2,6,6-tetramethylpiperidin-4-ylamino)pyrimidin-2-ylamino)-2-((1S,2S)-2-(trifluoromethyl)cyclopropyl)phenyl)-4-methyl-1H-tetrazol-5(4H)-one (I-70)

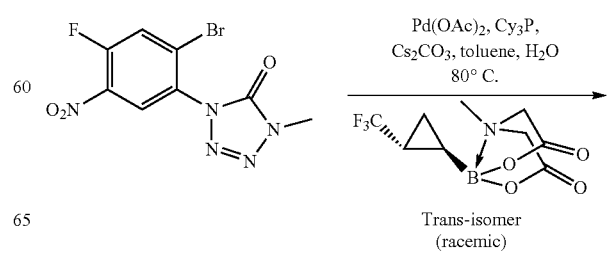

Trans-isomer (racemic)

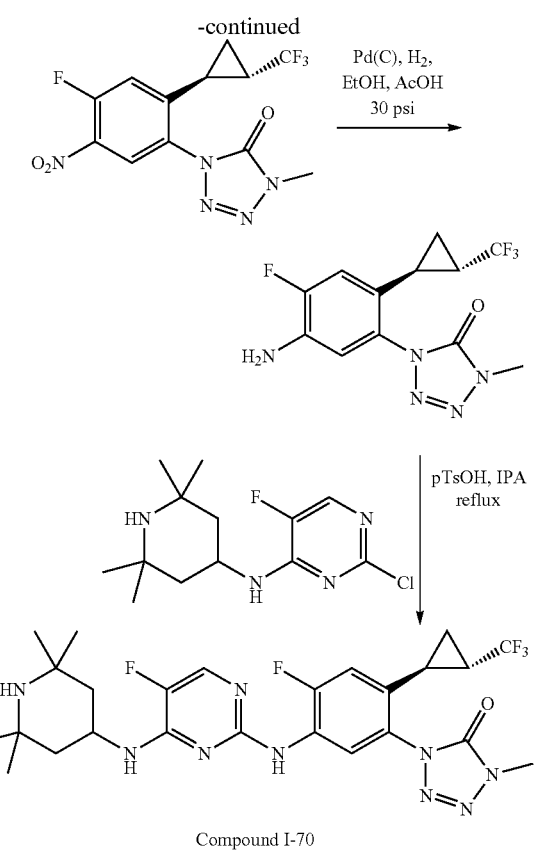

Compound I-70

Example 202

Preparation of Trans-2-(trifluoromethyl)cyclopropylboronic Acid MIDA Ester

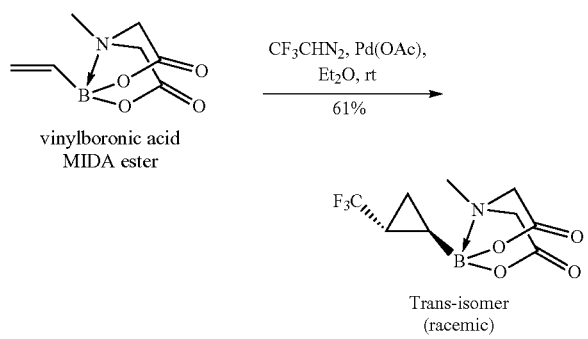

Trans-isomer (racemic)

Step 1: Preparation of Trifluoromethyl Diazomethane

Sodium nitrite (4.6 g, 66 mmol) in water (10 mL) was added in one portion to a stirred solution of 2,2,2-trifluoroethylamine hydrochloride (8.1 g, 60 mmol) in water (25 mL) and ether (45 mL) at 0° C. The reaction vessel was sealed with a teflon stopper and the mixture stirred from 0° C. to room temperature and stirred at room temperature for approximately 3 hours. The mixture was then partitioned in a separating funnel and the ether layer containing the product was used directly in the next step without further purification. The yield of the trifluoromethyl diazomethane product was assumed to be approximately 50% based on literature citation herein (=3.32 g).

A safety notice for the procedure: Diazo compounds are potentially explosive. The reaction was performed behind a blast shield in glassware free from cracks or prominent scratches and glassware was inspected prior to use.

Reference for the procedure is made to *J. Am. Chem. Soc.* 1943, 65, 1458, which is hereby incorporated by reference in its entirety.

Step 2: Preparation of Trans-2-(trifluoromethyl)cyclopropylboronic Acid MIDA Ester A mixture of trifluoromethyl diazomethane (3.32 g, 30 mmol) in $Et_2O$ (45 mL) was added dropwise to a stirred suspension of vinylboronic acid MIDA ester (Sigma-Aldrich, St. Louis, Mo.; 1.65 g, 9.0 mmol) and $Pd(OAc)_2$ (50 mg) in $Et_2O$ at room temperature. After adding for 10 minutes (about a quarter of the trifluoromethyl diazomethane had been added at this stage), more $Pd(OAc)_2$ (50 mg) and $Et_2O$ (100 mL) was added, and trifluoromethyl diazomethane was added dropwise for another 20 minutes (approximately three quarters added after this time). EtOAc (50 mL) and $Pd(OAc)_2$ (50 mg) were added at this point and the remaining trifloromethyl diazomethane was added dropwise over 10 minutes. After complete addition of the trifloromethyl diazomethane the mixture was analysed by TLC which indicated complete reaction. The solvent was removed under vacuum and the residue was dry-loaded on to silica gel and purified by column chromatography on silica gel using EtOAc as eluent to give the product (1.45 g, 61%) as a solid. A sample was recrystallised from EtOAc, and then a small sample recrystallized again from 1,2-dichloroethane, to give crystals suitable for analysis by x-ray crystallography. X-ray studies confirmed the material to be the trans-isomer.

Reference for the procedure is made to *Tetrahedron Letters* 2010, 51, 1009-1011, which is hereby incorporated by reference in its entirety. Reference for the procedure and procedures below is made to U.S. Provisional Patent Application Ser. No. 61/418,654, entitled "Cyclopropyl MIDA Boronate," filed concurrently herewith, which is hereby incorporated by reference in its entirety.

$^1$H NMR (DMSO-$d_6$, 300 MHz): δ 3.99-3.72 (m, 4H), 2.70 (s, 3H), 1.28 (m, 1H), 0.53 (m, 1H), 0.31 (m, 1H), 0.00 (m, 1H). 19F NMR (DMSO-$d_6$, 282 MHz): -65.4.

Example 203

Preparation of Trans-1-(4-fluoro-2-(2-(trifluoromethyl)cyclopropyl)-5-nitrophenyl)-4-methyl-1H-tetrazol-5(4H)-one

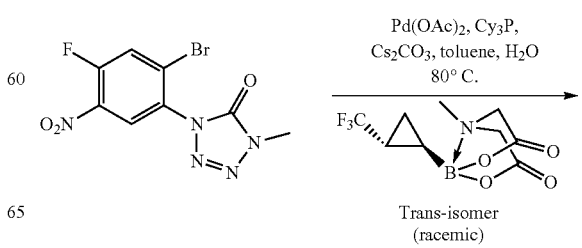

Trans-isomer (racemic)

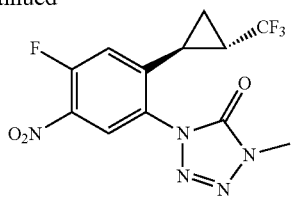

A mixture of 1-(2-bromo-4-fluoro-5-nitrophenyl)-4-methyl-1H-tetrazol-5(4H)-one (145 mg, 0.46 mmol), trans-2-(trifluoromethyl)cyclopropylboronic acid MIDA ester (240 mg, 0.91 mmol), Pd(OAc)$_2$ (20 mg, 0.09 mmol), Cy$_3$P (50 mg, 0.18 mmol) and Cs$_2$CO$_3$ (593 mg, 1.82 mmol) in toluene (6 mL) and H$_2$O (2 mL) was de-gassed with N$_2$ for 10 minutes, then placed under a nitrogen atmosphere and heated to 80° C. overnight (a reflux condenser was used in the apparatus). After completion of the reaction (Note: TLC showed product and starting material to be very close), the mixture was cooled and partitioned between EtOAc (50 mL) and H$_2$O (50 mL). The aqueous and organic layers were partitioned and the organic layer was washed with brine (1×20 mL), dried (MgSO$_4$), filtered and the solvent removed under vacuum to leave a crude residue. The residue was dry-loaded on to silica gel and purified by column chromatography on silica gel using EtOAc/hexane (3:7 to 4:6) as eluent to give the product (107 mg, 67%).

The above reaction was also undertaken starting with 106 mg of 1-(2-bromo-4-fluoro-5-nitrophenyl)-4-methyl-1H-tetrazol-5(4H)-one to give the product (55 mg, 47%).

$^1$H NMR (CDCl$_3$, 300 MHz): δ 8.19 (dd, 1H), 7.22 (d, 1H), 3.74 (s, 3H), 2.69-2.62 (m, 1H), 1.78-1.69 (m, 1H), 1.50-1.43 (m, 1H), 1.29-1.22 (m, 1H). $^{19}$F NMR (CDCl$_3$, 282 MHz): −67.6, −112.9. m/z=389.2 (M$^+$MeCN+H)$^+$.

Example 204

Preparation of trans-1-(5-amino-4-fluoro-2-(2-(trifluoromethyl)cyclopropyl)phenyl)-4-methyl-1H-tetrazol-5(4H)-one

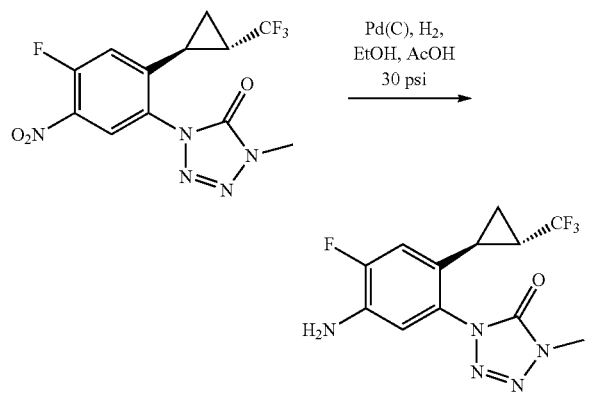

Palladium on charcoal, wet (Degussa grade E101; 29 mg) was added to a mixture of trans-1-(4-fluoro-2-(2-(trifluoromethyl)cyclopropyl)-5-nitrophenyl)-4-methyl-1H-tetrazol-5(4H)-one (145 mg, 0.46 mmol), EtOH (10 mL) and AcOH (75 µL) under nitrogen. The mixture was evacuated and filled with hydrogen—this procedure was repeated another two times. The mixture was hydrogenated at 30 psi for 7 days (topping-off the hydrogen if necessary). More Pd on charcoal, wet (Degussa grade E101; 15 mg) was added and the mixture hydrogenated at 30 psi for another 10 days (LC/MS was used to monitor the progression of the reaction over the 2 week experiment). After complete reaction, the mixture was filtered through a small plug of Celite and the filter cake washed with EtOH (3×10 mL). The filtrate was concentrated under vacuum (dry-loaded on to silica) and purified by column chromatography on silica gel using EtOAc/hexane (1:4 to 2:3) as eluent to give the product (117 mg, 89%) as a solid.

$^1$H NMR (d$_6$-DMSO, 300 MHz): δ 6.99 (d, 1H), 6.78 (dd, 1H), 5.53 (br. s, 2H), 3.58 (s, 3H), 2.18-2.11 (m, 1H), 1.92-1.87 (m, 1H), 1.23-1.09 (m, 2H). $^{19}$F NMR (d$_6$-DMSO, 282 MHz): −65.5, −132.0. m/z=318.1 (M+H)$^+$.

Example 205

Preparation of trans-1-(5-(4-(2,2,6,6-tetramethylpiperidin-4-ylamino)-5-fluoropyrimidin-2-ylamino)-4-fluoro-2)2-(trifluoromethyl)cyclopropyl)phenyl)4-4methyl-1H-tetrazol-5(4H)-one (I-70)

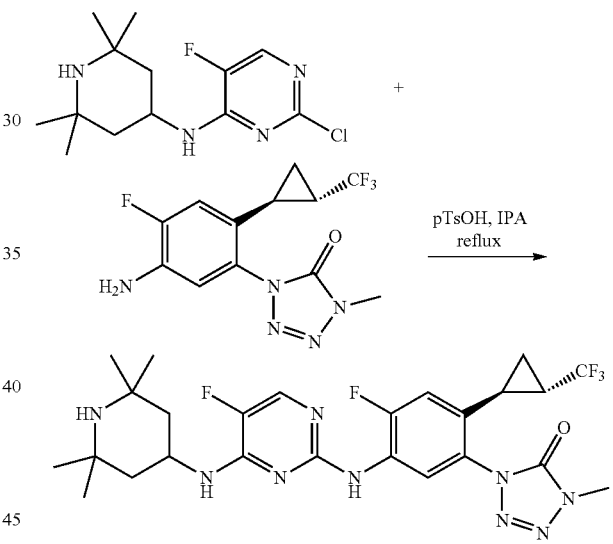

A mixture of trans-1-(5-amino-4-fluoro-2-(2-(trifluoromethyl)cyclopropyl)phenyl)-4-methyl-1H-tetrazol-5(4H)-one (110 mg, 0.35 mmol), 2-chloro-5-fluoro-N4-(2,2,6,6-tetramethylpiperidin-4-yl)-4-pyrimidineamine hydrochloride (112 mg, 0.35 mmol) and para-toluenesulfonic acid monohydrate (66 mg, 0.35 mmol) in IPA (7.5 mL) was heated to reflux and stirred for 7 days. After allowing to cool, 3-aminobenzoic acid (100 mg) added and the mixture stirred at reflux overnight. After cooling, the mixture was concentrated under vacuum and the residue portioned between EtOAc (30 mL) and 1N NaOH (30 mL). The aqueous and organic layers were partitioned and the organic layer was dried (MgSO$_4$), filtered and the solvent removed under vacuum to leave a residue (LC/MS indicates this to be product and unreacted aniline). The residue was triturated with Et$_2$O and the emerging precipitate was filtered and the filter cake washed with Et$_2$O to give the product (48 mg, 24%) as a solid. [Note: there is still a lot of product in the filtrate].

$^1$H NMR (d$_6$-DMSO, 300 MHz): δ 8.56 (br. s, 1H), 7.92 (d, 1H), 7.84 (d, 1H), 7.25-7.19 (m, 2H), 4.22 (m, 1H), 3.58

(s, 3H), 2.23 (m, 1H), 2.02 (m, 1H), 1.57 (m, 2H), 1.26 (m, 2H), 1.14-1.07 (m, 2H), 0.97 (s, 12H). 19F NMR (d$_6$-DMSO, 282 MHz): −65.6, −120.1, −165.8. m/z=568.7 (M+H)$^+$.

Synthesis of 1-(4-fluoro-3-(5-fluoro-4-(2,2,6,6-tetramethylpiperidin-4-ylamino)pyrimidin-2-ylamino)phenyl)-4-methyl-1H-tetrazol-5(4H)-one (I-71)

extracts were combined and EtOAc (100 mL) was added. The mixture was acidified to pH<2 using 6M HCl. The aqueous and organic layers were partitioned and the organic layer was dried (MgSO$_4$), filtered and the solvent removed under vacuum to leave the product (1.96 g, 78%) as a solid.

$^1$H NMR (d$_6$-DMSO, 300 MHz): δ 8.64-8.62 (m, 1H), 8.28-8.22 (m, 1H), 7.83-7.77 (m, 1H). $^{19}$F NMR (d$_6$-DMSO, 282 MHz): −119.7. m/z=224.0 (M−H)$^+$.

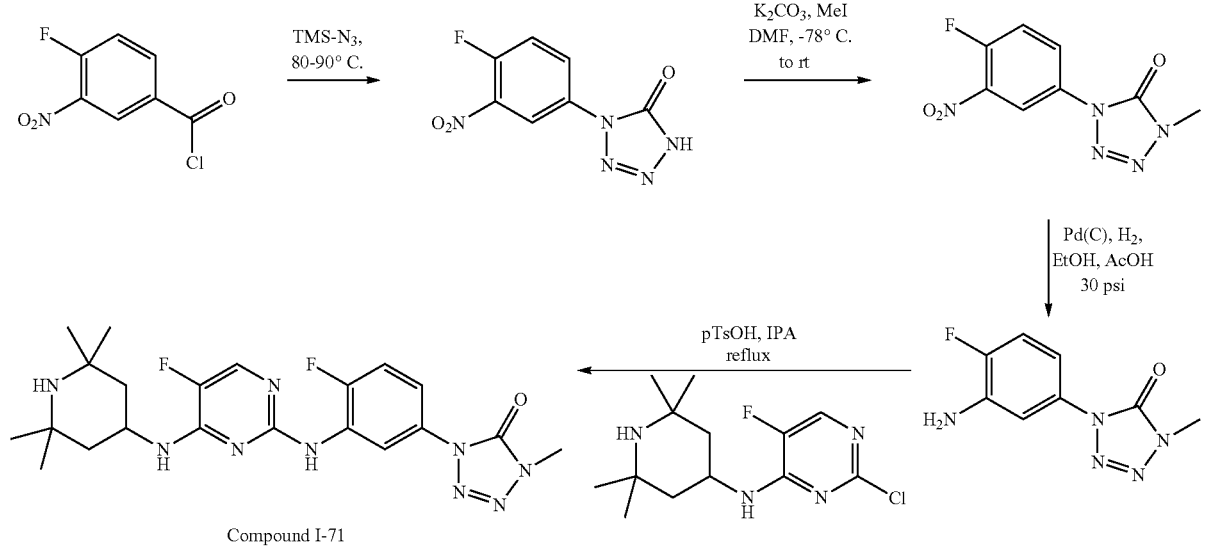

Compound I-71

Example 206

Preparation of 1-(4-fluoro-3-nitrophenyl)-1H-tetrazol-5(4H)-one

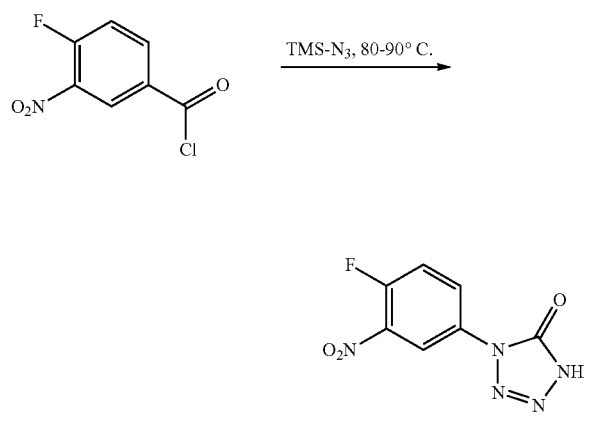

A mixture of 4-fluoro-3-nitro-benzoyl chloride (2.04 g, 10 mmol) and azidotrimethylsilane (7.9 mL, 60 mmol) was slowly heated to 80-90° C. and the mixture was stirred overnight. The reaction was performed behind a blast shield. After allowing to cool, the solvent was removed under vacuum and the residue partitioned between EtOAc (50 mL) and H$_2$O (50 mL). The organic layer was extracted with saturated NaHCO$_3$ (3×50 mL—until TLC indicated all desired product removed from organic layer). The aqueous Example 207

Preparation of 1-((4-fluoro-3-nitrophenyl)-4-methyl-1H-tetrazol-5(4H)-one

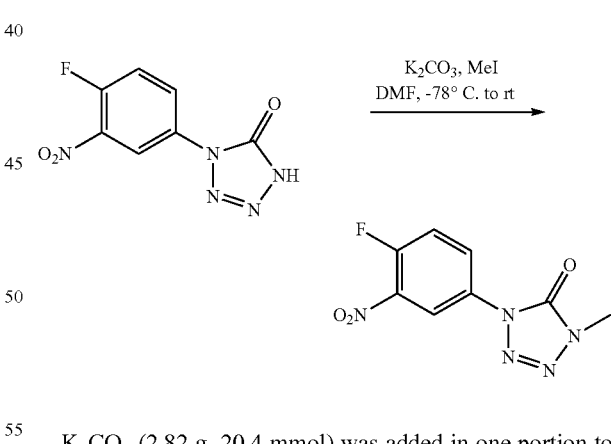

K$_2$CO$_3$ (2.82 g, 20.4 mmol) was added in one portion to a stirred mixture of 1-(4-fluoro-3-nitrophenyl)-1H-tetrazol-5(4H)-one (1.84 g, 8.2 mmol) and MeI (2.32 g, 16.3 mmol) in DMF (17.5 mL) under nitrogen at −78° C. The mixture was allowed to warm to room temperature overnight. Analysis by TLC indicated complete reaction, so the mixture was poured in to EtOAc (50 mL) and H$_2$O (75 mL). The aqueous and organic layers were partitioned and the organic layer was washed with H$_2$O (2×75 mL). The combined aqueous layers were back-extracted with EtOAc (1×50 mL) and the combined organic extracts were dried (MgSO$_4$), filtered and the solvent removed under vacuum to leave a crude residue.

The residue (dry-loaded on to silica) was purified by column chromatography on silica gel using EtOAc/hexane (3:7 to 4:6) as eluent to give the product (1.68 g, 86%) as a solid.

¹H NMR (d₆-DMSO, 300 MHz): δ 8.62-8.58 (m, 1H), 8.28-8.22 (m, 1H), 7.84-7.77 (m, 1H), 3.62 (s, 3H). 19F NMR (d₆-DMSO, 282 MHz): −119.2. m/z=281.1 (M⁺MeCN+H)⁺.

Example 208

Preparation of 1-(3-amino-4-fluorophenyl)-4-methyl-1H-tetrazol-5(4H)-one

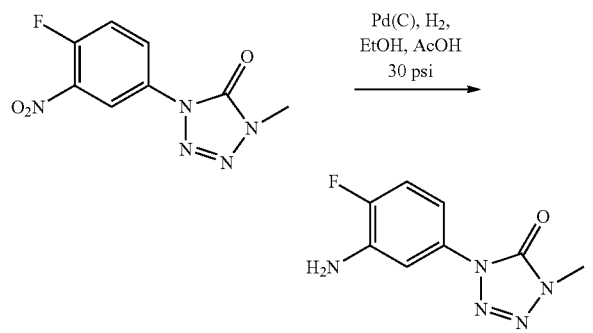

Palladium on charcoal, wet (Degussa grade E101; 25 mg) was added to a mixture of 1-(4-fluoro-3-nitrophenyl)-4-methyl-H-tetrazol-5(4H)-one (120 mg, 0.5 mmol), EtOH (15 mL) and AcOH (120 µL) under nitrogen. The mixture was evacuated and filled with hydrogen—this procedure was repeated another two times. The mixture was hydrogenated at 30 psi overnight (LC/MS was used to monitor the progression of the reaction). After complete reaction, the mixture was filtered through a small plug of Celite and the filter cake washed with EtOH. The filtrate was concentrated under vacuum to give the product (106 mg, 100%) as a solid.

¹H NMR (d₆-DMSO, 300 MHz): δ 7.27 (m, 1H), 7.16-7.10 (m, 1H), 6.97-6.92 (m, 1H), 5.53 (br. s, 2H), 3.58 (s, 3H). 19F NMR (d₆-DMSO, 282 MHz): −135.6. m/z=210.0 (M+H)⁺.

Example 209

Preparation of 1-(3-(4-(2,2,6,6-tetramethylpiperidin-4-ylamino)-5-fluoropyrimidin-2-ylamino)-4-fluorophenyl)-4-methyl-1H-tetrazol-5(4H)-one (I-71)

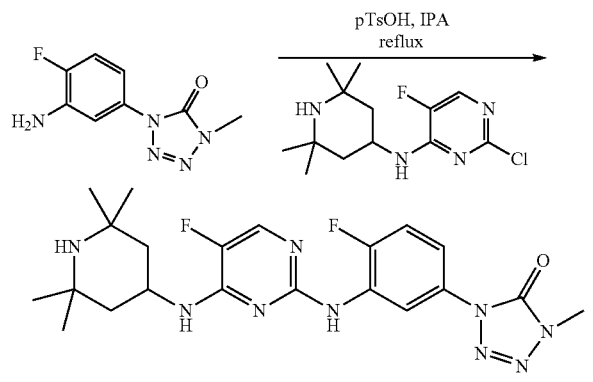

A mixture of 1-(3-amino-4-fluorophenyl)-4-methyl-1H-tetrazol-5(4H)-one (96 mg, 0.46 mmol), 2-chloro-5-fluoro-N4-(2,2,6,6-tetramethylpiperidin-4-yl)-4-pyrimidineamine hydrochloride (141 mg, 0.44 mmol) and para-toluenesulfonic acid monohydrate (84 mg, 0.44 mmol) suspended in IPA (7.5 mL) was heated to reflux and stirred for 3 days. The mixture was then cooled, and 3-aminobenzoic acid (100 mg) was added and the mixture stirred at reflux overnight. After allowing to cool, the mixture was concentrated under vacuum and the residue partitioned between saturated NaHCO₃ (30 mL) and EtOAc (30 mL). The aqueous and organic layers were partitioned and the organic layer was washed with saturated NaHCO₃ (1×30 mL), dried (MgSO₄), filtered and the solvent removed under vacuum to leave a crude residue (ca. 180 mg). The residue was triturated with Et₂O (solid emerges) and the Et₂O mixture cooled in a −18° C. freezer for 15 minutes before filtering. The filter cake was washed with Et₂O (2×10 mL) to give the product (78 mg, 39%) as a solid.

¹H NMR (d₆-DMSO, 300 MHz): δ 8.62 (br. s, 1H), 8.29 (m, 1H), 7.85 (d, 1H), 7.42-7.32 (m, 2H), 7.17 (d, 1H), 4.21 (m, 1H), 3.57 (s, 3H), 1.57 (m, 2H), 1.10-1.02 (m, 2H), 0.95 (s, 6H), 0.90 (s, 6H). 19F NMR (d₆-DMSO, 282 MHz): −124.2, −165.8. m/z=460.4 (M+H)⁺

Synthesis of 1-(2-cyclopropyl-4-fluoro-5-(5-fluoro-4-(2,2,6,6-tetramethylpiperidin-4-ylamino)pyrimidin-2-ylamino)phenyl-4-(deuteriomethyl)-1H-tetrazol-5(4H)-one (I-72)

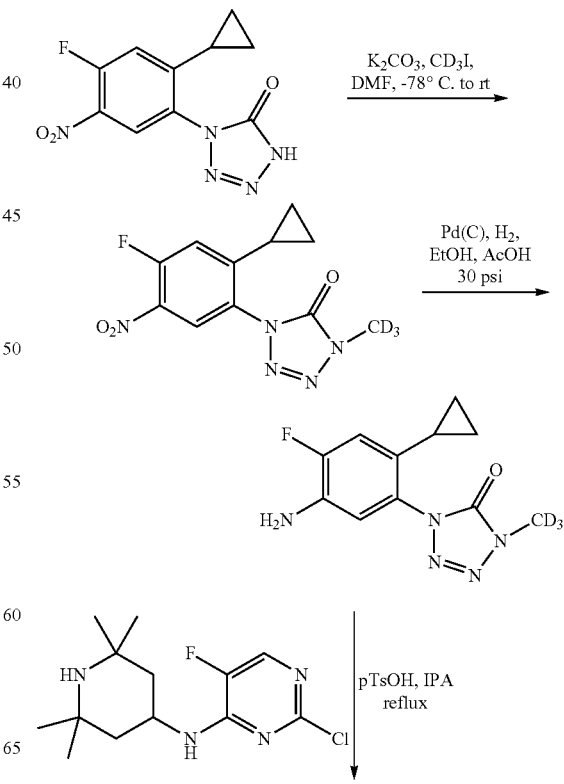

-continued

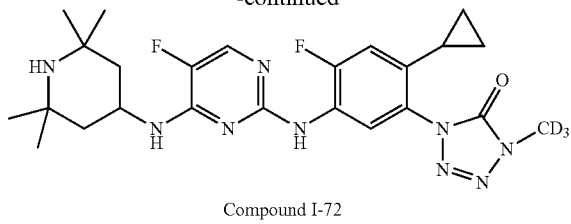

Compound I-72

Example 210

Preparation of 1-(2-cyclopropyl-4-fluoro-nitrophenyl)-4-deuteriomethyl-1H-tetrazol-5(4H)-one

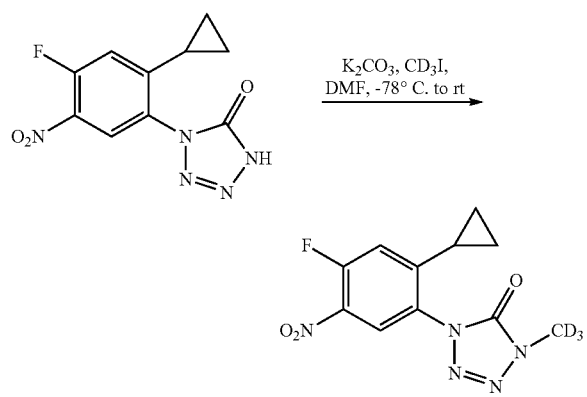

K$_2$CO$_3$ (276 mg, 2.0 mmol) was added in one portion to a stirred mixture of 1-(2-cyclopropyl-4-fluoro-5-nitrophenyl)-1H-tetrazol-5(4H)-one (265 mg, 1.0 mmol) and d3-iodomethane (Aldrich; 187 μL, 3.0 mmol) in DMF (3 mL) under nitrogen at −78° C. (mixture solidified after K$_2$CO$_3$ addition). The mixture was allowed to warm to room temperature overnight. The mixture was poured in to EtOAc (50 mL) and H$_2$O (50 mL). The aqueous and organic layers were partitioned and the organic layer was washed with H$_2$O (2×30 mL), then brine (1×30 mL). The organic layer was dried (MgSO$_4$), filtered and the solvent removed under vacuum to leave the product (257 mg, 91%) as a solid.

$^1$H NMR (d$_6$-DMSO, 300 MHz): δ 8.38 (d, 1H), 7.29 (d, 1H), 1.88-1.82 (m, 1H), 1.10-1.04 (m, 2H), 0.96-0.91 (m, 2H) [Note: no Me peak in $^1$H NMR as CD$_3$ analogue]. $^{19}$F NMR (d$_6$-DMSO, 282 MHz): −115.3. m/z=283.1 (M+H)$^+$.

Example 211

Preparation of 1-(5-amino-2-cyclopropyl-4-fluorophenyl)-4-dueteriomethyl-1H-tetrazol-5(4H)-one

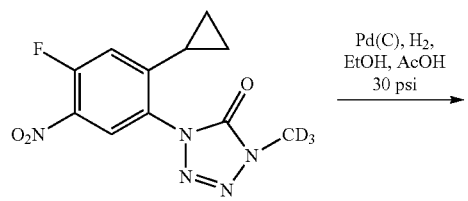

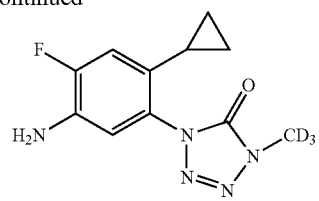

Palladium on charcoal, wet (Degussa grade E101; 50 mg) was added to a mixture of 1-(2-cyclopropyl-4-fluoro-5-nitrophenyl)-4-deuteriomethyl-1H-tetrazol-5(4H)-one (250 mg, 0.89 mmol) in EtOH (15 mL) under nitrogen. The mixture was evacuated and filled with hydrogen—this procedure was repeated another two times. The mixture was hydrogenated at 30 psi for 3-4 hours (LC/MS was used to monitor the progression of the reaction). After complete reaction, the mixture was filtered through a small plug of Celite and the filter cake washed with EtOH (3×20 mL). The filtrate was concentrated under vacuum to give the product, which was used directly in the next step (yield assumed quantitative=222 mg).

m/z=253.1 (M+H)$^+$

Example 212

Preparation of N2-{4-cyclopropyl-6-fluoro-[3-(4-dueteriomethyl)-1,2,3,4-tetrazol-5-one-1-yl]}phenyl-5-fluoro-N4-(2,2,6,6-tetramethylpiperidin-4-yl)-2,4-pyrimidinediamine (I-72)

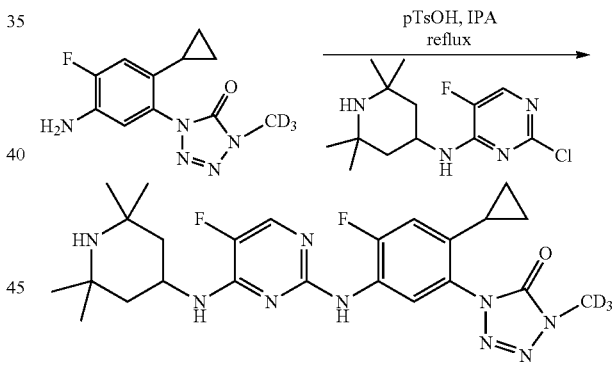

A mixture of 1-(5-amino-2-cyclopropyl-4-fluorophenyl)-4-deuteriomethyl-1H-tetrazol-5(4H)-one (222 mg, 0.89 mmol), 2-chloro-5-fluoro-N4-(2,2,6,6-tetramethylpiperidin-4-yl)-4-pyrimidineamine hydrochloride (270 mg, 0.83 mmol) and para-toluenesulfonic acid monohydrate (159 mg, 0.83 mmol) suspended in IPA (5 mL) was heated to reflux and stirred for 2 days. The mixture was then cooled, and 3-aminobenzoic acid (100 mg) was added and the mixture stirred at reflux overnight. After allowing to cool, the mixture was concentrated under vacuum and the residue partitioned between 1N NaOH (50 mL) and EtOAc (50 mL). The aqueous and organic layers were partitioned and the organic layer was washed with brine (1×30 mL), dried (MgSO$_4$), filtered and the solvent removed under vacuum to leave a crude residue. The residue was triturated with MeCN and filtered to give the product (140 mg, 34%) as a solid.

$^1$H NMR (d$_6$-DMSO, 300 MHz): δ 8.49 (br. s, 1H), 7.81-7.76 (m, 2H), 7.19 (d, 1H), 6.94 (d, 1H), 4.21 (m, 1H), 1.65-1.56 (m, 3H), 1.30-1.05 (m, 2H), 0.98-0.96 (s, 12H), 0.81-0.78 (m, 2H), 0.59-0.57 (m, 2H) [Note: no Me peak in $^1$H NMR as CD$_3$ analogue]. 19F NMR (d$_6$-DMSO, 282 MHz): −120.1, −166.8. m/z=503.4 (M+H)$^+$.

Example 213

1-(2-cyclopropyl-4-fluoro-5-nitrophenyl)-4-isopropyl-1H-tetrazol-5(4H)-one

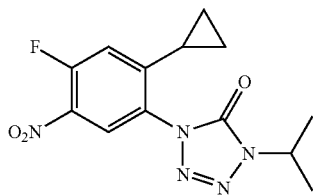 [SMILES: CC(C)n1nnn(-c2cc([N+](=O)[O-])c(F)cc2C2CC2)c1=O]

1-(2-Cyclopropyl-4-fluoro-5-nitrophenyl)-1H-tetrazol-5(4H)-one (500 mg, 1.9 mmol) was dissolved into DMF (9.4 ml), the solution was chilled to −70° C. K$_2$CO$_3$ (780 mg, 5.7 mmol) was added to this solution and followed by 2-iodopropane (0.23 ml, 2.28 mmol). The mixture was allowed to warm up to room temperature overnight with stirring. Ethyl acetate and brine were added to this mixture, the 2 layers were separated. The organic layer was dried with Na$_2$SO$_4$, filtered off solid and concentrated under reduced pressure to give the product (208 mg, 75% pure).

$^1$H NMR (300 MHz, DMSO-d$_6$) δ 8.43 (d, J=6.9 Hz, 1H), 7.33 (d, J=12.6 Hz, 1H), 4.45 (m, 1H), 1.82 (m, 1H), 1.47 (s, 3H), 1.45 (s, 3H), 1.05 (m, 2H), 0.95 (m, 2H); LCMS (m/z): 307.11 (MH$^+$).

Example 214

1-(5-amino-2-cyclopropyl-4-fluorophenyl)-4-isopropyl-1H-tetrazol-5(4H)-one

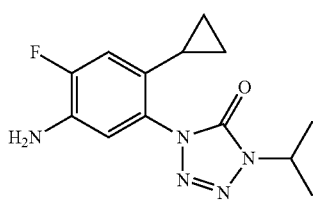

1-(2-Cyclopropyl-4-fluoro-5-nitrophenyl)-4-isopropyl-1H-tetrazol-5(4H)-one (208 mg, 0.7 mmol) was added to ethyl alcohol (4.8 ml), SnCl$_2$.2H$_2$O (501 mg, 2.7 mmol) and conc. HCl (0.6 ml) were added to the solution. The mixture was heated at 80° C. for 1 hour. The solution was allowed to cool to room temperature, and concentrated under reduced pressure. Ethyl acetate was added and washed with saturated K$_2$CO$_3$, the 2 layers were separated. The organic layer was washed with brine and dried with Na$_2$SO$_4$. Solid was filtered off and mother liquor was concentrated under reduced pressure to give the product (140 mg) as a white solid.

$^1$H NMR (300 MHz, DMSO-d$_6$) δ 6.83 (d, J=12.3 Hz, 1H), 6.75 (d, J=8.7 Hz, 1H), 5.36 (s, 2H), 4.43 (m, 1H), 1.54 (m, 1H), 1.44 (s, 3H), 1.42 (s, 3H), 0.65 (m, 2H), 0.43 (m, 2H); LCMS (m/z): 278.11 (MH$^+$).

Example 215

N2-{4-cyclopropyl-6-fluoro-[3-(4-isopropyl)-1,2,3,4-tetrazol-5-one-1-yl]}phenyl-5-5fluoro-N4-(2,2,6,6-tetramethylpiperidin-4-yl)-2,4-pyrimidinediamine (I-73)

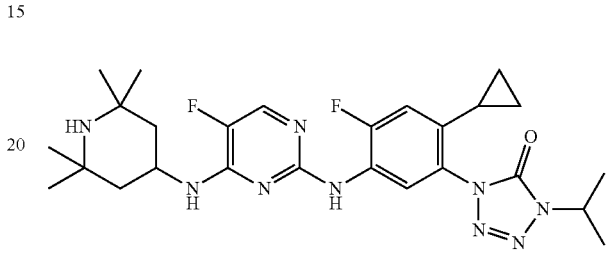

$^1$H NMR (DMSO-d$_6$, 300 MHz): δ 8.49 (s, 1H), 7.81 (bs, 1H), 7.76 (d, J=7.2 Hz, 1H), 7.19 (bs, 1H), 6.99 (d, J=11.7 Hz, 1H), 4.43 (m, 1H), 4.25 (bs, 1H), 1.6 (m, 2H), 1.45 (s, 3H), 1.43 (s, 3H), 1.51 (m, 2H), 0.97 (m, 12H), 0.77 (m, 2H), 0.53 (m, 2H); LCMS (m/z): 528.40 (MH$^+$).

Example 216

1-(5-amino-2-cyclopropyl-4-fluorophenyl)-1H-tetrazol-5(4H)-one

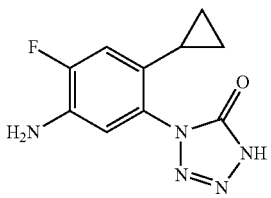 [SMILES: Nc1cc(-n2nn[nH]c2=O)c(C2CC2)cc1F]

1-(2-Cyclopropyl-4-fluoro-5-nitrophenyl)-4-H-1H-tetrazol-5(4H)-one (145 mg, 0.5 mmol) was added to ethyl alcohol (4.0 ml), SnCl$_2$.2H$_2$O (409 mg, 2.2 mmol) and concentrated HCl (0.47 ml) were added to the solution. The mixture was heated at 80° C. for 1 hour. The solution was allowed to cool to room temperature, and concentrated under reduced pressure. Ethyl acetate was added and washed first with water (2×10 ml), and then brine (10 ml). The 2 layers were separated and the organic layer was dried with Na$_2$SO$_4$. Solid was filtered off and mother liquor was concentrated under reduced pressure to give the product (95.1 mg, 74% yield) as a white solid.

$^1$H NMR (300 MHz, DMSO-d$_6$) δ 6.8 (d, J=12.6 Hz, 1H), 6.72 (d, J=8.4 Hz, 1H), 5.33 (s, 2H), 1.56 (m, 1H), 0.67 (d, J=7.8 Hz, 2H), 0.45 (d, J=4.5 Hz, 2H); LCMS (m/z): 236.05 (MH$^+$).

Example 217

N2-{4-cyclopropyl-6-fluoro-3-(1,2,3,4-tetrazol-5-one-1-yl)}phenyl-5-fluoro-N4-(2,2,6,6-tetramethyl-piperidin-4-yl)-2,4-pyhrimidinediamine, Formate Salt (I-74)

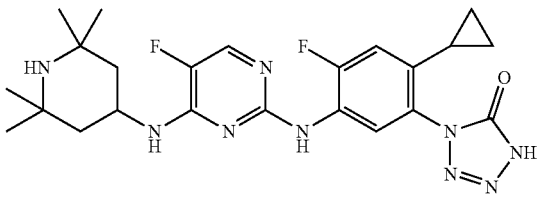 [SMILES: CC1(C)CC(Nc2nc(Nc3cc(-n4nn[nH]c4=O)c(C4CC4)cc3F)ncc2F)CC(C)(C)N1]

$^1$H NMR (DMSO-d$_6$, 300 MHz): δ 8.88 (bs, 1H), 8.55 (d, J=12.3 Hz, 1H), 7.95 (d, J=3.3 Hz, 1H), 7.69 (d, J=7.5 Hz, 1H), 7.45 (d, J=7.5 Hz, 1H), 7.09 (d, J=7.5 Hz, 1H), 7.03 (d, J=11.7 Hz, 1H), 4.26 (m, 1H), 2.71 (bs, 1H), 1.84 (d, J=11.7 Hz, 2H), 1.66 (m, 1H), 1.49 (t, J=12.9 Hz, 2H), 1.32 (s, 6H), 1.21 (s, 6H), 0.85 (m, 2H), 0.6 (m, 2H); LCMS (m/z): 486.13 (MH$^+$).

Example 218

N2-{4-Cyclopropyl-6-Fluoro-[3-(4-Methyl)-1,2,3,4-Tetrazol-5-One-1-yl]}Phenyl-5-Fluoro-N4-(2,2,6,6-Tetramethylpiperidin-4-yl)-2,4-Pyrimidinediamine Citrate Salt (I-75)

N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine (50 mg) was dissolved into isopropyl alcohol (4 ml) in a 20 ml scintillation vial, citric acid monohydrate (21.1 mg, 1.0 eq.) was added to the solution, solid formed immediately. The turbid solution was heated to 60° C. in an oil bath until the solution turned clear, turned off the heat and the vial was left in the oil bath until the temperature returned to room temperature (25° C.). The vial was removed from the bath and left in the cabinet for two days. The product was collected by filtering through a Buchner funnel fitted with filter paper, and pumped under reduced pressure overnight to remove residual solvent, gave 40 mg of white solid.

$^1$H NMR (300 MHz, DMSO-d$_6$) δ 8.61 (s, 1H), 7.88 (s, 1H), 7.72 (d, J=7.2 Hz, 1H), 7.49 (d, J=7.8 Hz, 1H), 6.99 (d, J=12.3 Hz, 1H), 4.31 (bs, 1H), 3.6 (s, 3H), 1.84 (d, J=13.5 Hz, 2H), 1.66 (m, 1H), 1.45 (t, J=12.6 Hz, 2H), 1.29 (s, 6H), 1.21 (s, 6H), 0.83 (m, 2H), 0.61 (m, 2H); LCMS (m/z): 500.20 (MH$^+$).

Example 219

N2-{4-Cyclopropyl-6-Fluoro-[3-(4-Methyl)-1,2,3,4-Tetrazol-5-One-1-yl]}Phenyl-5-Fluoro-N4-(2,2,6,6-Tetramethylpiperidin-4-yl)-2,4-Pyrimidinediamine Maleate Salt (I-76)

N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine (100 mg) was suspended in water (4 ml), maleic acid (23.3 mg, 10. eq.) was added to the suspension, a clear solution formed. A few minutes later tiny crystals can be seen forming at the bottom of vial. The vial was left inside the cabinet for 1 week. Product was collected by filtering off water, and dried under reduced pressure overnight, gave 85 mg of white solid.

$^1$H NMR (300 MHz, DMSO-d$_6$) δ 8.62 (s, 1H), 8.48 (d, J=13.2 Hz, 1H), 7.88 (d, J=3.9 Hz, 1H), 7.71 (d, J=6.9 Hz, 1H), 7.65 (bs, 1H), 7.51 (d, J=7.5 Hz, 1H), 6.99 (d, J=12.3 Hz, 1H), 5.99 (s, 2H), 4.31 (bs, 1H), 3.6 (s, 3H), 1.86 (d, J=12 Hz, 2H), 1.65 (m, 1H), 1.49 (t, J=12.3 Hz, 2H), 1.31 (s, 6H), 1.22 (s, 6H), 0.83 (m, 2H), 0.6 (m, 2H); LCMS (m/z): 500.20 (MH$^+$).

Example 220

N2-{4-Cyclopropyl-6-Fluoro-[3-(4-Methyl)-1,2,3,4-Tetrazol-5-One-1-yl]}Phenyl-5-Fluoro-N4-(2,2,6,6-Tetramethylpiperidin-4-yl)-2,4-Pyrimidinediamine Fumarate Salt (2:1 Ratio) (I-77)

N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine (50 mg) was suspended in 2 ml of H$_2$O in a 20 ml scintillation vial, fumaric acid (11.65 mg, 1.0 eq.) was added, a clear solution was obtained. The vial was left for 1 week at room temperature inside the cabinet, white stringy solid formed. The product was collected by filtering through a Buchner funnel fitted with filter paper and then pumped overnight under reduced pressure to dry, gave around 15 mg of white solid.

$^1$H NMR (300 MHz, DMSO-d$_6$) δ 8.52 (s, 1H), 7.84 (bs, 1H), 7.75 (d, J=7.5 Hz, 1H), 7.34 (bs, 1H), 6.97 (d, J=12 Hz, 1H), 6.38 (s, 1H), 4.24 (bs, 1H), 3.6 (s, 3H), 1.67 (m, 3H), 1.29 (t, J=11.4 Hz, 2H), 1.14 (s, 6H), 1.09 (s, 6H), 0.83 (m, 2H), 0.6 (m, 2H); LCMS (m/z): 500.20 (MH$^+$).

Example 221

N2-{4-Cyclopropyl-6-Fluoro-[3-(4-Methyl)-1,2,3,4-Tetrazol-5-One-1-yl]}Phenyl-5-Fluoro-N4-(2,2,6,6-Tetramethylpiperidin-4-yl)-2,4-Pyrimidinediamine L-Tartarate Salt (I-78)

N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine (50 mg) in a 20 ml scintillation vial was dissolved into isopropyl alcohol (3 ml) at 55° C. in an oil bath. 1.0 eq of L-tartaric acid (15.3 mg, 1.0 eq.) was added, without stirring, temperature increased to 75° C. (salt precipitates at about 55° C.) to minimize quick salt formation. Heating was turned off after 10 minutes at 75° C. and vial was left inside the oil bath to cool down overnight. White solid was obtained after filtering off the solvent and was dried under reduced pressure for 3 days, and then overnight at 60° C. under high vacuum to give 30 mg of white solid.

$^1$H NMR (300 MHz, DMSO-d$_6$) δ 8.53 (s, 1H), 7.85 (d, J=3.6 Hz, 1H), 7.75 (d, J=7.8 Hz, 1H), 7.35 (bs, 1H), 6.98 (d, J=12 Hz, 1H), 4.25 (bs, 1H), 3.73 (s, 2H), 3.6 (s, 3H), 1.69 (m, 3H), 1.28 (m, 2H), 1.14 (s, 6H), 1.09 (s, 6H), 0.81 (m, 2H), 059 (m, 2H); LCMS (m/z): 500.20 (MH$^+$).

Example 222

N2-{4-Cyclopropyl-6-Fluoro-[3-(4-Methyl)-1,2,3,4-Tetrazol-5-One-1-yl]}Phenyl-5-Fluoro-N4-(2,2,6,6-Tetramethylpiperidin-4-yl)-2,4-Pyrimidinediamine Hydrogen Sulfate Salt (I-79)

N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine (100 mg) was suspended in water (2 ml), 1N $H_2SO_4$ (0.2 ml, 1.0 eq.) was added, a clear solution was formed. The hydrogen sulfate salt was obtained by lyophilizing for 2 days and confirmed by $^1$H NMR. This salt (50 mg) was added to a 20 ml scintillation vial and dissolved in 10 ml of MeOH, the solution was filtered through filter paper to ensure clear solution were obtained. The vial was put into a glass jar filled with THF, kept in the cabinet with the lid closed. After 3 days, with no signs of crystal formation, THF was poured out and replaced with diethyl ether. The jar was again kept with the lid closed and inside the cabinet for 9 days, long needle shaped crystals can be seen forming at the bottom and the wall of the vial. The solution from the vial was carefully poured out onto a funnel fitted with filter paper. The solid (15 mg) collected was washed with ether, and dried under reduced pressure for 48 hours.

$^1$H NMR (300 MHz, DMSO-$d_6$) δ 8.56 (s, 1H), 7.86 (d, J=3.6 Hz, 1H), 7.74 (d, J=7.8 Hz, 1H), 7.41 (bs, 1H), 6.99 (d, J=12.3 Hz, 1H), 4.28 (bs, 1H), 3.6 (s, 3H), 1.74 (m, 2H), 1.65 (m, 1H), 1.14 (m, 14H), 0.82 (m, 2H), 0.59 (m, 2H); LCMS (m/z): 500.20 (MH$^+$).

Example 223

N2-{4-Cyclopropyl-6-Fluoro-[3-(4-Methyl)-1,2,3,4-Tetrazol-5-One-1-yl]}Phenyl-5-Fluoro-N4-(2,2,6,6-Tetramethylpiperidin-4-yl)-2,4-Pyrimidinediamine Hydrogen Chloride Salt (I-80)

N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine (100 mg) suspended in water in a 20 ml scintillation vial, 1 N HCl (0.2 ml, 1.0 eq.) was added and a clear solution was obtained. Water was removed by lyophilizing over two days to give white solid. Salt formation was confirmed by $^1$H NMR, 50 mg of this salt was dissolved completely into ethyl alcohol (6 ml) in a 20 ml scintillation vial and it was placed into a glass TLC chamber filled with EtOAc. After 3 days with no signs of crystal formation, EtOAc was removed from the TLC chamber, and replaced with ether. The TLC chamber was closed with a glass top, left inside the cabinet. Crystals started to form at the bottom of the vial after sitting inside the cabinet for two days and it was left there for around 9 days. The vial was carefully removed from the chamber and the solid was collected by filtering through a funnel fitted with filter paper. The solid (30 mg) was dried under reduced pressure for 48 hours.

$^1$H NMR (300 MHz, DMSO-$d_6$) δ 8.9 (bs, 1H), 8.61 (s, 1H), 7.88 (d, J=3.6 Hz, 1H), 7.72 (d, J=7.8 Hz, 1H), 7.52 (d, J=7.2 Hz, 1H), 6.99 (d, J=12 Hz, 1H), 4.33 (bs, 1H), 3.6 (s, 3H), 1.83 (d, J=11.7 Hz, 2H) 1.66 (m, 1H), 1.5 (t, J=13.2 Hz, 2H), 1.34 (s, 6H), 1.23 (s, 6H), 0.81 (m, 2H), 0.6 (m, 2H); LCMS (m/z): 500.20 (MH$^+$).

Example 224

N2-{4-Cyclopropyl-6-Fluoro-[3-(4-Methyl)-1,2,3,4-Tetrazol-5-One-1-yl]}Phenyl-5-Fluoro-N4-(2,2,6,6-Tetramethylpiperidin-4-yl)-2,4-Pyrimidinediamine Benzoate Salt (I-81)

N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine (100 mg) was suspended in water, benzoic acid (24.5 mg, 1.0 eq) was added. Solution remained milky even after sonication, left in cabinet for 1 week. Filtered off solid to get a clear solution, small sparkling crystal started to form in mother liquor while sitting inside the cabinet. It was left undisturbed for 2 more weeks, filtered to get around 25 mg of solid.

$^1$H NMR (300 MHz, DMSO-$d_6$) δ 8.49 (s, 1H), 7.9 (d, J=6.9 Hz, 2H), 7.83 (d, J=3.6 Hz, 1H), 7.77 (d, J=8.1 Hz, 1H), 7.53 (m, 1H), 7.43 (m, 2H), 7.24 (d, J=7.8 Hz, 1H), 6.97 (d, J=12.3 Hz, 1H), 4.26 (bs, 1H), 3.6 (s, 3H), 1.63 (m, 3H), 1.17 (t, J=12 Hz, 2H), 1.05 (s, 6H), 1.02 (s, 6H), 0.81 (m, 2H), 0.59 (m, 2H); LCMS (m/z): 500.20 (MH$^+$).

Example 225

N2-{4-Cyclopropyl-6-Fluoro-[3-(4-Methyl)-1,2,3,4-Tetrazol-5-One-1-yl]}Phenyl-5-Fluoro-N4-(2,2,6,6-Tetramethylpiperidin-4-yl)-2,4-Pyrimidinediamine Tosylate Salt (I-82)

N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine (50 mg) in a 20 ml scintillation vial was dissolved into anhydrous THF (1 ml), para-TSA (19.1 mg, 1.0 eq.) was added, a clear solution was obtained, small crystal started to form at the bottom of vial. It was left inside the cabinet for 3 days, removed THF by filtering through Buchner funnel fitted with filter paper. White solid (40 mg) collected was dried under reduced pressure for 2 days.

$^1$H NMR (300 MHz, DMSO-$d_6$) δ 8.62 (s, 1H), 8.49 (d, J=12.6 Hz, 1H), 7.89 (d, J=3.6 Hz, 1H), 7.72 (d, J=7.8 Hz, 1H), 7.51 (d, J=8.1 Hz, 1H), 7.46 (d, J=7.8 Hz, 2H), 7.09 (d, J=8.4 Hz, 2H), 7.0 (d, J=12 Hz, 1H), 4.3 (bs, 1H), 3.6 (s, 3H), 2.27 (s, 3H), 1.86 (d, J=12 Hz, 2H), 1.67 (m, 1H), 1.48 (t, J=11.7 Hz, 2H), 1.31 (s, 6H), 1.22 (s, 6H), 0.83 (m, 2H), 0.60 (m, 2H); LCMS (m/z): 500.20 (MH$^+$).

Example 226

N2-{4-Cyclopropyl-6-Fluoro-[3-(4-Methyl)-1,2,3,4-Tetrazol-5-One-1-yl]}Phenyl-5-Fluoro-N4-(2,2,6,6-Tetramethylpiperidin-4-yl)-2,4-Pyrimidinediamine Besylate Salt (I-83)

N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine (50 mg) in a 20 ml scintillation vial was dissolved into anhydrous THF (1 ml), benzenesulfonic acid (15.8 mg, 1.0 eq.) was added, a clear solution was obtained, no crystal formed right away. It was left inside the cabinet for 3 days, crystals formed at the bottom of the vial. It was collected after THF was removed by filtering through Buchner funnel fitted with filter paper. White solid (25 mg) collected was pumped under reduced pressure for 2 days.

$^1$H NMR (300 MHz, DMSO-$d_6$) δ 8.62 (s, 1H), 8.49 (d, J=12.6 Hz, 1H), 7.89 (d, J=3.6 Hz, 1H), 7.72 (d, J=7.5 Hz, 1H), 7.59 (m, 3H), 7.3 (m, 2H), 7.0 (d, J=12 Hz, 1H), 4.31 (bs, 1H), 3.6 (s, 3H), 1.86 (d, J=13.8 Hz, 2H), 1.66 (b,s, 1H), 1.48 (t, J=12.3 Hz, 2H), 1.31 (s, 6H), 1.22 (s, 6H), 0.82 (m, 2H), 0.6 (m, 2H); LCMS (m/z): 500.20 (MH$^+$).

Example 227

N2-{4-Cyclopropyl-6-Fluoro-[3-(4-Methyl)-1,2,3,4-Tetrazol-5-One-1-yl]}Phenyl-5-Fluoro-N4-(2,2,6,6-Tetramethylpiperidin-4-yl)-2,4-Pyrimidinediamine Mesylate Salt (I-84)

N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine (50 mg) in a 20 ml scintillation vial dissolved into 1 ml of anhydrous THF, methanesulfonic acid (6.5 µl, 1.0 eq) was added, a milky solution formed, heated at 70° C. until clear solution obtained, cooled to room temperature in oil bath. Filtered off liquid the next day and dried under reduced pressure for 3 days, gave around 38 mg of white solid.

$^1$H NMR (300 MHz, DMSO-$d_6$) δ 9.07 (s, 1H), 8.54 (d, J=10.5 Hz, 1H), 8.08 (s, 1H), 8.01 (s, 1H), 7.73 (s 1H), 7.68 (d, J=7.8 Hz, 1H), 7.05 (d, J=11.7 Hz, 1H), 4.28 (bs, 1H), 3.6 (s, 3H), 2.29 (s, 3H), 1.83 (d, J=12.6 Hz, 2H), 1.68 (m, 1H), 1.50 (t, J=12.6 Hz, 2H), 1.32 (s, 6H), 1.19 (s, 6H), 0.85 (m, 2H), 0.63 (m, 2H); LCMS (m/z): 500.20 (MH$^+$).

Example 228

N2-{4-Cyclopropyl-6-Fluoro-[3-(4-Methyl)-1,2,3,4-Tetrazol-5-One-1-yl]}Phenyl-5-Fluoro-N4-(2,2,6,6-Tetramethylpiperidin-4-yl)-2,4-Pyrimidinediamine Acetate Salt (I-85)

N2-{4-Cyclopropyl-6-fluoro-[3-(4-methyl)-1,2,3,4-tetrazol-5-one-1-yl]}phenyl-5-fluoro-N4-(2,2,6,6-tetramethylpiperidin-4-yl)-2,4-pyrimidinediamine (50 mg) was dissolved into anhydrous THF in a 20 ml scintillation vial. Acetic acid (5.7 µl, 1.0 eq.) was added to the solution, a clear solution formed, this solution was put inside the refrigerator for 4 days. Solid formed at the bottom of the vial was collected by filtering off THF through filter paper to obtain white solids (25 mg). It was dried under reduced pressure for 4 days.

$^1$H NMR (300 MHz, DMSO-$d_6$) δ 8.46 (s, 1H), 7.81 (m, 2H), 7.17 (d, J=8.4 Hz, 1H), 6.96 (d, J=12 Hz, 1H), 4.23 (bs, 1H), 3.6 (s, 2H), 1.88 (s, 3H), 1.60 (m, 3H), 1.09 (t, J=12 Hz, 2H), 0.98 (s, 12H), 0.81 (m, 2H), 0.59 (m, 2H); LCMS (m/z): 500.20 (MH$^+$).

Example 229

4-fluoro-2-methoxyaniline

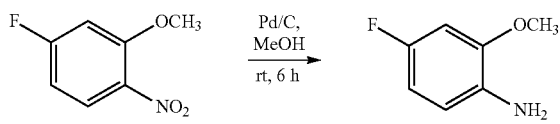 [SMILES: COc1cc(F)ccc1[N+](=O)[O-] ; COc1cc(F)ccc1N]

A solution of 5-fluoro-2-nitroanisole (5.0 g, 29.22 mmol, 1 equiv) in the presence of 250 mg of Pd/C (5%) in MeOH (60 mL) was hydrogenated at room temperature for 6 hours. The reaction mixture was filtered over a pad of Celite and then concentrated to give a brown oil (4.06 g, 98%) which was directly used in the next step. m/z=142 (M+H)$^+$.

Example 230

4-fluoro-2-methoxyphenylisocyanate

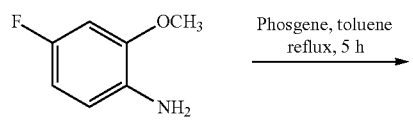

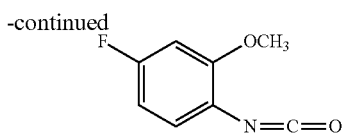

A solution of 4-fluoro-2-methoxyaniline (2.0 g, 14.2 mmol, 1 equiv) in 20% of phosgene in toluene (15 mL, 28.4 mmol, 2 equiv) was refluxed for 5 hours. The reaction mixture was then concentrated and the resulting residue was directly used in the next step.

Example 231

1-(4-fluoro-2-methoxyphenyl)-4,5-dihydro-5H-tetrazol-5-one

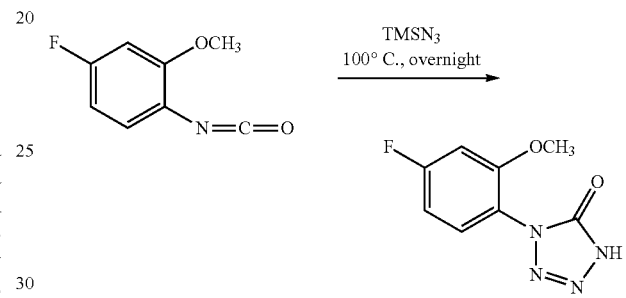

To the above residue of Example 230, 3.77 mL of TMSN$_3$ (28.4 mmol, 2 equiv) was added and then the resulting mixture was heated at 100° C. overnight. After being cooled to room temperature, the reaction mixture was concentrated. The residue was diluted with EtOAc (50 mL) and saturated aqueous NaHCO$_3$ (50 mL). The aqueous layer was separated, neutralized with 2 N HCl to pH 4~5 and extracted with EtOAc (2×50 mL). The organic layers were combined, dried over MgSO$_4$ and concentrated to give a white solid (450 mg, 15% two steps) which was directly used in the next step. m/z=211 (M+H)$^+$.

Example 232cl 1-(4-fluoro-2-methoxyphenyl)-4-methyl-5H-tetrazol-5-one

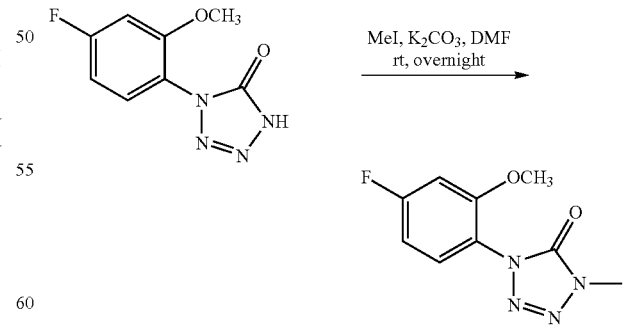

To a mixture of 1-(4-fluoro-2-methoxyphenyl)-4,5-dihydro-5H-tetrazol-5-one (450 mg, 2.14 mmol, 1 equiv) and K$_2$CO$_3$ (887 mg, 6.43 mmol, 3 equiv) in 6 mL of DMF was added MeI (0.4 mL, 6.43 mmol, 3 equiv) and the resulting mixture was stirred at room temperature overnight. The reaction mixture was diluted with water and extracted with EtOAc. The organic layer was separated and concentrated. The residue was triturated in water to give 410 mg of product (85%) as an off-white solid. m/z=270 (M+H)$^+$.

Example 233

1-(4-fluoro-2-methoxy-5-nitrophenyl)-4-methyl-5H-tetrazol-5-one

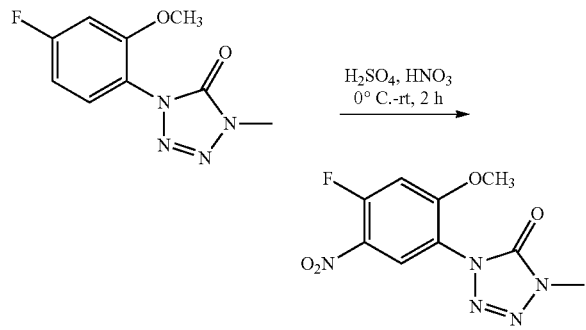

90% HNO$_3$ (0.056 mL, 1.13 mmol, 1.1 equiv) was added dropwise to a mixture of 1-(4-fluoro-2-methoxyphenyl)-4-methyl-5H-tetrazol-5-one (230 mg, 1.03 mmol, 1 equiv) in 2 mL of fuming H$_2$SO$_4$ at 0° C. Then the mixture was left to room temperature and stirred for 2 hours. Poured into ice and the aqueous phase was extracted with EtOAc. The organic layer was separated, washed with saturated NaHCO$_3$ and concentrated to give 277 mg of product (quantitative) as a yellow solid.

$^1$H NMR (CDCl$_3$, 300 MHz): δ 8.28 (d, J=7.8 Hz, 1H), 6.94 (d, J=12.0 Hz, 1H), 3.98 (s, 3H), 3.72 (s, 3H); m/z=270 (M+H)$^+$.

Example 234

1-(5-amino-4-fluoro-2-methoxyphenyl)-4-methyl-5H-tetrazol-5-one

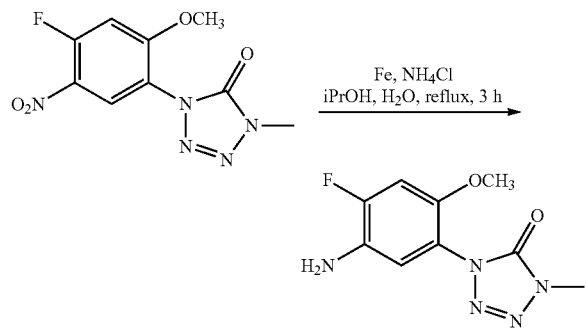

A mixture of 1-(4-fluoro-2-methoxy-5-nitrophenyl)-4-methyl-5H-tetazol-5-one (320 mg, 1.2 mmol, 1 equiv), iron powder (332 mg, 6.0 mmol, 5 equiv) and ammonium chloride (318 mg, 6.0 mmol, 5 equiv) in iPrOH (6 mL) and water (1.2 mL) was refluxed for 3 hours. After cooling to room temperature, the reaction mixture was filtered through a pad of Celite, and the pad of Celite was rinsed with EtOAc (50 mL). The filtrate was washed with water. The organic layer was separated, dried over MgSO$_4$ and evaporated to give the product quantitatively. m/z=240 (M+H)$^+$.

Example 235

N2-(4-fluoro-2-methoxy-3-(4-methyl-4,5-dihydro-5-oxo-1H-tetrazol-1-yl)phenyl)-5-fluoro-N4-(2,2,6,6-tetramethylpiperidin-4-yl)pyrimidine-2,4-diamine

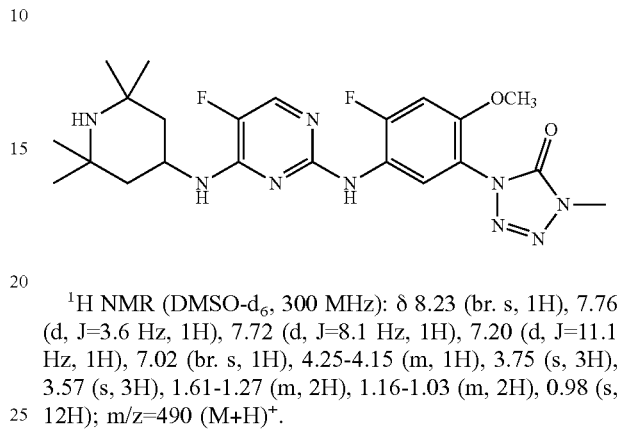

$^1$H NMR (DMSO-d$_6$, 300 MHz): δ 8.23 (br. s, 1H), 7.76 (d, J=3.6 Hz, 1H), 7.72 (d, J=8.1 Hz, 1H), 7.20 (d, J=11.1 Hz, 1H), 7.02 (br. s, 1H), 4.25-4.15 (m, 1H), 3.75 (s, 3H), 3.57 (s, 3H), 1.61-1.27 (m, 2H), 1.16-1.03 (m, 2H), 0.98 (s, 12H); m/z=490 (M+H)$^+$.

Example 236

N2-(4-fluoro-2-methoxy-3-(4-methyl-4,5-dihydro-5-oxo-1H-tetrazol-1-yl)phenyl)-5-fluoro-N4-(1,2,2,6,6-pentamethylpiperidin-4-yl)pyrimidine-2,4-diamine (I-87)

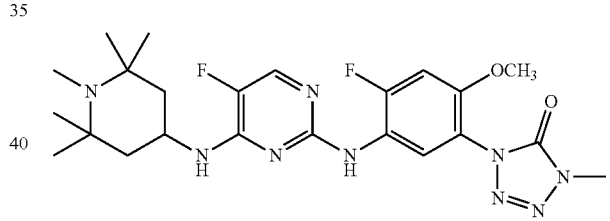

$^1$H NMR (DMSO-d$_6$, 300 MHz): δ 8.50 (br. s, 1H), 7.85 (d, J=3.9 Hz, 1H), 7.62 (d, J=8.4 Hz, 1H), 7.47 (d, J=7.5 Hz, 1H), 7.26 (d, J=12.0 Hz, 1H), 4.28-4.18 (m, 1H), 3.77 (s, 3H), 3.58 (s, 3H), 2.66 (s, 3H), 2.00-1.90 (m, 2H), 1.73-1.65 (m, 2H), 1.35 (s, 6H), 1.18 (s, 6H); m/z=504 (M+H)$^+$.

BIOLOGICAL EXAMPLES

Example 237: PKC Assay

The inhibition of PKC-alpha, PKC-beta, PKC-delta, PKC epsilon and PKC-theta activity is determined via ELISA as follows: NUNC MAXISORP (#436110) or Costar High Binding (#3922) plates are coated with 0.01 mg/mL Neutravidin (Pierce #PI-31000) in 1×PBS (100 µL/well) for 18-24 hours at 4° C. When ready to be used, plates are washed with 1×PBST and then blocked with 2% BSA in 1×PBST (100 µL/well) for a minimum of 1 hour at room temperature. The reactions are conducted in a volume of 60 µL/well. When ready to begin, the plates are washed with 1×PBST to remove the 2% BSA blocking solution. Reaction solution containing the necessary buffer components as well as the appropriate concentrations of ATP and peptide substrate is then added to each well (see Table 3). Appropriate concentrations of test compound is then added—with the volume added should taking into consideration the DMSO tolerance of the kinases being about 0.2%. The reaction is then initiated by the addition of kinase—the approximate final concentration of which is listed in Table 3 (note that this will vary depending on the batch to batch variability in the activity of enzymes). After allowing the reaction to stand at room temperature for 20 minutes, the plates are then washed with 1×PBST.

TABLE 3

| Kinase | Buffer components | [ATP] (uM) | [peptide] (uM) | Time (min) | 1° and 2° antibodies | Notes |
|---|---|---|---|---|---|---|
| PKCs α: ~8 ng/mL β: ~16 ng/mL δ: ~13 ng/mL ε: ~13 ng/mL θ: ~8 ng/mL | 20 mM Hepes pH 7.4 5 mM MgCl$_2$ 0.2 mM CaCl$_2$ 1 mM DTT 0.05% Chaps | 1 µM | 1 µM PKC peptide (biotin-RFARKGSLRQKNV) (Invitrogen #P2760) (SEQ ID NO: 2) | 20 min | Rabbit pSer PKC substrate Ab (Cell Signaling #2261); HRP-goat a-rabbit (Jackson Immunoresearch #111-035-003) | 0.15 mg/mL DAG (Sigma #D0138) 0.75 mg/mL Phosphoserine (Sigma #P6641) DMSO tolerance ~0.2% |

After removal of the reaction mixture from the plate and washing with 1×PBST, an antibody developing solution containing a 1:10,000 dilution of the appropriate primary and secondary antibodies (Table 3) in a 0.1% BSA solution in 1×PBST is then added to each well (100 µL/well). This is then allowed to stand at room temperature for a minimum of 1 hour. After this time, the plates are once again washed with 1×PBST. The SuperSignal ELISA Pico Chemiluminescent substrate (Pierce #PI-37069) is then added (100 µL/well) and the plate is read on a luminescence plate reader.

Example 238: PKC Assay

Alternatively, the inhibition of PKC activity is measured by monitoring the production of phosphorylated peptide by fluorescence polarization at different concentrations of the inhibitor. Reactions are carried out in 96-well plate format with a total volume of 20 µL containing 20 mM HEPES, pH 7.4, 5 mM MgCl$_2$, 0.2 mM CaCl$_2$, 1 mM DTT, 0.02% Brij-35, 0.1 mg/mL phosphatidylserine, 0.02 mg/mL dioleoyl-sn-glycerol and 5 µM each of ATP and the peptide substrate. Compounds are first diluted serially in DMSO and then transferred to a solution containing the above concentrations of HEPES, MgCl$_2$, CaCl$_2$, DTT, and Brij-35 to yield 5× compound solutions in 2% DMSO, which is then added to the reaction solution. Reactions are initiated by the addition of PKC at a typical concentration as described in Table 4, and then allowed to incubate at room temperature for 20 minutes. At the end of this time, a combination of quench (EDTA) and detection (peptide tracer and antibody) reagents is added using the protocol of Invitrogen P2748. After a 30 minutes period of incubation, the amount of phosphorylated peptide generated is measured by fluorescence polarization (Ex=485 nm, Em=535 nm) using a Tecan Polarian instrument.

TABLE 4

| Peptide substrate | | SEQ ID | Enzyme source | Typical enzyme concentration |
|---|---|---|---|---|
| PKC theta | RFARKGSLRQKNV | Seq ID No. 1 | Upstate Biotechnologies, Temecula, CA, cat. #14-444 | 40 ng/mL |
| PKC epsilon | RFARKGSLRQKNV | Seq ID No. 1 | Upstate Biotechnologies, Temecula, CA, cat. #14-518 | 50 ng/mL |

Example 239: Calcium Influx

HEK-FLPTREX cells are stably transfected with pcDNA5/FRT/TO+hTRPV4a, rat TRPV1-HA or rTRPA1-HA are grown in Dulbecco's Modified Eagle's Medium (DMEM) containing 10% tetracycline-free fetal bovine serum, hygromycin (50 µg/ml) and blasticidin (10 µg/ml). Cells are treated with tetracycline (0.1 µg/ml, 20H) to induce TRP expression. DRG from thoracic and lumbar spinal cord of rats or mice are minced in cold Hank's Balanced Salt Solution (HBSS) and incubated for 60 at 37° C. in DMEM containing 1 mg/ml of collagenase type IA and 0.1 mg/ml of DNAse type IV, pelleted and incubated with 0.25% trypsin for 30 minutes. Neurons are pelleted, suspended in DMEM containing 10% fetal bovine serum, 10% horse serum, 100 U/ml penicillin, 0.1 mg/ml streptomycin, 2 mM glutamine, dissociated by gentle trituration until the solution appears cloudy and homogeneous and plated on glass coverslips coated with PolyOnitine/laminin. Neurons are cultured for 3-4 days before the experiment.

Cells grown on coverslips or on a 96 multiwell plate are incubated in HBSS (pH 7.4) containing Ca2+ and Mg2+, 20 mM HEPES buffer, 0.1% BSA, 100 U/ml penicillin, 100 µg/ml streptomycin, with 2.5-5 µM Fura-2AM (Invitrogen) for 20-45 minutes at 37° C. Cells are washed and fluorescence is measured at 340 nm and 380 nm excitation and 510 nm emission in a F-2500 spectrophotometer, or in a Flexstation 3 Microplate Reader III (for the measurement of the calcium in the cell population) or using a Zeiss Axiovert microscope, an ICCD video camera and a video microscopy acquisition program (for the measurement of the calcium influx in the single neurons). Substances are injected directly into the chamber (20 ml into 2 ml, for the spectrophotometer; 20 ml in 200 ml for the Flexstation, 50 ml in 350 ml in the chamber for the single cells).

Example 240: In Vivo Hyperplasia

Mechanical pain is quantified as the number of times the hind paw is withdrawn in response to 5 applications of a 0.173 mN von Frey hair. Responses are expressed as a percentage (e.g. 3 withdrawals out of 5 are recorded as 60%) and mechanical hyperalgesia defined as increase in the percentage of withdrawal compared to basal measurement. 2) Mechanical pain is quantified using the 'up-down paradigm', determining the 50% response threshold to the von Frey filaments applied to the mid-plantar surface for 5 s or until a withdrawal response occurred. Von Frey filaments are in this range of intensities: 1.65, 2.44, 2.83, 3.22, 3.61, 3.84, 4.08.

Thermal hyperalgesia is assessed in mice using a plantar test apparatus and quantified as the latency of paw withdrawal to a radiant heat. Thermal hyperalgesia is defined as a decrease in the withdrawal latency compared to the basal measurement. After measuring basal level mice, under light halothane anesthesia (5%), are injected with testing compound into the left or right paws (5-10 µl intraplantar injection) and paw withdrawal measurements repeated at different time point. To assess PAR2 TRPV1, TRPV4 and TRPA1 mediated hyperalgesia and potentiation of TRPV-mediated responses, mice are treated with PAR2-AP for 15 minutes followed by capsaicin, 4αPDD or HNE. To assess the role of protein kinases, the antagonists or the corresponding vehicles are injected 20-30 minutes before the challenge with agonists. The effects induced by the different treatments are evaluated within the same rat comparing the responses recorded in the right paw (receiving for example saline, or vehicle) with the responses obtained in the left paw (receiving for example PAR2-AP or 4(PDD).

Formalin induced hyperalgeisa is assessed using 5% solution of formalin administered by intradermal injection into the dorsal surface of the mouse or rat forepaw to induce a painful behavior. Pain is accessed on a four-level scale related to posture: 0, normal posture; 1, with the injected paw remaining on the ground but not supporting the animal; 2, with the injected paw clearly raised; and 3, with the injected paw being licked, nibbled, or shaken. Animals are observed and scored for behavior at 3 minutes after the injection (defined as initial phase that results from the direct stimulation of nociceptors), and then at 30-60 minutes after the injection (defined as second phase that involves a period of sensitization during which inflammatory phenomena occur). The nociceptive behavioral score for each 3-minutes interval is calculated as the weighted average of the number of seconds spent in each behavior. 2.5% solution of formalin is administered by intraplantar injection and thermal and mechanical pain measured as described above after 30-60 minutes. To assess the role of protein kinases, antagonists or their vehicles (control) are injected into the right paws 20-30 minutes before formalin. Nociceptive behavior will be scored for each rats and compared to control.

Example 241: IL-2 ELISA, Human Primary T Cell, Anti CD3+CD28+

Human primary T cell isolation and culture: Human primary T cells were prepared as follows. Whole blood was obtained from a healthy volunteer, mixed 1:1 with PBS, layered on to Ficoll Hypaque (Amersham Pharmacia Biotech, Piscataway, N.J., Catalog #17-1440-03) in 2:1 blood/PBS:ficoll ratio and centrifuged for 30 minutes at 4° C. at 1750 rpm. The cells at the serum: ficoll interface were recovered and washed twice with 5 volumes of PBS. These freshly isolated human peripheral blood mononuclear cells were cultured in Yssel's medium containing 40 U/mL IL2 in a flask pre-coated with 1 µg/mL αCD3 and 5 µg/mL αCD28 (Anti-Human CD3, BD Pharmingen Catalog #555336, Anti-Human CD28, Beckman Coulter Catalog #IM1376). The cells were stimulated for 3-4 days, then transferred to a fresh flask and maintained in RPMI (RPMI-1640 with L-Glutamine; Mediatech, Inc., Herndon Va., cat. #10-040-CM) with 10% FBS and 40 U/mL IL-2. The primary T-cells were then washed twice with PBS to remove the IL-2.

Primary T cell stimulation and IL2 ELISA: Human primary T cells (100,000 cells per well) were pre-incubated with or without test compound in Yssel's medium for 1 hour at 37° C. Cells were then stimulated by transferring them to round-bottom 96-well plates pre-coated with 1 µg/ml αCD3 and 5 µg/ml αCD28. For counter assay, cells were instead stimulated by adding 8x stock solutions of PMA and ionomycin in Yssels (for final concentrations of 0.5 ng/ml PMA and 0.1 uM ionomycin, both from Calbiochem). Cells were incubated at 37° C. for 24 hours before 100 µL supernatants were harvested for quantification of IL-2 by ELISA using Human IL-2 Duoset ELISA Kit from R and D Systems, Cat. # DY202E.

Table 5 shows the $IC_{50}$ values for compounds tested in the assays described in this example. For ELISA data in Table 5, "A" indicates an $IC_{50}$ in the indicated assay of less than 0.5 µM; "B" is 0.51-2.99 µM; "C" is 3-25 µM; and "D" is from greater than 25 µM.

TABLE 5

| Compound | $IC_{50}$ |
|---|---|
| I-1 | C |
| I-2 | D |
| I-3 | A |
| I-4 | A |
| I-5 | B |
| I-6 | B |
| I-7 | B |
| I-8 | A |
| I-9 | A |
| I-10 | A |
| I-11 | A |
| I-12 | B |
| I-13 | B |
| I-14 | A |
| I-15 | A |
| I-16 | A |
| I-17 | A |
| I-18 | A |
| I-19 | A |
| I-20 | A |
| I-21 | A |
| I-22 | A |
| I-23 | A |
| I-24 | A |
| I-25 | A |
| I-26 | A |
| I-27 | A |
| I-28 | A |
| I-29 | A |
| I-30 | A |
| I-31 | A |
| I-32 | A |
| I-33 | A |
| I-34 | A |
| I-35 | A |
| I-36 | A |
| I-37 | B |
| I-38 | A |
| I-39 | A |
| I-40 | A |
| I-41 | A |
| I-42 | A |

TABLE 5-continued

| Compound | IC$_{50}$ |
|---|---|
| I-43 | A |
| I-44 | A |
| I-45 | A |
| I-46 | A |
| I-47 | A |
| I-48 | A |
| I-49 | A |
| I-50 | A |
| I-51 | A |
| I-52 | A |
| I-53 | A |
| I-54 | A |
| I-55 | A |
| I-56 | A |
| I-57 | A |
| I-58 | A |
| I-59 | A |
| I-60 | A |
| I-61 | C |
| I-62 | A |
| I-63 | A |
| I-64 | A |
| I-65 | C |
| I-66 | C |
| I-67 | C |
| I-68 | A |
| I-69 | A |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of formula (V):

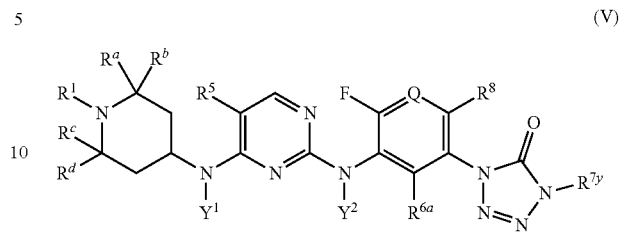

wherein

R$^5$ is selected from alkyl, substituted alkyl, hydroxy, alkoxy, substituted alkoxy, amino, substituted amino, carboxyl, carboxyl ester, cyano, halogen, acyl, aminoacyl, nitro, alkenyl, substituted alkenyl, alkynyl, and substituted alkynyl;

Y$^1$ and Y$^2$ are independently selected from hydrogen, alkyl, and acyl;

R$^1$ is selected from hydrogen, alkyl, substituted alkyl, cycloalkyl, acyl, and oxy radical;

R$^a$ and R$^b$ are independently selected from hydrogen and alkyl;

R$^c$ and R$^d$ are independently selected from hydrogen and alkyl;

Q is selected from N and CR$^{7b}$;

R$^{6a}$, R$^{7b}$ and R$^8$ are independently selected from hydrogen, alkyl, substituted alkyl, halogen, cyano, hydroxyl, alkoxy, substituted alkoxy, amino, substituted amino, acylamino, aminocarbonyloxy, heteroaryl, substituted heteroaryl, heterocyclyl, substituted heterocyclyl, alkenyl, substituted alkenyl, alkynyl, substituted alkynyl, cycloalkyl, substituted cycloalkyl, aryl, substituted

SEQUENCE LISTING

<160> NUMBER OF SEQ ID NOS: 2

<210> SEQ ID NO 1
<211> LENGTH: 13
<212> TYPE: PRT
<213> ORGANISM: Artificial Sequence
<220> FEATURE:
<223> OTHER INFORMATION: Synthetic peptide

<400> SEQUENCE: 1

Arg Phe Ala Arg Lys Gly Ser Leu Arg Gln Lys Asn Val
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal biotinylation

<400> SEQUENCE: 2

Arg Phe Ala Arg Lys Gly Ser Leu Arg Gln Lys Asn Val
1               5                   10 aryl, alkoxycarbonylamino, aminocarbonylamino, acyl, carboxyl, carboxyl ester, aminoacyl, sulfonyl, sulfonylamino, aminosulfonyl, and —O-alk-A;

alk is a bond, alkylene or substituted alkylene;

A is selected from aryl, cycloalkyl, heteroaryl, and heterocyclyl;

wherein the A ring can be substituted or unsubstituted; and $R^{7y}$ is selected from hydrogen, alkyl, and substituted alkyl;

or a salt or stereoisomer thereof.

2. The compound of claim 1, wherein $R^5$ is cyano or halogen.

3. The compound of claim 1, wherein $R^5$ is halogen.

4. The compound of claim 1, wherein $R^5$ is fluoro.

5. The compound of claim 1, wherein $R^5$ is cyano.

6. The compound of claim 1, wherein $R^8$ is selected from hydrogen, alkyl, substituted alkyl, halogen, alkoxy, substituted alkoxy, cycloalkyl, and substituted cycloalkyl.

7. The compound of claim 1, wherein $R^8$ is selected from alkyl, substituted alkyl, cycloalkyl, and substituted cycloalkyl.

8. The compound of claim 1, wherein $R^8$ is cycloalkyl or substituted cycloalkyl.

9. The compound of claim 1, wherein $R^8$ is cyclopropyl.

10. The compound of claim 1, wherein $Y^1$ and $Y^2$ are each hydrogen.

11. The compound of claim 1, wherein $R^1$ is hydrogen.

12. The compound of claim 1, wherein $R^1$ is alkyl.

13. The compound of claim 1, wherein $R^a$, $R^b$, $R^c$ and $R^d$ are each alkyl.

14. The compound of claim 1, wherein $R^{6a}$ is selected from hydrogen, alkyl, substituted alkyl, and halogen.

15. The compound of claim 1, wherein $R^{6a}$ is hydrogen.

16. The compound of claim 1, wherein Q is $CR^{7b}$, and $R^{7b}$ is selected from hydrogen, alkyl, and substituted alkyl.

17. The compound of claim 16, wherein $R^{7b}$ is hydrogen.

18. The compound of claim 1, wherein $R^{7y}$ is alkyl.

19. The compound of claim 1, wherein the compound is 1-(2-cyclopropyl-4-fluoro-5-(5-fluoro-4-(2,2,6,6-tetramethylpiperidin-4-ylamino)pyrimidin-2-ylamino)phenyl)-4-methyl-1H-tetrazol-5(4H)-one (Compound I-14).

20. The compound of claim 1, wherein the compound is 1-{2-Cyclopropyl-4-fluoro-5-[5-fluoro-4-(1,2,2,6,6-pentamethyl-piperidin-4-ylamino)-pyrimidin-2-ylamino]-phenyl}-4-methyl-1,4-dihydro-tetrazol-5-one (Compound (I-16).

21. A pharmaceutical composition comprising a compound of claim 1 and a pharmaceutically acceptable carrier.

22. A method of inhibiting a protein kinase C (PKC) activity, wherein the method comprises:

contacting a PKC with a compound of claim 1, wherein the contacting results in inhibition of the PKC activity.

23. The method of claim 22, wherein the contacting comprises administering a therapeutically effective amount of the compound of formula (V) to a subject in need of treatment of a disease or disorder that is mediated or sustained through the PKC activity, and wherein the administering results in treatment of the disease or disorder that is mediated or sustained through the PKC activity.

24. The method of claim 23, wherein the disease or disorder is associated with activation of T cells.

25. The method of claim 23, wherein the disease or disorder is an inflammatory disease.

26. The method of claim 23, wherein the disease or disorder is an autoimmune disease.

27. The method of claim 23, wherein the disease or disorder is an ocular disease or disorder involving inflammatory and/or neovascular events.

* * * * *